US011155815B2

(12) United States Patent
Rigo

(10) Patent No.: US 11,155,815 B2
(45) Date of Patent: *Oct. 26, 2021

(54) COMPOSITIONS AND METHODS FOR MODULATING TAU EXPRESSION

(71) Applicant: Ionis Pharmaceuticals, Inc., Carlsbad, CA (US)

(72) Inventor: Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/472,110

(22) Filed: Mar. 28, 2017

(65) Prior Publication Data

US 2018/0051283 A1 Feb. 22, 2018

Related U.S. Application Data

(63) Continuation of application No. 14/776,561, filed as application No. PCT/US2014/029752 on Mar. 14, 2014, now Pat. No. 9,644,207.

(60) Provisional application No. 61/943,931, filed on Feb. 24, 2014, provisional application No. 61/785,177, filed on Mar. 14, 2013.

(51) Int. Cl.
*C12N 15/113* (2010.01)
*C12Q 1/68* (2018.01)

(52) U.S. Cl.
CPC ........ *C12N 15/113* (2013.01); *C12N 2310/11* (2013.01); *C12N 2310/31* (2013.01); *C12N 2310/315* (2013.01); *C12N 2310/3181* (2013.01); *C12N 2310/32* (2013.01); *C12N 2310/321* (2013.01); *C12N 2310/322* (2013.01); *C12N 2310/3231* (2013.01); *C12N 2310/3233* (2013.01); *C12N 2310/3341* (2013.01); *C12N 2310/345* (2013.01); *C12N 2310/346* (2013.01); *C12N 2310/351* (2013.01); *C12N 2320/33* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 4,880,635 A | 11/1989 | Janoff et al. |
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 5,034,506 A | 7/1991 | Summerton et al. |
| 5,130,302 A | 7/1992 | Spielvogel et al. |
| 5,134,066 A | 7/1992 | Rogers et al. |
| 5,149,797 A | 9/1992 | Pederson et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner |
| 5,457,187 A | 10/1995 | Gmelner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,801,154 A | 9/1998 | Baracchini et al. |
| 5,830,653 A | 11/1998 | Froehler et al. |
| 5,837,853 A | 11/1998 | Takashima et al. |

(Continued)

FOREIGN PATENT DOCUMENTS

| CN | 1696294 | 11/2005 |
|---|---|---|
| WO | WO 1998/039352 | 9/1998 |

(Continued)

OTHER PUBLICATIONS

International Search Report and Written Opinion for application PCT/US2017/054540 dated Jan. 18, 2018, 11 pages.
Sazani et al., "Therapeutic potential of antisense oligonucleotides as modulators of alternative splicing," J. Clinical Invest (2003) 112 481-486.
Buck et al., "Design Strategies and Performance of Custom DNA Sequencing Primers," Biotechniques, 1999, 27(3): 528-536.
GenBank Accession No. NM_001285455.1.
Chernolovskaya et al., "Chemical Modification of siRNA," Current Opinion in Molecular Therapeutics, 2010, 12(2):1-10.
Agrawal et al., "Site-specific excision from RNA by Rnase H and mixed-phosphate-backbone oligodeoxynucleotides" Proc. Nat'l Acad. Sci (1990) 87:1401-1405.

(Continued)

*Primary Examiner* — Sean McGarry
(74) *Attorney, Agent, or Firm* — McNeill Baur PLLC

(57) ABSTRACT

Disclosed are methods for modulating splicing of Tau mRNA in an animal with Tau antisense compounds. Also disclosed herein are methods for reducing expression of Tau mRNA and protein in an animal with Tau antisense compounds. Such compounds and methods are useful to treat, prevent, or ameliorate neurodegenerative diseases in an individual in need thereof. Examples of neurodegenerative diseases that can be treated, prevented, and ameliorated with the administration Tau antisense oligonucleotides include Alzheimer's Disease, Fronto-temporal Dementia (FTD), FTDP-17, Progressive Supranuclear Palsy, Chronic Traumatic Encephalopathy, Epilepsy, and Dravet's Syndrome.

33 Claims, 1 Drawing Sheet
Specification includes a Sequence Listing.

(56) References Cited

U.S. PATENT DOCUMENTS

| | | | |
|---|---|---|---|
| 6,005,096 A | 12/1999 | Matteucci et al. | |
| 6,268,490 B1 | 7/2001 | Imanishi et al. | |
| 6,525,191 B1 | 2/2003 | Ramasamy | |
| 6,582,908 B2 | 6/2003 | Fodor et al. | |
| 6,670,461 B1 | 12/2003 | Wengel et al. | |
| 6,673,661 B1 | 1/2004 | Liu et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,084,125 B2 | 8/2006 | Wengel | |
| 7,217,805 B2 | 5/2007 | Imanishi et al. | |
| 7,314,923 B2 | 1/2008 | Kaneko et al. | |
| 7,399,845 B2 | 7/2008 | Seth et al. | |
| 7,427,672 B2 | 9/2008 | Imanishi et al. | |
| 7,547,684 B2 | 6/2009 | Seth et al. | |
| 7,569,575 B2 | 8/2009 | Sorensen et al. | |
| 7,696,345 B2 | 4/2010 | Allerson et al. | |
| 7,741,457 B2 | 6/2010 | Seth et al. | |
| 7,858,747 B2 | 12/2010 | Woldike et al. | |
| 8,178,503 B2 | 5/2012 | Rigoutsos et al. | |
| 8,329,890 B2 | 12/2012 | Davidson et al. | |
| 8,871,729 B2 | 10/2014 | Yague et al. | |
| 9,084,813 B2 | 7/2015 | Roberson et al. | |
| 9,198,982 B2 | 12/2015 | Roberson et al. | |
| 9,644,207 B2 | 5/2017 | Rigo et al. | |
| 9,683,235 B2 | 6/2017 | Freier | |
| 10,407,680 B2 | 9/2019 | Kordasiewicz | |
| 2001/0053519 A1 | 12/2001 | Fodor et al. | |
| 2002/0018995 A1 | 2/2002 | Ghetti et al. | |
| 2003/0219770 A1 | 11/2003 | Eshleman et al. | |
| 2003/0228597 A1 | 12/2003 | Cowsert et al. | |
| 2004/0054156 A1 | 3/2004 | Draper et al. | |
| 2004/0171570 A1 | 9/2004 | Allerson et al. | |
| 2004/0241651 A1 | 12/2004 | Olek et al. | |
| 2005/0108783 A1 | 5/2005 | Koike et al. | |
| 2005/0130923 A1 | 6/2005 | Bhat et al. | |
| 2005/0153336 A1 | 7/2005 | Bennett et al. | |
| 2005/0244851 A1 | 11/2005 | Blume et al. | |
| 2005/0255487 A1 | 11/2005 | Khvorova et al. | |
| 2006/0216722 A1 | 9/2006 | Betsholtz et al. | |
| 2007/0031844 A1 | 2/2007 | Khvorova et al. | |
| 2007/0203333 A1 | 8/2007 | McSwiggen et al. | |
| 2007/0287831 A1 | 12/2007 | Seth et al. | |
| 2008/0003570 A1* | 1/2008 | Rogers | C07K 14/47 435/6.16 |
| 2008/0039618 A1 | 2/2008 | Allerson et al. | |
| 2008/0249058 A1 | 10/2008 | Roberson et al. | |
| 2008/0318210 A1 | 12/2008 | Bentwich | |
| 2009/0012281 A1 | 1/2009 | Swayze et al. | |
| 2009/0162365 A1 | 6/2009 | Feinstein et al. | |
| 2009/0076725 A1 | 7/2009 | Morrissey et al. | |
| 2009/0176728 A1 | 7/2009 | Yague et al. | |
| 2010/0261175 A1 | 10/2010 | Rasmussen et al. | |
| 2011/0054005 A1 | 3/2011 | Naito et al. | |
| 2011/0150897 A1 | 6/2011 | Meyer et al. | |
| 2011/0244561 A1 | 10/2011 | Davidson et al. | |
| 2011/0263687 A1 | 10/2011 | Mattick et al. | |
| 2013/0046007 A1 | 2/2013 | Bennett et al. | |
| 2013/0123133 A1 | 5/2013 | Ward et al. | |
| 2014/0155462 A1* | 6/2014 | Brown | A61K 31/713 514/44 A |
| 2014/0315983 A1* | 10/2014 | Brown | A61K 31/713 514/44 A |
| 2015/0057329 A1 | 2/2015 | Bhanot et al. | |
| 2017/0211064 A1 | 7/2017 | Rigo | |
| 2018/0094261 A1 | 4/2018 | Kordasiewicz et al. | |
| 2018/0119145 A1 | 5/2018 | Kordasiewicz | |
| 2019/0211332 A1 | 7/2019 | Kordasiewicz | |

FOREIGN PATENT DOCUMENTS

| | | |
|---|---|---|
| WO | WO 1999/014226 | 3/1999 |
| WO | WO 1999/062548 | 12/1999 |
| WO | WO 2000/063364 | 10/2000 |
| WO | WO 2001/032703 | 5/2001 |
| WO | WO 2002/081494 | 10/2002 |
| WO | WO 2003/004602 | 1/2003 |
| WO | WO 2004/017072 | 2/2004 |
| WO | WO 2004/035765 | 4/2004 |
| WO | WO 2004/058940 | 7/2004 |
| WO | WO 2004/011613 | 9/2004 |
| WO | WO 2004/106356 | 12/2004 |
| WO | WO 2005/017143 | 2/2005 |
| WO | WO 2005/021570 | 3/2005 |
| WO | WO 2005/040180 | 5/2005 |
| WO | WO 2006/047673 | 5/2006 |
| WO | WO 2007/027775 | 3/2007 |
| WO | WO 2007/107789 | 9/2007 |
| WO | WO 2007/134181 | 11/2007 |
| WO | WO 2008/101157 | 8/2008 |
| WO | WO 2008/124066 | 10/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036698 | 4/2010 |
| WO | WO 2010/148249 | 12/2010 |
| WO | WO 2011/005786 | 1/2011 |
| WO | WO 2011/005793 | 1/2011 |
| WO | WO 2011/017521 | 5/2011 |
| WO | WO 2011/131693 | 10/2011 |
| WO | WO 2011/139702 | 11/2011 |
| WO | WO 2012/005898 | 1/2012 |
| WO | WO 2012/018881 | 2/2012 |
| WO | WO 2012/177639 | 12/2012 |
| WO | WO 2013/148260 | 10/2013 |
| WO | WO 2013/148283 | 10/2013 |
| WO | WO 2013/173647 | 11/2013 |
| WO | WO 2014/012081 | 1/2014 |
| WO | WO 2014/114937 | 7/2014 |
| WO | WO 2015/010135 | 1/2015 |
| WO | WO 2016/151523 | 9/2016 |
| WO | WO 2018/064593 | 4/2018 |

OTHER PUBLICATIONS

Albaek et al., "Analogues of a Locked Nucleic Acid with Three-Carbon 2',4'Linkages: Synthesis by Ring-Closing Metathesis and Influence of Nucleic Acid Duplex Stability" J. Org. Chem. (2006)71:7731-7740.

Allshire, "RNAi and Heterochromatin—a Hushed-Up Affair" Science (2002) 297: 1818-1819.

Altmann et al., "Second Generation Antisense Oligonucleotides—Inhibition of PKC-a and c-RAF Kinase Expression by Chimeric Oligonucleotides Incorporating 6'Substituted Carbocyclic Nucleosides and 2'-O-Ethylene Glycol Substituted Ribonucleosides" Nucleosides Nucleotides (1997) 16: 917-926.

Altmann et al., "Second Generation of Antisense Oligonucleotides: From Nuclease Resistance to Biological Efficacy in Animals" Chimia (1996) 50: 168-176.

Altmann et al., "Second-generation antisense oligonucleotides: structure-activity relationships and the design of improved signal-transduction inhibitors." Biochem. Soc. Trans. (1996) 24: 630-637.

Altschul et al., "Basic Local Alignment Search Tool" J. Mol. Biol. (1990) 215:403-410.

Andorfer et al., "Hyperphosphorylation and aggregation of tau in mice expressing normal human tau isoforms" Journal of Neurochemistry (2003) 86: 582-590.

Australian Patent Examination Report for Application No. 2013202595 dated Jul. 4, 2014 (15 pages).

Badiola et al., "Tau phosphorylation and aggregation as a therapeutic target in tauopathies" CNS Neurol Discord Drug Targets (2010) 9(6):727-740.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1

(56) References Cited

OTHER PUBLICATIONS

Translation Initiation Complex in Human Umbilical Vein Endothelial Cells" J. Biol. Chern., (1997) 272: 11944-12000.
Baker et al., "Effects of oligo sequence and chemistry on the efficiency of oligodeoxyribonucleotide-mediated mRNA cleavage" (1990) 18(12):3537-3543.
Bevins et al., "Object recognition in rats and mice: a one-trial non-matching-to-sample learning task to study 'recognition memory'" Nature Protocols (2006) 1: 1306-1311.
Bi et al., "Tau-Targeted Immunization Impedes Progression of Neurofibrillary Histopathology in Aged P301L Tau Transgenic Mice" Plos ONE (2011) 6(12):e26860.
Boiziau et al., "Antisense 2'-O-alkyl oligoribonucleotides are efficient inhibitors of reverse transcription" Nucleic Acids Research, (1995) 23(l):64-71.
Braasch et al., "Locked nucleic acid (LNA): fine-tuning the recognition of DNA and RNA" Chem. Biol. (2001) 8:1-7.
Braasch et al., "Novel antisense and peptide nucleic acid strategies for controlling gene expression" Biochemistry (2002) 41(14):4503-4510.
Branch et al., "A good antisense molecule is hard to find," TIBS (1998) 23:45-50.
Caceres et al., "Inhibition of neurite polarity by tau antisense oligonucleotides in primary cerebellar neurons" Nature (1990) 343:461-463.
Caceres et al., "The Effect of Tau Antisense Oligonucleotides on Neurite Formation of Cultured Cerebellar Macroneurons" J. Neuroscience (1991) 11(6): 1515-1523.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Craig et al., "Towards a small molecule inhibitor of tau exon 10 splicing: Identification of compounds that stabilise the 5'-splice site stem-loop" Alzheimer's & Dementia: The Journal of the Alzheimer's Association (2012) 8(4): P636.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Davies et al., (2003) "Hyperphosphorylation and aggregation of tau in mice expressing normal human tau isoforms" Journal of Neurochemistry 86:582-590.
Dawson et al., "The tau N279K exon 10 splicing mutation recapitulates frontotemporal dementia and parkinsonism linked to chromosome 17 tauopathy in a mouse model." (2007) 27(34):9155-9168.
Dawson, "Tau Exon 10 Splicing Tauopathy", presentation given at CurePSP 2010 International Research Symposium, Nov. 18, 2010, San Diego, CA.
Dawson, "The Effects of the CBD-Associated Tau Gene H1 Haplotype on Tau Expression," Abstract presented at CurePSP 2010 International Research Symposium, Nov. 18, 2010, San Diego, CA (retrieved online Jan. 13, 2016).
Deacon, "Assessing nest building in mice" Nat. Protocol. (2006) 1:1117-1119.
Devos et al., "Antisense oligonucleotides: treating neurodegeneration at the level of RNA" Neurotherapeutics (2013) 10(3): 486-497.
Devos et al., "Antisense Reduction of Human Tau in the CNS of P301S mice both Prevents and Reverses Hyperphosphorylated Tau Deposition" abstract presented at Keystone Symposium: Long Noncoding RNAs: Marching toward Mechanism, Feb. 27-Mar. 4, 2014, Santa Fe, NM.
Devos et al., "Antisense Reduction of Tau in Adult Mice Protects against Seizures" J. Neuroscience (2013) 33(31): 12887-12897.
Devos et al., "Antisense Reduction of the Human Tau Transgene in the CNS of P301S mice Robustly Decreases Tau Deposition" abstract presented at Keystone Symposia: New Frontiers in Neurodegenerative Disease Research, Feb. 3-8, 2013, Santa Fe, NM.
Devos et al., "Reducing Human Tau in the CNS of P301S mice Dramatically Reverses Tau Pathology" abstract presented at l4th International Conference on Alzheimer's Drug Discovery, Sept. 9-10, 2013, Jersey City, NJ.
Devos et al., "Using antisense oligonucleotides to knockdown endogenous brain tau in vivo" Alzheimer's & Dementia: The Journal of the Alzheimer's Association (2012) 8(4): P205.
Devos et al., "Using antisense oligonucleotides to knockdown endogenous brain tau in vivo" poster presentation at AAIC 2012; Jul. 14-19, 2012.
Donahue et al., "Stabilization of the Tau Exon 10 Stem Loop Alters Pre-mRNA Splicing" J. Biol. Chern. (2006) 281(33):23302-23306.
Duff et al., "Characterization of Pathology in Transgenic Mice Over-Expressing Human Genomic and cDNA Tau Transgenes" Neurobiology of Disease (2000) 7:87-98.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Angewandte Chemie, International Edition (1991) 30(6): 613-629.
European Examination Report for Application No. 13770075.3 dated Oct. 2, 2015.
European Examination Report for Application No. 14767904.7 dated Sep. 19, 2016.
Freiek et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Frost et al., "Retinal Screening for Early Detection of Alzheimer's Disease" Digital Telerential Screening, K. Yogesaneds., 2012, 91-100.
Furdon et al., "RNase H cleavage of RNA hybridized to oligonucleotides containing methylphosphonate, phosphorothioate and phosphodiester bonds" Nucleic Acids Res. (1989) 17(22): 9193-9204.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
GenBank Accession No. AK226139.1.
GenBank Accession No. NM_001123066.3.
GenBank Accession No. NM_001123067.3.
GenBank Accession No. NM_001203251.1.
GenBank Accession No. NM_001203252.1.
GenBank Accession No. NM_005910.5.
GenBank Accession No. NM_016834.4.
GenBank Accession No. NM_016835.4.
GenBank Accession No. NM_016841.4.
GenBank Accession No. NT_010783.14.
GenBank Accession No. NT_010783.15.
Goedert et al., "Cloning and Sequencing of the cDNA Encoding a Core Protein of the Paired Helical Filament of Alzheimer Disease: Identification as the Microtubule-Associated Protein Tau" PNAS (1988) 85(11):4051-4055.
Goedert et al., "Monoclonal antibody AT8 recognises tau protein phosphorylated at both serine 202 and threonine 205." Neurosci. Lett. (1995) 189(3): 167-169.
Gordon et al., "Antisense suppression of tau in cultured rat olgodendrocytes inhibits process formation," Journal of Neuroscience Research (2008) 86: 2591-2601.
Gupta et al., "Retinal tau pathology in human glaucomas" Can. J. Ophtalmol. (2008) 43: 53-60.
Hall et al., "Establishment and Maintenance of a Heterochromatin Domain" Science (2002) 297: 2232-2237.
Hatta et al., "Mechanisms of the inhibition of reverse transcription by unmodified and modified antisense oligonucleotides" FEBS Lett. (1993) 330(2): 161-164.
Ho et al., "Review: Tauopathy in the retina and optic nerve: does it shadow pathological changes in the brain?" Molecular Vision (2012) 18: 2700-2710.

(56) References Cited

OTHER PUBLICATIONS

International Search Report for application PCT/US2013/31500 dated Jun. 5, 2013 (12 pages).
International Search Report for application PCT/US2014/029752 dated Sep. 18, 2014.
Jenuwein, "Molecular biology. An RNA-guided pathway for the epigenome." Science (2002) 297(5590): 2215-2218.
Jiang et al., "Aberrant Splicing of tau Pre-mRNA Caused by Intronic Mutations Associated with the Inherited Dementia Frontotemporal Dementia with Parkinsonsism Linked to Chromosome 17" Mol. Cell Biol. (2000) 20(11):4036-4048.
Jones et al., "RNA Quantitation by Fluorescence-Based Solution Assay: RiboGreen Reagent Characterization" Analytical Biochemistry (1998) 265: 368-374.
Jones et al., "Targeting hyperphosphorylated tau with sodium selenate suppresses seizures in rodent models" Neurobiology of Disease (2012) 45:897-901.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.
Kalbfuss, B. et al., "Correction of Alternative Splicing of Tau in Frontotemporal Dementia and Parkinsonism Linked to Chromosome 17," Journal of Biological Chemistry, (2001) 276:42986-42993.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, The Concise Encyclopedia of Polymer Science and Engineering, John Wiley & Sons, 1990, 858-859.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Maher et al., "Comparative hybrid arrest by tandem antisense oligodeoxy ribonucleotides or oligodeoxyribonucleoside methylphosphonates in a cell-free system" Nuc. Acid. Res. (1988) 16:3341-3358.
Manoharan et al., "Chemical Modifications to Improve Uptake and Bioavailability of Antisense Oligonucleotides" Ann N.Y. Acad. Sci. (1992) 660:306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Martin, "Ein neuer Zugang zu 2'-O-Alkylribonucleosiden und Eigenschaften deren Oligonucleotide" Helv. Chim Acta (1995) 78: 486-504.
Mishra et al., "Improved leishmanicidal effect of phosphorotioate antisense oligonucleotides by LDL-mediated delivery" Biochim Biophys. Acta (1995) 1264:229-237.
Morita et al., "Synthesis and Properties of 2'-O,4'-C-Ethylene-Bridged Nucleic Acids (ENA) as Effective Antisense Oligonucleotides" Bioorganic Medicinal Chemistry (2003) 11: 2211-2226.
New England Biolabs 1998/99 Catalog (cover page and pp. 121 and 284).
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curt. OpinionMol. Ther. (2001) 3:239-243.
Pal-Bhadra et al., "Heterochromatic silencing and HP1 localization in *Drosophila* are dependent on the RNAi machinery." Science (2004) 303(5658): 669-672.
Peacey et al., "Targeting a pre-mRNA structure with bipartite antisense molecules modulates tau alternative splicing" Nucleic Acids Research (2012) 40(19):9836-9849.
Pizzi et al., "Antisense Strategy Unravels Tan Proteins as Molecular Risk Factors for Glutamate-Induced Neurodegeneration" Cellular and Molecular Neurobiology (1994) 14(5):569-578.
Reynolds et al., "Rational siRNA design for RNA interference" Nature Biotechnology (2004) 22(3):326-330.
Rodriguez-Martin et al., "Reprogramming of tau alternative splicing by spliceosome-mediatedRNA trans-splicing: implications fortauopathies." Proc Natl Acad Sci USA (2005) 102(43): 15659-15664.
Saison-Behmoaras et al., "Short modified antisense oligonucleotides directed against Ha-ras point mutation induce selective cleavage of the mRNA and inhibit T24 cells proliferation" Embo J. (1991) 10(5):1111-1118.
Sanghvi et al., "Heterocyclic Base Modifications in Nucleic Acids and Their Applications in Antisense Oligonucleotides" Antisense Research and Applications (1993) pp. 273-288.
Sapir et al., "Tau's role in the developing brain: implications for intellectual disability" Human Molecular Genetics (2012) 21(8): 1681-1692.
Schoch et al., "Antisense oligonucleotide-mediated tau splicing reduces behavioral deficits and tau pathology in a tauopathy model" abstract presented at Keystone Symposium: Alzheimer's Disease, Mar. 2-7, 2014, Keystone, CO.
Schoch et al., "Antisense oligonucleotide-mediated tau splicing reduces behavioral deficits and tau pathology in a tauopathy model" poster presented at Keystone Symposium: Alzheimer's Disease, Mar. 2-7, 2014, Keystone, CO.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Smith et al., "Comparison of Biosequences" Adv. Appl. Math. (1981) 2: 482-489.
Spicakova et al., "Expression and silencing of the microtubule-associated protein Tau in breast cancer cells," Molecular Cancer Therapeutics (2010) 9: 2970-2981.
Sproat et al., "Highly efficient chemical synthesis of 2'-O-methyloligoribonucleotides and tetrabiotinylated derivatives; novel probes that are resistant to degradation by RNA or DNA specific nucleases" Nucleic Acids Res. (1989) 17(9): 3373-3386.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Usman et al., "Exploiting the chemical synthesis of RNA," Trends in Biochemical Sciences, Elsevier, Haywards, GB (1992) 17(9): 334-339.
Verdel et al., "RNAi-Mediated Targeting of Heterochromatin by the RITS Complex" Science (2004) 303: 672-676.
Volpe et al., "Regulation of Heterochromatic Silencing and Histone H3 Ly sine-9 Methylation by RNAi" Science (2002) 297: 1833-1837.

(56) References Cited

OTHER PUBLICATIONS

Wahlesiedt et al., "Potent and nontoxic antisense oligonucleotide containing locked nucleic acids" Proc. Natl. Acad. Sci. USA (2000) 97: 5633-5638.

Walder et al., "Role of RNase H in hybrid-arrested translation by antisense oligonucleotides." Proc. Natl. Acad. Sci. USA (1988) 85(14): 5011-5015.

Wang et al., "A Novel Tau Transcript in Cultured Human Neuroblastoma Cells Expression Nuclear Tau" J. Cell Biol. (1993) 121(2):257-267.

Wolfe M.S., "The Roll of Tau in Neurodegenerative Diseases and Its Potential as a Therapeutic Target" Scientifica (2012) 1-20.

Wolfe M.S., "Tau Mutations in Neurodegemative Diseases" J. Biol Chem (2009) 284(10):3021-3025.

Woolf et al., "Specificity of antisense oligonucleotides in vivo" Proc. Natl. Acad. Sci. USA (1992) 89:7305-7309.

Yamada et al., "In vivo microdialysis reveals age-dependent decrease of brain interstitial fluid tau levels in P30 Is human tau transgenic mice." Neurosci. (2011) 31: 13110-13117.

Yoshiyama et al., "Synapse Loss and Microglial Activation Precede Tangles in a P301S Tauopathy Mouse Model" Neuron (2007) 53: 337-351.

Zhang et al., "PowerBLAST: A New Network BLAST Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Extended Examination Report for EP 20181501.6 dated Dec. 1, 2020.

Lebedeva at al., "Phosphorothioate oligodeoxynucleotides as inhibitors of gene expression: antisense and non-antisense effects" Applications of antisense therapies to restenosis, Kluwer Academic Publishers, 1999, pp. 99-118.

\* cited by examiner

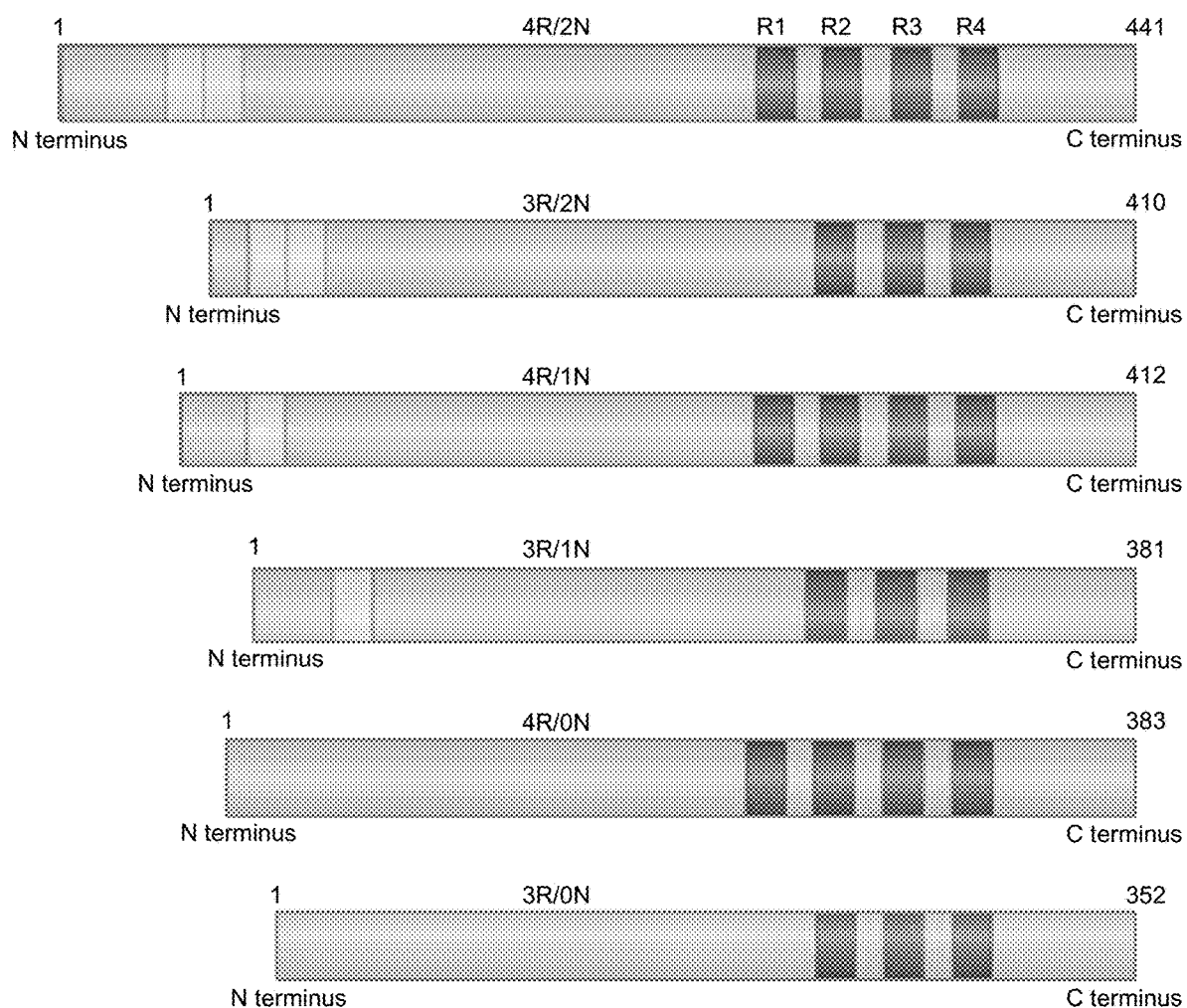

COMPOSITIONS AND METHODS FOR MODULATING TAU EXPRESSION

SEQUENCE LISTING

The present application is being filed along with a Sequence Listing in electronic format. The Sequence Listing is provided as a file entitled BIOL0220USC1SEQ_ST25.txt created Mar. 28, 2017, which is approximately 228 KB in size. The information in the electronic format of the sequence listing is incorporated herein by reference in its entirety.

BACKGROUND

1. Field

Disclosed herein are compositions and methods related to the fields of antisense compounds biochemistry, molecular biology, and medicine. Embodiments described herein relate to compounds, compositions, and methods for treating, preventing, or ameliorating neurodegenerative diseases, including tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome by inhibiting expression of Tau or modulating the splicing of Tau in a cell and/or in an animal.

2. Description

The primary function of Tau is to bind to and stabilize microtubules, which are important structural components of the cytoskeleton involved in mitosis, cytokinesis, and vesicular transport. Tau is found in multiple tissues, but is particularly abundant in axons of neurons. In humans, there are six isoforms of Tau that are generated by alternative splicing of exons 2, 3, and 10. Splicing of exons 2 and 3 at the N-terminus of the protein leads to inclusion of zero, one, or two 29 amino acid acidic domains and is termed 0N, 1N, or 2N Tau respectively. The influence of these domains on Tau function is not fully clear, though may play a role in interactions with the plasma membrane. Inclusion of exon 10 at the C-terminus leads to inclusion of the microtubule binding domain encoded by exon 10. Since there are 3 microtubule binding domains elsewhere in Tau, this Tau isoform (with exon 10 included) is termed 4R Tau, where 'R' refers to the number of repeats of microtubule binding domains. Tau without exon 10 is termed 3R Tau. Since more microtubule binding domains (4R compared with 3R) increases the binding to microtubules, 4R Tau presumably significantly increases microtubule binding and assembly. The ratio of 3R/4R Tau is developmentally regulated, with fetal tissues expressing exclusively 3R Tau and adult human tissues expressing approximately equal levels of 3R/4R Tau. Deviations from the normal ratio of 3R/4R Tau are characteristic of neurodegenerative FTD Tauopathies. It is not known how changing the 3R/4R Tau ratio at a later stage in the adult animal will affect Tau pathogenesis.

Serine-threonine directed phosphorylation regulates the microtubule binding ability of Tau. Hyperphosphorylation promotes detachment of Tau from microtubules. Other post translational modifications of Tau have been described; however the significance of these is unclear. Phosphorylation of Tau is also developmentally regulated with higher phosphorylation in fetal tissues and much lower phosphorylation in the adult. One characteristic of neurodegenerative disorders is aberrantly increased Tau phosphorylation.

The microtubule network is involved in many important processes within the cell including structural integrity needed for maintaining morphology of cells and operating transport machinery. Since binding of Tau to microtubules stabilizes microtubules, Tau is likely to be a key mediator of some of these processes and disruption of normal Tau in neurodegenerative diseases may disrupt some of these key cellular processes.

One of the early indicators that Tau may be important in neurodegenerative syndromes was the recognition that Tau is a key component of neurofibrillary inclusions in Alzheimer's disease. In fact, neurofibrillary inclusions are aggregates of hyperphosphorylated Tau protein. Along with amyloid beta containing plaques, neurofibrillary inclusions are a hallmark of Alzheimer's disease and correlate significantly with cognitive impairment. 95% of Tau accumulations in AD are found in neuronal processes and is termed neuritic dystrophy. The process(es) whereby this microtubule associated protein becomes disengaged from microtubules and forms accumulations of proteins and how this relates to neuronal toxicity is not well understood.

Neuronal Tau inclusions are a pathological characteristic of not only Alzheimer's disease, but also a subset of Frontotemporal dementia (FTD), PSP, and CBD. The link between Tau and neurodegeneration was solidified by the discovery that mutations in the Tau gene cause a subset of FTD. These genetic data have also highlighted the importance of the 3R:4R ratio of Tau. Many of the Tau mutations that cause FTD lead to a change in Tau splicing which leads to preferential inclusion of exon 10, and thus to increased 4R Tau. The overall Tau levels are normal. Whether the Tau isoform change or the amino acid change or both cause neurodegeneration remains unknown. Recent data suggest that PSP may also be associated with an increased 4R:3R Tau ratio and thus may be amenable to a similar splicing strategy.

To help understand the influence of Tau ratios on neurodegeneration, a mouse model based on one of the splicing Tau mutations (N279K) has been generated using a minigene that includes the Tau promoter and the flanking intronic sequences of exon 10. As in humans, these mice demonstrate increased levels of 4R Tau compared with transgenics expressing WT Tau and develop behavioral and motor abnormalities as well as accumulations of aggregated Tau in the brain and spinal cord.

The protein "Tau" has been associated with multiple diseases of the brain including Alzheimer's disease, frontotemporal dementia, progressive supranuclear palsy, corticobasal ganglionic degeneration, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration and others. Tau-associated disorders such as AD are the most common cause of dementia in the elderly. AD affects an estimated 15 million people worldwide and 40% of the population above 85 years of age. AD is characterized by two pathological hallmarks: Tau neurofibrillary inclusions (NFT) and amyloid-β (Aβ) plaques.

In seizure disorders, the brain's electrical activity is periodically disturbed, resulting in some degree of temporary brain dysfunction. Normal brain function requires an orderly, organized, coordinated discharge of electrical impulses. Electrical impulses enable the brain to communicate with the spinal cord, nerves, and muscles as well as within itself. Seizures may result when the brain's electrical activity is disrupted. There are two basic types of seizures; epileptic and nonepileptic. Epileptic seizures have no apparent cause or trigger and occur repeatedly. Nonepileptic seizures are triggered orprovoked by a disorder or another condition that irritates the brain. Certain mental disorders can cause seizure symptoms referred to as psychogenic nonepileptic seizures.

Alzheimer's Disease(AD) is known to be a clinical risk factor for late onset seizures. Multiple AD mouse models recapitulate this increased seizure susceptibility. Within the last 5 years, many of these AD models have been studied in the setting of mouse tau knockout (tau−/−). Increased seizure susceptibility was ameliorated in these amyloid-depositing tau knockout lines. Further, tau−/− alone interestingly appeared to be protective against chemically induced seizures.

Anticonvulsants represent the common treatment regime for seizues. However, anticonvulsants are ineffective in a significant percent of people with a seizure disorder and for these individuals, surgery is the only option. Amidst the lack of available treatments for seizure disorders and neurodegenerative diseases, certain methods of the present embodiments provide methods for treating, preventing or ameliorating a seizure disorder and neurodegenerative diseases by inhibiting expression of Tau or modulating the splicing of Tau in an animal.

SUMMARY

Provided herein are methods for modulating splicing of Tau mRNA in cells, tissues, and animals. Also provided herein are methods for modulating the expression product of a Tau mRNA in cells, tissues, and animals.

In certain embodiments, modulation can occur in a cell or tissue. In certain embodiments, the cell or tissue is in an animal. In certain embodiments, the animal is human. In certain embodiments, Tau mRNA levels are reduced. In certain embodiments, Tau protein levels are reduced. In certain embodiments, splicing of Tau mRNA is modulated. In certain embodiments, the expression product of a Tau mRNA is modulated. In certain embodiments, exclusion of Tau exon 10 is promoted. In certain embodiments, expression of the 4R isoform of Tau RNA or protein is reduced. In certain embodiments, expression of the 3R isoform of Tau RNA or protein is increased. In certain embodiments, expression of the 4R isoform of Tau RNA or protein is reduced and expression of the 3R isoform of Tau RNA or protein is increased. In certain embodiments, hyperphosphorylated Tau is reduced. Such reduction and modulation can occur in a time-dependent manner or in a dose-dependent manner.

Several embodiments are drawn to methods of reducing or decreasing one or more symptoms of a tau-associated disorder. In certain embodiments, the symptom is a seizure. In certain embodiments, the tau-associated disorder or neurodegenerative disorder is Alzheimer's disease, frontotemporal dementia, progressive supranuclear palsy, corticobasal ganglionic degeneration, dementia pugilistica, parkinsonism linked to chromosome, Lytico¬Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration. Certain embodiments are drawn to a method of decreasing seizures in a subject with a high 4R:3R tau isoform ratio. In certain embodiments, the methods comprise administering an antisense agent to the subject, wherein the agent decreases expression of tau or decreases the 4R:3R tau ratio in the central nervous system of the subject.

Also provided are methods useful for preventing, treating, and ameliorating diseases, disorders, and conditions associated with Tau. In certain embodiments, such diseases, disorders, and conditions associated with Tau are neurodegenerative diseases. In certain embodiments, the neurodegenerative disease is any of Alzheimer's Disease, Fronto temporal Dementia (FTD), FTDP-17, Progressive Supranuclear Palsy, Chronic Traumatic Encephalopathy, Epilepsy, or Dravet's Syndrome. In certain embodiments, one or more symptoms of a neurodegenerative disease is ameliorated, prevented, or delayed (progression slowed). In certain embodiments, the symptom is memory loss, anxiety, or loss of motor function. In certain embodiments, neurodegenerative function is improved. In certain embodiments, neurofibrillary inclusions are reduced.

Such diseases, disorders, and conditions can have one or more risk factors, causes, or outcomes in common. Certain risk factors and causes for development of a neurodegenerative disease include genetic predisposition and older age.

In certain embodiments, methods of treatment include administering a Tau antisense compound to an individual in need thereof. The antisense compound may inhibit expression of Tau or modulate splicing of Tau. In certain embodiments, the antisense compound is a single-stranded antisense oligonucleotide. In certain embodiments, the single-stranded antisense oligonucleotide is complementary to a Tau nucleic acid.

In certain embodiments, the present invention provides compounds comprising oligonucleotides. In certain embodiments, such oligonucleotides are complementary to a Tau transcript. In certain such embodiments, oligonucleotides are complementary to a target region of the Tau transcript comprising exon 10. In certain such embodiments, oligonucleotides are complementary to a target region of the Tau transcript comprising an intron adjacent to exon 10. In certain such embodiments, oligonucleotides are complementary to a target region of the Tau transcript comprising an intron adjacent to exon 10 and downstream of exon 10. In certain such embodiments, oligonucleotides are complementary to a target region of the Tau transcript comprising an intron adjacent to exon 10 and upstream of exon 10. In certain embodiments, the Tau transcript comprises an exonic splice silencer for exon 10. In certain embodiments, oligonucleotides inhibit inclusion of exon 10. In certain embodiments, oligonucleotides promote skipping of exon 10. In certain such embodiments, 3R Tau mRNA is increased. In certain such embodiments, Tau mRNA with exon 10 mRNA is decreased. In certain embodiments, the 4R isoform of the Tau protein is decreased. In certain embodiments, the 3R isoform of the Tau protein is increased.

In certain embodiments, including, but not limited to any of the above numbered embodiments, the Tau transcript is in a human. In certain embodiments, including, but not limited to any of the above numbered embodiments, the Tau transcript is in a mouse.

The present disclosure provides the following non-limiting numbered embodiments:

Embodiment 1

A compound comprising a modified oligonucleotide consisting of 8 to 30 linked nucleosides and having a nucleobase sequence comprising a complementary region comprising at least 8 contiguous nucleobases complementary to a target region of equal length of a Tau transcript.

Embodiment 2

The compound of embodiment 1, wherein the complementary region of the modified oligonucleotide is 100% complementary to the target region.

Embodiment 3

The compound of embodiment 1 or 2, wherein the complementary region of the nucleobase sequence of the modified oligonucleotide comprises at least 10 contiguous nucleobases.

Embodiment 4

The compound of embodiment 1 or 2, wherein the complementary region of the nucleobase sequence of the modified oligonucleotide comprises at least 15 contiguous nucleobases.

Embodiment 5

The compound of embodiment 1 or 2, wherein the complementary region of the nucleobase sequence of the modified oligonucleotide comprises at least 18 contiguous nucleobases.

Embodiment 6

The compound of any of embodiments 1-5, wherein the nucleobase sequence of the modified oligonucleotide is at least 80% complementary to an equal-length region of the Tau transcript, as measured over the entire length of the oligonucleotide.

Embodiment 7

The compound of any of embodiments 1-5, wherein the nucleobase sequence of the modified oligonucleotide is at least 90% complementary to an equal-length region of the Tau transcript, as measured over the entire length of the oligonucleotide.

Embodiment 8

The compound of any of embodiments 1-5, wherein the nucleobase sequence of the modified oligonucleotide is 100% complementary to an equal-length region of the Tau transcript, as measured over the entire length of the oligonucleotide.

Embodiment 9

The compound of any of embodiments 1-8, wherein the target region is within exon 10 of the Tau transcript.

Embodiment 10

The compound of any of embodiments 1-8, wherein the target region is within intron 9 of the Tau transcript.

Embodiment 11

The compound of any of embodiments 1-8, wherein the target region is within intron 10 of the Tau transcript.

Embodiment 12

The compound of any of embodiments 1-8, wherein the target region comprises a portion of intron 9 and a portion of exon 10.

Embodiment 13

The compound of any of embodiments 1-8, wherein the target region comprises a portion of exon 10 and a portion of intron 10.

Embodiment 14

The compound of any of embodiments 1-8, wherein the target region comprises a portion of exon 10 and a portion of the intron at the 5'-end of exon 10.

Embodiment 15

The compound of any of embodiments 1-8, wherein the target region comprises a portion of exon 10 and a portion of the intron at the 3'-end of exon 10.

Embodiment 16

The compound of any of embodiments 1-15, wherein the target region is within nucleobase 121708 and nucleobase 122044 of SEQ ID NO.: 1.

Embodiment 17

The compound of any of embodiments 1-9, wherein the target region is within nucleobase 121796 and nucleobase 122044 of SEQ ID NO.: 1.

Embodiment 18

The compound of any of embodiments 1-9, wherein the target region is within nucleobase 121796 and nucleobase 121885 of SEQ ID NO.: 1.

Embodiment 19

The compound of any of embodiments 1-9, wherein the target region is within nucleobase 121873 and nucleobase 121898 of SEQ ID NO.: 1.

Embodiment 20

The compound of any of embodiments 1-9, wherein the target region is within nucleobase 121869 and nucleobase 121943 of SEQ ID NO.: 1.

Embodiment 21

The compound of any of embodiments 1-9, wherein the target region is within nucleobase 122020 and nucleobase 122044 of SEQ ID NO.: 1.

Embodiment 22

The compound of any of embodiments 1-9, wherein the target region is within nucleobase 121881 and nucleobase 121898 of SEQ ID NO.: 1.

Embodiment 23

The compound of any of embodiments 1-9, wherein the target region is within nucleobase 121880 and nucleobase 121897 of SEQ ID NO.: 1.

Embodiment 24

The compound of any of embodiments 1-9, wherein the target region is within nucleobase 121879 and nucleobase 121896 of SEQ ID NO.: 1.

Embodiment 25

The compound of any of embodiments 1-9, wherein the target region is within nucleobase 121878 and nucleobase 121895 of SEQ ID NO.: 1.

Embodiment 26

The compound of any of embodiments 1-9, wherein the target region is within nucleobase 121877 and nucleobase 121894 of SEQ ID NO.: 1.

Embodiment 27

The compound of any of embodiments 1-9, wherein the target region is within nucleobase 121876 and nucleobase 121893 of SEQ ID NO.: 1.

Embodiment 28

The compound of any of embodiments 1-9, wherein the target region is within nucleobase 121875 and nucleobase 121892 of SEQ ID NO.: 1.

Embodiment 29

The compound of any of embodiments 1-9, wherein the target region is within nucleobase 121874 and nucleobase 121891 of SEQ ID NO.: 1.

Embodiment 30

The compound of any of embodiments 1-9, wherein the target region is within nucleobase 121873 and nucleobase 121890 of SEQ ID NO.: 1.

Embodiment 31

The compound of any of embodiments 1-15, wherein the nucleobase sequence of the modified oligonucleotide comprises the nucleobase sequence of any of SEQ ID NOs: 8-200.

Embodiment 32

The compound of any of embodiments 1-15, wherein the nucleobase sequence of the modified oligonucleotide consists of the nucleobase sequence of any of SEQ ID NOs: 8-200.

Embodiment 33

The compound of any of embodiments 1-15, wherein the nucleobase sequence of the modified oligonucleotide comprises the nucleobase sequence of any of SEQ ID NOs: 33, 34, 147, 148, 149, 150, 151, 152, or 153.

Embodiment 34

The compound of any of embodiments 1-15, wherein the nucleobase sequence of the modified oligonucleotide consists of the nucleobase sequence of any of SEQ ID NOs: 33, 34, 147, 148, 149, 150, 151, 152, or 153.

Embodiment 35

The compound of any of embodiments 1-15, wherein the nucleobase sequence of the modified oligonucleotide comprises the nucleobase sequence of any of SEQ ID NOs: 31, 33, 34, 35, 36, 37, 45, 72, 79, 82, 83, 97, 106, 107, 112, 113, 130, 140, 141, 142, 143, 144, 145, 146, 147, 148, 149, 150, 151, 152, 153, 154, 157, 158, 160, or 200.

Embodiment 36

The compound of any of embodiments 1-15, wherein the nucleobase sequence of the modified oligonucleotide consists of the nucleobase sequence of any of SEQ ID NOs: 31, 33, 34, 35, 36, 37, 45, 72, 79, 82, 83, 97, 106, 107, 112, 113, 130, 140, 141, 142, 143, 144, 145, 146, 147, 148, 149, 150, 151, 152, 153, 154, 157, 158, 160, or 200.

Embodiment 37

The compound of any of embodiments 1-36, wherein the modified oligonucleotide comprises at least one modified nucleoside.

Embodiment 38

The compound of embodiment 37, wherein at least one modified nucleoside comprises a modified sugar moiety.

Embodiment 39

The compound of embodiment 37, wherein at least one modified sugar moiety is a 2'-substituted sugar moiety.

Embodiment 40

The compound of embodiment 39, wherein the 2'-substituent of at least one 2'-substituted sugar moiety is selected from among: 2'-OMe, 2'-F, and 2'-MOE.

Embodiment 41

The compound of embodiment 39, wherein the 2'-substituent of at least one 2'-substituted sugar moiety is a 2'-MOE.

Embodiment 42

The compound of any of embodiments 37-38, wherein at least one modified sugar moiety is a bicyclic sugar moiety.

Embodiment 43

The compound of embodiment 42, wherein at least one bicyclic sugar moiety is LNA or cEt.

Embodiment 44

The compound of any of embodiments 37-43, wherein at least one sugar moiety is a sugar surrogate.

Embodiment 45

The compound of embodiment 44, wherein at least one sugar surrogate is a morpholino.

Embodiment 46

The compound of embodiment 44, wherein at least one sugar surrogate is a modified morpholino.

Embodiment 47

The compound of any of embodiment 1-46, wherein the modified oligonucleotide comprises at least 5 modified nucleosides, each independently comprising a modified sugar moiety.

Embodiment 48

The compound of embodiment 47, wherein the modified oligonucleotide comprises at least 10 modified nucleosides, each independently comprising a modified sugar moiety.

Embodiment 49

The compound of embodiment 47, wherein the modified oligonucleotide comprises at least 15 modified nucleosides, each independently comprising a modified sugar moiety.

Embodiment 50

The compound of embodiment 47, wherein each nucleoside of the modified oligonucleotide is a modified nucleoside and each independently comprises a modified sugar moiety, wherein the modified sugar moieties of each modified nucleosides are each the same as one another.

Embodiment 51

The compound of embodiment 47, wherein each nucleoside of the modified oligonucleotide is a modified nucleoside, each independently comprising a modified sugar moiety.

Embodiment 52

The compound of any of embodiments 1-51, wherein the modified oligonucleotide comprises at least two modified nucleosides comprising modified sugar moieties that are the same as one another.

Embodiment 53

The compound of any of embodiments 1-52, wherein the modified oligonucleotide comprises at least two modified nucleosides comprising modified sugar moieties that are different from one another.

Embodiment 54

The compound of any of embodiments 1-53, wherein the modified oligonucleotide comprises a modified region comprising at least 5 contiguous modified nucleosides.

Embodiment 55

The compound of embodiment 54, wherein the modified oligonucleotide comprises a modified region comprising at least 10 contiguous modified nucleosides.

Embodiment 56

The compound of embodiment 54, wherein the modified oligonucleotide comprises a modified region comprising at least 15 contiguous modified nucleosides.

Embodiment 57

The compound of embodiment 54, wherein the modified oligonucleotide comprises a modified region comprising at least 18 contiguous modified nucleosides.

Embodiment 58

The compound of embodiment 54, wherein the modified oligonucleotide comprises a modified region comprising at least 20 contiguous modified nucleosides.

Embodiment 59

The compound of any of embodiments 53-58, wherein each modified nucleoside of the modified region has a modified sugar moiety independently selected from among: 2'-F, 2'-OMe, 2'-MOE, cEt, LNA, morpholino, and modified morpholino.

Embodiment 60

The compound of any of embodiments 54-59, wherein the modified nucleosides of the modified region each comprise the same modification as one another.

Embodiment 61

The compound of embodiment 60, wherein the modified nucleosides of the modified region each comprise the same 2'-substituted sugar moiety.

Embodiment 62

The compound of embodiment 61, wherein the 2'-substituted sugar moiety of the modified nucleosides of the region of modified nucleosides is selected from 2'-F, 2'-OMe, and 2'-MOE.

Embodiment 63

The compound of embodiment 61, wherein the 2'-substituted sugar moiety of the modified nucleosides of the region of modified nucleosides is 2'-MOE.

Embodiment 64

The compound of embodiment 59, wherein the modified nucleosides of the region of modified nucleosides each comprise the same bicyclic sugar moiety.

Embodiment 65

The compound of embodiment 64, wherein the bicyclic sugar moiety of the modified nucleosides of the region of modified nucleosides is selected from LNA and cEt.

Embodiment 66

The compound of embodiment 59, wherein the modified nucleosides of the region of modified nucleosides each comprises a sugar surrogate.

Embodiment 67

The compound of embodiment 66, wherein the sugar surrogate of the modified nucleosides of the region of modified nucleosides is a morpholino.

Embodiment 68

The compound of embodiment 66, wherein the sugar surrogate of the modified nucleosides of the region of modified nucleosides is a modified morpholino.

Embodiment 69

The compound of any of embodiments 1-68, wherein the modified nucleotide comprises no more than 4 contiguous naturally occurring nucleosides.

Embodiment 70

The compound of any of embodiments 1-68, wherein each nucleoside of the modified oligonucleotide is a modified nucleoside.

Embodiment 71

The compound of embodiment 70 wherein each modified nucleoside comprises a modified sugar moiety.

Embodiment 72

The compound of embodiment 71, wherein the modified nucleosides of the modified oligonucleotide comprise the same modification as one another.

Embodiment 73

The compound of embodiment 72, wherein the modified nucleosides of the modified oligonucleotide each comprise the same 2'-substituted sugar moiety.

Embodiment 74

The compound of embodiment 73, wherein the 2'-substituted sugar moiety of the modified oligonucleotide is selected from 2'-F, 2'-OMe, and 2'-MOE.

Embodiment 75

The compound of embodiment 74, wherein the 2'-substituted sugar moiety of the modified oligonucleotide is 2'-MOE.

Embodiment 76

The compound of embodiment 72, wherein the modified nucleosides of the modified oligonucleotide each comprise the same bicyclic sugar moiety.

Embodiment 77

The compound of embodiment 76, wherein the bicyclic sugar moiety of the modified oligonucleotide is selected from LNA and cEt.

Embodiment 78

The compound of embodiment 72, wherein the modified nucleosides of the modified oligonucleotide each comprises a sugar surrogate.

Embodiment 79

The compound of embodiment 78, wherein the sugar surrogate of the modified oligonucleotide is a morpholino.

Embodiment 80

The compound of embodiment 78, wherein the sugar surrogate of the modified oligonucleotide is a modified morpholino.

Embodiment 81

The compound of any of embodiments 1 to 36, wherein the modified oligonucleotide has an A-$B_2$-A-$B_2$-A-$B_2$-A-$B_2$-A-$B_2$-A-$B_2$-$A_2$ motif, wherein each A comprises a bicyclic sugar moiety, and wherein each B is selected from a 2'-substituted sugar moiety and an unmodified 2'-deoxy sugar moiety.

Embodiment 82

The compound of embodiment 81, wherein each A is a cEt sugar moiety.

Embodiment 83

The compound of embodiment 81, wherein each A is an LNA sugar moiety.

Embodiment 84

The compound of any of embodiments 81 to 83, wherein each B is an unmodified 2'-deoxy sugar moiety.

Embodiment 85

The compound of any of embodiments 81 to 83, wherein each B is 2'-MOE sugar moiety.

Embodiment 86

The compound of any of embodiments 1-85, wherein the modified oligonucleotide comprises at least one modified internucleoside linkage.

Embodiment 87

The compound of embodiment 86, wherein each internucleoside linkage is a modified internucleoside linkage.

Embodiment 88

The compound of embodiment 86 or 87, comprising at least one phosphorothioate internucleoside linkage.

Embodiment 89

The compound of any of embodiments 1-85, wherein each internucleoside linkage is a modified internucleoside linkage and wherein each internucleoside linkage comprises the same modification.

Embodiment 90

The compound of embodiment 89, wherein each internucleoside linkage is a phosphorothioate internucleoside linkage.

Embodiment 91

The compound of embodiment 86, wherein the modified oligonucleotide comprises 4 phosphodiester internucleoside linkages.

Embodiment 92

The compound of embodiment 86, wherein the modified oligonucleotide comprises 5 phosphodiester internucleoside linkages.

Embodiment 93

The compound of embodiment 86, wherein the modified oligonucleotide comprises 6 phosphodiester internucleoside linkages.

Embodiment 94

The compound of embodiment 86, wherein the modified oligonucleotide comprises 7 phosphodiester internucleoside linkages.

Embodiment 95

The compound of any of embodiments 91 to 94, wherein each remaining internucleoside linkage is a phosphodiester internucleoside linkage.

Embodiment 96

The compound of any of embodiments 1-85, wherein the compound has an $N_SN_SN_ON_SN_ON_SN_ON_SN_ON_SN_ON_SN_O N_SN_ON_SN_SN$ internucleoside linkage motif, wherein each N represents a nucleoside, each S represents a phosphorothioate internucleoside linkage, and each O represents a phosphodiester internucleoside linkage.

Embodiment 97

The compound of any of embodiments 1-85, wherein the compound has an $N_SN_ON_ON_ON_SN_SN_SN_SN_SN_SN_SN_O N_ON_ON_SN_SN$ internucleoside linkage motif, wherein each N represents a nucleoside, each S represents a phosphorothioate internucleoside linkage, and each O represents a phosphodiester internucleoside linkage.

Embodiment 98

The compound of any of embodiments 1-97 comprising at least one conjugate.

Embodiment 99

The compound of any of embodiments 1-98 consisting of the modified oligonucleotide.

Embodiment 100

The compound of any of embodiments 1-99, wherein the compound modulates splicing of the Tau transcript.

Embodiment 101

The compound of any of embodiments 1-99, wherein the compound decreases expression of the 4R Tau isoform.

Embodiment 102

The compound of any of embodiments 1-99, wherein the compound decreases expression Tau mRNA comprising exon 10.

Embodiment 103

The compound of any of embodiments 1-99, wherein the compound decreases expression Tau protein comprising amino acids encoded from exon 10 mRNA.

Embodiment 104

The compound of any of embodiments 1-8 or 30-103, having a nucleobase sequence comprising any of the sequences as set forth in SEQ ID NOs. 8-200.

Embodiment 105

The compound of any of embodiments 1-8 or 30-103, having a nucleobase sequence comprising any of the sequences as set forth in SEQ ID NOs. 33, 34, 147, 148, 149, 150, 151, 152, or 153.

Embodiment 106

The compound of any of embodiments 1-8 or 30-103, having a nucleobase sequence consisting of any of the sequences as set forth in SEQ ID NOs. 8-200.

Embodiment 107

The compound of any of embodiments 1-8 or 30-103, having a nucleobase sequence consisting of any of the sequences as set forth in SEQ ID NOs. 33, 34, 147, 148, 149, 150, 151, 152, or 153.

Embodiment 108

A double stranded compound comprising the compound of any of embodiments 1-107.

Embodiment 109

A compound consisting of ISIS 670011.

Embodiment 110

A compound consisting of ISIS 670012.

Embodiment 111

A compound consisting of ISIS 670013.

Embodiment 112

A compound consisting of ISIS 670014.

Embodiment 113

A compound consisting of ISIS 670015.

Embodiment 114

A compound consisting of ISIS 670016.

Embodiment 115

A compound consisting of ISIS 670017.

Embodiment 116

A compound consisting of ISIS 670018.

Embodiment 117

A compound consisting of ISIS 670019.

Embodiment 118

A compound consisting of ISIS 670020.

Embodiment 119

A compound consisting of ISIS 670021.

Embodiment 120

A compound consisting of ISIS 670022.

Embodiment 121

A compound consisting of ISIS 670023.

Embodiment 122

A compound consisting of ISIS 670024.

Embodiment 123

A compound consisting of ISIS 670025.

Embodiment 124

A compound consisting of ISIS 670026.

Embodiment 125

A compound consisting of ISIS 670027.

Embodiment 126

A compound consisting of ISIS 670028.

Embodiment 127

A compound consisting of ISIS 678329.

Embodiment 128

A compound consisting of ISIS 678330.

Embodiment 129

A compound consisting of ISIS 678331.

Embodiment 130

A compound consisting of ISIS 678332.

Embodiment 131

A compound consisting of ISIS 678333.

Embodiment 132

A compound consisting of ISIS 678334.

Embodiment 133

A compound consisting of ISIS 693840.

Embodiment 134

A compound consisting of ISIS 693841.

Embodiment 135

A compound consisting of ISIS 693842.

Embodiment 136

A compound consisting of ISIS 693843.

Embodiment 137

A compound consisting of ISIS 693844.

Embodiment 138

A compound consisting of ISIS 693845.

Embodiment 139

A compound consisting of ISIS 693846.

Embodiment 140

A compound consisting of ISIS 693847.

Embodiment 141

A compound consisting of ISIS 693848.

Embodiment 142

A compound consisting of ISIS 693849.

Embodiment 143

A compound consisting of ISIS 549577.

Embodiment 144

A compound consisting of ISIS 549580.

Embodiment 145

A compound consisting of ISIS 549581.

Embodiment 146

A compound consisting of ISIS 549582.

Embodiment 147

A compound consisting of ISIS 549583.

Embodiment 148

A compound consisting of ISIS 549584.

Embodiment 149

A compound consisting of ISIS 549585.

Embodiment 150

A compound consisting of ISIS 549586.

Embodiment 151

A compound consisting of ISIS 617341.

Embodiment 152

A compound consisting of ISIS 617351.

Embodiment 153

A compound consisting of ISIS 617352.

Embodiment 154

A compound consisting of ISIS 617353.

Embodiment 155

A compound consisting of ISIS 617358.

Embodiment 156

A compound consisting of ISIS 617360.

Embodiment 157

A compound consisting of ISIS 617361.

Embodiment 158

A compound consisting of ISIS 617362.

Embodiment 159

A method of modulating splicing of a Tau transcript in a cell comprising contacting the cell with a compound according to any of embodiments 1-158.

Embodiment 160

The method of embodiment 158, wherein the cell is in vitro.

Embodiment 161

The method of embodiment 158, wherein the cell is in an animal.

Embodiment 162

A method of modulating the expression of Tau protein in a cell, comprising contacting the cell with a compound according to any of embodiments 1-158.

Embodiment 163

The method of embodiment 162, wherein expression of the 4R isoform of Tau protein is decreased.

Embodiment 164

The method of embodiment 162, wherein expression of the 3R isoform of Tau protein is increased.

Embodiment 165

The method of any of embodiments 162 to 164, wherein the cell is in vitro.

Embodiment 166

The method of any of embodiments 162 to 164, wherein the cell is in an animal.

Embodiment 167

A method of reducing or ameliorating one or more symptoms associated with a tau-associated disorder, comprising contacting a cell with a compound according to any of embodiments 1-158.

Embodiment 168

The method of embodiment 167, wherein the symptom is seizure.

Embodiment 169

The method of any of embodiments 167-168, wherein the cell is in an animal.

Embodiment 170

A pharmaceutical composition comprising a compound according to any of embodiments 1-158 and a pharmaceutically acceptable carrier or diluent.

Embodiment 171

The pharmaceutical composition of embodiment 170, wherein the pharmaceutically acceptable carrier or diluent is sterile saline.

Embodiment 172

A method comprising administering the pharmaceutical composition of embodiments 170 or 171 to an animal.

Embodiment 173

The method of embodiment 172, wherein the administration is by injection.

Embodiment 174

The method of embodiment 172 or 173, wherein the administration is systemic.

Embodiment 175

The method of embodiment 172 or 173, wherein the administration is to the CNS.

Embodiment 176

The method of any of embodiments 172-175, wherein the animal has one or more symptoms associated with one or more tau-associated disorders.

Embodiment 177

The method of embodiment 176, wherein the administration results in amelioration of one or more symptoms associated with one or more tau-associated disorders.

Embodiment 178

The method of any of embodiments 172-175, wherein the animal has one or more symptoms associated with Alzheimer's disease.

Embodiment 179

The method of embodiment 178, wherein the administration results in amelioration of one or more symptoms associated with Alzheimer's disease.

Embodiment 180

The method of any of embodiments 172-179, wherein the animal is a mouse.

Embodiment 181

The method of any of embodiments 172-179, wherein the animal is a human.

Embodiment 182

Use of the compound of any of embodiments 1 to 158 or the composition of embodiments 170-171 for the preparation of a medicament for use in the treatment of a tau-associated disorder.

Embodiment 183

Use of the compound of any of embodiments 1 to 158 or the composition of embodiments 170-171 for the preparation of a medicament for use in the amelioration of one or more symptoms associated a tau-associated disorder.

Embodiment 184

The compound, composition, or method of any of embodiments 1-183, wherein the nucleobase sequence does not consist of the nucleobase sequence as set forth in SEQ ID NO.: 45, 66, 68, 69, or 200.

Embodiment 185

The compound, composition, or method of any of embodiments 1-183, wherein the nucleobase sequence does not consist of the nucleobase sequence CCAGCTTCTTAT-TAATTATC or TAAGATCCAGCTTCTTATTA.

Embodiment 186

The compound, composition, or method of any of embodiments 1-183, wherein the target region is not within nucleobase 121828 and nucleobase 121847 of SEQ ID NO.: 1.

Embodiment 187

The compound, composition, or method of any of embodiments 1-183, wherein the target region is not within nucleobase 121834 and nucleobase 121853 of SEQ ID NO.: 1.

Embodiment 188

The compound, composition, or method of any of embodiments 1-183, wherein the target region is not within nucleobase 121840 and nucleobase 121859 of SEQ ID NO.: 1.

Embodiment 189

The compound, composition, or method of any of embodiments 1-183, wherein the target region is not within nucleobase 121924 and nucleobase 121941 of SEQ ID NO.: 1.

Embodiment 190

The compound, composition, or method of any of embodiments 1-183, wherein the target region is not within nucleobase 121012 and nucleobase 121029 of SEQ ID NO.: 1.

Embodiment 191

The compound, composition, or method of any of embodiments 1-183, wherein the target region is not within nucleobase 121020 and nucleobase 121037 of SEQ ID NO.: 1.

Embodiment 192

The compound, composition, or method of any of embodiments 1-183, wherein the target region is not within nucleobase 121024 and nucleobase 121041 of SEQ ID NO.: 1.

BRIEF DESCRIPTION OF THE FIGURES

FIG. 1 depicts a graphical representation of Tau isoforms. The isoforms can differ from each other in the number of tubulin-binding domains (three or four repeats located in the C-terminal half of the protein) and are referred to as 3R or 4R Tau isoforms, respectively. They can also differ in the presence or absence of either one or two 29-amino-acid-long, highly acidic inserts at the N-terminal portion of the protein (the projection domain). Between the projection domain and the microtubule-binding domain lies a basic proline-rich region.

DETAILED DESCRIPTION

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "Tau transcript" means a transcript transcribed from a Tau gene. In certain embodiments, a Tau transcript is represented by GENBANK Accession No NT_010783.15, truncated from nucleotides 9240000 to 9381000 (SEQ ID NO: 1), or a variant thereof.

As used herein, "Tau gene" means a gene that encodes a Tau protein and any Tau protein isoforms. In certain embodiments, Tau protein isoforms include the 3R isoform and the 4R isoform.

As used herein, "3R" means a Tau transcript that includes does not include exon 10.

As used herein, "3R Tau isoform" means a Tau protein isoform that does not include amino acids encoded from exon 10.

As used herein, "4R" means a Tau transcript that includes exon 10.

As used herein, "4R Tau isoform" means a Tau protein isoform that includes amino acids encoded from exon 10.

As used herein, "Tau-associated disease" means any neurological or neurodegenerative disease associated with Tau. Non-limiting examples of Tau-associated disorders include Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, supranuclear palsy, corticobasal degeneration, frontotemporal dementia, or frontotemporal lobar degeneration.

As used herein, "Tauopathy" means disorders characterized by a build-up of Tau protein in the brain.

As used herein, "Tau-specific inhibitor" includes but is not limited to a "antisense compound" targeted to Tau.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($-C(O)R_{aa}$), carboxyl ($-C(O)O-R_{aa}$), aliphatic groups, alicyclic groups, alkoxy, substituted oxy ($-O-R^{aa}$), aryl, aralkyl, heterocyclic radical, heteroaryl, heteroarylalkyl, amino ($-N(R_{bb})(R_{cc})$), imino($=NR_{bb}$), amido ($-C(O)N(R_{bb})(R_{cc})$ or $-N(R_{bb})C(O)R_{aa}$), azido ($-N_3$), nitro ($-NO_2$), cyano ($-CN$), carbamido ($-OC(O)N(R_{bb})(R_{cc})$ or $-N(R_{bb})C(O)OR_{aa}$), ureido ($-N(R_{bb})C(O)N(R_{bb})(R_{cc})$), thioureido ($-N(R_{bb})C(S)N(R_{bb})-(R_{cc})$), guanidinyl ($-N(R_{bb})C(=NR_{bb})N(R_{bb})(R_{cc})$), amidinyl ($-C(=NR_{bb})N(R_{bb})(R_{cc})$ or $-N(R_{bb})C(=NR_{bb})(R_{aa})$), thiol ($-SR_{bb}$), sulfinyl ($-S(O)R_{bb}$), sulfonyl ($-S(O)_2R_{bb}$) and sulfonamidyl ($-S(O)_2N(R_{bb})(R_{cc})$ or $-N(R_{bb})S-(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula $-C(O)-X$ where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N (Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH (CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.*, 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-($CH_2$)$_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, and (J) propylene carbocyclic (4'-($CH_2$)$_3$-2') BNA as depicted below.

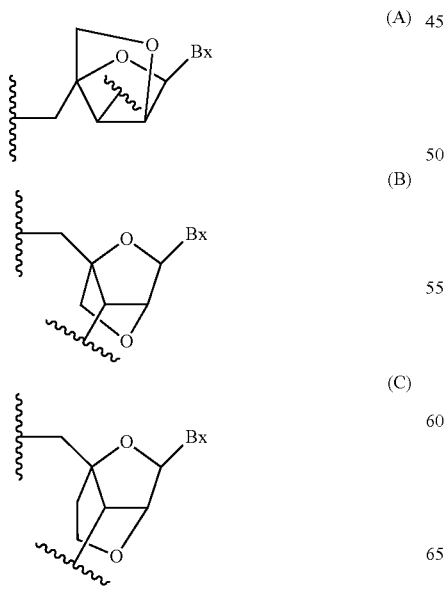

(A)

(B)

(C)

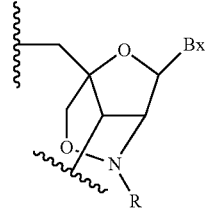

(D)

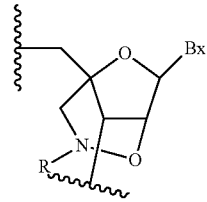

(E)

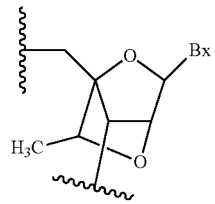

(F)

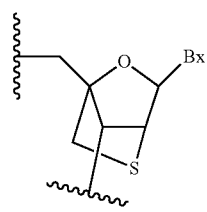

(G)

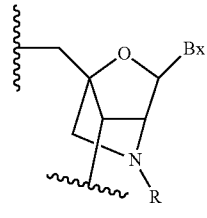

(H)

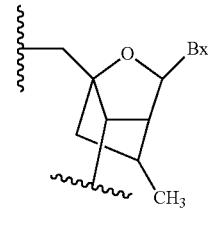

(I)

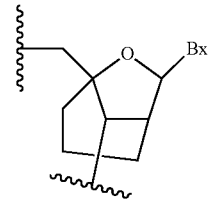

(J)

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630;

Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

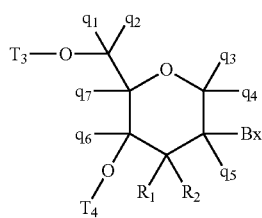

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following structure:

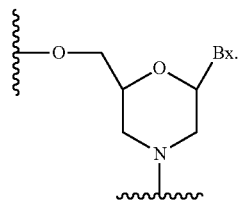

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, phosphoramidate, and phosphorothioates (P═S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C (O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(═O)—N(H)-5'), amide-4 (3'-CH$_2$—N(H)—C(═O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, compounds and compositions, including modified oligonucleotides, are delivered to the CNS. In certain embodiments, compounds and compositions, including modified oligonucleotides, are delivered to the CNS via intracerebroventricular administration or intracerebroventricular bolus administration. In certain embodiments, one or more modified oligonucleotides may exhibit high potency and high selectivity toward a nucleic acid target, but may possess certain degrees of acute toxicity when delivered into the CNS via intracerebroventricular administration. In certain embodiments, introduction of one or more modifications to the internucleoside linkages of the modified oligonucleotide ameliorates or reduces acute toxicity associated with CNS delivery via intracerebroventricular administration. In certain embodiments, introduction of one or more phosphodiester internucleoside linkages into the modified oligonucleotide ameliorates or reduces acute toxicity associated with CNS delivery via intracerebroventricular administration.

In certain embodiments, an oligomeric compound has an internucleoside linkage motif selected from the table below, wherein each "N" represents a nucleoside, each subscript "s" represents a phosphorothioate internucleoside linkage, and each subscript "o" represents a phosphodiester internucleoside linkage:

| Internucleoside Linkage Motifs |
|---|
|  |
| $N_SN_ON_ON_ON_SN_SN_SN_SN_SN_SN_SN_SN_ON_ON_ON_SN_SN$ |

In certain embodiments, the inclusion of 3, 4, 5, 6, 7, 8, or 9 phosphodiester internucleoside linkages into the modified oligonucleotide ameliorates or reduces acute toxicity associated with CNS delivery via intracerebroventricular administration.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654) a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Certain Modified Oligonucleotides

In certain embodiments, a modified oligonucleotide has the sequence of SEQ ID NO. 31. In certain embodiments, a modified oligonucleotide has the sequence of SEQ ID NO. 33. In certain embodiments, a modified oligonucleotide has the sequence of SEQ ID NO.34. In certain embodiments, a modified oligonucleotide has the sequence of SEQ ID NO.35. In certain embodiments, a modified oligonucleotide has the sequence of SEQ ID NO. 36. In certain embodiments, a modified oligonucleotide has the sequence of SEQ ID NO. 37. In certain embodiments, a modified oligonucleotide has the sequence of SEQ ID NO. 45.

In certain embodiments, a modified oligonucleotide has the sequence of SEQ ID NO. 72. In certain embodiments, a modified oligonucleotide has the sequence of SEQ ID NO. 79. In certain embodiments, a modified oligonucleotide has the sequence of SEQ ID NO. 82. In certain embodiments, a modified oligonucleotide has the sequence of SEQ ID NO. 83. In certain embodiments, a modified oligonucleotide has the sequence of SEQ ID NO. 97. In certain embodiments, a modified oligonucleotide has the sequence of SEQ ID NO. 106. In certain embodiments, a modified oligonucleotide has the sequence of SEQ ID NO. 107. In certain embodiments, a modified oligonucleotide has the sequence of SEQ ID NO. 112. In certain embodiments, a modified oligonucleotide has the sequence of SEQ ID NO. 113. In certain embodiments, a modified oligonucleotide has the sequence of SEQ ID NO. 130. In certain embodiments, a modified oligonucleotide has the sequence of SEQ ID NO. 140.

In certain embodiments, a modified oligonucleotide has the sequence of SEQ ID NO. 141. In certain embodiments, a modified oligonucleotide has the sequence of SEQ ID NO. 142. In certain embodiments, a modified oligonucleotide has the sequence of SEQ ID NO. 143. In certain embodiments, a modified oligonucleotide has the sequence of SEQ ID NO. 144. In certain embodiments, a modified oligonucleotide has the sequence of SEQ ID NO. 145. In certain embodiments, a modified oligonucleotide has the sequence of SEQ ID NO. 146. In certain embodiments, a modified oligonucleotide has the sequence of SEQ ID NO. 147. In certain embodiments, a modified oligonucleotide has the sequence of SEQ ID NO. 148. In certain embodiments, a modified oligonucleotide has the sequence of SEQ ID NO. 149.

In certain embodiments, a modified oligonucleotide has the sequence of SEQ ID NO. 150. In certain embodiments, a modified oligonucleotide has the sequence of SEQ ID NO. 151. In certain embodiments, a modified oligonucleotide has the sequence of SEQ ID NO. 152. In certain embodiments, a modified oligonucleotide has the sequence of SEQ ID NO. 153. In certain embodiments, a modified oligonucleotide has the sequence of SEQ ID NO. 157. In certain embodiments, a modified oligonucleotide has the sequence of SEQ ID NO. 158. In certain embodiments, a modified oligonucleotide has the sequence of SEQ ID NO. 160. In certain embodiments, a modified oligonucleotide has the sequence of SEQ ID NO. 200.

Certain Pathways and Mechanisms Associated with Neurodegenerative Disorders

In certain embodiments, a neurodegenerative syndrome or disorder may be any neurodegenerative syndrome or disorder associated with Tau. Non limiting examples of a neurodegenerative disorder associated with Tau may include Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, supranuclear palsy, corticobasal degeneration, frontotemporal dementia, or frontotemporal lobar degeneration. In some embodiments, the method of the invention comprises modifying frontotemporal dementia (FTD). In other embodiments, the method of the invention comprises modifying Alzheimer's disease (AD). In yet other embodiments, the method of the invention comprises modifying progressive supranuclear palsy. In other embodiments, the method of the invention comprises modifying corticobasalganglionic degeneration.

In certain embodiments, described herein are compositions and methods of modifying a neurodegenerative syndrome by altering the splicing of a nucleic acid encoding Tau. Tau is a protein found in multiple tissues, but is particularly abundant in axons of neurons. The primary function of Tau is to bind to and stabilize microtubules, which are important structural components of the cytoskeleton involved in mitosis, cytokinesis and vesicular transport. In humans, there are six isoforms of Tau that are generated by alternative splicing of exons 2, 3, and 10. Splicing of exons 2 and 3 at the N-terminus of the protein leads to inclusion of zero, one or two 29 amino acid, acidic domains and is termed 0N, 1N, or 2N Tau respectively. Inclusion of exon 10 at the C-terminus leads to inclusion of the microtubule binding domain encoded by exon 10. Since there are 3 mictrotubule binding domains elsewhere in Tau, this Tau isoform (with exon 10 included) is termed 4R Tau, where R refers to the number of repeats of microtubule binding domains. (FIG. 1). Tau without exon 10 is termed 3R Tau. In healthy subjects, the ratio of 3R:4R Tau is developmentally regulated, with fetal tissues expressing almost exclusively 3R Tau and adult human tissues expressing approximately equal levels of 3R/4R Tau. Deviations from the normal ratio of 3R/4R Tau are characteristic of neurodegenerative syndromes such as FTD Tauopathies.

In certain embodiments, the 4R:3R Tau ratio in the central nervous system of the subject may be normal, low or high. As used herein, a "normal 4R:3R Tau ratio" in the central nervous system signifies a 4R:3R Tau ratio in the central nervous system that is substantially the same as the 4R:3R Tau ratio in the central nervous system of a subject from the same species and of approximately the same age not suffering from a neurodegenerative disease. In certain embodiments, certain antisense oligonucleotide compositions and/or methods decrease the normal 4R:3R Tau ratio in the central nervous system of a subject. In other embodiments, certain antisense oligonucleotide compositions and/or methods decreases a low 4R:3R Tau ratio in the central nervous system of a subject.

In certain embodiments, certain antisense oligonucleotide compositions and/or methods decrease a high 4R:3R Tau ratio in the central nervous system of a subject. In certain embodiments, certain antisense oligonucleotide compositions and/or methods decreases a high 4R:3R Tau ratio caused by a defect in splicing of the nucleic acid encoding Tau in the subject. Defects in splicing of the nucleic acid encoding Tau in the subject may be caused, for instance, by genetic mutations altering the splicing of the nucleic acid encoding Tau and leading to a high 4R:3R Tau ratio. A mutation may be either a substitution mutation or a deletion mutation which creates a new, aberrant, splice element. Non-limiting examples of genetic mutations that may alter the splicing of the nucleic acid encoding Tau and lead to a high 4R:3R Tau ratio may include N279K, P301S, 280, L284L, N296H, N296N, 296N, P301S, G303V, E10+11, E10+12, E10+13, E+10+14 and E10+16, and E10+19.

In certain embodiments, administration of an antisense oligonucleotide decreases the 4R:3R Tau ratio in the central nervous system of a subject by altering the splicing of a nucleic acid encoding Tau.

In certain embodiments, increasing exclusion of exon 10 of a Tau transcript inhibits one or more tau-associated disorders. In certain embodiments, the tau-associated disorder may be any of Alzheimer's Disease, frontotemporal Dementia (FTD), FTDP-17, Progressive Supranuclear Palsy (PSP), Chronic Traumatic Encephalopathy (CTE), Corticobasal Ganglionic Degeneration (CBD), epilepsy, Dravet's Syndrome, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, supranuclear palsy, corticobasal degeneration, or frontotemporal lobar degeneration.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, the target nucleic acid is a tau transcript. In certain embodiments, the target RNA is a Tau pre-mRNA.

In certain embodiments, an antisense compound is complementary to a region of Tau pre-mRNA. In certain embodiments, an antisense compound is complementary within a region of Tau pre-mRNA comprising an exon encoding the 4R isoform. In certain embodiments, an antisense compound is complementary to a region of Tau pre-mRNA comprising an intron-exon splice junction. In certain embodiments, an antisense compound is complementary to a region of Tau pre-mRNA comprising the intron-exon splice junction adjacent to exon 10. In certain embodiments, an antisense compound is complementary to a region of Tau pre-mRNA comprising the intron-exon splice junction between intron 9 and exon 10. In certain embodiments, an antisense compound is complementary to a region of Tau pre-mRNA comprising the intron-exon splice junction between exon 10 and intron 10. In certain embodiments, an antisense compound is complementary within a region of Tau pre-mRNA consisting of exon 10.

In certain embodiments, an antisense compound is complementary within a region of Tau pre-mRNA comprising an exonic splicing silencer within exon 10. In certain embodiments, an antisense compound is complementary within a region of Tau pre-mRNA comprising an exonic splicing enhancer within exon 10.

In certain embodiments, an antisense compound comprises a modified oligonucleotide consisting of 8 to 30 linked nucleosides and having a nucleobase sequence comprising a complementary region comprising at least 8 contiguous nucleobases complementary to a target region of equal length of a Tau transcript.

In certain embodiments, the target region is within nucleobase 121708 and nucleobase 122044 of SEQ ID NO.: 1. In certain embodiments, the target region is within nucleobase 121796 and nucleobase 122044 of SEQ ID NO.: 1. In certain embodiments, the target region is within nucleobase 121796 and nucleobase 121885 of SEQ ID NO.: 1. In certain embodiments, the target region is within nucleobase 121873 and nucleobase 121898 of SEQ ID NO.: 1. In certain embodiments, the target region is within nucleobase 121869 and nucleobase 121943 of SEQ ID NO.: 1. In certain embodiments, the target region is within nucleobase 122020 and nucleobase 122044 of SEQ ID NO.: 1. In certain embodiments, the target region is within nucleobase 121881 and nucleobase 121898 of SEQ ID NO.: 1. In certain embodiments, the target region is within nucleobase 121880 and nucleobase 121897 of SEQ ID NO.: 1. In certain embodiments, the target region is within nucleobase 121879 and nucleobase 121896 of SEQ ID NO.: 1.

In certain embodiments, the target region is within nucleobase 121878 and nucleobase 121895 of SEQ ID NO.: 1. In certain embodiments, the target region is within nucleobase 121877 and nucleobase 121894 of SEQ ID NO.: 1. In certain embodiments, the target region is within nucleobase 121876 and nucleobase 121893 of SEQ ID NO.: 1. In certain embodiments, the target region is within nucleobase 121875 and nucleobase 121892 of SEQ ID NO.: 1. In certain embodiments, the target region is within nucleobase 121874 and nucleobase 121891 of SEQ ID NO.: 1. In certain embodiments, the target region is within nucleobase 121873 and nucleobase 121890 of SEQ ID NO.: 1.

In certain embodiments, an antisense oligonucleotide modulates splicing of a pre-mRNA. In certain embodiments, an antisense oligonucleotide modulates splicing a Tau premRNA. In certain embodiments, an antisense oligonucleotide increases the amount of Tau 3R mRNA. In certain embodiments, an antisense oligonucleotide increases the exclusion of exon 10 in Tau mRNA. In certain embodiments, an antisense oligonucleotide decreases the inclusion of exon 10 in Tau mRNA. In certain embodiments, an antisense oligonucleotide increases the amount of 3R Tau mRNA. In certain embodiments, an antisense oligonucleotide decreases the amount of 4R Tau mRNA.

In certain embodiments it is desirable to alter the splicing of Tau pre-mRNA to exclude exon 10. By altering the splicing of Tau pre-mRNA to exclude exon 10, expression of 3R Tau will increase and expression of 4R Tau will decrease. In certain embodiments it is desirable to alter the splicing of Tau pre-mRNA to decrease expression of 4R Tau.

In certain embodiments, an antisense oligonucleotide decreases the amount of Tau 3R mRNA. In certain embodiments, an antisense oligonucleotide decreases the exclusion of exon 10 in Tau mRNA. In certain embodiments, an antisense oligonucleotide increases the inclusion of exon 10 in Tau mRNA. In certain embodiments, an antisense oligonucleotide decreases the amount of 3R Tau mRNA. In certain embodiments, an antisense oligonucleotide increases the amount of 4R Tau mRNA. In certain embodiments it is desirable to alter the splicing of Tau pre-mRNA to include exon 10, for example to produce a phenotypic effect in a mouse or animal model.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

In certain embodiments, a pharmaceutical composition is administered to an animal having at least one Tau-associated disorder. In certain embodiments, such administration results in reduction in expression of the 4R isoform. In certain embodiments, a pharmaceutical composition is administered to an animal having at least one symptom associated with a Tau-associated disorder. In certain embodiments, such administration results in amelioration of at least one symptom. In certain embodiments, administration of a pharmaceutical composition to an animal results in a decrease of 4R mRNA in a cell of the animal. In certain embodiments, such administration results in an increase in 3R mRNA. In certain embodiments, such administration results in a decrease in 4R protein and an increase 3R protein. In certain embodiments, a 3R protein is preferred over a 4R protein. In certain embodiments, the administration of certain antisense oligonucleotides delays the onset of one or more Tau-associated disorders. In certain embodiments, the administration of certain antisense oligonucleotides prevents or reduces seizures. In certain embodiments, the administration of certain antisense oligonucleotides causes the amount of 4R protein to decrease in the CNS. In certain embodiments, the administration of certain antisense oligonucleotides rescues cellular phenotype.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Effects of Uniform 2'-MOE Modified Oligonucleotides on Human Tau Exon 10

A series of modified oligonucleotides were designed to target exon 10 of human Tau and were screened for their effects in reducing exon 10 inclusion in vitro. These modified oligonucleotides were designed by shifting 4 nucleotides upstream or downstream (i.e. microwalk) across the target site. They are 18 nucleosides in length, wherein each nucleoside has a 2'-MOE modification. Each internucleoside linkage throughout the modified oligonucleotide are phosphorothioate internucleoside linkages (P=S). All cytosine residues throughout the modified oligonucleotides are 5-methylcytosines.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 5 nM concentration of modified oligonucleotide. After a treatment period of approximately 24 hours, RNA was isolated from the cells and the mRNA levels of Tau transcripts containing exon 10 were measured by quantitative real-time PCR. Human primer probe set 9_10 or 10_11 was used to measure mRNA levels. Tau exon 10 mRNA levels were adjusted according to total RNA content, as measured by RIBOGREEN®. Results are presented as percent of Tau exon 10 mRNA expression, relative to untreated control levels and is denoted as "% UTC."

Human primer probe set 9_10 (forward sequence CACTGAGAACCTGAAGCACC, designated herein as SEQ ID NO: 2; reverse sequence GGACTGGACGTTGCTAAGATC, designated as SEQ ID NO: 3; probe sequence TTAATTATCTGCACCTTCCCGCCTCC, designated herein as SEQ ID NO: 4).

Human primer probe set 10_11 (forward sequence GGATAATATCAAACACGTCCCG, designated herein as SEQ ID NO: 5; reverse sequence TGCCTAATGAGCCACACTTG, designated as SEQ ID NO: 6; probe sequence GTCTACAAACCAGTTGACCTGAGC, designated herein as SEQ ID NO: 7).

As illustrated in Tables 1 and 2, ISIS 549583, 549584, 549585, 549586, 549595, 549571, 549566, 549570, 549587, 549568, 549617, 549567, 549576, 549577, 549580, and 549581 show 70% or greater reduction in human Tau exon 10 inclusion comparing to untreated control.

TABLE 1

Effects of uniform 2'-MOE modified oligonucleotides on human Tau exon 10 using Primer Probe Set 9_10

| ISIS NO | Sequence | % UTC | SEQ ID NO: 1 Start Site | SEQ ID NO: 1 Stop Site | SEQ ID NO |
|---|---|---|---|---|---|
| 549543 | CCCGCCTACTTGCTCGCA | 130 | 121708 | 121725 | 8 |
| 549544 | TGGACCCGCCTACTTGCT | 119 | 121712 | 121729 | 9 |
| 549545 | ACCCTGGACCCGCCTACT | 106 | 121716 | 121733 | 10 |
| 549546 | CATGCGCCACCCTGGACC | 84 | 121724 | 121741 | 11 |
| 549547 | GTGACATGCGCCACCCTG | 78 | 121728 | 121745 | 12 |
| 549548 | ATGAGTGACATGCGCCAC | 63 | 121732 | 121749 | 13 |
| 549549 | TTCGATGAGTGACATGCG | 70.0 | 121736 | 121753 | 14 |
| 549550 | CACTTTCGATGAGTGACA | 69 | 121740 | 121757 | 15 |
| 549551 | CCTCCACTTTCGATGAGT | 103 | 121744 | 121761 | 16 |
| 549552 | GACGCCTCCACTTTCGAT | 148 | 121748 | 121765 | 17 |
| 549553 | CAAGGACGCCTCCACTTT | 116 | 121752 | 121769 | 18 |
| 549554 | CTCGCAAGGACGCCTCCA | 80 | 121756 | 121773 | 19 |
| 549555 | CTTGCTCGCAAGGACGCC | 102 | 121760 | 121777 | 20 |

TABLE 1-continued

Effects of uniform 2'-MOE modified oligonucleotides on human Tau exon 10 using Primer Probe Set_9_10

| ISIS NO | Sequence | % UTC | SEQ ID NO: 1 Start Site | SEQ ID NO: 1 Stop Site | SEQ ID NO |
| --- | --- | --- | --- | --- | --- |
| 549556 | CCTGCTTGCTCGCAAGGA | 109 | 121764 | 121781 | 21 |
| 549557 | CCCGCCTGCTTGCTCGCA | 100 | 121768 | 121785 | 22 |
| 549558 | TGGACCCGCCTGCTTGCT | 111 | 121772 | 121789 | 23 |
| 549559 | ACCCTGGACCCGCCTGCT | 108 | 121776 | 121793 | 24 |
| 549560 | CGCCACCCTGGACCCGCC | 88 | 121720 121780 | 121737 121797 | 25 |
| 549561 | GACACGCCACCCTGGACC | 83 | 121784 | 121801 | 26 |
| 549562 | GAGTGACACGCCACCCTG | 77 | 121788 | 121805 | 27 |
| 549563 | GGATGAGTGACACGCCAC | 58 | 121792 | 121809 | 28 |
| 549564 | AAAAGGATGAGTGACACG | 49 | 121796 | 121813 | 29 |
| 549565 | AGAAAAAAGGATGAGTGA | 35 | 121800 | 121817 | 30 |
| 549566 | AGCCAGAAAAAGGATGA | 21 | 121804 | 121821 | 31 |
| 549567 | TGGTAGCCAGAAAAAAGG | 32 | 121808 | 121825 | 32 |
| 549583 | TTATCCTTTGAGCCACAC | 11 | 121876 | 121893 | 33 |
| 549584 | GATATTATCCTTTGAGCC | 11 | 121880 | 121897 | 34 |
| 549585 | GTTTGATATTATCCTTTG | 13 | 121884 | 121901 | 35 |
| 549586 | ACGTGTTTGATATTATCC | 17 | 121888 | 121905 | 36 |
| 549587 | CGGGACGTGTTTGATATT | 24 | 121892 | 121909 | 37 |
| 549588 | CTCCCGGGACGTGTTTGA | 52 | 121896 | 121913 | 38 |
| 549589 | CCGCCTCCCGGGACGTGT | 57 | 121900 | 121917 | 39 |
| 549590 | ACTGCCGCCTCCCGGGAC | 84 | 121904 | 121921 | 40 |
| 549591 | TCACACTGCCGCCTCCCG | 48 | 121908 | 121925 | 41 |
| 549592 | GTACTCACACTGCCGCCT | 30 | 121912 | 121929 | 42 |
| 549593 | GAAGGTACTCACACTGCC | 35 | 121916 | 121933 | 43 |
| 549594 | GTGTGAAGGTACTCACAC | 63 | 121920 | 121937 | 44 |
| 549595 | GGACGTGTGAAGGTACTC | 20 | 121924 | 121941 | 45 |
| 549596 | CATGGGACGTGTGAAGGT | 125 | 121928 | 121945 | 46 |
| 549597 | GGCGCATGGGACGTGTGA | 216 | 121932 | 121949 | 47 |
| 549598 | GCACGGCGCATGGGACGT | 242 | 121936 | 121953 | 48 |
| 549599 | CACAGCACGGCGCATGGG | 158 | 121940 | 121957 | 49 |
| 549600 | AAGCCACAGCACGGCGCA | 162 | 121944 | 121961 | 50 |
| 549601 | ATTCAAGCCACAGCACGG | 175 | 121948 | 121965 | 51 |
| 549602 | AATAATTCAAGCCACAGC | 164 | 121952 | 121969 | 52 |
| 549603 | TCCTAATAATTCAAGCCA | 200 | 121956 | 121973 | 53 |
| 549604 | CACTTCCTAATAATTCAA | 133 | 121960 | 121977 | 54 |
| 549605 | ACACCACTTCCTAATAAT | 113 | 121964 | 121981 | 55 |
| 549606 | ACTCACACCACTTCCTAA | 136 | 121968 | 121985 | 56 |

TABLE 1-continued

Effects of uniform 2'-MOE modified oligonucleotides on human Tau exon 10 using Primer Probe Set 9_10

| ISIS NO | Sequence | % UTC | SEQ ID NO: 1 Start Site | SEQ ID NO: 1 Stop Site | SEQ ID NO |
| --- | --- | --- | --- | --- | --- |
| 549608 | GTGTACGCACTCACACCA | 80.6 | 121976 | 121993 | 57 |
| 549609 | GCAAGTGTACGCACTCAC | 49.9 | 121980 | 121997 | 58 |
| 549610 | TCTCGCAAGTGTACGCAC | 86.5 | 121984 | 122001 | 59 |
| 549611 | AGTGTCTCGCAAGTGTAC | 62.4 | 121988 | 122005 | 60 |
| 549612 | ATGCAGTGTCTCGCAAGT | 46.4 | 121992 | 122009 | 61 |
| 549613 | TTCTATGCAGTGTCTCGC | 46.6 | 121996 | 122013 | 62 |
| 549614 | TTTATTCTATGCAGTGTC | 33.2 | 122000 | 122017 | 63 |
| 549615 | AGGATTTATTCTATGCAG | 34.3 | 122004 | 122021 | 64 |
| 549616 | AAGAAGGATTTATTCTAT | 46.5 | 122008 | 122025 | 65 |
| 549617 | GCCCAAGAAGGATTTATT | 29.6 | 122012 | 122029 | 66 |
| 549618 | GAGAGCCCAAGAAGGATT | 38.6 | 122016 | 122033 | 67 |
| 549619 | TCCTGAGAGCCCAAGAAG | 36.9 | 122020 | 122037 | 68 |
| 549620 | CAGATCCTGAGAGCCCAA | 38.3 | 122024 | 122041 | 69 |

TABLE 2

Effects of uniform 2'-MOE modified oligonucleotides on human Tau exon 10 using Primer Probe Set 10_11

| ISIS NO | Sequence | % UTC | SEQ ID NO: 1 Start Site | SEQ ID NO: 1 Stop Site | Mis-matches | SEQ ID NO |
| --- | --- | --- | --- | --- | --- | --- |
| 549543 | CCCGCCTACTTGCTCGCA | 128 | 121708 121768 | 121725 121785 | 0 1 | 8 |
| 549544 | TGGACCCGCCTACTTGCT | 117 | 121712 121772 | 121729 121789 | 0 1 | 9 |
| 549545 | ACCCTGGACCCGCCTACT | 98 | 121716 121776 | 121733 121793 | 0 1 | 10 |
| 549546 | CATGCGCCACCCTGGACC | 78 | 121724 | 121741 | 0 | 11 |
| 549547 | GTGACATGCGCCACCCTG | 75 | 121728 | 121745 | 0 | 12 |
| 549548 | ATGAGTGACATGCGCCAC | 63 | 121732 | 121749 | 0 | 13 |
| 549549 | TTCGATGAGTGACATGCG | 74 | 121736 | 121753 | 0 | 14 |
| 549550 | CACTTTCGATGAGTGACA | 76 | 121740 | 121757 | 0 | 15 |
| 549551 | CCTCCACTTTCGATGAGT | 107 | 121744 | 121761 | 0 | 16 |
| 549552 | GACGCCTCCACTTTCGAT | 137 | 121748 | 121765 | 0 | 17 |
| 549553 | CAAGGACGCCTCCACTTT | 108 | 121692 121752 | 121709 121769 | 1 0 | 18 |
| 549554 | CTCGCAAGGACGCCTCCA | 71 | 121696 121756 | 121713 121773 | 1 0 | 19 |
| 549555 | CTTGCTCGCAAGGACGCC | 108 | 121700 121760 | 121717 121777 | 1 0 | 20 |
| 549556 | CCTGCTTGCTCGCAAGGA | 106 | 121704 121764 | 121721 121781 | 1 0 | 21 |

TABLE 2-continued

Effects of uniform 2'-MOE modified oligonucleotides on human Tau exon 10 using Primer Probe Set 10_11

| ISIS NO | Sequence | % UTC | SEQ ID NO: 1 Start Site | SEQ ID NO: 1 Stop Site | Mis-matches | SEQ ID NO |
|---------|----------|-------|-------------------------|------------------------|-------------|-----------|
| 549557 | CCCGCCTGCTTGCTCGCA | 93 | 121708<br>121768 | 121725<br>121785 | 1<br>0 | 22 |
| 549558 | TGGACCCGCCTGCTTGCT | 111 | 121712<br>121772 | 121729<br>121789 | 1<br>0 | 23 |
| 549559 | ACCCTGGACCCGCCTGCT | 100 | 121716<br>121776 | 121733<br>121793 | 1<br>0 | 24 |
| 549560 | CGCCACCCTGGACCCGCC | 89 | 121720<br>121780 | 121737<br>121797 | 0<br>0 | 25 |
| 549561 | GACACGCCACCCTGGACC | 80 | 121784 | 121801 | 0 | 26 |
| 549562 | GAGTGACACGCCACCCTG | 81 | 121788 | 121805 | 0 | 27 |
| 549563 | GGATGAGTGACACGCCAC | 54 | 121792 | 121809 | 0 | 28 |
| 549564 | AAAAGGATGAGTGACACG | 45 | 121796 | 121813 | 0 | 29 |
| 549565 | AGAAAAAAGGATGAGTGA | 34 | 121800 | 121817 | 0 | 30 |
| 549566 | AGCCAGAAAAAGGATGA | 19 | 121804 | 121821 | 0 | 31 |
| 549567 | TGGTAGCCAGAAAAAAGG | 31 | 121808 | 121825 | 0 | 32 |
| 549568 | CCTTTGGTAGCCAGAAAA | 23 | 121812 | 121829 | 0 | 70 |
| 549569 | TGCACCTTTGGTAGCCAG | 53 | 121816 | 121833 | 0 | 71 |
| 549570 | TAATTATCTGCACCTTTG | 26 | 121824 | 121841 | 0 | 72 |
| 549571 | TTCTTAATTATCTGCACC | 21 | 121828 | 121845 | 1 | 73 |
| 549572 | CTTCTTCTTAATTATCTG | 30 | 121832 | 121849 | 1 | 74 |
| 549573 | CCAGCTTCTTCTTAATTA | 34 | 121836 | 121853 | 1 | 75 |
| 549574 | AGATCCAGCTTCTTCTTA | 43 | 121840 | 121857 | 1 | 76 |
| 549575 | GCTAAGATCCAGCTTCTT | 25 | 121844 | 121861 | 0 | 77 |
| 549576 | CGTTGCTAAGATCCAGCT | 18 | 121848 | 121865 | 0 | 78 |
| 549577 | TGGACGTTGCTAAGATCC | 16 | 121852 | 121869 | 0 | 79 |
| 549578 | GGACTGGACGTTGCTAAG | 44 | 121856 | 121873 | 0 | 80 |
| 549579 | ACTTGGACTGGACGTTGC | 36 | 121860 | 121877 | 0 | 81 |
| 549580 | CCACACTTGGACTGGACG | 19 | 121864 | 121881 | 0 | 82 |
| 549581 | TGAGCCACACTTGGACTG | 16 | 121868 | 121885 | 0 | 83 |
| 549595 | GGACGTGTGAAGGTACTC | 20 | 121924 | 121941 | 0 | 45 |
| 549596 | CATGGGACGTGTGAAGGT | 128 | 121928 | 121945 | 0 | 46 |
| 549597 | GGCGCATGGGACGTGTGA | 199 | 121932 | 121949 | 0 | 47 |
| 549598 | GCACGGCGCATGGGACGT | 199 | 121936 | 121953 | 0 | 48 |
| 549599 | CACAGCACGGCGCATGGG | 149 | 121940 | 121957 | 0 | 49 |
| 549600 | AAGCCACAGCACGGCGCA | 156 | 121944 | 121961 | 0 | 50 |
| 549601 | ATTCAAGCCACAGCACGG | 166 | 121948 | 121965 | 0 | 51 |
| 549602 | AATAATTCAAGCCACAGC | 159 | 121952 | 121969 | 0 | 52 |
| 549603 | TCCTAATAATTCAAGCCA | 179 | 121956 | 121973 | 0 | 53 |

TABLE 2-continued

Effects of uniform 2'-MOE modified oligonucleotides on human Tau exon 10 using Primer Probe Set 10_11

| ISIS NO | Sequence | % UTC | SEQ ID NO: 1 Start Site | SEQ ID NO: 1 Stop Site | Mis-matches | SEQ ID NO |
|---|---|---|---|---|---|---|
| 549604 | CACTTCCTAATAATTCAA | 123 | 121960 | 121977 | 0 | 54 |
| 549605 | ACACCACTTCCTAATAAT | 113 | 121964 | 121981 | 0 | 55 |
| 549606 | ACTCACACCACTTCCTAA | 119 | 121968 | 121985 | 0 | 56 |
| 549608 | GTGTACGCACTCACACCA | 77.2 | 121976 | 121993 | 0 | 57 |
| 549609 | GCAAGTGTACGCACTCAC | 53.0 | 121980 | 121997 | 0 | 58 |
| 549610 | TCTCGCAAGTGTACGCAC | 87.4 | 121984 | 122001 | 0 | 59 |
| 549611 | AGTGTCTCGCAAGTGTAC | 69.2 | 121988 | 122005 | 0 | 60 |
| 549612 | ATGCAGTGTCTCGCAAGT | 43.3 | 121992 | 122009 | 0 | 61 |
| 549613 | TTCTATGCAGTGTCTCGC | 41.4 | 121996 | 122013 | 0 | 62 |
| 549614 | TTTATTCTATGCAGTGTC | 29.2 | 122000 | 122017 | 0 | 63 |
| 549615 | AGGATTTATTCTATGCAG | 30.9 | 122004 | 122021 | 0 | 64 |
| 549616 | AAGAAGGATTTATTCTAT | 45.8 | 122008 | 122025 | 0 | 65 |
| 549617 | GCCCAAGAAGGATTTATT | 31.8 | 122012 | 122029 | 0 | 66 |
| 549618 | GAGAGCCCAAGAAGGATT | 41.8 | 122016 | 122033 | 0 | 67 |
| 549619 | TCCTGAGAGCCCAAGAAG | 41.7 | 122020 | 122037 | 0 | 68 |
| 549620 | CAGATCCTGAGAGCCCAA | 35.6 | 122024 | 122041 | 0 | 69 |

Example 2: Effects of Uniform 2'-MOE Modified Oligonucleotides on Human Tau Exon 10

A series of modified oligonucleotides were designed to target exon 10 of human Tau and were screened for their effects in reducing exon 10 inclusion in vitro. These modified oligonucleotides were designed by shifting 1 nucleotide upstream or downstream (i.e. microwalk) across the target site. They are 18 nucleosides in length, wherein each nucleoside has a 2'-MOE modification. Each internucleoside linkage throughout the modified oligonucleotide are phosphorothioate internucleoside linkages (P=S). All cytosine residues throughout the modified oligonucleotides are 5-methylcytosines.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 5 nM concentration of modified oligonucleotide. After a treatment period of approximately 24 hours, RNA was isolated from the cells and the mRNA levels of Tau transcripts containing exon 10 were measured by quantitative real-time PCR. Human Tau primer probe set 10_11 or 9_10 R5 was used to measure mRNA levels. Tau exon 10 mRNA levels were adjusted according to total RNA content, as measured by RIBOGREEN®. Results are presented as percent of Tau exon 10 mRNA expression, relative to untreated control levels and is denoted as "% UTC."

Human primer probe set 10_11 (forward sequence GGATAATATCAAACACGTCCCG, designated herein as SEQ ID NO: 5; reverse sequence TGCCTAATGAGCCACACTTG, designated herein as SEQ ID NO: 6; probe sequence GTCTACAAACCAGTTGACCTGAGC, designated herein as SEQ ID NO: 7).

Human Tau primer probe set 9_10 R5 (forward sequence CACTGAGAACCTGAAGCACC, designated herein as SEQ ID NO: 2; reverse sequence GGACGTTGCTAAGATCCAGCT, designated herein as SEQ ID NO: 3; probe sequence TTAATTATCTGCACCTTCCCGCCTCC, designated herein as SEQ ID NO: 4).

TABLE 3

Effects of uniform 2'-MOE modified oligonucleotides on human Tau exon 10 using Human Tau primer probe set 10_11

| ISIS NO | Sequence | % UTC | SEQ ID NO: 1 Start Site | SEQ ID NO: 1 Stop Site | SEQ ID NO |
|---|---|---|---|---|---|
| 549564 | AAAAGGATGAGTGACACG | 43 | 121796 | 121813 | 29 |
| 617296 | AAAAAGGATGAGTGACAC | 38 | 121797 | 121814 | 84 |

TABLE 3-continued

Effects of uniform 2'-MOE modified oligonucleotides on human Tau exon 10 using Human Tau primer probe set 10_11

| ISIS NO | Sequence | % UTC | SEQ ID NO: 1 Start Site | SEQ ID NO: 1 Stop Site | SEQ ID NO |
|---|---|---|---|---|---|
| 617297 | AAAAAAGGATGAGTGACA | 40 | 121798 | 121815 | 85 |
| 617298 | GAAAAAAGGATGAGTGAC | 39 | 121799 | 121816 | 86 |
| 549565 | AGAAAAAAGGATGAGTGA | 45 | 121800 | 121817 | 30 |
| 617299 | CAGAAAAAAGGATGAGTG | 39 | 121801 | 121818 | 87 |
| 617300 | CCAGAAAAAAGGATGAGT | 34 | 121802 | 121819 | 88 |
| 617301 | GCCAGAAAAAAGGATGAG | 34 | 121803 | 121820 | 89 |
| 549566 | AGCCAGAAAAAAGGATGA | 21 | 121804 | 121821 | 31 |
| 617302 | TAGCCAGAAAAAAGGATG | 26 | 121805 | 121822 | 90 |
| 617303 | GTAGCCAGAAAAAAGGAT | 27 | 121806 | 121823 | 91 |
| 617304 | GGTAGCCAGAAAAAAGGA | 32 | 121807 | 121824 | 92 |
| 549567 | TGGTAGCCAGAAAAAAGG | 39 | 121808 | 121825 | 32 |
| 617305 | TTGGTAGCCAGAAAAAAG | 34 | 121809 | 121826 | 93 |
| 617306 | TTTGGTAGCCAGAAAAAA | 49 | 121810 | 121827 | 94 |
| 617307 | CTTTGGTAGCCAGAAAAA | 37 | 121811 | 121828 | 95 |
| 549568 | CCTTTGGTAGCCAGAAAA | 27 | 121812 | 121829 | 70 |
| 617308 | ACCTTTGGTAGCCAGAAA | 31 | 121813 | 121830 | 96 |
| 617309 | CACCTTTGGTAGCCAGAA | 23 | 121814 | 121831 | 97 |
| 617310 | GCACCTTTGGTAGCCAGA | 59 | 121815 | 121832 | 98 |
| 549569 | TGCACCTTTGGTAGCCAG | 59 | 121816 | 121833 | 71 |
| 617311 | CTGCACCTTTGGTAGCCA | 59 | 121817 | 121834 | 99 |
| 617312 | TCTGCACCTTTGGTAGCC | 58 | 121818 | 121835 | 100 |
| 617313 | ATCTGCACCTTTGGTAGC | 53 | 121819 | 121836 | 101 |
| 415866 | TATCTGCACCTTTGGTAG | 41 | 121820 | 121837 | 102 |
| 617314 | TTATCTGCACCTTTGGTA | 36 | 121821 | 121838 | 103 |
| 617315 | ATTATCTGCACCTTTGGT | 31 | 121822 | 121839 | 104 |
| 617316 | AATTATCTGCACCTTTGG | 38 | 121823 | 121840 | 105 |
| 549570 | TAATTATCTGCACCTTTG | 21 | 121824 | 121841 | 72 |
| 617317 | TTAATTATCTGCACCTTT | 23 | 121825 | 121842 | 106 |
| 617318 | ATTAATTATCTGCACCTT | 25 | 121826 | 121843 | 107 |
| 617319 | TATTAATTATCTGCACCT | 27 | 121827 | 121844 | 108 |
| 617320 | TTATTAATTATCTGCACC | 27 | 121828 | 121845 | 109 |
| 617321 | CTTATTAATTATCTGCAC | 26 | 121829 | 121846 | 110 |
| 617322 | TCTTATTAATTATCTGCA | 25 | 121830 | 121847 | 111 |
| 617323 | TTCTTATTAATTATCTGC | 25 | 121831 | 121848 | 112 |
| 617324 | CTTCTTATTAATTATCTG | 25 | 121832 | 121849 | 113 |
| 617325 | GCTTCTTATTAATTATCT | 26 | 121833 | 121850 | 114 |

TABLE 3-continued

Effects of uniform 2'-MOE modified oligonucleotides on human Tau exon 10 using Human Tau primer probe set 10_11

| ISIS NO | Sequence | % UTC | SEQ ID NO: 1 Start Site | SEQ ID NO: 1 Stop Site | SEQ ID NO |
|---|---|---|---|---|---|
| 617326 | AGCTTCTTATTAATTATC | 32 | 121834 | 121851 | 115 |
| 617327 | CAGCTTCTTATTAATTAT | 31 | 121835 | 121852 | 116 |
| 617328 | CCAGCTTCTTATTAATTA | 29 | 121836 | 121853 | 117 |
| 617329 | TCCAGCTTCTTATTAATT | 35 | 121837 | 121854 | 118 |
| 617330 | ATCCAGCTTCTTATTAAT | 29 | 121838 | 121855 | 119 |
| 617331 | GATCCAGCTTCTTATTAA | 33 | 121839 | 121856 | 120 |
| 617332 | AGATCCAGCTTCTTATTA | 33 | 121840 | 121857 | 121 |
| 617333 | AAGATCCAGCTTCTTATT | 37 | 121841 | 121858 | 122 |
| 617334 | TAAGATCCAGCTTCTTAT | 42 | 121842 | 121859 | 123 |
| 617335 | CTAAGATCCAGCTTCTTA | 34 | 121843 | 121860 | 124 |
| 549575 | GCTAAGATCCAGCTTCTT | 29 | 121844 | 121861 | 77 |
| 617336 | TGCTAAGATCCAGCTTCT | 42 | 121845 | 121862 | 125 |
| 617337 | TTGCTAAGATCCAGCTTC | 36 | 121846 | 121863 | 126 |
| 617338 | GTTGCTAAGATCCAGCTT | 35 | 121847 | 121864 | 127 |
| 549576 | CGTTGCTAAGATCCAGCT | 26 | 121848 | 121865 | 78 |
| 617339 | ACGTTGCTAAGATCCAGC | 25 | 121849 | 121866 | 128 |
| 617340 | GACGTTGCTAAGATCCAG | 30 | 121850 | 121867 | 129 |
| 617341 | GGACGTTGCTAAGATCCA | 24 | 121851 | 121868 | 130 |
| 549577 | TGGACGTTGCTAAGATCC | 25 | 121852 | 121869 | 79 |
| 617342 | CTGGACGTTGCTAAGATC | 27 | 121853 | 121870 | 131 |
| 617343 | ACTGGACGTTGCTAAGAT | 29 | 121854 | 121871 | 132 |
| 617344 | GACTGGACGTTGCTAAGA | 34 | 121855 | 121872 | 133 |
| 549578 | GGACTGGACGTTGCTAAG | 40 | 121856 | 121873 | 80 |
| 617345 | TGGACTGGACGTTGCTAA | 51 | 121857 | 121874 | 134 |
| 617346 | TTGGACTGGACGTTGCTA | 43 | 121858 | 121875 | 135 |
| 617347 | CTTGGACTGGACGTTGCT | 38 | 121859 | 121876 | 136 |
| 549579 | ACTTGGACTGGACGTTGC | 34 | 121860 | 121877 | 81 |
| 617348 | CACTTGGACTGGACGTTG | 39 | 121861 | 121878 | 137 |
| 617349 | ACACTTGGACTGGACGTT | 30 | 121862 | 121879 | 138 |
| 617350 | CACACTTGGACTGGACGT | 32 | 121863 | 121880 | 139 |
| 549580 | CCACACTTGGACTGGACG | 27 | 121864 | 121881 | 82 |
| 617351 | GCCACACTTGGACTGGAC | 23 | 121865 | 121882 | 140 |
| 617352 | AGCCACACTTGGACTGGA | 23 | 121866 | 121883 | 141 |
| 617353 | GAGCCACACTTGGACTGG | 26 | 121867 | 121884 | 142 |
| 549581 | TGAGCCACACTTGGACTG | 24 | 121868 | 121885 | 83 |

TABLE 4

Effects of uniform 2'-MOE modified oligonucleotides on human Tau exon 10 using Human Tau primer probe set 9_10_R5

| ISIS NO | Sequence | % UTC | SEQ ID NO: 1 Start Site | SEQ ID NO: 1 Stop Site | SEQ ID NO |
|---------|----------|-------|-------------------------|------------------------|-----------|
| 617354 | TTGAGCCACACTTGGACT | 21 | 121869 | 121886 | 143 |
| 617355 | TTTGAGCCACACTTGGAC | 22 | 121870 | 121887 | 144 |
| 617356 | CTTTGAGCCACACTTGGA | 16 | 121871 | 121888 | 145 |
| 549582 | CCTTTGAGCCACACTTGG | 14 | 121872 | 121889 | 146 |
| 617357 | TCCTTTGAGCCACACTTG | 17 | 121873 | 121890 | 147 |
| 617358 | ATCCTTTGAGCCACACTT | 17 | 121874 | 121891 | 148 |
| 617359 | TATCCTTTGAGCCACACT | 19 | 121875 | 121892 | 149 |
| 549583 | TTATCCTTTGAGCCACAC | 20 | 121876 | 121893 | 33 |
| 617360 | ATTATCCTTTGAGCCACA | 21 | 121877 | 121894 | 150 |
| 617361 | TATTATCCTTTGAGCCAC | 15 | 121878 | 121895 | 151 |
| 617362 | ATATTATCCTTTGAGCCA | 16 | 121879 | 121896 | 152 |
| 549584 | GATATTATCCTTTGAGCC | 17 | 121880 | 121897 | 34 |
| 565989 | TGATATTATCCTTTGAGC | 17 | 121881 | 121898 | 153 |
| 565990 | TTGATATTATCCTTTGAG | 20 | 121882 | 121899 | 154 |
| 565991 | TTTGATATTATCCTTTGA | 28 | 121883 | 121900 | 155 |
| 549585 | GTTTGATATTATCCTTTG | 22 | 121884 | 121901 | 35 |
| 617363 | TGTTTGATATTATCCTTT | 25 | 121885 | 121902 | 156 |
| 617364 | GTGTTTGATATTATCCTT | 22 | 121886 | 121903 | 157 |
| 617365 | CGTGTTTGATATTATCCT | 20 | 121887 | 121904 | 158 |
| 549586 | ACGTGTTTGATATTATCC | 21 | 121888 | 121905 | 36 |
| 617366 | GACGTGTTTGATATTATC | 24 | 121889 | 121906 | 159 |
| 617367 | GGACGTGTTTGATATTAT | 16 | 121890 | 121907 | 160 |
| 617368 | GGGACGTGTTTGATATTA | 33 | 121891 | 121908 | 161 |
| 549587 | CGGGACGTGTTTGATATT | 20 | 121892 | 121909 | 37 |
| 617369 | CCGGGACGTGTTTGATAT | 25 | 121893 | 121910 | 162 |
| 617370 | CCCGGGACGTGTTTGATA | 43 | 121894 | 121911 | 163 |
| 617371 | TCCCGGGACGTGTTTGAT | 52 | 121895 | 121912 | 164 |
| 549588 | CTCCCGGGACGTGTTTGA | 53 | 121896 | 121913 | 38 |
| 549590 | ACTGCCGCCTCCCGGGAC | 48 | 121904 | 121921 | 40 |
| 617372 | CACTGCCGCCTCCCGGGA | 71 | 121905 | 121922 | 165 |
| 617373 | ACACTGCCGCCTCCCGGG | 60 | 121906 | 121923 | 166 |
| 617374 | CACACTGCCGCCTCCCGG | 40 | 121907 | 121924 | 167 |
| 549591 | TCACACTGCCGCCTCCCG | 47 | 121908 | 121925 | 41 |
| 617375 | CTCACACTGCCGCCTCCC | 33 | 121909 | 121926 | 168 |
| 617376 | ACTCACACTGCCGCCTCC | 34 | 121910 | 121927 | 169 |
| 617377 | TACTCACACTGCCGCCTC | 34 | 121911 | 121928 | 170 |
| 549592 | GTACTCACACTGCCGCCT | 31 | 121912 | 121929 | 42 |

TABLE 4-continued

Effects of uniform 2'-MOE modified oligonucleotides on human Tau exon 10 using Human Tau primer probe set 9_10 R5

| ISIS NO | Sequence | % UTC | SEQ ID NO: 1 Start Site | SEQ ID NO: 1 Stop Site | SEQ ID NO |
|---|---|---|---|---|---|
| 617378 | GGTACTCACACTGCCGCC | 29 | 121913 | 121930 | 171 |
| 617379 | AGGTACTCACACTGCCGC | 34 | 121914 | 121931 | 172 |
| 617380 | AAGGTACTCACACTGCCG | 43 | 121915 | 121932 | 173 |
| 549593 | GAAGGTACTCACACTGCC | 33 | 121916 | 121933 | 43 |
| 617381 | TGAAGGTACTCACACTGC | 28 | 121917 | 121934 | 174 |
| 617382 | GTGAAGGTACTCACACTG | 41 | 121918 | 121935 | 175 |
| 617383 | TGTGAAGGTACTCACACT | 43 | 121919 | 121936 | 176 |
| 549594 | GTGTGAAGGTACTCACAC | 68 | 121920 | 121937 | 44 |
| 617384 | CGTGTGAAGGTACTCACA | 35 | 121921 | 121938 | 177 |
| 617385 | ACGTGTGAAGGTACTCAC | 34 | 121922 | 121939 | 178 |
| 617386 | GACGTGTGAAGGTACTCA | 29 | 121923 | 121940 | 179 |
| 549595 | GGACGTGTGAAGGTACTC | 26 | 121924 | 121941 | 45 |
| 617387 | GGGACGTGTGAAGGTACT | 36 | 121925 | 121942 | 180 |
| 617388 | TGGGACGTGTGAAGGTAC | 36 | 121926 | 121943 | 181 |
| 617389 | ATGGGACGTGTGAAGGTA | 94 | 121927 | 121944 | 182 |
| 549596 | CATGGGACGTGTGAAGGT | 141 | 121928 | 121945 | 46 |
| 617390 | GCATGGGACGTGTGAAGG | 297 | 121929 | 121946 | 183 |
| 510184 | CGCATGGGACGTGTGAAG | 295 | 121930 | 121947 | 184 |
| 617391 | GCGCATGGGACGTGTGAA | 274 | 121931 | 121948 | 185 |
| 549597 | GGCGCATGGGACGTGTGA | 284 | 121932 | 121949 | 47 |
| 510185 | CGGCGCATGGGACGTGTG | 276 | 121933 | 121950 | 186 |
| 617392 | ACGGCGCATGGGACGTGT | 304 | 121934 | 121951 | 187 |
| 510186 | CACGGCGCATGGGACGTG | 268 | 121935 | 121952 | 188 |
| 549598 | GCACGGCGCATGGGACGT | 305 | 121936 | 121953 | 48 |
| 617393 | AGCACGGCGCATGGGACG | 237 | 121937 | 121954 | 189 |
| 510187 | CAGCACGGCGCATGGGAC | 144 | 121938 | 121955 | 190 |
| 617394 | ACAGCACGGCGCATGGGA | 170 | 121939 | 121956 | 191 |
| 549599 | CACAGCACGGCGCATGGG | 183 | 121940 | 121957 | 49 |
| 549619 | TCCTGAGAGCCCAAGAAG | 42 | 122020 | 122037 | 68 |
| 617395 | ATCCTGAGAGCCCAAGAA | 38 | 122021 | 122038 | 192 |
| 617396 | GATCCTGAGAGCCCAAGA | 44 | 122022 | 122039 | 193 |
| 617397 | AGATCCTGAGAGCCCAAG | 35 | 122023 | 122040 | 194 |
| 549620 | CAGATCCTGAGAGCCCAA | 35 | 122024 | 122041 | 69 |
| 617398 | CCAGATCCTGAGAGCCCA | 39 | 122025 | 122042 | 195 |
| 617399 | GCCAGATCCTGAGAGCCC | 47 | 122026 | 122043 | 196 |
| 617400 | AGCCAGATCCTGAGAGCC | 38 | 122027 | 122044 | 197 |

Example 3: Inhibitory Effect of Uniform 2'-MOE Modified Oligonucleotides on Human Tau Exon 10

Several modified oligonucleotides from Tables 3 and 4 were selected and further evaluated for their effects on inhibiting human Tau exon 10 expression in vitro. ISIS 549595 was included in the study for comparison.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 0, 0.1, 0.3, 1, 3, 10, or 30 nM concentration of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels, except for ISIS 549581. Human Tau primer probe set 10_11 was used for this oligonucleotide. Human Tau exon 10 mRNA levels were adjusted according to total RNA content, as measured by RIBOGREEN®.

The half maximal inhibitory concentration ($IC_{50}$) of each oligonucleotide is presented in the table below and was calculated by plotting the concentrations of oligonucleotides used versus the percent inhibition of human Tau exon 10 mRNA expression achieved at each concentration, and noting the concentration of oligonucleotide at which 50% inhibition of human Tau exon 10 mRNA expression was achieved compared to the control. Results are presented below.

Example 4: Inhibitory Effect of Uniform 2'-MOE Modified Oligonucleotides on Human Tau Exon 10

Several modified oligonucleotides from Table 4 were selected and further evaluated for their effects on inhibiting human Tau exon 10 expression in vitro. ISIS 549595 was included in the study for comparison.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 0, 0.1, 0.3, 1, 3, 10, or 30 nM concentration of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels. Human Tau exon 10 mRNA levels were adjusted according to total RNA content, as measured by RIBOGREEN®.

The $IC_{50}$ of each oligonucleotide was calculated in the same manner as illustrated in Example 3 and the results are presented below.

TABLE 5

Inhibitory effect of uniform 2'-MOE modified oligonucleotides on human Tau exon 10 expression

| ISIS NO | Sequence | $IC_{50}$ (nM) | SEQ ID NO: 1 Start Site | SEQ ID NO: 1 Stop Site | SEQ ID NO |
|---|---|---|---|---|---|
| 549581 | TGAGCCACACTTGGACTG | 1.20 | 121868 | 121885 | 83 |
| 617354 | TTGAGCCACACTTGGACT | 1.39 | 121869 | 121886 | 143 |
| 617355 | TTTGAGCCACACTTGGAC | 1.08 | 121870 | 121887 | 144 |
| 617356 | CTTTGAGCCACACTTGGA | 0.74 | 121871 | 121888 | 145 |
| 549582 | CCTTTGAGCCACACTTGG | 0.49 | 121872 | 121889 | 146 |
| 617357 | TCCTTTGAGCCACACTTG | 0.64 | 121873 | 121890 | 147 |
| 617358 | ATCCTTTGAGCCACACTT | 0.44 | 121874 | 121891 | 148 |
| 617359 | TATCCTTTGAGCCACACT | 0.54 | 121875 | 121892 | 149 |
| 549583 | TTATCCTTTGAGCCACAC | 0.37 | 121876 | 121893 | 33 |
| 617360 | ATTATCCTTTGAGCCACA | 0.39 | 121877 | 121894 | 150 |
| 617361 | TATTATCCTTTGAGCCAC | 0.38 | 121878 | 121895 | 151 |
| 549595 | GGACGTGTGAAGGTACTC | 0.97 | 121924 | 121941 | 4 5 |

TABLE 6

Inhibitory effect of uniform 2'-MOE modified oligonucleotides on human Tau exon 10 expression

| ISIS NO | Sequence | IC$_{50}$ (nM) | SEQ ID NO: 1 Start Site | SEQ ID NO: 1 Stop Site | SEQ ID NO |
|---|---|---|---|---|---|
| 617362 | ATATTATCCTTTGAGCCA | 0.27 | 121879 | 121896 | 152 |
| 549584 | GATATTATCCTTTGAGCC | 0.40 | 121880 | 121897 | 34 |
| 565989 | TGATATTATCCTTTGAGC | 0.58 | 121881 | 121898 | 153 |
| 565990 | TTGATATTATCCTTTGAG | 1.23 | 121882 | 121899 | 154 |
| 549585 | GTTTGATATTATCCTTTG | 0.71 | 121884 | 121901 | 35 |
| 617364 | GTGTTTGATATTATCCTT | 0.61 | 121886 | 121903 | 157 |
| 617365 | CGTGTTTGATATTATCCT | 0.74 | 121887 | 121904 | 158 |
| 549586 | ACGTGTTTGATATTATCC | 0.93 | 121888 | 121905 | 36 |
| 617367 | GGACGTGTTTGATATTAT | 0.64 | 121890 | 121907 | 160 |
| 549587 | CGGGACGTGTTTGATATT | 0.97 | 121892 | 121909 | 37 |
| 549620 | CAGATCCTGAGAGCCCAA | 3.46 | 122024 | 122041 | 69 |
| 549595 | GGACGTGTGAAGGTACTC | 1.25 | 121924 | 121941 | 45 |

Example 5: Inhibitory Effect of Uniform 2'-MOE Modified Oligonucleotides on Human Tau Exon 10

Several modified oligonucleotides from Tables 3 and 4 were selected and further evaluated for their effects on inhibiting human Tau exon 10 expression in vitro. ISIS 549595 was included in the study for comparison.

"Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

A172 cells were transfected using Lipofectamine2000® with 0, 0.1, 0.3, 1, 3, 10, or 30 nM concentrations of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 10_11 was used to measure mRNA levels, except for ISIS 549595. Human Tau primer probe set 9_10 R5 was used for this oligonucleotide. Human Tau exon 10 mRNA levels were adjusted according to total RNA content, as measured by RIBOGREEN®.

The IC$_{50}$ of each oligonucleotide was calculated in the same manner as illustrated in Example 3 and the results are presented below.

TABLE 7

Inhibitory effect of uniform 2'-MOE modified oligonucleotides on human Tau exon 10 expression

| ISIS NO | Sequence | IC$_{50}$ (nM) | SEQ ID NO: 1 Start Site | SEQ ID NO: 1 Stop Site | SEQ ID NO |
|---|---|---|---|---|---|
| 549566 | AGCCAGAAAAAAGGATGA | 1.00 | 121804 | 121821 | 31 |
| 617309 | CACCTTTGGTAGCCAGAA | 1.11 | 121814 | 121831 | 97 |
| 549570 | TAATTATCTGCACCTTTG | 1.39 | 121824 | 121841 | 72 |
| 617317 | TTAATTATCTGCACCTTT | 1.26 | 121825 | 121842 | 106 |
| 617318 | ATTAATTATCTGCACCTT | 1.21 | 121826 | 121843 | 107 |
| 617323 | TTCTTATTAATTATCTGC | 0.96 | 121831 | 121848 | 112 |
| 617324 | CTTCTTATTAATTATCTG | 1.06 | 121832 | 121849 | 113 |
| 617341 | GGACGTTGCTAAGATCCA | 0.82 | 121851 | 121868 | 130 |
| 549577 | TGGACGTTGCTAAGATCC | 0.87 | 121852 | 121869 | 79 |

TABLE 7-continued

Inhibitory effect of uniform 2'-MOE modified oligonucleotides on human Tau exon 10 expression

| ISIS NO | Sequence | $IC_{50}$ (nM) | SEQ ID NO: 1 Start Site | SEQ ID NO: 1 Stop Site | SEQ ID NO |
|---|---|---|---|---|---|
| 617351 | GCCACACTTGGACTGGAC | 0.91 | 121865 | 121882 | 140 |
| 617352 | AGCCACACTTGGACTGGA | 0.79 | 121866 | 121883 | 141 |
| 549595 | GGACGTGTGAAGGTACTC | 0.73 | 121924 | 121941 | 45 |

Example 6: Inhibitory Effect of Uniform 2'-MOE Modified Oligonucleotides on Human Tau Exon 10

Several modified oligonucleotides from Tables 1 and 4 were selected and further evaluated for their effect on inhibiting human Tau exon 10 expression in vitro. ISIS 617782, 617781, and 415833 were included in the study for comparison. "Start site" indicates the 5'-most nucleoside to which the modified oligonucleotide is targeted.

"Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

ISIS 617782 is 21 nucleosides in length, wherein each nucleoside has a 2'-OCH$_3$ modification and is denoted as the subscript "m". Each internucleoside linkage throughout the modified oligonucleotide are phosphorothioate internucleoside linkages (P=S).

ISIS 617781 is 18 nucleosides in length, wherein each nucleoside has a 2'-OCH$_3$ modification and is denoted as the subscript "m". Each internucleoside linkage throughout the modified oligonucleotide are phosphorothioate internucleoside linkages (P=S).

ISIS 415833 is 20 nucleosides in length, wherein each nucleoside has a 2'-MOE modification. Each internucleoside linkage throughout the modified oligonucleotide are phosphorothioate internucleoside linkages (P=S). All cytosine residues throughout the modified oligonucleotides are 5-methylcytosines.

A172 cells were transfected using Lipofectamine2000® with 0, 0.1, 0.3, 1, 3, 10, or 30 nM concentration of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels, except for ISIS 617781 and 415883. Human Tau primer probe set 10_11 was used for these two oligonucleotides. Human Tau exon 10 mRNA levels were adjusted according to total RNA content, as measured by RIBOGREEN®.

The $IC_{50}$ of each oligonucleotide was calculated in the same manner as illustrated in Example 3 and the results are presented below.

TABLE 8

Inhibitory effect of uniform 2'-MOE modified oligonucleotides on human Tau exon 10 expression

| ISIS NO | Sequence | $IC_{50}$ (nM) | SEQ ID NO: 1 Start Site | SEQ ID NO: 1 Stop Site | SEQ ID NO |
|---|---|---|---|---|---|
| 617357 | TCCTTTGAGCCACACTTG | 0.48 | 121873 | 121890 | 147 |
| 617358 | ATCCTTTGAGCCACACTT | 0.34 | 121874 | 121891 | 148 |
| 617359 | TATCCTTTGAGCCACACT | 0.41 | 121875 | 121892 | 149 |
| 549583 | TTATCCTTTGAGCCACAC | 0.27 | 121876 | 121893 | 33 |
| 617360 | ATTATCCTTTGAGCCACA | 0.33 | 121877 | 121894 | 150 |
| 617361 | TATTATCCTTTGAGCCAC | 0.24 | 121878 | 121895 | 151 |
| 617362 | ATATTATCCTTTGAGCCA | 0.27 | 121879 | 121896 | 152 |
| 549584 | GATATTATCCTTTGAGCC | 0.19 | 121880 | 121897 | 34 |
| 565989 | TGATATTATCCTTTGAGC | 0.39 | 121881 | 121898 | 153 |
| 617782 | U$^m$G$^m$A$^m$A$^m$G$^m$G$^m$U$^m$A$^m$C$^m$U$^m$C$^m$A$^m$C$^m$A$^m$C$^m$U$^m$G$^m$C$^m$C$^m$G$^m$C$^m$ | 4.33 | 121914 | 121934 | 198 |
| 617781 | U$^m$A$^m$U$^m$C$^m$U$^m$G$^m$C$^m$A$^m$C$^m$C$^m$U$^m$U$^m$U$^m$G$^m$G$^m$U$^m$A$^m$G$^m$ | 20.25 | 121820 | 121837 | 199 |
| 415883 | TCTTATTAATTATCTGCACC | 0.65 | 121828 | 121847 | 200 |

Example 7: Modified Oligonucleotides Targeting Exon 10 of Human Tau

A series of modified oligonucleotides were designed to target exon 10 of human Tau. "Start site" indicates the 5'-most nucleoside to which the modified oligonucleotide is targeted. "Stop site" indicates the 3'-most nucleoside to which the modified oligonucleotide is targeted. Each modified oligonucleotide listed in the tables below is targeted to SEQ ID NO: 1 (GENBANK Accession No NT_010783.15 truncated from nucleotides 9240000 to 9381000).

In the table below, "$^mC$" indicates 5-methylcytosine, subscript "e" indicates 2'-O-methoxyethyl, subscript "f" indicates 2'-deoxyfluoro, subscript "d" indicates 2'-deoxy, subscript "p" indicates a peptide nucleic acid monomer, subscript "s" indicates a phosphorothioate internucleoside linkage, subscript "o" indicates a phosphodiester internucleoside linkage, "P-" indicates an O-linker at the 5'-end (PNA Bio, Thousand Oaks, Calif.), "—N" indicates a 3'-end carboxy amide.

TABLE 9

Modified oligonucleotides targeting hu$^m$an Tau

| ISIS NO | Sequence | SEQ ID NO: 1 Start Site | SEQ ID NO: 1 Stop Site | SEQ ID NO |
|---|---|---|---|---|
| 549607 | $A_{es}{}^mC_{es}G_{es}{}^mC_{es}A_{es}{}^mC_{es}T_{es}{}^mC_{es}A_{es}{}^mC_{es}A_{es}{}^mC_{es}{}^mC_{es}A_{es}{}^mC_{es}T_{es}T_{es}{}^mC_e$ | 121972 | 121989 | 201 |
| 565985 | $^mC_eG_{es}{}^mC_{es}{}^mC_{es}T_{es}A_{es}{}^mC_{es}T_{es}T_{es}G_{es}{}^mC_{es}T_{es}{}^mC_{es}G_{es}{}^mC_{es}A_{es}A_{es}G_e$ | 121706 | 121723 | 202 |
| 565986 | $G_{es}A_{es}{}^mC_{es}{}^mC_{es}{}^mC_{es}G_{es}{}^mC_{es}{}^mC_{es}T_{es}A_{es}{}^mC_{es}T_{es}T_{es}G_{es}{}^mC_{es}T_{es}{}^mC_{es}G_e$ | 121710 | 121727 | 203 |
| 565987 | $G_{es}A_{es}{}^mC_{es}{}^mC_{es}{}^mC_{es}G_{es}{}^mC_{es}{}^mC_{es}T_{es}G_{es}{}^mC_{es}T_{es}T_{es}G_{es}{}^mC_{es}T_{es}{}^mC_{es}G_e$ | 121770 | 121787 | 204 |
| 565988 | $^mC_{es}{}^mC_{es}T_{es}G_{es}G_{es}A_{es}{}^mC_{es}{}^mC_{es}{}^mC_{es}G_{es}{}^mC_{es}{}^mC_{es}T_{es}G_{es}{}^mC_{es}T_{es}T_{es}G_e$ | 121774 | 121791 | 205 |
| 566007 | $^mC_{es}G_{es}C_{fs}C_{fs}U_{fs}A_{fs}C_{fs}U_{fs}U_{fs}G_{fs}C_{fs}U_{fs}C_{fs}G_{fs}C_{fs}A_{fs}A_{es}G_e$ | 121706 | 121723 | 206 |
| 566012 | $^mC_{es}{}^mC_{es}U_{fs}G_{fs}G_{fs}A_{fs}C_{fs}C_{fs}C_{fs}G_{fs}C_{fs}C_{fs}U_{fs}G_{fs}C_{fs}U_{fs}T_{es}G_e$ | 121774 | 121791 | 207 |
| 566013 | $T_{es}G_{es}A_{fs}U_{fs}A_{fs}U_{fs}U_{fs}A_{fs}U_{fs}C_{fs}C_{fs}U_{fs}U_{fs}G_{fs}A_{fs}G_{es}{}^mC_e$ | 121881 | 121898 | 208 |
| 566014 | $T_{es}T_{es}G_{fs}A_{fs}U_{fs}A_{fs}U_{fs}U_{fs}A_{fs}U_{fs}C_{fs}C_{fs}U_{fs}U_{fs}G_{fs}A_{es}G_e$ | 121882 | 121899 | 209 |
| 566015 | $T_{es}T_{es}U_{fs}G_{fs}A_{fs}U_{fs}A_{fs}U_{fs}U_{fs}A_{fs}U_{fs}C_{fs}C_{fs}U_{fs}U_{fs}U_{fs}G_{es}A_e$ | 121883 | 121900 | 210 |
| 566016 | $^mC_{es}A_{es}C_{fs}U_{fs}U_{fs}C_{fs}C_{fs}U_{fs}A_{fs}A_{fs}U_{fs}A_{fs}A_{fs}U_{fs}U_{fs}C_{fs}A_{es}A_e$ | 121960 | 121977 | 211 |
| 566017 | $A_{es}{}^mC_{es}A_{fs}C_{fs}C_{fs}A_{fs}C_{fs}U_{fs}U_{fs}C_{fs}C_{fs}U_{fs}A_{fs}A_{fs}U_{fs}A_{es}T_e$ | 121964 | 121981 | 212 |
| 566018 | $A_{es}{}^mC_{es}U_{fs}C_{fs}A_{fs}C_{fs}A_{fs}C_{fs}C_{fs}A_{fs}C_{fs}U_{fs}U_{fs}C_{fs}C_{fs}U_{fs}A_{es}A_e$ | 121968 | 121985 | 213 |
| 568409 | $^mC_{es}{}^mC_{es}C_{fs}G_{fs}C_{fs}C_{fs}U_{fs}A_{fs}C_{fs}U_{fs}U_{fs}G_{fs}C_{fs}U_{fs}C_{fs}G_{fs}{}^mC_{es}A_e$ | 121708 | 121725 | 214 |
| 568410 | $G_{es}A_{es}C_{fs}C_{fs}C_{fs}G_{fs}C_{fs}C_{fs}U_{fs}A_{fs}C_{fs}U_{fs}U_{fs}G_{fs}C_{fs}U_{fs}{}^mC_{es}G_e$ | 121710 | 121727 | 215 |
| 568411 | $G_{es}A_{es}C_{fs}C_{fs}C_{fs}G_{fs}C_{fs}C_{fs}U_{fs}G_{fs}C_{fs}U_{fs}U_{fs}G_{fs}C_{fs}U_{fs}{}^mC_{es}G_e$ | 121770 | 121787 | 216 |
| 568412 | $T_{es}G_{es}G_{fs}A_{fs}C_{fs}C_{fs}C_{fs}G_{fs}C_{fs}C_{fs}U_{fs}G_{fs}C_{fs}U_{fs}U_{fs}G_{fs}{}^mC_{es}T_e$ | 121772 | 121789 | 217 |
| 624464 | $U_{ms}C_{ms}U_{ms}U_{ms}A_{ms}U_{ms}U_{ms}A_{ms}A_{ms}U_{ms}U_{ms}A_{ms}U_{ms}C_{ms}G_{ms}C_{ms}A_{ms}C_{ms}C_m$ | 121828 | 121847 | 218 |
| 624465 | $T_{ks}{}^mC_{ds}T_{ds}T_{ks}A_{ds}T_{ds}T_{ks}A_{ds}A_{ds}T_{ks}T_{ds}A_{ds}T_{ks}{}^mC_{ds}T_{ds}G_{ks}{}^mC_{ds}A_{ds}{}^mC_{ks}{}^mC_k$ | 121828 | 121847 | 200 |
| 624466 | $T_{ks}{}^mC_{es}T_{es}T_{ks}A_{es}T_{es}T_{ks}A_{es}A_{es}T_{ks}T_{es}A_{es}T_{ks}{}^mC_{es}T_{es}G_{ks}{}^mC_{es}A_{es}{}^mC_{ks}{}^mC_k$ | 121828 | 121847 | 200 |

TABLE 9-continued

Modified oligonucleotides targeting human Tau

| ISIS NO | Sequence | SEQ ID NO: 1 Start Site | SEQ ID NO: 1 Stop Site | SEQ ID NO |
|---|---|---|---|---|
| 624467 | $T_{ks}{}^mC_{es}T_{es}T_{k0}A_{es}T_{es}T_{k0}A_{es}A_{es}T_{k0}T_{es}A_{es}T_{k0}{}^mC_{es}T_{es}G_{k0}{}^mC_{es}A_{es}{}^mC_{ks}{}^mC_k$ | 121828 | 121847 | 200 |
| 624468 | $T_{ks}{}^mC_{ds}T_{ds}T_{k0}A_{ds}T_{ds}T_{k0}A_{ds}A_{ds}T_{k0}T_{ds}A_{ds}T_{k0}{}^mC_{ds}T_{ds}G_{k0}{}^mC_{ds}A_{ds}{}^mC_{ks}{}^mC_k$ | 121828 | 121847 | 200 |
| 626881 | $\text{P-}T_pC_pT_pT_pA_pT_pT_pA_pA_pT_pT_pA_pT_pC_pTpG_pC_pA_pC_pC_p\text{-N}$ | 121828 | 121847 | 200 |
| 670011 | $G_{es}G_{es}A_{eo}{}^mC_{es}G_{eo}T_{es}T_{eo}G_{es}{}^mC_{eo}T_{es}A_{eo}A_{es}G_{eo}A_{es}T_{eo}{}^mC_{es}{}^mC_{es}A_e$ | 121851 | 121868 | 130 |
| 670012 | ${}^mC_{es}{}^mC_{es}T_{eo}T_{es}T_{eo}G_{es}A_{eo}G_{es}{}^mC_{eo}{}^mC_{es}A_{eo}{}^mC_{es}A_{eo}{}^mC_{es}T_{eo}T_{es}G_{es}G_e$ | 121872 | 121889 | 146 |
| 670013 | $A_{es}T_{es}{}^mC_{eo}{}^mC_{es}T_{eo}T_{es}T_{eo}G_{es}A_{eo}G_{es}{}^mC_{eo}{}^mC_{es}A_{eo}{}^mC_{es}A_{eo}{}^mC_{es}T_{es}T_e$ | 121874 | 121891 | 148 |
| 670014 | $T_{es}T_{es}A_{eo}T_{es}{}^mC_{eo}{}^mC_{es}T_{eo}T_{es}T_{eo}G_{es}A_{eo}G_{es}{}^mC_{eo}{}^mC_{es}A_{eo}{}^mC_{es}A_{es}{}^mC_e$ | 121876 | 121893 | 33 |
| 670015 | $A_{es}T_{es}T_{eo}A_{es}T_{eo}{}^mC_{es}{}^mC_{es}T_{eo}T_{es}T_{eo}G_{es}A_{es}G_{eo}{}^mC_{es}{}^mC_{eo}A_{es}{}^mC_{es}A_e$ | 121877 | 121894 | 150 |
| 670016 | $T_{es}A_{es}T_{eo}T_{es}A_{eo}T_{es}{}^mC_{eo}{}^mC_{es}T_{eo}T_{es}T_{eo}G_{es}A_{eo}G_{es}{}^mC_{eo}{}^mC_{es}A_{es}{}^mC_e$ | 121878 | 121895 | 151 |
| 670017 | $A_{es}T_{es}A_{eo}T_{es}T_{eo}A_{es}T_{eo}{}^mC_{es}{}^mC_{eo}T_{es}T_{eo}T_{es}G_{eo}A_{es}G_{eo}{}^mC_{es}{}^mC_{es}A_e$ | 121879 | 121896 | 152 |
| 670018 | $G_{es}A_{es}T_{eo}A_{es}T_{eo}T_{es}A_{eo}T_{es}{}^mC_{eo}{}^mC_{es}T_{eo}T_{es}T_{eo}G_{es}A_{eo}G_{es}{}^mC_{es}{}^mC_e$ | 121880 | 121897 | 34 |
| 670019 | $G_{es}T_{es}T_{eo}T_{es}G_{eo}A_{es}T_{eo}A_{es}T_{es}A_{eo}T_{es}{}^mC_{eo}{}^mC_{es}T_{eo}T_{es}T_{es}G_e$ | 121884 | 121901 | 35 |
| 670020 | $G_{es}G_{eo}A_{eo}{}^mC_{eo}G_{es}T_{es}T_{es}G_{es}{}^mC_{es}T_{es}A_{es}A_{es}G_{eo}A_{eo}T_{eo}{}^mC_{es}{}^mC_{es}A_e$ | 121851 | 121868 | 130 |
| 670021 | ${}^mC_{es}{}^mC_{eo}T_{eo}T_{eo}T_{es}G_{es}A_{es}G_{es}{}^mC_{es}{}^mC_{es}A_{es}{}^mC_{es}A_{eo}{}^mC_{eo}T_{eo}T_{es}G_{es}G_e$ | 121872 | 121889 | 146 |
| 670022 | $A_{es}T_{eo}{}^mC_{eo}{}^mC_{es}T_{es}T_{es}T_{es}G_{es}A_{es}G_{es}{}^mC_{es}{}^mC_{es}A_{eo}{}^mC_{eo}A_{eo}{}^mC_{es}T_{es}T_e$ | 121874 | 121891 | 148 |
| 670023 | $T_{es}T_{eo}A_{eo}T_{eo}{}^mC_{es}{}^mC_{es}T_{es}T_{es}T_{es}G_{es}A_{es}G_{es}{}^mC_{eo}{}^mC_{eo}A_{eo}{}^mC_{es}A_{es}{}^mC_e$ | 121876 | 121893 | 33 |
| 670024 | $A_{es}T_{eo}T_{eo}A_{eo}T_{es}{}^mC_{es}{}^mC_{es}T_{es}T_{es}T_{es}G_{es}A_{es}G_{eo}{}^mC_{eo}{}^mC_{eo}A_{es}{}^mC_{es}A_e$ | 121877 | 121894 | 150 |
| 670025 | $T_{es}A_{eo}T_{eo}T_{eo}A_{es}T_{es}{}^mC_{es}{}^mC_{es}T_{es}T_{es}T_{es}G_{es}A_{eo}G_{eo}{}^mC_{eo}{}^mC_{es}A_{es}{}^mC_e$ | 121878 | 121895 | 151 |
| 670026 | $A_{es}T_{eo}A_{eo}T_{eo}T_{es}A_{es}T_{es}{}^mC_{es}{}^mC_{es}T_{es}T_{es}T_{es}G_{eo}A_{eo}G_{eo}{}^mC_{es}{}^mC_{es}A_e$ | 121879 | 121896 | 152 |
| 670027 | $G_{es}A_{eo}T_{eo}A_{eo}T_{es}T_{es}A_{es}T_{es}{}^mC_{es}{}^mC_{es}T_{es}T_{es}T_{eo}G_{eo}A_{eo}G_{es}{}^mC_{es}{}^mC_e$ | 121880 | 121897 | 34 |
| 670028 | $G_{es}T_{eo}T_{eo}T_{eo}G_{es}A_{es}T_{es}A_{es}T_{es}A_{es}T_{es}{}^mC_{eo}{}^mC_{eo}T_{eo}T_{es}T_{es}G_e$ | 121884 | 121901 | 35 |
| 678329 | $G_{es}{}^mC_{es}{}^mC_{eo}A_{es}{}^mC_{eo}A_{es}{}^mC_{eo}T_{es}T_{eo}G_{es}G_{eo}A_{es}{}^mC_{eo}T_{es}G_{eo}G_{es}A_{es}{}^mC_e$ | 121865 | 121882 | 140 |
| 678330 | $A_{es}G_{es}{}^mC_{eo}{}^mC_{es}A_{eo}{}^mC_{es}A_{eo}{}^mC_{es}T_{eo}T_{es}G_{eo}G_{es}A_{eo}{}^mC_{es}T_{eo}G_{es}G_{es}A_e$ | 121866 | 121883 | 141 |
| 678331 | $T_{es}G_{es}A_{eo}G_{es}{}^mC_{es}{}^mC_{es}A_{eo}{}^mC_{es}A_{eo}{}^mC_{es}T_{eo}T_{es}G_{eo}G_{es}A_{eo}{}^mC_{es}T_{es}G_e$ | 121868 | 121885 | 83 |
| 678332 | $G_{es}{}^mC_{eo}{}^mC_{eo}A_{eo}{}^mC_{es}A_{es}{}^mC_{es}T_{es}T_{es}G_{es}G_{es}A_{es}{}^mC_{eo}T_{eo}G_{eo}G_{es}A_{es}{}^mC_e$ | 121865 | 121882 | 140 |

TABLE 9-continued

Modified oligonucleotides targeting human Tau

| ISIS NO | Sequence | SEQ ID NO: 1 Start Site | SEQ ID NO: 1 Stop Site | SEQ ID NO |
|---|---|---|---|---|
| 678333 | $A_{es}G_{eo}{}^mC_{eo}{}^mC_{es}A_{es}{}^mC_{es}A_{es}{}^mC_{es}T_{es}T_{es}G_{es}G_{es}A_{eo}{}^mC_{eo}T_{eo}G_{es}G_{es}A_e$ | 121866 | 121883 | 141 |
| 678334 | $T_{es}G_{eo}A_{eo}G_{eo}{}^mC_{es}{}^mC_{es}A_{es}{}^mC_{es}A_{es}{}^mC_{es}T_{es}T_{es}G_{eo}G_{eo}A_{eo}{}^mC_{es}T_{es}G_e$ | 121868 | 121885 | 83 |
| 693840 | $T_{es}G_{es}G_{eo}A_{es}{}^mC_{eo}G_{es}T_{eo}T_{es}G_{eo}{}^mC_{es}T_{eo}A_{es}A_{eo}G_{es}A_{eo}T_{es}{}^mC_{es}{}^mC_e$ | 121852 | 121869 | 79 |
| 693841 | ${}^mC_{es}{}^mC_{es}A_{eo}{}^mC_{es}A_{eo}{}^mC_{es}T_{eo}T_{es}G_{eo}G_{es}A_{eo}{}^mC_{es}T_{eo}G_{es}G_{eo}A_{es}{}^mC_{es}G_e$ | 121864 | 121881 | 82 |
| 693842 | $A_{es}{}^mC_{es}G_{eo}T_{es}G_{eo}T_{es}T_{eo}T_{es}G_{eo}A_{es}T_{eo}A_{es}T_{eo}T_{es}A_{eo}T_{es}{}^mC_{es}{}^mC_e$ | 121888 | 121905 | 36 |
| 693843 | $G_{es}G_{es}A_{eo}{}^mC_{es}G_{eo}T_{es}G_{eo}T_{es}G_{eo}A_{es}A_{eo}G_{es}G_{eo}T_{es}A_{eo}{}^mC_{es}T_{es}{}^mC_e$ | 121924 | 121941 | 45 |
| 693844 | $G_{es}A_{es}G_{eo}{}^mC_{es}{}^mC_{eo}A_{es}{}^mC_{eo}A_{es}{}^mC_{eo}T_{es}T_{eo}G_{es}G_{eo}A_{es}{}^mC_{es}T_{es}G_{es}G_e$ | 121867 | 121884 | 142 |
| 693845 | $T_{es}G_{eo}G_{eo}A_{eo}{}^mC_{es}G_{es}T_{es}T_{es}G_{es}{}^mC_{es}T_{es}A_{es}A_{eo}G_{eo}A_{eo}T_{es}{}^mC_{es}{}^mC_e$ | 121852 | 121869 | 79 |
| 693846 | ${}^mC_{es}{}^mC_{eo}A_{eo}{}^mC_{eo}A_{es}{}^mC_{es}T_{es}T_{es}G_{es}G_{es}A_{es}{}^mC_{es}T_{eo}G_{eo}G_{eo}A_{es}{}^mC_{es}G_e$ | 121864 | 121881 | 82 |
| 693847 | $A_{es}{}^mC_{eo}G_{eo}T_{eo}G_{es}T_{es}T_{es}T_{es}G_{es}A_{es}T_{es}A_{es}T_{eo}T_{eo}A_{eo}T_{es}{}^mC_{es}{}^mC_e$ | 121888 | 121905 | 36 |
| 693848 | $G_{es}G_{eo}A_{eo}{}^mC_{eo}G_{es}T_{es}G_{es}T_{es}G_{es}A_{es}A_{es}G_{es}G_{eo}T_{eo}A_{eo}{}^mC_{es}T_{es}{}^mC_e$ | 121924 | 121941 | 45 |
| 693849 | $G_{es}A_{es}G_{eo}{}^mC_{eo}{}^mC_{es}A_{es}{}^mC_{es}A_{es}{}^mC_{es}T_{es}T_{es}G_{es}G_{eo}A_{eo}{}^mC_{eo}T_{es}G_{es}G_e$ | 121867 | 121884 | 142 |

Example 8: In Vivo Analysis of Oligonucleotides Targeting Human Tau Exon 10

Sprague Dawley rats were separated into groups of 3 rats for the experiment presented in Table 11 and into groups of 2 or 4 rats for the experiment presented in Table 12. Each rat in each group of rats was administered a single 3 mg intrathecal (IT) dose of an oligonucleotide selected from Table 3, 4, or 9. At various time points after injection from 3 hours to 8 weeks, the movement of 7 different parts of the body was evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; and (7) the rat's head. For each of the 7 different body parts, each rat was given a sub-score of 0 if the body part was moving or 1 if the body part was paralyzed. After each of the 7 body parts were evaluated, the sub-scores were summed for each rat and then averaged for each group. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Saline treated rats generally receive a score of 0. A score of at the top end of the range would be suggestive of toxicity. Results are presented as the average score for each treatment group in Tables 11 and 12.

TABLE 11

3 mg IT bolus in vivo study

| ISIS No. | Score 3 hours after injection | Score 2 weeks after injection | Score 8 weeks after injection | SEQ ID NO. |
|---|---|---|---|---|
| 670020 | 1.0 | 2.7 | 2.7 | 130 |
| 670011 | 2.3 | 2.3 | 2.3 | 130 |
| 617341 | 3.0 | 0.0 | 0.0 | 130 |
| 678329 | 2.3 | 0.0 | 0.0 | 140 |
| 678332 | 3.0 | 0.0 | 1.3 | 140 |
| 617351 | 7.0 | 0.0 | 4.0 | 140 |
| 678330 | 2.7 | 2.3 | 3.0 | 141 |
| 678333 | 2.7 | 2.3 | 2.3 | 141 |
| 617352 | 7.0 | 0.0 | 2.0 | 141 |
| 678331 | 3.0 | 0.0 | 0.0 | 83 |
| 678334 | 4.3 | 2.3 | 2.3 | 83 |
| 549581 | 7.0 | 0.0 | 0.3 | 83 |
| 670012 | 2.7 | 0.0 | 0.0 | 146 |
| 670021 | 3.0 | 0.0 | 1.0 | 146 |
| 549582 | 4.3 | 0.0 | 0.0 | 146 |
| 670013 | 0.3 | 2.3 | 2.3 | 148 |
| 670022 | 2.0 | 2.3 | 3.0 | 148 |
| 617358 | 3.7 | 0.0 | 1.3 | 148 |
| 670014 | 0.0 | 0.0 | 0.0 | 33 |
| 670023 | 2.0 | 1.0 | 0.3 | 33 |
| 549583 | 2.3 | 0.0 | 0.0 | 33 |
| 670015 | 1.0 | 2.0 | 0.7 | 150 |
| 670024 | 1.0 | 0.7 | 0.0 | 150 |
| 617360 | 5.3 | 0.0 | 1.0 | 150 |
| 670025 | 0.3 | 5.3 | 5.3 | 151 |
| 670016 | 2.3 | 1.3 | 1.7 | 151 |
| 617361 | 3.0 | 0.0 | 0.3 | 151 |
| 670017 | 0.0 | 1.7 | 1.3 | 152 |

TABLE 11-continued 3 mg IT bolus in vivo study

| ISIS No. | Score 3 hours after injection | Score 2 weeks after injection | Score 8 weeks after injection | SEQ ID NO. |
|---|---|---|---|---|
| 670026 | 1.0 | 3.7 | 3.3 | 152 |
| 617362 | 4.7 | 3.7 | 2.7 | 152 |
| 670018 | 0.3 | 0.3 | 0.3 | 34 |
| 670027 | 1.0 | 0.7 | 0.7 | 34 |
| 549584 | 5.0 | 2.7 | 3.7 | 34 |
| 670028 | 2.0 | 0.0 | 0.0 | 35 |
| 670019 | 3.0 | 0.0 | 0.0 | 35 |
| 549585 | 4.7 | 5.3 | 7.0 | 35 |

TABLE 12

3 mg IT bolus in vivo study

| ISIS No. | No. of rats in treatment group | Score 3 hours after injection | SEQ ID NO. |
|---|---|---|---|
| 549577 | 4 | 3.3 | 79 |
| 693840 | 4 | 1.8 | 79 |
| 693845 | 4 | 0.0 | 79 |
| 549580 | 4 | 7.0 | 82 |
| 693841 | 4 | 1.8 | 82 |
| 693846 | 4 | 2.5 | 82 |
| 617353 | 4 | 7.0 | 142 |
| 693844 | 2 | 3.5 | 142 |
| 693849 | 4 | 5.0 | 142 |
| 549582 | 4 | 4.3 | 146 |
| 549586 | 4 | 5.0 | 36 |
| 693847 | 2 | 1.0 | 36 |
| 549595 | 4 | 6.5 | 45 |
| 693843 | 2 | 2.0 | 45 |
| 693848 | 2 | 7.0 | 45 |

Example 9: Inhibitory Effect In Vivo of a Modified Oligonucleotide Targeting Human Tau Exon 10

B6.Cg-Mapttm1(EGFP)Klt Tg(MAPT)8cPdav/J mice (The Jackson Laboratory) express the 3R and 4R isoforms of human Tau. The effect of oligonucleotides selected from Table 3, 4, or 8 on shifting of the 4R isoform to 3R isoform was assessed in this mouse model.

Groups of four B6.Cg-Mapttm1(EGFP)Klt Tg(MAPT) 8cPdav/J mice (3-4 months of age) were administered 500 µg of oligonucleotide via an intracerebroventricular (ICV) bolus injection. A control group of four mice was similarly treated with PBS. Two weeks after the dose, animals were sacrificed and RNA was extracted from the cerebral cortex, hippocampus, and/or spinal cord. mRNA expression of the 4R isoform and total human Tau were analyzed by qRT-PCR. The 4R isoform was analyzed using primer probe set hTau 9_10 junction (forward sequence 5'-CACTGAGAACCTGAAGCACC-3', SEQ ID NO: 219; reverse sequence 5'-GTTGCTAAGATCCAGCTTCTT-3', SEQ ID NO: 220; probe sequence 5'-TTAAT-TATCTGCACCTTCCCGCCTCC-3', SEQ ID NO: 221) or primer probe set hTau 10_11 junction (forward sequence 5'-AATATCAAACACGTCCCGGGAG-3', SEQ ID NO: 222; reverse sequence 5'-TGCCTAATGAGCCACACTTG-3', SEQ ID NO: 223; probe sequence 5'-GTCTA-CAAACCAGTTGACCTGAGC-3', SEQ ID NO: 224). Total Tau was analyzed using primer probe set RTS3104 (forward sequence 5'-AAGATTGGGTCCCTGGACAAT-3', SEQ ID NO: 225; reverse sequence 5'-AGCTTGTGGGTTTCAATCTTTTTATT-3', SEQ ID NO: 226; probe sequence 5'-CACC-CACGTCCCTGGCGGA-3', SEQ ID NO: 227). The ratio of 4R isoform to total Tau mRNA levels was normalized to mouse GAPDH levels, which were analyzed using primer probe set mGapdh_LTS00102 (forward sequence 5'-GGCAAATTCAACGGCACAGT-3', SEQ ID NO: 228; reverse sequence 5'-GGGTCTCGCTCCTGGAAGAT-3', SEQ ID NO: 229; probe sequence 5'-AAGGCCGAGAATGGGAAGCTTGTCATC-3', SEQ ID NO: 230). The results are presented in Tables 13-15 as the average ratio of 4R isoform to total Tau mRNA normalized to GAPDH levels for each treatment group divided by the average ratio for the PBS group. "ND" indicates no data.

Inflammation was also assessed by performing RT-PCT to determine the expression levels of AIF1 in the cortex, hippocampus, and/or spinal cord. After normalization of all samples to GADPH, the average AIF1 value for each treatment group was divided by the average AIF1 value for the PBS control group. The results are presented in Tables 13-15.

TABLE 13

Effect of modified oligonucleotides on Tau exon 10 skipping in transgenic mice

| ISIS NO. | 4R cortex | 4R hippo | 4R spinal cord | AIF1 cortex | AIF1 hippo | AIF1 spinal cord | SEQ ID NO. |
|---|---|---|---|---|---|---|---|
| 415883 | 0.50 | 0.46 | 0.56 | 1.35 | 1.27 | 1.44 | 200 |
| 549566 | 0.54 | 0.54 | 0.66 | 1.09 | 1.13 | 1.46 | 31 |
| 549570 | 0.58 | 0.60 | 0.64 | 1.17 | 1.16 | 1.39 | 72 |
| 549577 | 0.25 | 0.30 | 0.38 | 2.92 | 3.27 | 4.39 | 79 |
| 549581 | 0.25 | ND | ND | 1.04 | 1.07 | 1.40 | 83 |
| 549582 | 0.07 | 0.10 | 0.12 | 0.89 | 0.95 | 1.15 | 146 |
| 549583 | 0.25 | 0.26 | 0.25 | 0.97 | 0.94 | 1.09 | 33 |
| 617309 | 0.36 | 0.36 | 0.51 | 1.06 | 1.06 | 1.09 | 97 |

TABLE 14

Effect of modified oligonucleotides on Tau exon 10 skipping in transgenic mice

| ISIS NO. | 4R cortex | 4R hippo | 4R spinal cord | AIF1 spinal cord | SEQ ID NO. |
|---|---|---|---|---|---|
| 549582 | 0.21 | 0.21 | 0.23 | 0.97 | 146 |
| 549584 | 0.32 | 0.28 | 0.28 | 1.12 | 34 |
| 549585 | 0.30 | 0.27 | 0.30 | 1.05 | 35 |
| 565989 | 0.36 | 0.32 | 0.36 | 1.03 | 153 |
| 565990 | 0.50 | 0.46 | 0.53 | 0.97 | 154 |
| 617341 | 0.25 | 0.28 | 0.28 | 1.16 | 130 |
| 617351 | 0.13 | 0.18 | 0.14 | 1.01 | 140 |
| 617352 | 0.09 | 0.13 | 0.09 | 1.06 | 141 |
| 617354 | 0.31 | ND | ND | 1.21 | 143 |
| 617355 | 0.43 | 0.50 | 0.37 | 1.18 | 144 |
| 617356 | 0.30 | 0.40 | 0.49 | 0.98 | 145 |
| 617357 | 0.33 | 0.33 | 0.27 | 1.31 | 147 |
| 617358 | 0.27 | 0.27 | 0.34 | 1.12 | 148 |
| 617359 | 0.32 | 0.32 | 0.37 | 0.95 | 149 |
| 617360 | 0.21 | 0.19 | 0.29 | 1.19 | 150 |
| 617361 | 0.26 | 0.21 | 0.37 | 1.04 | 151 |
| 617362 | 0.26 | 0.27 | 0.34 | 0.90 | 152 |
| 617364 | 0.39 | 0.33 | 0.43 | 1.09 | 157 |

TABLE 15

Effect of modified oligonucleotides on Tau exon 10 skipping in transgenic mice

| ISIS NO. | 4R cortex | 4R hippo | 4R spinal cord | AIF1 cortex | AIF1 spinal cord | SEQ ID NO. |
|---|---|---|---|---|---|---|
| 549582 | 0.26 | 0.34 | 0.29 | 0.74 | 1.03 | 146 |
| 549586 | 0.25 | 0.43 | 0.38 | 0.97 | 0.98 | 36 |
| 549587 | 0.39 | 0.47 | 0.46 | 0.96 | 1.17 | 37 |
| 549595 | 0.27 | 0.39 | 0.39 | 0.84 | 0.92 | 45 |
| 617317 | 0.62 | 0.83 | 0.53 | 0.88 | 1.05 | 106 |
| 617318 | 0.57 | 0.69 | 0.49 | 0.94 | 1.06 | 107 |
| 617323 | 0.60 | 0.82 | 0.49 | 0.92 | 1.10 | 112 |
| 617324 | 0.72 | 0.88 | 0.49 | 0.70 | 1.03 | 113 |
| 617365 | 0.31 | 0.42 | 0.27 | 0.79 | 0.87 | 158 |
| 617367 | 0.39 | 0.46 | 0.35 | 0.90 | 1.29 | 160 |

Example 10: Effect In Vivo of Mixed Backbone Oligonucleotides on Human Tau Exon 10 Skipping Groups of four B6.Cg-Mapttml(EGFP)Klt Tg(MAPT) 8cPdav/J mice (see Example 9) were administered 125 µg of an oligonucleotide selected from Table 3, 4, or 9 or PBS via ICV bolus injection. Two weeks after the dose, animals were sacrificed and RNA was extracted from the cerebral cortex and/or hippocampus and analyzed as described in Example 9. The results are presented in Tables 16 and 17 as the average ratio of the 4R isoform to total Tau mRNA normalized to PBS for each treatment group.

Expression of allograft inflammatory factor (AIF1) was tested as a measure of inflammation by performing RT-PCT to determine the expression levels of AIF1 in the cortex and spinal cord. After normalization of all samples to GADPH, the average AIF1 value for each treatment group was divided by the average AIF1 value for the PBS control group. The results are presented in Tables 16 and 17.

TABLE 16

Effect of modified oligonucleotides on Tau exon 10 skipping in transgenic mice

| ISIS NO. | 4R Cortex | AIF1 cortex | AIF1 spinal cord | SEQ ID NO. |
|---|---|---|---|---|
| 549582 | 0.42 | 1.0 | 0.9 | 146 |
| 549583 | 0.71 | 0.9 | 1.2 | 33 |

TABLE 16-continued

Effect of modified oligonucleotides on Tau exon 10 skipping in transgenic mice

| ISIS NO. | 4R Cortex | AIF1 cortex | AIF1 spinal cord | SEQ ID NO. |
|---|---|---|---|---|
| 617341 | 0.64 | 1.0 | 0.9 | 130 |
| 617361 | 0.63 | 1.1 | 1.1 | 151 |
| 670011 | 0.78 | 1.0 | 1.0 | 130 |
| 670012 | 0.47 | 0.9 | 1.1 | 146 |
| 670013 | 0.63 | 1.0 | 0.9 | 148 |
| 670014 | 0.90 | 0.9 | 1.0 | 33 |
| 670015 | 0.70 | 0.9 | 0.9 | 150 |
| 670018 | 0.75 | 1.0 | 1.0 | 34 |
| 670019 | 0.58 | 1.1 | 1.0 | 35 |
| 670020 | 0.67 | 0.9 | 0.9 | 130 |
| 670023 | 0.87 | 1.0 | 1.0 | 33 |
| 670024 | 0.60 | 1.0 | 1.1 | 150 |
| 670025 | 0.72 | 1.1 | 0.9 | 151 |
| 670027 | 0.79 | 1.0 | 0.9 | 34 |
| 670028 | 0.66 | 1.1 | 1.0 | 35 |
| 678329 | 0.13 | 1.0 | 1.0 | 140 |
| 678330 | 0.51 | 0.9 | 0.9 | 141 |
| 678331 | 1.12 | 0.9 | 1.0 | 83 |
| 678332 | 0.27 | 0.9 | 1.0 | 140 |
| 678333 | 0.56 | 0.9 | 0.9 | 141 |
| 678334 | 1.10 | 0.9 | 1.2 | 83 |

TABLE 17

Effect of modified oligonucleotides on Tau exon 10 skipping in transgenic mice

| ISIS No. | 4R Cortex | AIF1 cortex | AIF1 spinal cord | SEQ ID NO. |
|---|---|---|---|---|
| 549577 | 0.56 | 1.4 | 1.6 | 79 |
| 549580 | 0.52 | 0.9 | 1.2 | 82 |
| 549582 | 0.27 | 0.9 | 1.0 | 146 |
| 549586 | 0.90 | 1.1 | 1.3 | 36 |
| 549595 | 0.90 | 1.0 | 1.4 | 45 |
| 617353 | 1.35 | 1.0 | 1.3 | 142 |
| 693840 | 0.80 | 0.9 | 1.2 | 79 |
| 693841 | 0.91 | 1.1 | 1.1 | 82 |
| 693842 | 1.20 | 1.0 | 0.8 | 36 |
| 693843 | 1.31 | 1.0 | 1.6 | 45 |
| 693844 | 2.22 | 1.1 | 1.6 | 142 |
| 693845 | 0.86 | 1.0 | 1.4 | 79 |
| 693846 | 0.84 | 1.0 | 1.4 | 82 |
| 693847 | 0.89 | 1.0 | 1.8 | 36 |
| 693848 | 0.76 | 0.9 | 1.9 | 45 |
| 693849 | 2.08 | 0.8 | 1.8 | 142 |

The invention claimed is:

1. A single-stranded modified oligonucleotide consisting of 12 to 30 linked nucleosides and having a nucleobase sequence comprising at least 8 contiguous nucleobases of any of SEQ ID NO: 140, wherein at least one nucleoside of the modified oligonucleotide comprises a modified sugar moiety and/or at least one internucleoside linkage of the modified oligonucleotide is a modified internucleoside linkage.

2. The single-stranded modified oligonucleotide of claim 1, wherein the nucleobase sequence of the modified oligonucleotide is at least 90% complementary to SEQ ID NO: 1.

3. The single-stranded modified oligonucleotide of claim 1, wherein the nucleobase sequence of the modified oligonucleotide is 100% complementary to SEQ ID NO: 1.

4. The single-stranded modified oligonucleotide of claim 2, wherein the modified oligonucleotide consists of 16 to 22 linked nucleosides.

5. The single-stranded modified oligonucleotide of claim 2, wherein at least one nucleoside of the modified oligonucleotide comprises a modified sugar moiety.

6. The single-stranded modified oligonucleotide of claim 5, wherein at least one nucleoside of the modified oligonucleotide comprises a 2'-substituted sugar moiety.

7. The single-stranded modified oligonucleotide of claim 6, wherein the 2'-substituted sugar moiety is selected from 2'-OMe, 2'-F, and 2'-MOE.

8. The single-stranded modified oligonucleotide of claim 5, wherein at least one nucleoside of the single-stranded modified oligonucleotide comprises a bicyclic sugar moiety.

9. The single-stranded modified oligonucleotide of claim 8, wherein the bicyclic sugar moiety is LNA or cEt.

10. The single-stranded modified oligonucleotide of claim 5, wherein at least one nucleoside of the single-stranded modified oligonucleotide comprises a sugar surrogate.

11. The single-stranded modified oligonucleotide of claim 10, wherein the sugar surrogate is a morpholino.

12. The single-stranded modified oligonucleotide of claim 5, wherein at least one nucleoside of the single-stranded modified oligonucleotide comprises a naturally occurring sugar moiety.

13. The single-stranded modified oligonucleotide of claim 2, wherein each nucleoside of the modified oligonucleotide comprises a modified sugar moiety.

14. The single-stranded modified oligonucleotide of claim 13, wherein the modified sugar moiety is a 2'-substituted sugar moiety.

15. The single-stranded modified oligonucleotide of claim 14, wherein the 2'-substituted sugar moiety is selected from: 2'-OMe, 2'-F, and 2'-MOE.

16. The single-stranded modified oligonucleotide of claim 13, wherein the modified sugar moiety is a bicyclic sugar moiety.

17. The single-stranded modified oligonucleotide of claim 16, wherein the bicyclic sugar moiety is LNA or cEt.

18. The single-stranded modified oligonucleotide of claim 13, wherein the modified sugar moiety is a sugar surrogate.

19. The single-stranded modified oligonucleotide of claim 18, wherein the sugar surrogate is a morpholino.

20. The single-stranded modified oligonucleotide of claim 1, wherein at least one nucleobase of the modified oligonucleotide is a modified nucleobase.

21. The single-stranded modified oligonucleotide of claim 20, wherein the modified nucleobase is a 5-methylcytosine.

22. The single-stranded modified oligonucleotide of claim 2, wherein the modified oligonucleotide comprises at least one modified internucleoside linkage.

23. The single-stranded modified oligonucleotide of claim 22, wherein the modified oligonucleotide comprises at least one phosphorothioate internucleoside linkage.

24. The single-stranded modified oligonucleotide of claim 23, wherein the modified oligonucleotide comprises at least one naturally occurring internucleoside linkage.

25. The single-stranded modified oligonucleotide of claim 2, wherein each internucleoside linkage is a modified internucleoside linkage.

26. The single-stranded modified oligonucleotide of claim 25, wherein each modified internucleoside linkage is a phosphorothioate internucleoside linkage.

27. An oligomeric compound comprising the single-stranded modified oligonucleotide of claim 5 and a conjugate group.

28. A single-stranded modified oligonucleotide consisting of 18 linked nucleosides and having a nucleobase sequence comprising 18 contiguous nucleobases of any of SEQ ID NO: 140, wherein each nucleoside of the modified oligonucleotide comprises a 2'-substituted sugar moiety and each internucleoside linkage is selected from a phosphorothioate internucleoside linkage and a phosphodiester internucleoside linkage.

29. The single-stranded modified oligonucleotide of claim 28, wherein the 2'-substituted sugar moiety is 2'-MOE.

30. The single-stranded modified oligonucleotide of claim 29, wherein each internucleoside linkage is a phosphorothioate internucleoside linkage.

31. A pharmaceutical composition comprising a single-stranded modified oligonucleotide according to claim 28 and a pharmaceutically acceptable carrier or diluent.

32. The pharmaceutical composition of claim 31, wherein the single-stranded modified oligonucleotide is a sodium salt.

33. A method of reducing or ameliorating one or more symptoms associated with a tau-associated disorder, comprising contacting a cell with the single-stranded modified oligonucleotide of claim 28.

* * * * *

SEQUENCE LISTING

<160> NUMBER OF SEQ ID NOS: 232

<210> SEQ ID NO 1
<211> LENGTH: 141001
<212> TYPE: DNA
<213> ORGANISM: Homo sapiens

<400> SEQUENCE: 1

```
aatttataaa ggaaaaaggt ttaattgact cacagttcag catgtctggg gaagtgttag      60
gaaacttaca atcatggcag aagagaaagc aaaccatcct ttctcacatg gtgacaggaa     120
gagcaaagcg gggtaagccc cttacaaaac caccagatct catgagaact cactatcacg     180
agaacaccat ggaggtaact gccccatga ttcaattacc tcccaccagg tccctcccac      240
gacatgtggg gattatgcga actccaactc aagatgagat ttgggtgggg acacagccaa     300
```

| | |
|---|---|
| accatatcag aagcttaacc ttctttggag catgattatt cagttgaacc taagttcagt | 360 |
| agtcacccag ttatgctgtc ttcagctact attttccata tgtttctcaa acatctgata | 420 |
| tatcacactg gctagtgcac tttcttccac cagcatacca tctcaattta ccactttaac | 480 |
| aattggactg ccactttgtg tcagggacta tctgtgctcc aactactaca agtgataagg | 540 |
| tcctcactga cagccaggga gcaagtgatc cagctctaaa actcaccttc tcatctgctt | 600 |
| tcctagacca ctcctaacaa ccaactattc tgggttgagt tctccaagag gcagagagtt | 660 |
| caggatacag aatgttgttt tgttttttgtt gttgttgctg ttgttgtttg tgtgtgtgtt | 720 |
| tgggcttttt tgagacggag tctcactctg ttgcccaggt agaagtgcag tggcatgatc | 780 |
| tcagctccct gcaacctcca cctcctgggt ttaagtgatt cccctgcctc cacctcctga | 840 |
| gtagctggga ctacaagtgt gcgccaccac acccagctaa ttttgtgtt tttagtagaa | 900 |
| atggggtttt accatgttgg ctaggctgct cccaaactcc tgacctccag tgatccacct | 960 |
| acctctgcct cccaaagtgc tgggattaca ggcgtgagcc accacaccca gcccagaatg | 1020 |
| tttattagaa tgcacaatta ataccagagg cagtgggaa ggaaggactg agcagaggag | 1080 |
| gaagttgagt tgtgattcaa cccaacaact gcctggctgg catggggagc tctggagtta | 1140 |
| aatagggcca tcagactttc ccagtgtggg gccaacatga ctgggtcttt ataccccac | 1200 |
| ctctgtcagt cactcaacgt ggtctccctg caacaaggtg actcttgcag ccgagacaat | 1260 |
| ccctgaaggg acagagggct gaagcctgtc tgccaacagc actcccagtg gctggaacaa | 1320 |
| gtccttccct atagggggaat ctgggcggca cacctccatc tccatgtcca tcacatacga | 1380 |
| tatcacagac atttaaatat tttgataact gtacataaga gtttccttta taatcttata | 1440 |
| gatcttattt tatgcatttg aaaatattct tctgagacag ggcttttatc atattgccat | 1500 |
| agggtgccac gatataaaaa aggttaaata ctctctgatt cagaagtatc caatgatgac | 1560 |
| ttctctctca tgcatttaat tgaaaatctg gttttctcc ttctctgcta gttctctacc | 1620 |
| tctctcccca cctcccacat catagcctat tcacatatgt ctgaatctca tgatagacaa | 1680 |
| gttcaggttc tttttcccagg ttcttttttac cacatccccc cacccccaca taaaaagtat | 1740 |
| atatggcaca gcctaggttc caccccaaatc ctttctcctc ttcttcctgg gcccacaact | 1800 |
| ctcctacata cattggtata ccttgcgctt agggatggcc atgtgactaa gttctaacag | 1860 |
| tggaacatga tcagatgcca cttccagcct ctaagacagc cagtgtgttt cctccataag | 1920 |
| ctccttctct tcctcccaac tggagactct aaatgatgac cctgcctcaa gcaagcaaac | 1980 |
| aacaagtccc tcagggggtgg tgtaggctgc aaatggaagg agcttgagtc ccaaaccttc | 2040 |
| cacggagaag gctggctacc aacctggatc actcacccaa gactgctcga agagttggtt | 2100 |
| tgaaccattg tgtttggggg tctatttatt acaacagttt agcttgcttt gtgaatagat | 2160 |
| ttagtggcag agcctccaaa ttctatagat acattgatct cagtcctaac cgcatctgga | 2220 |
| acaccattaa ataaaggaat tgcaaaccca gagaaggtaa tgaatttgtc taaggtcata | 2280 |
| caagatggct aggatcagga cccaactctc cagttttctt tcttctctgc tattctgcct | 2340 |
| tctgtgatcc tacataagtg ggcatgattg tataacatat gcggccatga gatttctctt | 2400 |
| tcagcaagag aaagggacag gaagaaagag agggaatgca ttttcttggc ctgaattagt | 2460 |
| gtgagccatt agttacctac attgactaaa ttatctggaa tgaacattca actctacatc | 2520 |
| acatatagtt aaaatgacag atctgcttaa gattgtttct agcatacgtt atttcaattt | 2580 |
| aggcaaatgt gaccattcag tgtgagggga ccatactgtc attaggtccc tgtcagttct | 2640 |

```
caattatact gttatcttag aggggggaaaa atgtgaaatt tgaatgtaga cgagtgttga   2700
tttgactgct acagtttatt ttacgtatag aaataaaata atgtgtagca aaagcattat   2760
tacaaagatg ataatgaaat aactagtatt tataatagta taatagtata gtatttataa   2820
tagtatgata gtttaatgac tatttgtcag atgttgtgta agaaacttta tacacacaca   2880
cacacacacc tcatttaatt cctgtatcaa tcaggataca ggacgctgtg gtaacaactc   2940
ctcaaatctc ggtggcttgc acaacaaatg cttatttctt ttttttttt gacaccaagt   3000 cttgctctgt aacaggctgg agtgcaatgg tgcaatctcg gctcactgca gcctctgcct   3060
cctgggttca gcgattctc ctgcctcagt ctctcgagta gctgggaaca caggcacgcg   3120
ccaccacatc tggctaattt ttgtgatttt agtagagatg ggatttcacc atgttgctca   3180
ggctggcctt gaactcctga cctcaagcga tccacccacc tcagcctccc aaagtgctgg   3240
gattacaggc atgagccact gcgcccagcc ccaaatgttt atttcttgct catgtgacat   3300
gtacttcctc gagttttttcc ttcctgagat ctaagctgaa ggaacagctc tctggagcca   3360
cgccattctg gtggcggaaa ggaagagtaa aagtggtaga accttgcaat gctcttgaag   3420
cgcctatttg gaatgtctac atcatgtaaa tggtaatgga caagtatgta taatccccac   3480
accaaaaaaa ggggacacta ttggggacaa taaccacatt tcaatgctgc aagacggata   3540
ttgactgcac cccttccca ctttcagaaa gaagaagagt aattttgctg aactccttct   3600
agagactgga aatgtcccct ccagttgggg tgattaggga aggctttggt aaaatttgag   3660
ctagagtttg aaggttaggt agactactgg tgggtgaaga aagaacaagg acctttgtag   3720
gcaaaggaaa acctcagaat tacagaggtg gaaaagagt tctagtcaag ccacttcagc   3780
tggctacaga gtaggtggga aagaaaatgg gaggacaagg gctcagatga tgggggggttg   3840 gggcattggg gggacacttg aaagctaaac taagggggttg aacttaattt aggaggcagt   3900
tagaagcttt tacatatttt tgagcaagag agtgacataa ttaaaatgat ctgggccagg   3960
tgtggtggct cacacctgta atcccagcac tttgggaggc tgaggagctt gggtcacctg   4020
aggtcaggag atcgagacca gcctggccaa catggtgaaa tcccgtccta ctaaaaatac   4080
aaaaattagc cgggagtggt ggcatatgcc tgtaatccca gtagctggga ggctgagaca   4140
ggaaaatcgc ttgaacccgg gaaacaggtt gcagtgagcc gagatcgtgc cactgcactc   4200
cagcctgggc aacagagcga gactccatct caaaaaaaca aaacaaacac acacaaaaaa   4260
ccaaaaataa ataaataaaa tgatcacttc tgaatactga tctaactagg ggttgcaggg   4320
tgggctgata tagggagaaa ctggagagca aggagatcac taaggtccct acatgtccag   4380
aaccaagata gaggtcttga actaggatgg tggcagttag aacaacaaca acaaaaagtc   4440
aattccaggc tgagtgcagt ggctcatgcc tgtaatccca cgctttggg aggctgaggt   4500 gggagttaga aagcagcctg gcaacactg caagacctcc tctctaaaaa aaaaaaaaa   4560 aaaaagttag ccaggtgtgg tggtgcccac ctgtagtccc agcaactcag aaggctgagg   4620
tgggaagatt gcttgagccc caggagttca agcttgccgt gagctacgat tgtgccactg   4680
cactccagcc tgagcaagac cttgtctcca aaaaaggtc aattccactg acttttctaa   4740
ggtgtacacc atcaaggggc agctccatct ccaggccatt ggctcatgag acattctgta   4800
gtcagaaggc tagggcagat tgctttgagc aagcccccat ggtggttctc actcctactt   4860
ctttgggtat atgcccctct gtttaaaaat aaagttaata tgcatttaaa aaaaaaaagg   4920
agaaaaaggt cagttccaga aactgtgtga ataaagcatt ttacttgctt tttctattaa   4980
tctataacat atgttgattt tttaaaaaga atataagagc tatgcaaatt ggagcttcaa   5040
```

```
gacaacttcc catctcccta ggaggagatg gctgccctaa accccctac atagaaatca    5100 tcccactgct tgggcttaaa cttgatgttg gggaaatgaa aaatccaagc taaggccgaa    5160
gcctggggcc tgggcgacca gcagaatgag gaccactggt cagtttcagg ctgaggtgcg    5220
tcttccaggg gacaatctct agctggccct taaacattca gacttcaagc tctatttaca    5280
gcataaaggt gtttcaaaag acgtgataca aataactgca aatgctctgc gatgtgttaa    5340
gcactgtttg aaattcgtct aatttaagat tttttttct gacgtaacgg ttagattcac     5400
gtttcttttt ttttaagtac agttctactg tattgtaact gagttagctt gctttaagcc    5460
gatttgttaa ggaaaggatt caccttggtc agtaacaaaa aaggtgggaa aaaagcaagg    5520
agaaaggaag cagcctgggg gaaagagacc ttagccaggg gggcggtttc gggactacga    5580
agggtcgggg cggacggact cgagggccgg ccacgtggaa ggccgctcag gacttctgta    5640
ggagaggaca ccgccccagg ctgactgaaa gtaaagggca gcggacccag cggcggagcc    5700
actggccttg ccccgacccc gcatggcccg aaggaggaca cccaccccg caacgacaca     5760 aagactccaa ctacaggagg tggagaaagc gcgtgcgcca cggaacgcgc gtgcgcgctg    5820
cggtcagcgc cgcggcctga ggcgtagcgg gaggggacc gcgaaagggc agcgccgaga     5880
ggaacgagcc gggagacgcc ggacggccga gcggcagggc gctcgcgcgc gcccactagt    5940
ggccggagga gaaggctccc gcggaggccg cgctgcccgc cccctcccct ggggaggctc    6000
gcgttcccgc tgctcgcgcc tgcgccgccc gccggcctca ggaacgcgcc ctcttcgccg    6060
gcgcgcgccc tcgcagtcac cgccacccac cagctccggc accaacagca gcgccgctgc    6120
caccgcccac cttctgccgc cgccaccaca gccaccttct cctcctccgc tgtcctctcc    6180
cgtcctcgcc tctgtcgact atcaggtaag cgccgcggct ccgaaatctg cctcgccgtc    6240
cgcctctgtg caccctgcg ccgccgcccc tcgcctccc tctccgcaga ctggggcttc      6300
gtgcgccggg catcggtcgg ggccaccgca gggcccctcc ctgcctcccc tgctcggggg    6360
ctggggccag ggcggcctgg aaagggacct gagcaaggga tgcacgcacg cgtgagtgcg    6420
cgcgtgtgtg tgtgctggag ggtcttcacc accagattcg cgcagacccc aggtggaggc    6480
tgtgccggca gggtggggcg cggcggcggt gacttggggg aggggctgc ccttcactct     6540 cgactgcagc cttttgccgc aatgggcgtg tgtgtgtgtg tgtgtgtgtg tgtgtgtgtg    6600
tgtgtgtgtg gaggggtccg ataacgaccc ccgaaaccga atctgaaatc cgctgtccct    6660
gccgctgttc gccatcagct ctaagaaaga cgtggatcgg gttctagaaa agatgactcc    6720
ctgcacgccc tccctgcac ctcccgagca gtgattccga cagggccttc actgcccctg     6780
attttaggcg ggggccggcc ccctcccctt ttcctccttc agaaacccgt aggggacatt    6840 tggggggctgg gagaaatcga ggagatgggg aggggtccac gcgctgtcac tttagttgcc   6900
cttccccctg cgcacgcctg gcacagagac gcgagcagcg ccgtgcctga aacagtgcg     6960 cggatcccac tgtgcacgct cgcaaaggca gggttcacct ggcctggcga tgtggacgga    7020
ctcggcggcc gctggtcccc gttcgcgggc acgcacagcc gcagccacgc acggatgggc    7080
gcggggctgc aggtgcatct cggggcggat ttctttctca gcgctcggag cgcagggcgc    7140
ccggcgtgtg cgctccctgc cggaggcgcg ggctggcgc gcagggctcg ccctcactg      7200 cggcagtggg tgtggaccct ggtgggcgag gaaggggag gataggctgt gcctcctccc    7260
actcccgccc ccagccccc tttttttccc cctcggaacg cgaggtgcca tctttttcg      7320 gcgtgtcacg tctttacggt gccatgccaa accgggtggc cgggcttcat aggacagggc    7380
```

```
ggggcctggc attaaaggga gggggacaat cagcgctgaa atcttggcgt tttgctgctg    7440
cgggcgtgag cactggggc gttcgcccag caccttcttc gggggctctt tgctttgtct     7500
gtagaggtta cgtgatctgc gctcccagcc ctggtttctg gcttttattc tgagggtgtt    7560
cagtcaacct cccccctacg cccatgcgcc tctctttcct ttttcgctcc tcatttccga    7620
gcccattgtt ggatctcgag gcttgctggg ttcgatgaac tcgagtcaac cccccgaccc    7680
ccggcacgca tggaacgggc gtgaccgcgc gcagcctcgt ctcggagtct gccggcgccg    7740
ggaagcttct gaagggatgg gattcgagtc tccgtgcgcg ctgcgggcgg cggcagaggg    7800
atctcgcccc tccctacacc ccaagtgtcc tgagggccac gccacaccag gttgcccagc    7860
gagggacgct ggctacccat ccggggatgg gtggggagcc ctggcgggc ctctccggct     7920 ttacgccctg ttgcttcgcc tggccggaga atgtgaggaa ggggcataag gttactggtg    7980
cttcggccac acccatcttt ctgagcccac tggactgggc gcagagggg gattgccatg     8040 gaaaccacag gtgtccggag aggggatctt ggggctggcc tcacccttc cctgcggaga     8100 ttggggaccc tggggtaggg ggagccgcgc ccagtcggcc tcctggagga cacgggagga    8160
agccccgaac cccgcgcct gaggctgttt ctgattggcc cctggaggcc gcagacacgc     8220
agataggcgg ccctgggtgt atttttatta atattatgtc cgtactgatt aatattattt    8280
atcttaaata aatttcaccc gtgtccaagt tcaccgcgcc cccaaaaccg agtctggggc    8340
ggcaggggga actcctggcc aacgaattcca tgcctcgccc tcctgtgatg aacctggtac    8400
gcacggtttt ctggttaatt ctatcgctga aaactggtgc ggggggcgca cttctgagac    8460
ggaagagcat ctaggagctg aatcctccac gcgggtcgcc caggttgatc tgaatttctg    8520
gggaatggct tggctgcccg cccgggacca ggccgaccct ccttgacggt ggcgtagagg    8580
gctggagcct gggtactgcg aggctcctcg catggctggg cccgccgcga ggggttgcag    8640
agcggctcag ggatcgattc aagcatcgtc tctcctccct cgcccccaga cagagctggg    8700
cgcggggttc cccttccaga tggagcgagg gtctcggggt ggccccggaa aaggggagcc    8760
cgcggccacg gctacgtatt gccatctcgc gagcagagat gtcacctcct gcctttggag    8820
gaaagggagc ccgtgggga tgagcgcatt tagcccaatg ctgggaacaa agcgcactcc     8880
gcgcttctgc gatttcgctc cattttgaaa tgtgttggcg ctttggtggg gccgctgcgg    8940
tgggcaaggc cgggggcgct gttaatggag gaacctcagg gggacggtcc ttcgtaggaa    9000
actctatcct ggctctgcgc gcgctttaag gaaatggctt ccctccagga cctcgaggga    9060
tgcagctttt gcgcggatga cggtggggtg ctgaaccagc cggtgcgcct ctggaaatgt    9120
ctgggcacgg atcctggggc catcgacgac tcctccccat tcccagcagg cgggagctct    9180
tacattccga gcgagtgacc cctctcaccc tctggcgctc acacacctgt aactccaaac    9240
ctccgtctca gaatggtcca ggctggaagg gatgatgggg gctccgacag cgactgccta    9300
gctcacccct ctgcgtgctc aggctccagg ctcagcagga ccaatttgag ttctatctga    9360
tccccctcgg ccccttaact gacccatcct acaggagaca gggaaatgtc tttcctaccg    9420
cggttgattc tgggggtgtca ttttgtgttt tgtgatggct gcttatattt actgtataag    9480
cattgtattt actgtataag cattgtatta taattactgt ataagctgct tatatttact    9540
gtataagcat ctccaaatcc tccctctacg taaacaaatt aatggataaa cagataagtg    9600 tatccctgc ccccacccct gctacgcagg tccggagtga ctcttgaagc tcatacattc     9660
cttggccaag tttgcttctc taacagatgt ttatatagca ataacctggc ttggctcttg    9720
ggttcacctt tggacgattt ggggaagggg cttgttggct ttgctgggtt ttggatgagt    9780
```

```
gacagtccat gactgttcct gctggaaggg cgtgacttttt aagtggtttc taatatcagg    9840
cattgctcct ccgacaggaa caaaagaaat ggatactgcc cataaattgt tagaaaactt    9900
agaatcgctt tgattgagga aaggttagat ttattccggt tggaaaaagt ggcctttcta    9960
ttaaacgtgc cctttgaccc tcatgccctt ggaggtcggt gccagcctgg agatgggata   10020
agattgtggt tttccttctg ccttttttaac atctgttgtt acagtccatt tgttgaaaat   10080
ttaaagaaac tgttttattc cactttccct cagcatttat gtgtgtggtt tcagtagctc   10140
tgtggctata tgtacgaaca cgtgttattt ttccaattgg acatgtgata attttccaac   10200
tggaccttgc cttctattga tgtatttatt tagcatcttc cttactccct ccttgaaaaa   10260
gaatcactca aaacaaata aaaacagccg taggggccta atacagtgct agacatacaa   10320
gaggtattcg gtccatacca aatggatttt atccatgaag gataaatggg gaaatacagt   10380
gggaagcagg tgggaaactg cgtttgactc tgctcttttcc tccaccacca ctttcctcat   10440
caccgtgttc agagaccccc aaagccccct cacactccca gaaacacccc cctggccact   10500
cctaacttgc catgcccagg agttaggtgc ttccactagt gacatggagc tggcgtttgg   10560
ggggcacctc agcaggtgac gggaagagaa gaccccagcc tcaccagctg ggctgcagca   10620
gggagaggag tcctcatgtt ccagcaggga ctctcagctg ttttcctgta aaaccatggt   10680
tctcaactgg gggccactga gatgtctaga gagatgtttt tgttttcaca actcggggag   10740
ggtgctactg acatcttgtg ggtagaggcc aggaatgctg ttaaacatcc tacaaggaag   10800
gcacaggaca gtctcctaca tcaaaatatg acccagtccc aatgtcacca ctgctggggt   10860
tgacactggc actgctatct taattacatt cattgagtgt cttttaggag gcccctattct  10920
aagtgcttgc taagattatc tcatttaatc ctcacaacac ttccgctatg tagcaggtgc   10980
tgttattatc tccgtgatgg ggaaactgaa gcacagagag ggttagtaac ttgctaaagg   11040
tcacagagcc agtgggtggt ggagctggtt gcctgacact agttccctcc cctctcagcc   11100
acatgtgggt ttacttggcc attgtggact agtctgggaa cccagatatg atctataaca   11160
ttgacccagt agaatattga ttccaaaacc actgtctcac aaatgaattt ttacaagagt   11220
ctgtaatcgg agcatgaccc agaataaggt tagggagatg tggagttaaa gctctcaatt   11280
tcttatctgg ccccgacaca gagagcaagg catttcactc tacattggtg ctctgtttat   11340
aaaacaaaga gcaaatatct cttcctaagg tccttaaacc tcttccccca atccaggggtt  11400
tctggactgc tctgccatat gacggggcag ctggtttgat tgacccaggg aaggctggaa   11460
atcaagactg ggggatcaag acgtagattc agtgtggcca aggtcaagtc tctgaggttt   11520
agggacatca gatccccagc ttaggttctg tacctcggca aggtgaaagc gttggcgccc   11580
actgatgagg cctgctctga gattgtgggt gtgggttgag ttgggtgggc ataggcaagt   11640
cctcttgtaa gaatcttttg gcaaagatgg gcctgggagg ctttctcac ttcctggggc    11700
ccaggctttg caataagtat tccattatac tgtggtacct tggggctacc tgagaatcct   11760
ctgtctcgcc cctgttgcct tgccaaagag tttgctgtcc aagaattcct ttcctgtctc   11820
caggtgccat gctcctgcca cctctgccag gttccctgcc tgcccagatg gctcccaact   11880
gagtgtgagg aggaatttga gacaggtttt gagcttctg ggttctccag ttaggaaact    11940
ttctgtaagc atgcagatag aatgggcttc agcaaaatac aaactcgaac aacttccatg   12000
tatagtccct taatttctct tgcttttttc atatttcatc aggctccatg ctgagcccaa   12060
tcagggaccc gatagaaatc caaacaccat gtcagcgagt ccccaagaaa tgcattttgt   12120
```

```
gccaaggcta ttcaaggaag gtttgggagc agctcaaggg cagacactgt taccctcccc    12180
caggtcccca gtgcagggca gtgttctgca tgtggaggca gtttggccta atggttaagg    12240
aggtaggctc tgatcgggcc tcctgggcac aaatcccagc tccctgctca ctgtgagacc    12300
taagccatat tgtttagctg cttggagagt tttttgtcat ccacaacttg gagtatgatg    12360
gtacctgtct cacgggttgc catggggttc acacaagcta acccggtact cactagggcc    12420
aagcacatag taactgctca gtaaatggca tcatcggcgg tgtcctgtgg atgagtgctt    12480
gtgattggct gaatgaccag aggggtctaa agatcctggt gatggaatca gttgtacaga    12540
taaattgtta cactgagtag ggatcaagat aggaaaagtc ggcaactacc cagctcccct    12600
gcaccaaact gggcagaagt ggatcctctg aaaattgcac acacccatgt ttaaatgtac    12660
acacagaact cttgccacag gcaagcggag atttgtcatc tgctgtccct gcctcatctt    12720
cttcctgaaa tccactccat gccaggaata aactgcatgc tctccaccag cccaaactga    12780
cctgccttcc cgccagccat cccgggcagg gtgacctggc ttagtacatc gggttcagag    12840
atctttccag tttactcgtt gaataaaaag tgagggctga tcgagaaagt aatggcagtc    12900
agggaaggcg aaggaggtaa agaagagatt ttacaaatga agtaattcaa cagagtgctg    12960
acattggtaa actggcaaac agatttcagg gtggttggtt gagagtagag tagaaaagga    13020
ttaaataaag caaacttgtg gtgtactgaa tcttaggaat tccatgtatc caataagtat    13080
agtcatttat gaattaataa attcggccta agaagccttc ttatcgctta aatcaagact    13140
aagtaacaat atatcagttt taaaaagtca ttatatcaga aaatcattta aatgatacac    13200
atagatttcc aagattttac tttaaccgaa actatataaa tgtgaatttg ttcacccatc    13260
ttttgacaca gggctcaggt cttctcttgg tgtctggatc agccagttga aatttcttgt    13320
ctgttttgcc tatgccacat taataatgca ctgtctgggt cctccgattt cagtttggat    13380
tttgggttta cattgtggag tcatctgaat gcagaatcct tcagggattt tactttttt    13440 ttttttttc atggtctta ccatcccatt tgatagtaaa tattactcac ctttatgaag    13500
tctttccaaa acattcaact aaattttctt aaaatcattg aatgatttga agagcttatt    13560
cctcagcact tttactccat cagcttgcac cttatttttt aatcttttt tgagacggag    13620 tctcgctcta tcgcccaggc ttaagtgcaa tggcgcgatc ttggctcact gcgacctcca    13680
cctcctgggt tcaagcaatt ccgcctcagc ctccgccgta gccgggacta caggtacaca    13740
ccataatgct cggctgattt ttgtatttt gtagggatgg ggtatcgcca tgttggccag    13800
gctggtcccg aacttctgac ccaagtgatc cacccacctc ggcctcccaa agtgctggga    13860
ttacaggtgt gagccaccgc gcccggccag cttgcacctt atttaggata tgtgattatt    13920
atagcaagtc tggtgtacat acaagatttt gaatgggcac agatgacctt tagtaagtgc    13980
ttggctgtga taagaggcag tcctgactgc agatcaggct gtgtggaccc cagccttgca    14040
tgtttacaga ccttcatgtc ttattcttac agggtatcag aagaacacct actggggaaa    14100
cttataaatt agtaaaaggt gggcattctc cccgcccatc ttctgtctgt ctgccaggac    14160
tagcacagca ctttgaagtc attcacatag aatcccaact taagagggta aaatcctcct    14220
caacagactg aaaataagtt taaattccct tgctatatt aactcccctg aggaaagagt    14280
cttagatcaa tgtccaacac taaaaacagt tttaaatcag caagtgagaa ttaaatctga    14340
agcaattgat aataatgttt cattcattcc tctcctttgg ccccgtccac cctactgcta    14400
aatccaggca tcaaagagaa gagggacata attatctcta gtcccagctg ctggttttcc    14460
ttccagccta tggcccagtt ttctgtttta ctgagaaggc tggtgatgtt atcttgggat    14520
```

```
ctaagtctgc agtttcacca caaaaagtcc agggatgcac tttcatgctt gtgtcctcct    14580
ccctgggata gcaaggatat tagaagaccc ctggctctgt aattgcttgt catgtgctct    14640
acagacgcca cagaatgcca agaacgaagt gctgggaagg acaaattcat ggaaccgtgg    14700
gacggtgctc ctcccccagc gtaaaggaca gctcctcctc ctgaattgga gccagcgttc    14760
taaatcatgt gtcaacagag ttgtcctgga tcggatccag ttctgccatt gatttgcagg    14820
tcatttcagt ggtacctgtt tccagttgtt cttaattgaa cagtggcacc aaactattgt    14880
cttgcctcat ccccctccca tggcctgtcc cccaaaaaga gacttcttgg gtaattaatc    14940
agggcaacat caggcagtct gggcgcggtg gctcacgcct gtaatcccag cactttggga    15000
ggccgaggcg ggcagatcat gaggttagga gattgagacc atcctggctt tgtgaaaccc    15060
cgtctctact aaaaatacaa aaaattagcc gggcgtggtg gcgggcgcct gtagtcccag    15120
ctactcgaga ggctgaggca ggggaatggc gtgaacccgg gaggtggagg ttgcagtgag    15180
ccgagatcgc accactgcac tctagcctgg gcgacagagc tagacttctt ctcaaaaaaa    15240
aaaaaaaaaa ggaatctctt tggttttata tatattttt ttatatatat aatatatatt    15300
aaaatataat atatatattt atataatata atatataaat atattatata ttatatattt    15360
tatatattat atattatata tattatatat tatatattta tatatttata tattatatat    15420
atttatatat tatatattta tatatattat atatttatat ataatatata ttatatatta    15480
tatattatat attatatatt atatatttat atatattata tattatatat attatatatt    15540
atatatttat atattatata tttatatata ttatatatta tatattatat atttatatat    15600
tatatattta tatattatat atatttatat atattatata ttatatatta tatatgtata    15660
tattatatat gttatatatt atatatattt atatatataa tatattgtat atattatata    15720
tctaatatat tatatatatt atatatatta tatattataa tatatattat atattatata    15780
ttatatatat ttttatatat ataatatgta taatatataa tatatataaa aacatatata    15840
atatatatta tatattatat atatattata tatattatat atattaaata tattttatat    15900
atattatata tatatacaca tatatatata taaatgaggc caggctcggt ggctcacact    15960
tgtaatccca gcactgtggg aggatcactt gaagccagga gtctgagact agcctgggca    16020
acaaaacaag atcctgtctc tacaaaagga aactgtaaaa attagctggg catgatggca    16080
tgtgtctgta gccctagcta cttgggaggc cgaagcagga ggatcgcttg agcccaggag    16140
ttcaaggcta cagtgagcta tgattgtccc atagcactcc agcctgggta acacagcaag    16200
gccctgtctc taaacttttt tttttaatt ctatttatat ttacatgtat ttaaatgtga    16260
atattcacta cctatttgtt gcatgcctgc attttttata ctgggcttgc caaaaacccg    16320
aacagctttc tactttgaca atgtatcaga atttaaatca gcaatatgtt aataagccaa    16380
gcaaaggtta tatatgcaaa taaaactgtt gtctataacc tcctgttaca ctggggcaca    16440 gcaaagtca tggtgtagtc gcatgtgaac ctgtccctt catagctgct cattgccagg    16500
aaacatcagg aatagccatt tggaagagtc atcagccctc ccaccatccg ttttctgtct    16560 tgtctttcc ctatgagcag gggaaattcc acgctggccc caatcccag tgcagcggct    16620 cagcctctgc ctctgctgct ggtccccatg aggccagctt agaaacggag gattttgcag    16680
aacatcccta aatccgcttg aataatgaag tgatcattca taaactcacc tgaaccttat    16740
taaaacctat ttaatatttt tcctggataa tcctataggg ataacttgcc tcctgggctt    16800
ctctccaccg ggttcagttc ttcctttagt ggtgaagttc ctcccttctt agcatctcaa    16860
```

```
ctgtgcctga gaaaaggcca gtggcggctg cactctgttc cctgtggagt gttaataaag    16920
actgaataaa ttgaaataaa tcccttcaa tgtcattaag tgctataaat aatcatgaac    16980
caatgttcga tggctgatga gaaatgcaag aaaaaatttt taatcagtag gattcataag    17040
ttgacaatct gggccaagtt aaaaaaaata aaaataaaaa gactttaaa aagatcttat    17100 cgtttgttac cagtaagact gaattccaga agcaagctac tccctcattt gtgggcccct    17160
gttatcactg gctgcttagg gttgccaagc cctgaattca tttgtcaact aagagatttt    17220
tggccaagat taagatttcc catgcctcca tatttccatc tgagaaatgg agattatact    17280
gtcttccccc tcagaatgga tgataatgtg gtctctcttc tgttcgcata gtcatagaac    17340
tgaaataaaa caacttaaga gaattccttt gagcttctca gaagtgctgc agggctgggg    17400
gatgcctccc aggagccgca gtcaggtgct gatctgaagt ctttggtggg ctgactttag    17460
cctgacctga aatagtatag ctgctgccac ctggctccct tagcgtcagt cagacggtgc    17520
agctggttcc taggggtgag ggctgagcca gcagggtccg tgcccaggag ggatgcatgg    17580
gtggccacag cccagcctgc actgatcttg tctgtcccct tctttggaag gaaggagccc    17640
caaaccaggg tgcaagacag tgggtggggg tgccttgagc atgacctcaa gtgatttcca    17700 gccctgcca gtgctgactt ctctggggaa gggctgggac ttccttctgg gctcaagtca    17760
cgacccttgg atggaatttc ctgggagctt ttctgttttt tctggagttt tcagtttttt    17820
cctaaccaga cagggacttg gtacagaatc tcatattcta attatgccta ggagcagcct    17880
ctccccacca ctcacagtgt ttagcatgtg acaggaatcg attaaggcat gagtgattaa    17940
attaaagcca ggcattgact tggatggtgt aatattctga catctgtttg gtgtcaaagg    18000
cacggggcag gcgcgttaat tgaactgctt gcacctggca tttgaattga ccagagcgg    18060 ggctaaagtc agtttgcctt caccctgtaa atggaggtt tctccggagc gtggatggtg    18120
ggaggtattt cagggtgtat gcataacccc caccctgaca atggcccatc tcttctccag    18180
cgtggccagg tttgagtgcc agtcctgggt gtccagtggc cccatagcct tgcgttttag    18240
taaaatgctg ccccattac cacctggtct gtgcacttcg gtcactggaa tttgccatct    18300
tccagtcccg aatgtggcaa gccatggagc cttaagctct tctccctcca catcctggaa    18360
cagacccgcc agtttcttcc aggcattgcc tcagtttgcc cctctgtttc cagtcacact    18420
ctcaccagcg ataaaatgat tttagacctt atcatctcac cctcggatcc ttatggaaac    18480
aataatgagt tgttccctgt ttcaattcca aaattcatat ccaatccgtt ttgcatgcca    18540
ttgccaaatt cctcccagag caaccccgtc acctgccctg ccctctcca agtgtggtcc    18600 tgccatgggc atcgcctgct aagccaagct ggcctcgagc tgcctgcccg ggtccccaca    18660
ccttggctca cctccctgcc cagtcccgcc tcctgccagc ctgccctgtg gctccttcat    18720
agatgccgtg ctctttctgc cccttgctca cccatggcag cctttgccct ctctccctgc    18780
cccaccccct atttaaattg acctgacctt cctcagtgtc catcttcccc gaagctttcc    18840
ccagccttgg cactcaaggt ccagaggcta cgcgtttcct ctcacctgtg gcagcgccgt    18900
gctccccagt gcctcacagt ttccttcttg ccccgcttc ctgtgtagga ctcatctgcc    18960
cacaggttgc acgtcctgtg agggcaagga ctgtgtctta tgtgactttc cttctccagt    19020
cacagagctg ggcacataga tagctcaaaa ccctctttat taacacagtt ggatgttgag    19080
aaatcaaaca ggccaatgtc aaatgagctc tccttattta aatcaagtca gttctccacc    19140
tcctagcact cagttccagt actctatata catggaaata ataaaaaaca catttccttt    19200
gaaacattct ataatcgttc ctttgcccta cttcagacca acttaacgca ctccccattg    19260
```

```
gtccaaatga gttttgctat acgaagatgc tgataataat agcagcagtg gattattctg   19320
ctaaaaccat tgcctcgtta atcctcagtc ccgaggtggg gattattatc ctcattttgc   19380
agagaagcaa actgagactc agagatttca cagctgggga gggagccagc tcatccctct   19440
gtccaggccc aagctctctc ccgcttgcct tcctgcctct gcaacctcag gcatccccc    19500 atctggttct actgcctgtg ctagtcgtgc aggagccaaa agacacgtct ttagtgctaa   19560
ggactggaga agccatgccc tccagcctct gtgaatgggt catatgtaac atgagcctgg   19620
agaaattatt tgaaaccaaa ggcaagcctc taaaccaggc tgctgcttca tggcgccggt   19680
gacggcagaa ccaaatttag tgctgtgggc aggtccacac ttatcaaata gagaagctca   19740 ttttcttcc ggctcacatc aagcatgaaa aatgttcaca catacccccc acacacacat    19800
gctttccgga ggggtccatg tggctagagg ctggaagatg tggatgagag gagcctggca   19860
ggtaagccca gggaagatga cattcagctt cccagacagc atctacaggg agaaatttaa   19920
ttaaaagtgg ggcggtttcc ctgagcaagg cagacaaagt cagccctcta ctgttaagaa   19980
aaagggtcac agtgagaggg gaggtgagga gactgagtct gtattttcta gtctgttggg   20040
ctacactacc tgatccccct tcctcaaaaa tccactttac tttccccatg tctacaccaa   20100
tgtggttcac actctgggac caggaaaagg gggagtgatg gggaacagag aagggaggag   20160
ctcacacagc tgaggctggg gttatgcata tcgaattact tagaatttgc aacctcacag   20220
ggtactttca tggcgttgaa atacacttcc cacagccacc ctccctctaa ctaaaagcaa   20280
gagtcatttc tcagttctgg tcttgcctcc cacgttctcc tccacattta agaaaatcca   20340
ccagctacaa agtgaagata ccatatgtga tatcccaccc tagtttctgt tttatcaggg   20400
tttggagcag gtggagcagg cagagggatc atttcagcct ataaattgta ttaagggtga   20460
gtactgagtc attcttcaag aaaagtttta gaagcatcca aaactgaagg gtggagccac   20520
ctggagacag tatcatcagt cctggccccg agcatggcct gcataggccc ccatggatcc   20580
cagcgggagc tgcagagtgc gggcaccttg gcacacagcc ctgagtgcaa aattaggagc   20640
tgggcagagg gcatctctct gtcgccattg ggcagcccag ggcacactgg tcatagcctt   20700
agaccacgaa caccctgtgc ccgggggaca gatgcaacca gtgtgccctg ggctgcccaa   20760
tggcaacaga gagatcgaca cctggacccc atgtcacggg gactccacta ctaaggctcc   20820
taagactgcc accttccagt gggataagcc ctgcctccta ctgggcccac aatgtgcaga   20880
gaacacttgg gactacctgg ctttctggat acacaaatat tgatccaatc tggactaatt   20940
agaaggtcag tccaataac aaatcgaagt cagctgggcg tgatggctca ctcctataat    21000
cccagcactt tgggaggctg aggtgggcag atcatttgaa gccagaagtt caagaccagc   21060
ctgggcaaca tagcaaaacc ctgtctctac taaaaataca aataattagg ctgggtgtgg   21120
tggctcatgc ctgtaatccc aacagtttgg gaggctgagg caggtggtca cctgaggtca   21180
ggagtttgag accagcctgg ccaacagggt gaaaccccgt gtctactaaa aacataaaaa   21240
ttagccaagc atgatggcat gtgcctataa tcctggctac tagggaggct gagacaggag   21300
agaatcgctt gaatccagga ggtggttgca gtgagctgag atggtgccac tgcactccag   21360
cctggttgac agagcaagac tctgtctcaa aaaaaaaaa aaaaaaaaa aagccatgcc    21420 tggtggagca ctacgtgtaa tctcagctat ttgggaggct gaggcacgag aatcacttga   21480
acctgggagg cagtggttgc agtgagctga gatcgcgcca ctgcactcca gcctgggcga   21540
cagagtgagt gagactccat ttcaaaaaaa taataaatct gagtcacttt aatattgtta   21600
```

```
tttggatgtc aacctctagg tgtttgagac aggagagtga tatggggggca ctggaaacac   21660 acaggcacgg ggtgtcctca cacttgggta gcccacacga tgtgatttca gggtgctggg   21720 aggtccccccc actccccaaa ttactaacaa gtggatagta ctttacagtt tatatgatct   21780
catttgattc ttaacatgag cctgtgagtg aaaaattcct tcccctcttc tacagattag   21840
gacgttgaga ttcagggagg ttcagaggga ttcagggaag tcaagtggca cctggagtcc   21900
cgtggctaat ttgaggccgg tagggggattc gaacccagga tttgtgcttc ttatgcctgg   21960
gcttctgctc cctggggcat ggtcttcccc ctagctttcc cattcactgc tttagcctag   22020
gggtcctacc ctttattaaa ctgccagtgc ctcactgctt ttctccccca aagacaaaaa   22080
aaaagtgttt ttgcttttgt tttgtttttc atgggcagag acctggaatt tcagcttgag   22140
aatttgtgcc atatgataaa taaatcaaca gatggctttt tccttaaaaa aaaaaaaaaa   22200
aaaaactaag atgtatttgc agtgaggcat aatttgtacc aaaagtgct caccacactg   22260 tagtcatggg ggcaggaggc agccgcgggt gaagggagaa atcttggagt ccaggcagcc   22320
cccttctggg ctgaactggg gagctggggg tgctgccagc cctgccaggt tctcctagga   22380
ggcggcagct catatggctg tgggaggagg cagagggagc ctcatatgca cccacatttc   22440
cagggatcta aagacagaa ggaggaaaac caccatcatg ttaaagcaga cagttaggta   22500
acacatcctg taatacaagt tattttttcc acatctaaag gctaaaaata gttgttagaa   22560
tttaaagata attggtaaat gagtttctat ccttctagtt tcacatcaaa tggaatcatg   22620
ctgccttcac atcactagtg cccgttattt gtgtttaatt tccacaatgt tgtctaattc   22680 cactcttttgg gcttccccag ggatccagcc tccctcactc gcccatcgca gggagatgct   22740
ttattcatct ttgtgtcttc tgtgccgggc atagcgcatg gcacagaata agcactcagt   22800
aattgattca cgagtgaata aatggatgag tgggtgagtt caatattgac tacaaaaacc   22860
ctaaggccac actggtgagt ggctgcgcct gtagtcccag ctgctgggga atctgaggca   22920
ggaggatctc ttgagcccag gagtttgaaa ctagcctggg cgatatagcg agaacctgtc   22980
tcaaatgaca aaaacagggc caggtgcagt ggctcacgcc tggaatccca gcactttagg   23040
aggccaagat gggaggatca cttgaggcca ggagtccgag accagcctgg gcaacatagg   23100
gagaccctgt ctctacaaaa aatttttttaa aaattagctg ggcatggcgg tgtgcgcttg   23160
tagtcccagc tactcaggag gctgaggcag gaggatcact tgagcccagg aaattgaggc   23220
tgcagcgagc catgatggca ccactgcact gcagcctggg cgtcagaacg agacctgctc   23280
tcaaaaaaac aaacaaacaa caaaaaaaaa ggctttctta aagagacttg agaacagaaa   23340
ggggaacaga tacataactt atatatttat ttgttcatct ttccaccttc ctggagggtg   23400
gaggggaaca ggtctgtatt tggagttttg aatgctaaaa gtgggaatac atgtactgtt   23460
tgccatgatc tgttcaaaag ttaagccaaa tgccttagat tctcctgaaa actggaatgc   23520
cactgtaaac tataagcccc acttcaaaga taaaagatct tgatgaacag gctgggtct   23580 gtggactggg cctctcccca ccacacaagg aagggtggtg ccagttgaag gaaaatcact   23640
taaatccttg ctgtctccta ataaggtgtg gtcccaggta gggctgtcag aattagcaaa   23700
ttaaaacaca gggcatctgt gaaaattaga atttcagata acaacaaata attggcatag   23760
gctgcataat gtccctcaaa gatatcaggt cctaatctcc agaacctgta aatgtgatct   23820
tatttggaaa aggggtcttt gtagatgtgg ttaaattaag gattttgaga tgggggggatt   23880 atcctgtatt atctaggtag gtcctaaatg cagtcacact catccttgta agaggaagga   23940
agagagagat ggaaaacaca gaagagaaga caatgtggtg atggaggcag agattggagt   24000
```

```
gaggtggcca caagccaagg actgctggca gctaccagca gccagaaaag tccaggaacc  24060
aattctctct tggagctcca gagggagtgt ggccctgctg acaccttagc ttcaacctag  24120
tgatcctgat tttggacttt ggccttcaga agtgtgaggg aatgaatatc tgttgtttta  24180
agccaccaag tttatggtca tttcctacag cagccacagg aatcaaaaac agtaagtatg  24240
tcccatgcaa tgtttgtgac acacaccaaa aatattactt gttgttcacc tgaaattcaa  24300
atttaactgg gtctcctgta ttttatttgg ccaacctagt tcccaggccc aaagaaagag  24360
gcttttgaaa tttgcaagaa agctggttgg agctgtcaga aagtggactt tgtaaacaca  24420
gtaccaccga accaatttga actgtactac ctctagacaa aagagagggc agtcagacag  24480
ttgttcgtga tttcttcttt caacagtcat ttgagcactt actacaaaac agaagctatg  24540
tgtaagggtg gaggcgttag ctgttaatca ggacctccag gctaagtttc tgtattagtc  24600
cgttttcacg ctgctgataa agacataccc gagactgggg aatttacaaa agaaagaggt  24660
ttaattggac ttacagttcc aagtggctgg ggaagcctca caatcatggc agaaggcaag  24720
gaggagcaag ccacatctta catggatggc agcagacaga cagggagaga gagcttgtgc  24780
aggggaactc ctcttttaa aaccatcaga tctcgttaga cttattcact atcaagagaa  24840
cagcacagaa aagacctgcc cccatgattc agttacttcc caccagatcc ctcccacaac  24900
atgtgggaat tcaagatgag atttgttacc atatcagtta ccaacccttc cagataaatc  24960
acgtgaaata tcgccattaa cagagtgagc tcaggtggtt cttcagtgca tttctgatac  25020
ctgaaccttc cctgggaatt tcacagacca tcaggctctc caccctttga tagcaggata  25080
gcagggccca ggttctgcag gaggagatgt taccacaggc ctgaaaggga gggaggggca  25140
gatgctacag gaagatgctg gctctggatt cgctggagga gctttcaagg gaagtagata  25200
cacactgtct ccatcatttc atgtccatca cactctaaaa tgctttggac aagaagcaaa  25260
tgttaaagac aaatgtggcc cattttcctg tacaaagagg gctgctccca tgccaggcta  25320
ttggcactgg tgggcatgag gcttctctgc tgccctggcc gggggttct ctcactcacc  25380 attggctctc tgacacctgg agagaccacc acccttgggc tttcatgatg ctcacagaat  25440
ccacactgtt ggagctttaa ggagcctgga tcaactggaa caggcaggga gtactaggac  25500
agcccagcat tgccccaaaa tatccaggcc tgataaaaga gaaaacagg tagctcacag  25560 gaaaaggata aaaaaggag gagggattta acatgaaaag gtgcttgatc tccctcataa  25620 taaaagact gctgattcca tccaggcaag tgacagaaaa aaaaaatta atttaaaaag  25680 actgctgata aaaccacagc gagacactgc tgctcaggga tctgagggtg tgggcagcca  25740
ggctgccacg catcatgggt cggagaggaa gaccacaccc ctggagcaga gggcggctga  25800
tctgtcagat gcccttgac agcacctcag cttccaagaa ttaaccctt ctatgtgagc  25860 agaggcatcc atgggggac acactggtga atcatctgtt atgtagaagt ctggaaaaca  25920
tcaggatgga actggtgaaa taagtgtggc ctctgacgga atggagcggt ccgtctgcac  25980
tgctgcgggt gccctcaga tcctgtgggt cagtgagaaa agcagtgagg aacaaggcag  26040
gtactgtgta ctgtcctctg cgtgcaagga aggccagcgc atgcaacaga gtccacacag  26100
acatagccta actctggaag gaagaatgag aatgcagttt cagtggtggc ctctggtggg  26160
gagaaactgg gtgaagggag atgtcatttc catttctcta ctattaattt tgtattacca  26220
tgcttaaatg ttactttta ccttttttt tttttgag acagggtctc tctctgttgc  26280
ccaggcagga gtgcagtggt acaatcatgg ttcactgcag cctgaacctc ccaggctcaa  26340
```

```
gcaatcctcc cacctcagcc tcctgagtag ctgggactat aggcacgcat accaccgtgc  26400 ccagctatttt ttttaatca agatggagtt tttctatgtt gcccaggctg gtctcaagct  26460
cctggactca agcaatcctc ctgcctcagc ctcccaaagg gctgagatta aacgtgagt   26520 caccctgccc agccaattgc ttttaaaaa agattaaatg catgtatacg ctcaggcatc   26580
agcacacttg gaaaggatga aaatatccgg aagaagggtt cttttaaaag gctcctcaag  26640
tgatgctggc aggcatgacg aatgtccctg gtcacaaaag ctctgatctg gcctaaccct  26700
gtcatgttag agactggagt gcgtgtgtgt gcgcgcaaag tgtgggggga tgggggtgag  26760
tgtgtgtggt gtgtaagcat gagtgtgtat gtgtgtggtg tggggtgtgt gctgtgtga   26820 gcgtgtgtga gtctgtgtgt gtagtgtgtg tgtgaagtat gtggtgtgta tgtgtgacgt  26880
gaggtgtgtg tggtgtgtga gttgtgtatg gtgtgtgcat gagcatgtgt gtgggcatgt  26940
gatgtgtgtg tggtgtgtaa gcatgtgtga gtgtgtatgt ttgagcatgt gtggtgtgtt  27000
gtgatatgtg tgtggtgtgt gagcatgtgt gtgtgatgtg tctgtgtgtg gtgtgtgtga  27060
gcatgtgtgt tgtgtgtgtg gtgcatgtgt gtggcgtgtg agcgtgtgtg tgcattgtgt  27120
ctgtgagcat gtgtgagtgt gtgtgtgttc agcatatata aggcatgtaa ctgaacacag  27180
cactttagag ggctctcctg gagtcagagg gggtgggtag gaggagaagg gaggtgggct  27240
agtgtgctga agtatctact ccttgtcata gtctgtgaca acccagacta gcccatgagc  27300
caccctgttc cctgcatttc caatgagacc tcggtggaca tgttccctga ggtgaggctg  27360
actgatgtca tttgacgatc ttgatgccaa atcctttttat atcaaaaaca accagaacac  27420
tctcttttct cttagtgctt tcacccagat gaccacattt catcctccca gccactctgg  27480
gccaggtggc actgctggtt tgaaagggag gtctcccctg gagtaacttc cgtgggcgga  27540
ttcacaccct gcccacagtc ctgtcccagt cagcccacca tggtggtctc cggttcctcc  27600
agaattcccg ctttttcagct catccccaca ttcccggagg gactgagagc gcagccccag  27660
ggccctgctc tttgggggcc gtctctacac ccagagaagc agcaaggcat tcctaggttt  27720
ctctttcaga tgcagaactt cagtgttcag agatgttccc actggtcctg agagggctca  27780 gttcagctttt aatgactgcg ctgttgcgtg tgctctgcag agggcgggtg gcccagcgtg  27840
gctgactgca gttttcctga cgtggagccc gagcctgccc cgctgtttat taattaagga  27900
tcactctgct tgcagaaccc tgaactcccc agaactgtga ggtgggagaa ccccgagagg  27960
ccacctggcc ccacttccca cctgctgccc aaaccccctc tctgccttcc tgacagtcac  28020
cccaactccc agtgatcccc atcaaccatc tgacaagggg actgagaggg aagagaaagg  28080
aggggcccaa agaggaaggt aaaactgtcg ggaacagccc ccaaatgtgt gacagccttc  28140
agtggagttg cccactttcc cttttctcct ccctgcagga cctcccttct ccccagtcct  28200
ccccaacttc tgaggttaca ttgagaaaag tctgcagaga ggtgccagca tcacaaggtg  28260
ttaaggacca cgagtttggc atttttaacag atgccagagc cacttgagaa atgtggtaac  28320
taagcccaga gaggtacagt taacctcccc agagtcacac agcaggttca tggcaaagct  28380
ggactagcac aggtgtccctt cccctgcaga tcccccttctg tgccccacat cacctccctc  28440
cagtgtctgg gccacctgga gatgggccct cagactcacc cggccagagg tgccatctca  28500
tgggagaggt ctggccagga agcatcgata tttgagatcc caagaaatga agacttggcc  28560
tgtcagatga cagacttcgg tcatgggaac acgtgatctg ttttacacat gcgtcccctc  28620
agcagcagct ttccagaaca ttcccacttt ccttctgtagt gagaagaact cttttccctgc  28680 agcctcctgc ccaactcctc cttcagtgtc tttgcttcag tgtctttgat aaaccattct  28740
```

```
gctttgcaga gtgcgagctc tgccttgcag ggttcgcatc tgcctgtgct gagtaaccaa    28800
cgctaaggtc gagtggtcgg tcacctctca taagagctag ggttgtctca tgctgatgac    28860
taggacttgc cctcaaggag aaaaataaat caaaacaaaa gcaaaaacag caaacatgca    28920
tctcttaaag aaggctctga gtccaggtaa atttccttcc actgaagcag ccaggctgaa    28980
ttcgaattat ctttgcccct gcttaaaaac taatgcaaat tttcctagag aatatccact    29040
aattcctgga gggggcatgg gcattcctga tgcccatgag aggaccattt gctcttccct    29100
cagtatgcta ataacagaa gcgacatttg ttgctggaaa gtatcagtga agttaataag    29160 gttttcttg cccagggtga gggaacagtt cccaatgaca aatgctgtat gggaaggggc    29220
tgtagaactg ccagcccctt tggtccatcc gtaaagtgaa ctctgtggat cctggaggat    29280
tccagcgtct ttttttttt ttctttttt ttaagacaga gccttgctgt cacccaggct    29340
ggagtgcagt ggcacgatct cagttcactg caacctccgc ctcccgggtt caagcgattc    29400
tcatgtctcg gcctcccgag cagcaagact acaggtgcgc accaccatgc ccgactaatt    29460
tttgtattat tagtagagac gggggtttca ctctgttggc caggctggtc tcaaactcct    29520
gacctcaggt gatccacccg cctcagcctc ccaaagtgct gggattacag gcatgagcca    29580
ccatgcccag ccagcatctt tcattttct gtctgctttg gccctttcct ctctcactgt    29640
cttccttttc catttccaaa gtcagtccat ctcactatta gcacaaaaac tgctagagcg    29700
cttgtcattg gtcatctctc cctgcacctg gctggtctgt tcttggccac tgaagcgttt    29760
cccccagctg ttgctttaat cattttattg ttattatgcc ttacttaaga aatggatatg    29820
agatgcattt acctgtctct tcctgccact ctgcagagcc agtaagatgt ggtggaaagg    29880
gcccaggctt tggaggaggg ctggctgggg ttggatcttg gctgccccct actagctgtg    29940
tgaccttggg taagtagctg gacctctctg agcctggttc ggaatcatag cacctctctt    30000
tcagggctgc tgtaaggaat agcagtggtg tgtataaagc agagcgcaca gccagcaact    30060
ggcccctagc cacactgctg agcacctact gtgataagct gccattgtgg tgtgtgaagc    30120
aaaggggaaa catgcctgct gtagtgagct tcctgtaggg caggttgtag aaccagaggt    30180
gggttccaag gttacaaagg gactcttagt gtattagtct gttctcacat tactataaag    30240
acctacctga gactggatca tttataaaga aaagaggttt aattggctca cattggctgg    30300
gtgcggtggc tcacgcctgt aatcccagca ttttgggagg ccaaggccgg cggatcactt    30360
gaggtcagga atttgagacc agcctggcca acatggtgaa accctgtctc ttctaaaata    30420
aaatacaaaa attagctggc catggtggtg tgcgcctgga atcccagcta ctcaggaggc    30480
tgaggtggaa gaattgcttg agcccgggag gtggaggttg cagtgagcca agatcgcccc    30540
actgcactct agcctgggca gcagactgag actctgtctc aataaaaaaa aaaaaaaga    30600 aagaaaaag aattgcaaga aataaattat tgtttatgag ctatatggtc tgtggtacct    30660
tgttgtggga ctgggagtct tggcgtctcc ctgaccctgc tgttgctgc agcaccgctc    30720 agccctgcct gctccctacc tgcctcccct cggcctctcc tgcctccacc gggcccctgg    30780
tgcctcctct agagacagtc ctcctgggac cgattgtgtt ctcacttaca cgaggcatcc    30840
aggactacag ataaccagag gaaggggcgc cccccccgcc tgccctcctc cctggcatcc    30900
tcacgctgca gaggtcagag cctcatccca gccccttacc tgcccctact ctgtggagaa    30960
ccgtggtcag ttcgccaggc cggatccacg aacggccttg tggaagatgg tgagctcaca    31020
cccagagctg gctccgatga ccctgtctcc tttacatgtt tctaccttcc cctcccctacc    31080
```

```
ttcccccact gctgggcgca gagtggaggc agatgaggtt taaagctcag aagggcttaa   31140
acgggttggg gcgcagtggc tcatgcctgt aatcccggca ctttgggagg ccaaggcaga   31200
ggatcacttg agcccaggag ttcgagacca acctgagcaa catagtgaga ccgcgtctct   31260
acaaaaaata aaataaataa aattagcttt gcagggtggc atgcacctgc agtccctgct   31320
actcagaagg ctgaggtggg aggatcgctt gtgcccagga gtttgaggct gcagtgagct   31380
atgctggcac cacagcactc cagcctgagt aacagaatga gatcctgtct caaaacaaac   31440
aaacaaacaa acaaaagaag gcttaaaggg ggctccaggt gggcttggca gcacaaagct   31500
atgaagttct atcttagaca caagttctgt tactgggcct ttgcaggctg gcctgggtac   31560
ctggctgcca tagacaggga accttccaga tgagctgcag gcgtggagca caggagccag   31620
ggtgctcttc ctgggctctg tccacaggca gaacgtacac agtctttgta cacgtccggc   31680
ggctctggtg cctattttg tttgtgtttt tcttttgttt ggggggatgg atttggtttc   31740
ccccgagccc tctgtcctcc tgtcacctgg ctggtgctcg gcaatgttga ccagctgcct   31800
ggctggagtt ggcagtggct aaggctgtga cagctaacat gttcctgagt cctctcattt   31860
cttcaccata atgccctgtt gagtttgcag atactgtctc tgttttatc tcccggggaa   31920 actgaggctc agagtggcta ggccaccttc ccatggtccc tcagctcatg agggccacac   31980
agggcattgc ggtggccttc tcctcagcct tgaccctccg gccccagcat tgctgcctca   32040
aggggtctcc tctgctgagc cgtgcacctt ctgcctggca gctccaactc tgtggctgtg   32100
ttcagtggct cagcactgcc ccttgaccct cctggccttt ctgcggatgc cagactggag   32160
cactctgaca aggtctgggg tggttgtatg ggtcctgtga cctctataca cctcccagtg   32220
cctgggaatc ctgcagatac accctcctta gccgtcccta accatagagg acatttctga   32280 ggtcccgag agagtggggc acccctgcag gatccaactg ctgggcccag gaaggatagc   32340
agcagcatga ggggttccat tagccacaaa ctcacggcat ggaaccttca cccacctcgc   32400
ccctcatctg ctgtttagca cctggcacgc cgtgtatact tactgattat tacatttaa   32460 tggcaaatta tagtggcaaa cgtatgcatc tttgcacaat tgttgtacag catgatgaac   32520
aagtcattaa tagtaaagaa taaatgtgaa agtgagaaaa atctgactgc caaagttttt   32580
actccttcct tccctcccca gactttaaa tgaaagttta gggataatcc cttagttgtc   32640
ctgctagtag gacttgcaat taaaagaatt gggccaagaa cacttctacg cttctccttt   32700
taggtttggg tgtaaattcg gggtatttct cactgatgaa agcctggtgc agggcagacc   32760
gtgggaagct ttcatttccg gaatggacca tcaacatccc ttggagaaga attctcttct   32820
ccagacccag acctggtgtc ctggcaccca ttgggcaagt gggtcctaga agacaaacct   32880
ggtcagagcc tggaggctgc ttagcattcc ccacgcacat tagcagctcg gagagctcag   32940
gaagccgcag cccctccttg cctcaccagc ctggatcagg acagcatccc ctggaagaca   33000
cacagggcct ggcctctgat tacccagcct ggagggaaag ctcaatcgag catcatgtca   33060
cccggtgccc ccatgcaggg tggcactggt gagacccca agccaatgat accacctcac   33120
aggagtgcag gccattgtg gccagatcat cttgactttt caagataaat cagaaatcgt   33180
atttccatga gatatcccta tttgcaagtg atggtgacta aattagaagt ttttgaatat   33240
tgtaacatgt tcgtaggctg tttgtctggt ttaaactcta tctggaggaa ttcaagctag   33300
acttcaggaa taacttcttg aggcaaggat tttgagacct tagggaaaga aggacgtctt   33360
gggggtattc tgactgttgt cctcctggaa gggaagaaca gagaactaga agactgccct   33420
tagcgaagtt caaagcacct aagcccggga ccctcagcaa gtgttcttga gtcacagatt   33480
```

```
ctccctgagg cgcctctttc tggctccata gaatggctga ttctgtaact cggtgagttt    33540 gcttttttt  tttcctccat cacccaggct ggagtgcagt gaagctggag tgccgtggag    33600
cgatcactgc aacctctgtc tcccaggttc aagcaattct ccttcctcag cctcccaagt    33660
agctgggatt acaagcatgc agcaccacac ctggctaatt tttgtgtttt taatagagac    33720
ggcccgaagt gctaggatta caggcatgag ccaccgcggc cagccataac tctgtgactc    33780
ttgttacaaa ggcctatat  tttgctcttt gagggtggtt ttggtttgat gcctgttggt    33840
tgccatcttt taactaggga tgttttatca aaatgcccag ccaaagtgtc caaacaaatt    33900
ataccttaaa gtttgaaaat gtctggcact tctaattcaa tgcctgttgt gccaggcact    33960
gggctgctga ggaactgagt cccgtccctg caggctagct agagaacaca cacacacaca    34020
cacacacaca cacacacaga gtggtcttac aagtcagttt tatattctac ctatatgcaa    34080 taaggtatt  attatgttga ggtgccttga tataaaaatt tttcttaaag gagaggatgc    34140
ctaaaacagg cattacctga aacctcctct ctccagcatt ggttgtcttc tgtcatgact    34200
cagggttttc actgagaatg ggatggaaat gtggtctaaa gatagggcca atgttgggac    34260
tggatcccct ctgggaagtc agaccaggct agggcaggtc cttgaagcca tcaggaaaag    34320
cctctggagc cagaaacaaa acaaaaaaaa aatggtgtta actaaactca gtctcaaatc    34380
ctgaatagga ctcaagtcaa gcaaaataat taaaggagtt agcaaagggc aagtcagaga    34440
gaccgagcaa caccaatgtc ttccgggagc cctgtggcga gtgacagagc ctggactctg    34500
gagtagaact catcttgtgt cttcttctgc cactcgttag ctgggtgacc ttgagccaag    34560 cccccttaacc tcttggaccc tatgttctta tctctaagta ggggctggta atatcttccc    34620
ctttgaggaa tgccctctaa ggggtgttgt gaagattcgg taaggtggca ggggtaggac    34680
tcctggccag aaacaggcac ataataaatg ctaagtctct ccttctctcc acctgctgga    34740
tgctgtagat actaaggatt tcgatgtgaa tgagacaaaa cccctgcctt ccaggagcct    34800
ttgagaatca gagaactaga cccatttcca gaacaagggg atgcagggtc tggataaagt    34860 tttgggatc  aatagagcag agggctccca gaggatccca tagggttgac tcctaactca    34920
agggcatgag acaaccccca ggaagggcac cctggaaggg gtccggctgt ccctgattta    34980
cttgtgggca ctgggggaat gcccggagcc atccagccct cagggctctg tgtgattctg    35040
ggttcctccc ataaaagata atcagattct ttcacgttaa tgtctttctc cacctcattg    35100
cacatcatgc agctattcat tgactcagca agtatcagct ttgcatgcga ccttggccta    35160
cccactttag cttttagtaa tagctcccct cttgaataat acaaccagtg gggaaacaga    35220
acctaactct tacctctggg aggcttattt gctttgagaa catatgtcct gcagttttgt    35280
tcatatggca gtgaagtttc gtgcacacac tctagagcca ggcagcctgg gttcaaagcg    35340
cagctctgcc aggtcctaac tgcatgaatt tgggcaagtc gctcaacctc tccatgcctg    35400
agtttcctca tctgtaagat tggagcaatg gtaatacctg cttttaggg  ttgagaagag    35460 aattaaatga attaagatgg gtaaagtgct tagagtggag ctttgcaagt agtaagtgct    35520
atgtaagtgt tcgatttaaa atgaaagacc cttaaataca ttctttgttc atttcacaag    35580
cccttcattt cacaaccttta catttcacaa ccaagctctg tctccctctgg aatccagcca    35640 taactctgct cacaagtgtg agacaggccc cagcagagct gcacgaagag gagagaaggc    35700 agcccccag  actcccaacc ccctgtccaa gatggcaaaa ccagaacaca gcctctgtac    35760 cacccagca  ggtattcaga atctgcaatc tccaaagccc acttcaattg taaatgtaga    35820
```

```
gccacgtgcg ctttaagtca cctgtcactc tggaggctct tttgctcagt tcctcaccat   35880
tagcagggat gacagggagt gcaggagtgc ggtcgactcc cagatattgg agagcgctgg   35940
gctagctgcc cattctcccg gcctccactc ctctttgctg tccagccatc acttgctctt   36000
tgaaggcaaa caaaacagaa aacagtgcca aaagtatggg aagaaagcca gcttctcccc   36060
tggggtgcct gtgatgccat gcccaccctc cctgaccacg cagcccctgt ggaccctcag   36120
ggccccaagc ccccatttcc atcacatgcg tacacccatg tgtgtccata gccgccatc    36180 tcagtcaata aggctgctcc tgcccacttg gaatagtggt gacaaccagg agtggcttat   36240
gggaactatc ccaatggcct gacagcatgt ccgctgcaaa ccgctgaggt aggacactgc   36300
cctcatgtct agctgatcag caagaggcgc agttgctttc ttaggtaaca ttgctgctgt   36360
gtcctggcca ttgctggggg gtggcactta atctacacca gaattttccc tcctgtatct   36420
tccaagctgc ttggatcttg gtgctgaatt aggttggact ttgtcttgtg gggaagggag   36480
gactatagac cctcaacgta agcaatggtc agactattct aagaaaactc gccgaattaa   36540
agcatgaggt aaatttagtt ctgacttctg tccaccccac tgccactgtc ccttttatc    36600 ccatgatccc ttgcttttct ttcctcctc tctccctatc tcttgtgttt gacgcatgat    36660
aggaattcag aaatatatgt ttgtggattt gtttattcac gtagcaaacc atttcttgag   36720
tgcctaccat gggccaggta gaatgggcgg ccccgggctg cagtggtttc ttcagcccct   36780
ctccagggtt tacactgtgc aagacggttt gtgatgggtc ctcccatcga ggaccacact   36840
cttctttctc tgtgccccctt ggtcctcagt ctctgaccc acttcaaagg cagcattcac    36900
tcagggaagc tcccatacaa tgctagtcag agtaaaagtt tggacaaatt gccaggaagc   36960
agcttgtcag tatgcataaa cagcctttaa aatattacta ctctttgacc cagaatttca   37020
cttctaggaa tctgtcctaa ggaagtagtc acatgcaaaa gatttatgta ccaagatgtt   37080
catcaaagtg ttgttttata acaggaagtc tcagaagctg ataaatatc caacctctgg    37140 aaatggttag atagaatagt atgtagccat tagaaaatta tgtctatggg gtttaaaatg   37200
tcatgggaaa acacttctga cataaaagag catgagaact gtatatttag cataatctta   37260
actatgtttt agaatgcaca ggaaaaaaat gtacaaacat attcatagtg atgtctctgg   37320
tggtaggatt atgatcagta agtacttctg tctcttcata ttttcctgta tttgataata   37380
catgcatatg ttgtttttaa aataagaaaa attttaagtt taaaattgga gctgaaaagt   37440
gtttttaggt caggcgaggt ggctcacacc tgtaatagca ccactttggg aggctgaggc   37500
agtcagatca cttgagccca ggagttcgag accagcctgg ccaacatggt gaaaccccat   37560
ctctactaaa aataaaaaaa ttagccatgt gtggtggcac acatctgtaa tcccagctac   37620
ttgggaggct gaggcatgag aattgcttga acccaggagg tggaggttgc agtgagccaa   37680
gatcgtgcca ctgcactcta gtctgggcaa cagagtaaga ctctatgtca aagaaaaaaa   37740
aaaaagaaaa gccttttttaa acagtagcag acataactat ataatcctta ctaagctgtc   37800
ggtcaaattt ttatttatat atttatttta ttcatttatt attttagac agggtctcac    37860 tctgttgccc aggctggagt acagtggcgt gatcatggct ctcttcaaac ttgacctccc   37920
gggctcaagt gatcctccca tcttagcctc ccaagtagat gggaccacag gtgcatacca   37980
ccacacctgg ctaattttt ttattttta tttttagaga tggtgtttac tatgttgccc     38040
aggctagtct caaactcctg ggctcaagct atcctcccac ctcggcctcc cgaagtgctg   38100
gggttaccag catgagccac tgtacccagc cctcaaattt ttaaaatct ataagagaca    38160 ttattggaca attagagaaa ttcacatatg gacttataat agtatcagag tgtgtggtgt   38220
```

```
gatggttctg gagggaatgg acttttctt tggagacagg cttttctatg cccacccttt    38280
tatcttgcta acttatcatc atccaggttc cagcagaaac attacttccc ccaggaaatt    38340
tcttaagggt gcagtatcat gatgtctgca gcaaattctc aaatagctca ggaaaaaagt    38400
acgtgtgtgg tatgagtgtg tgtatgtatg tgtgtatata tatacacata tatacacata    38460
tatatacata tatgtgtata tatacacata tatgtgtata tatatacaca cacatacaca    38520
tatatataca cacacacata catacatgta tttttatata attatatatg cagagagtgc    38580
aaatgttgcc aagttaaaga ttggtgagtc taggtgaagg gaatatggta tttattgtat    38640
tatttgtgca acttttctta agtttgaaaa ttttcaaaac aaaaaattgg aggaagaagg    38700
catgccagtc taccccaagc cctccattgg aatgctgaaa atctaaacaa tgtgatttgg    38760
caatttcatt tcttttctgt tgtgggccag tagtccttag atgttgggga aggggggtagt    38820 cgctgaggtg tggttgactt aggatggaag aagcagaagt caagactccc agggtcaaag    38880
tggtttgctc tgctgaccca agtgtgggag gcccagagtc agcgtttcag gtgtgctaat    38940
tcagcatggt tctattcacg gccaaagtcc accctgggca cctctctggc agcaatcttg    39000
ggtgactcta ctaaggccag gcctccatga ccctatgtct ggatcccata tctccacctc    39060
tcccactgtc tcaggaacgg tgcttagctt tttcttttcc ctctcctgtc ttctttgcca    39120
gcatgtagaa agtttaaata attcccctct ttacaacaaa acaaaacata ccccttcag    39180 tcaaccaccc tagctctctt ctccttttcc cagccagatt tttttaaaag catcctaggc    39240
caggcgcggt gactcacgcc tgtaattcca gcactttggg aggccaaggt gggtggatca    39300
caaggtcagg agatcgagac catcctggct aacatggtga accccatct ctactaaaaa    39360 tacaaaaaag tagccgggag tggtggcagg tgcctgtagt cccagctact cgggaggctg    39420
aggcaggaga atggcgtgaa cctggtaggc ggaggttgca gtgagccgag atggcgccac    39480
tgcactccag cctgggtgac agagtgagac tccgtctcag gaaaaaaaaa aaaaaaaaa    39540 aaaaaagcat cctcagcact ttggcaactc catctcctcc caacatgtcc ctgttactgg    39600
aatccagcca ggactcagcc ccgatctttc tactctaacc agttgtctca gttaacaagg    39660
acaggtttat gctgcagtga caaacaagat cccaaattct tgtggcttca cacatctggc    39720
accacctcat cttccagcct taggagtcat cttttagttc cttgaaaact ctttacagtt    39780
ttctgttggg gccttgtcat atactattcc cctggaatgt tctttcctat cccctcccctt    39840 tcaccttgct aacttgtgcc catccttcag gtctcagcag aaacatcact tccttgggga    39900
agttttctcc aacacccaca ctacacaggt gtcccatcta cactcctatg actttgtggt    39960
acttgtctca cttcattttc cactgccttc cccacaaggc acctgcacaa gggcaaggac    40020
cgtaccactg tacctatgtc actcattgct gtggtcacct gcactctggc tgcctacctt    40080
aactacacat tagaatcacc tgaggagctt ttaaagccac aatgcaagac tccaccctag    40140
gccaattgga tccaaatccc tggggtaggg ccagacatca gtggagttat atatacatat    40200
atatattttg tttgtttgtt tgtttgtttt ttgagacaga gttttgctct gtcacccagg    40260
ctggagtgca gtggcgcgat cttggctcac tgcaagctcc gcctctcggg ttcacaccat    40320
tctcctgcct cagcctcctg agtggctgga actacaagtg ctcgccacca cgcccagcta    40380 attttttttgt gttttttagta gagatggggt ttcaccgtgt tagccaggat ggtctcgatc    40440
tcctgacctc atgatctgcc tgcctcatca gcctcccaga gtgctgggat tacaggcatg    40500
agccactgca cccggccatc agtggatata ttttttaaagc actgcagaga attctgttgc    40560
```

```
atcagcttga gaaccactga tctgccttgt gcttcacatt taaaactttt ttttaatgaa    40620
taaataaacc ccaaaaaatt aatctcccta agcctcccta gaagatagga tggtaaggat    40680
attttcctag gtaaaaatat gttaatttca tatttcatga aatttcatgt ttcatttcaa    40740
tcaagctctg tcatacacct tacatggggc aagcccagtg cctgggcagg gtgtaattat    40800
actcattaca caggcaagga aaagtcacat taggtgatgg agcacaaata ggcagttaat    40860
ggtttcaggg ctagttagga tatgtttgtc tttcaattgc aagtaataga agcccaaaga    40920
aattggttat ttatataata taattgattg gttcccaaat ttgaaaaatt caggaataga    40980
cccagcttag gtacagctgg atccagtcac tcaaacaatg tcacaaagaa ccctttgaca    41040
ggaatgtatc ctgtgttgac tctactttgc tctgagtagt ctttccccag gtgatgataa    41100
aaatggtcat catcgccagg cttgtgtcct gtttagtagg aatatacaag aagagctcag    41160
taaatgctgg ccccaccact aagcaaaaac aaaacttttg ttgttgttat tgttgtttta    41220
aataacagct tagaccttcc ttcttttcctt gttattctct ttcatctgta atccagtttt    41280
ctacttctga agtatagaat gttctgatga tttattcttc attcccaca acttgcacat    41340 gtttatttaa aaatgccagg attgcctggc cgttgtgtgc tgttaacctt tgtttgctgt    41400
tagtggatcc ctgaagttca ggctcccagg ggagcagata atgggtatcc agttcctgca    41460
atatccaccc tctggcaagc caagttcctt cctgggtaag gttttgccta cctgcattcc    41520
tagggaagtt tctgggcctg accaccaagc cagctctgag aaggggtgca taagccccac    41580
catgctttgg ctctgtccct atagaatatt ttatgttgtt actgaaaact aaaggaagat    41640
gggtgcggtg gctcatgcct gtaatcccag cactttggga ggccaagaca gattgatcac    41700
tcgatgccag gagttcaaga ccagcctggc caacatggtg aaaccttgtc tctacaaaaa    41760
caaaacaaaa caaaaattag ccgggtatgg tggcatgcac ctgtggtacc agctactcaa    41820
gaggctgagg cacaagaatc tcttgaacct gggaggtaga ggttgcagtg agccgagatc    41880
gcactactgc attccagcct gggtgacaga gcaagattct gtctccaaaa aaaaaaaaa    41940 aaagaaaagg aaagctaaag gagagagact aaaatgatat caggttcctg gagaacaaac    42000
agacatgatt ttgcttcatg gcaggacagc cggaagaagt gggattatat cctcacatta    42060
caaataagaa aactgagact cagaatggtt aagtcacttg tcccaggcca cacagccagt    42120
aaattacaga aacagaattt gaacccaaat cttccagctc caaagcttgt gttcttttca    42180
ctacctcctg cttaatttt taatttctaa gattagaccc ttcatctatc catgacacct    42240
gcctgtcatc ccctgaaaaa aggtgaacgc cgttcagaaa tttttctagc ctgagctcac    42300
tcccagttca cttattttg ctttgtcatg gctgcccagt ccccacttgt agaccaggaa    42360
taggtcatgg ctgcggggac tacacgctgt cgctgctgca agggccggcc tctgtttccg    42420
gggctgagtg ggggccagac ctgccaggag caccatcttc tgtgggtcct gcctggatgt    42480
cacatcccgg ccccaagaag tcactgcaaa ccttcgtatt attgagcttc acatcctaga    42540
atttgctgtc actgtggctg ctgcatgaag ttgtcctgag agaaacgggc attgtcatta    42600
acagggaaat tgatggtctg ggggaaaagt catcctcatt ctcttgcaga tctatgggtg    42660
attgagactg gctgatgttg aagggggtttc tcagccatcg tgtgccatgt tatgaacag    42720 tggtgtagcc agccatttga cacccagcgc tgacctttgt ttaacaacct cacctatata    42780
tgacaaaatg attgtcagaa ataatcgtgt aatgaaatga ctgtaataat ggccagaaaa    42840
gaaacgcaga tagtaaaatg tttctcttgt tgaactctgt acatataatt gcaccaggat    42900
ttttttcaaa taaaaagtaa atattatact acaaaaaagg gaaaaagcac aagcatttat    42960
```

```
taaatagctt tctatatctt tctgagtttt gatcctttga ttgcagactg atgtaatatt   43020
ttatgtaaat cattgcttgg ttactaagtg aactttaaga aaagtgagac gtctgcagaa   43080
gttgcccata atttagcagc tactgtattg taccattgat gtacggcttt attttcttga   43140
ttaattattt aaacaatata attcacaatt ttaaaataat aaatttccac ttaaaatggt   43200
atttaaactc agcaaaatat atcatctatg agtaaaattt gtatttacca agcaaaaata   43260
ttacagtttg tggttcacat gctgtctcac tgttttaaat tttaaataca aaaactccaa   43320
gtaggctggg tgtggtggct cacacctgta atcccagtac tttgggaggc tgaggcaggc   43380
atatcgcttg agttcaggag ttcaagattt gcctgggcaa catagtgaga tcctgtctct   43440
actgaaaaca attagctggg tgtggtggca catgcctgcg gtcccagcta ctcaggaggc   43500
tgagatagga ggatcacttg aaccctgggg gacagaggtt gcagtgaggc aagattgcac   43560
cactgcactc cagcctgggt gacagattga gaccctgtct caaaaaaga aaaaaaaaa    43620 agaaacacaa aaactccagg tggtcgcaca gaatgacagg actgaagtaa cttagctcca   43680
atttctgtct tcataatcac tgtcctacca ttgtctgtgc ttagaatcta cttgcttaat   43740
gcaggaacat gtgttctcac agagatgaa aatgcaaatg cgccagaag caagctggaa    43800 attctgaacc attaagaatt tactctctgc caggcacggt ggctcacgcc tgtaatccca   43860
ggactttggg aggctgaggc aggcagatca tctgaggtca ggagttcaag accagcctgg   43920
ccaacatggt gaaacttcat ctctacaaaa atacaaaaat tagccaggca tgatggtggg   43980
tgcctgtaat cccagctact cgggaggctg aggcaggaga atcgcttgca cctgagaggt   44040
ggaggttgca gtgagccgag atctatctgc accattgcac ttcagcctgg gagacagagt   44100
aagactccat ctcaaaaaaa aaaaaaaaa aaaagaactt actctcaaaa taaatacgtg     44160
tggctgactc cacatatggt agggccaact gtataactag aagttctcca ataacttct    44220 gtggagaaaa aaaagtttat taaggttaa cttttttaaa gtgctaacta gaaccttact   44280
aacactgaga tcgcaccaat tgtttataac ttagacaggg ccgggtgcag tggctcatgc   44340
ctataatccc aacactttgg gaggccgagg caggtggatc acttgatgtc aggagttcga   44400
gaccagccta accaacatga tgaaacccca tctctactaa aaatacaaaa attagccagg   44460
cacggtggta cacgcctgta atcccagcta ctggggaggg tgaggcagga gaatctcttg   44520
aacccaggag gcggagattg cagtgggcca agatcgcacc attgcactct agccccagca   44580
acaagagtga aactctgttt caaacaaaca aacaaaaaaa aaaacctctt ggaccaggaa   44640 aatattttt aagggaggag tattttatca ctggcattgt ttaggattgc aggcacatga    44700
tgctaatgaa aagcagacta actattagtt ggttttatta ctgtttttga actctctctc   44760
tccctttttt tttttttga cagagtct ctctctctgt cacccaggct ggaatgcagt      44820
gactgcagtc tcagctcact acatcctctg cctcctcagt tcaagtgatt ctcgtgcctc   44880
agcctcccga gtagctggga ttacaggca ccacaccagg ctaagttttt gtattttag     44940 tagaggcagg gtttcaccat gttgcccagg ctggtctcaa actcctggcc tcaagcgatc   45000
tgcccatctt gacctcccaa agtgttggga ttacaggcgt gagccaccgt gcctagccct   45060 gttttgaac tctctagaga cagtccagcc cctattact tgtcctgagg cagctgctcc     45120
cttcacctgg ccccccgcat tgtgttccgg accttgtcc tggtggtgct aaagaatatc    45180
tctgtcgatc ctttggggac tggggaaact gaggcccagt gccacgcgat gccatttgtt   45240
cagggaagat taggtcatct gctaggtccc cagtcacttg accttcttcc cagacaggaa   45300
```

```
gaagctgctc tgggtctctc agtgctccac gtgtctttgc acattgaaat gttttctgat    45360
tttttttttt ttttttttgct gttacattta cttttaaaaa ataacaagca ataaaatgtt    45420
acatttgaga aggttgaaat gagaattgat ttgagttaaa ttctagcaga tttttcttag    45480
aagaatgata tcatcatctc cagctacctg caattgatct actctgaatt aagaaagaga    45540
cttccatttg ttgtttatat tttgcactct tgatgtgttt ctttaaatta tggtcatggg    45600
ccaggtgtag gagctcacac ctgtaatccc agcaccttgg gactctgagg agggaggatc    45660
actggaggcc aggagttcaa gacctcgtct gtacagtaaa ttttaaaaat tagccaggca    45720
tggtagcatt cacctgtagt cttagctact gggaggctg agatgggagg attgcttgag    45780
ccagaacttt gaggctacag tgagttattt tcacgccact gccctctagc ctggctgaca    45840
gagcaagacc tgcctcaaaa aaataagtaa aaaataaatt aaatttcaat cattagcagt    45900
cattaggata tttaaataca gtatgttgaa tcaaagttac gcatgtgtgt attttttttt    45960
ccagagagtt gtttatcatg tgggttttaa tttaacttta aaaaaatgtt ggctggacag    46020
ttgcccaaat ggtatcatca gccatttggt tgagaacgta tgtcctgcgg gctcctctgt    46080
cactggagtt ttgctagctg acagccactg gctagttaga gactgcagtc agcacagatg    46140
caggcgtgga cttgcgcacg taaccatgtc aatgcaaagc catcacttct taaaaattct    46200
gaaccctgct gtctgagatg gtggtgcagc ggatagaact ctgctctaag aggcagtagc    46260
taattccatg tcttctttgc ccttgactag ctgagtgact ttgcacatgg ggcttgcctc    46320
tctgttgcct tgtctgcaaa gtggaatcat cttttccttg ctagacagaa ggtggaccct    46380
ggacctatgg cctttttgag tttcccccc gcttcttaga aggacctctg atcctactga    46440
gtttaatacc cacgggttaa taattgggaa aagcaaagga agcgcttctg tttaggtaat    46500
tatatgcatg ttttttgtctt tttctggctg gaaagatatc caagccactg ggaaggtccg    46560
tggctaccca gggtagccct ctctggggag ggctgctata tccaagagcc cctcatgaga    46620
atttgaaaat cgaccatggt agggcctgct gacttttgac agctaatggt gtgctgagaa    46680
ttgtccctcc aaagatgcct ttccattccc tcgggagagt ctgggcagcc cctactgggg    46740
gctgggatgc tggctcttcc ctcagcctcc accccaactg ctctcttccc tcctcccctc    46800
cccagccccc taatttctct cacaaggctt tgttctgcag caacctttcc taatgcagtc    46860
ctggcctctt cgcagcttca ttacataacc ttccgtggac tcctggtcca aggatcaccc    46920
cagaaagcca gtcagaggta ggcacgcagc tggggtccat ttacttacct tccccacccc    46980
ctcggaactc agaggtggtg caggaatttg gactccaaga attaacagct ccaccaccat    47040
caccagagcc aaaactcagg atgcatgtgc ttcatctgct gcttatttcc agctgagagc    47100
cagtggtgcc atggttcctt agggagccgg tccctgatg ccggctcctg ccccaaatc    47160 tctctgatcc gggctcttcc agaatgtctt gtctccacca tcgcctttga ccaatggtgt    47220 cccctttgcct ggtaatgtcc cctttgcctg atgatggccc tgtcactcct ctctttagca    47280
cagaggaggc tgtttcatcc cttcaagcct gccctccctt caagtcttag ctcaagttca    47340
ccttctccgc agagccttct ccaatcttct tgactacgtc tcctctcagc tccagcaacc    47400
tctgtctctg gcactgattc cttacttagc taagagaatc acagacactt ggggctcagg    47460
acaatctgct ttctctcttc ttacccatgg ccttggactg tgtgtacctc tttgtctcca    47520
ctcccaaacc caaccccag agggcagaga gcatgttgtc tgtcccttg ctcagcatga    47580 agccatgcgt gtggtagatc ggcagagttc cataacttgt gttgaccgag gggtcacttt    47640
gctctgaaat taccctgtg tccttcagta tttgcacaga tagcttcctg ccagaccga    47700
```

| | |
|---|---|
| atatatccaa gggcatggcc cacctctgct cctgtttcca ggtccctggt gggggttagt | 47760 |
| tcatgccttc ctcataatct gcccactggc ctggtcctca aggtcttccc aactgctcag | 47820 |
| ccagagttga gaaatgggt cgctccatcc tgtttgtgtc gttctctcct tcctggccca | 47880 |
| ctctcctgcc cacaggtatc cagggctgc ctgtagcatt agaggacata catgcacatg | 47940 |
| cgtgggcatg ggacactcac gtagcctcca agcacagcat caataatgca ttctgtgctt | 48000 |
| tatagcatgg aaagctgctc taaactttat tacacagtgg acatgtctga agcagctccc | 48060 |
| aaatccaccc ctgagtgtgt tggaattggc aagcctatca cttgggagtc tagttttttt | 48120 |
| gttcgttaat aatagatgct tcctgtggcc ccagcttggc aattttgatt taaagtgatc | 48180 |
| ttaactgaag agactaatgg acgggtctga atttgtgcct tttaagcaca aagtattgct | 48240 |
| cttaattaac tggattctat cctttgagca ggcagaggcc ttcccccaag ggcgtcatta | 48300 |
| acgatccaca tctggacatc ttccaaagcc ttcttctgtt tcaggccaac cgcaggtgtg | 48360 |
| ttcctgaaca cccaggaggc tatgagagcc acatatgcct cccaaataca cacagtgtgc | 48420 |
| atgcccaggg acatagagca gtgtgcaaag tcccattcca tctctctcca cctgggagag | 48480 |
| gatggctctt ctgtctgatt catggctcaa agtggtaaag gagctcccca ctccccgtcc | 48540 |
| cacgcctact cagagtctgc aaatatgtat gcgatatgag agctcgtcag ttagctgtct | 48600 |
| tcagtgtggc gcacatttga ggagtctgac tcccctccag cacaggccaa tgtgcactgc | 48660 |
| tctcctatct ttgtaccccc actgttgcac tgtgcagagg ttggagccat agaagtacca | 48720 |
| gagctgtgaa aggagaggcc ccctctcacc tctgccctgg tctccatccc cactttctct | 48780 |
| aggaagctag taggtgctga caggggagag aagggagggg aggggtccag aaacagtggc | 48840 |
| tcatgcctgc aatcctagca ctttgggagg ctgaggcagg aggatcattt gaggtcagga | 48900 |
| gtttgagacc agcctgggca atgtagcaag accctatctc tacaaaaaga aaaatgtaa | 48960 |
| ttagctgggt gtggtggtgg gcacctgtag tcctagctac ttgggaggat gaggtgggag | 49020 |
| gattgcttga gcccaagagt ttgaggttac agtaagctgt gattgcacca ctgcactcca | 49080 |
| gcctgggcaa cagagctgag accctatctc aaaaaaagaa aaaaaaaag aaaggagaga | 49140 |
| gagagaaaga aagaaaaga aaaaaaaaa agaagggaag ggaaagccca gaagagtgtg | 49200 |
| gggagaggag gcggccgtca ttctggggcc ctcagtgtgc acaaccagat aacacatgct | 49260 |
| ctgtgggctt ttgtaccatt ttgcttgagc ataaagaaag gaaggctgcc cctaaataga | 49320 |
| aagcactctg gaggcaaaca aatctgactc caatcctggc cctgccactt tcccagctga | 49380 |
| ggacttagac aagcacccta gcctcttgga cattctcaga gccatctgct gcaagtgggt | 49440 |
| gctgccatac ccaccttact gggcaggctt gggggaccaa gggtggtaaa tggctcagtc | 49500 |
| tttcatgatg cggccacaca gcaggtgcgc catccaggtc catttctttc cttcctttcc | 49560 |
| cccaaatcaa gttgtcatta aagtactagt ccacattaat gaaatcaact gtattaattt | 49620 |
| tctatttgct gctataataa atcatcagaa atttagtggc ttaaaccaac acaaatgtat | 49680 |
| taccttacag ttctggaggc cagaagccct ccataggtgt cactgggctg aaatcaaggt | 49740 |
| tttggcaagg ttgcggtcct ttctggaggg tccaggggag aatccatttt cttccttttt | 49800 |
| ccagcttcta aaggtttcat gcattccttg gctcatgatc ttctatagct atagtcagaa | 49860 |
| aaattttcca tcaatcatct tcaaagccag caatggcagg atgagtcctc acatcacctt | 49920 |
| gctctgacac cagttctctg cctccctctt ccacatgtca ggaccctcat gattactttg | 49980 |
| ggctcactct gataatctgg gatgatctct ctattttaga gtcagctgac tgggaacctt | 50040 |

```
aattccatct acaaccccaa ttcctctttg ccatgtacag tgacatattc acaggttctg    50100
gggattagga cgagcctgtc tctgaaaggc tactttacat gaaaattcat ttttttaatt    50160 aagattttt tttcctcttg agacaaggtc tcactctatg gttcaggctg gagtgcagtg    50220
gtatgatcac agctcactgc agcctcgacg tctctgggct caggtgatcc tcccacctca    50280
gcttccctag tagctggaac tacaggggtg agcccccatg cccagctaat tttttttttt    50340
tttttttttt gagacagagt ctcactcagt cacccaggct ggtgtgcagt ggtgcaatct    50400
cagctcacag caacctccgc ctcctgggtt caagtgattc ttgtgcctca gcctcccaag    50460
gagctgggac tacaggtgtg caccaccacg cccgactaat ttttgtattt ttagtaaaga    50520
tggggtttca ccatgttggc caggctggtc tcaaactcct gatctcaagt gatccaccaa    50580
cctcagcctc tcaaagtgct gggattacag gtgtaagcca acatgcccgg ccccagctaa    50640 ttttaaata ttttttttgt agagatgggg ttttaccatt ttgtctaggc tggtcttgaa    50700
ctcctgggct caagcaaacc tcccaccttg gtctcccaaa gtgctgggat tacagcatga    50760
gccactgcac tcggccttaa gagaagattt aataattaat actttacaac aagatctgga    50820
agaggtggga tgagtaacta aatgaggata caagtaaccc gggtcatatt tgctaatacc    50880
cttggtcaca ttgaacttga tatcttatca gattttccta atcagctcct ttagcagcag    50940
tgttgcagca tcttatctca ttttgttttt tgtttttttg cctagcacat gcctgtaaat    51000
cactggattg aggtgtttag atgtttgttg tcctttggat gcttcttata aatccatatt    51060
tcatggctcc ctggaaagtg ctatgcaaat gataagctgc aaggatggaa aggaaattgc    51120
agtgctcctg aattgtaaat gggcttttac gaggaggttt ctaattactc gctctttctc    51180
ttgaactgag gagttgaagt gtaggtggca gatccataac agataatcat gtgtgtgatg    51240
tgacttcagc ctgagcgtcg aggaccaagt cacagagcag gaacagccac tctccagtgt    51300
ccttggggct acgtctgagg agaacctggg atttcatata tgacctgcac tggctggggg    51360
gctctcttga cgtaacgtgt tccctctgag catgttacag attctgacat tcttatgttc    51420
cttctgtgga gagacatgta cttagtgacc taactcactt tagcatattt ttgctcatcg    51480
tttgtgtagc ttaaaggaat cagataatta ccccctcccc actactttcg gaagcacaaa    51540
tgcaatgccc tagaattgta ctggggactc aaaaagaaaa gagagtagta aaatctatta    51600
aaggggacaa agacagccta tatactacaa gctttctatt tttatggcag agaatgccat    51660
tttctaagta aacagagaac tgcatttgac ctgcaatatc aaatgcatgg atttgatgct    51720
ttggaaagca actgttttct gcgttaatct gggtgtcttc cgtgaaatgt cctcctgcct    51780
ttggcttaaa cactagcttt gtctacagcc attccatcct gaacctgccc aatcttgtct    51840
gaatcctggt ttcaccactg acaagctgtg tgtccttggg caagttactt cacctgtctg    51900
tgcttcagag tcctcatctg tgagttgggg aatctggaca gaatctaccc cataggggcgt    51960 agtgaggatg tgttgaatta tcccaagtgg ctacacagag taagcactca aatgatgtca    52020
tcgttgtcat gattgctgtt accagagcct agagttcatt ctgatactcg agtctgtggc    52080
ccatccagcc caggtaagga atagttggag gagttgggca tgttcagctt gaagaggaga    52140
cgacagggga tatgggatag ttgaatctgt gaagggcccc ctgggatgaa gaactggcat    52200
gttctgtgtg gctccagggc actgagcagg acccatttgc caaagtctca gggacacagt    52260
ttctagctat agacagaaaa attttctgtc actcagagga tgaaaataga atgagccccc    52320
ttaagaggta atgagctccc tgtcattgga aggattccag aagagctagg taaccacttt    52380
aggtgctatc aaggggcttt tttctttaaa gtccttttcca aaagcttctg agattgcata    52440
```

```
aacaatagga agccatcttg gtgctttaac acaaactctc cccagtgatg agggttgagc   52500
caaagccaga ttggcaagca gagaggagac ttgtgtacaa ggagttcctc gagtcaattg   52560 cttttttcctt gttctagcca gccagagggc tcctgttgga aaacaggaga ccggagaggc   52620
tgaggcctga ccaaaccagc ttctgcaggc cagctgggag gccacaactc ctacctacgg   52680
gaaaactgaa gggcatctct attttttagat tagcaaaaga aaataaattt aagtttgagt   52740
ctcctttgca acttttaaaa gacatcttta ttgagatgat cattcacatt ctataaaatt   52800
cccccacttt gagttacaat tcagtggttt tagtcttcct tgatgatttt gatggtcttt   52860
tcttaaggct cttggaagac ccagaagcct ctcagacaca ggtgggtgtg gagggcgtag   52920
cacagaggca gacttctcat ttcctgggtc tccccttaa tgactctcag agacccctcc    52980 ttcccccctgc ccctggcttc taccccaggg gtgtagagtt ttgccatttt ccaagcagaa  53040
cttcatttcc tcttctgtgt ctacactctt tgtgcttctt tcttgccagc ttttctcct   53100 ttgcccgccc ttccttcctt ccttccctcc ctccccccctt ccctccttcc ctctttccct  53160
ccttcccccc ttccacccctt ccccccttcc cccttccct ccttccttcc ttccttcctg   53220
cctgccttcc ttccttcctt ccttccttcc ttccttcctt ccttccttcc ttcctggtat   53280
gtgactaatt tctgtttcag gacataaatg ttgtccaggc tgttctttgg tctttctgtt   53340
ggataatgga catttggcat tgagagaggc tgcttttttct gaaatcatgt tcttggggcc   53400
cagaacctag gtgtgtgctt ctgactttgt tttcttcctg atccaaattc tgatatgtcc   53460
atttaaattg atctagaccc acagggcact gtgggacaga tcctcagtgg aacatgactc   53520
tgtaacgaga gcattttgtt ttgtcaaaat gagaacatat tattgccttt catctgattg   53580
taaacataat acatgtttat aaaacagtat aatgagacaa aaatgtagac actaataagg   53640
gaaaatctcc ctaattgtat ttctcttcac agagaaagcc cctgttgggc atatatactc    53700
tagtttgttt atttgtttga ctacacatat atgtattctt ttcttatgta taaaaattct    53760
gaacatgcac atttctgcaa ctactgtttt cacttgatga tgcatggacc tctctagagt    53820
gtacgtttct tcttccttac aaagcagttg gcttcgccca gggtgcacca ggacacggtt    53880
ttggctctgt cccagggtg tcacgggacc aggggatgat ctcacagggt ctgccatctg    53940
ccctgcctgg ccggaggctg catcgagagg gccaagggc accacgtgtc gtgggtactg    54000
tcaaacaaga gccttcagag ccttccacag tctttctttt gcttcccagc attgcttccc   54060
cgctggtgga ctctgaatct agaactagct ccaggcgcct ctccaaattc agacgggagc   54120
tggggcacta ttataatgca aatctaggca aagccctccc aataccagga tccagaatgg   54180 ggtgggccc tttgccctga aaagctgttt agtttgaaaa tacaaacagg agacagaaaa    54240
gtttggctaa attaatggat aaagttttaa cgatggtaac catagtaggg ttcatcgaca   54300
gccagcgatg gttctgaaca cttgacatgt attaactcac ctaatcccca cattttacag   54360
acaatgcaaa ggaggctctg ggaggttgag tgacttgccc caaagtcgca cagctcctaa   54420
gtgaaggatt cggagtggac tccaggcagc ctggtctgac tccctgcact gcgctgtgct   54480
tatctctggc cccaatgccg ccatgcagaa gtgtctgggg gcactttgtc tctgtcagac   54540
agaattcgga gatgtgtatg cttgccctgg tatggcactt ctctttttttt gagacagaat  54600 ctcactctgt caccctggct ggagtgcagt ggcatgatct cagctcactg caacctccgc   54660
ctcccaggtt caagcaattc ttgtgcctca gcctcccaag tagctgggat tatagatgtg   54720
caccatcgtg cctagctaaa ttttttgtact tttagtaaag atgttgttttt gctgtgttgg   54780
```

```
ccaagctgat ctcgaacttt tggcctcaag tgatctgcct acctcagcct cccaaagtgc   54840
tgggattaca ggcatgagcc accatgcctg gcagtgtggc acttcttacg tgtgttcagc   54900
ggacactgtt tatcttctgt ccctccaaga cggtgctgag ctcaggtcgt tcattactgg   54960
cagacaactg ctgatttcca acagaattgc catcctcttc tcccctgcga ctttcagagt   55020
gtgacctcag actcaaaaat tagaagtgaa aacatcttaa aaactatcac cttttcttcc   55080
taatcctcct ctcccctccc tgtcttcctt gttgtcccca tctaatgaac tatcatggca   55140
aaaagagccc atttctggtc attttctgtg cctttcaaa ctcccaccta ccccactgct    55200
cctgggtgca ttacccgaaa gctgagactt cagtgcagaa agtgccaggc cctctgtccc   55260
cccagatcgc cttccttgtc ttccctgtgc ttgcctgtca cattgtgtgg gttccagcgc   55320
tggaaggaat gaggaacaga ttctctggtt ctccttttga gtttacctt cgctccacca    55380 cttctgagac cttcccggaa gttgcccctt gtttctctcc tctccagggc tgccccagag   55440
ctgcctctca cctcttcctg ctgtcacccc accaccatca gggcagaagt tgggacaaag   55500
cctctcctac tggctcctgc ttttctccct taggtccagc ctcctcttct ccatcttcag   55560
gagtctcctt ctccactcac acgtcatgac ttcagcacct cgcatcagtc cagaatatga   55620
ctgcttgttc aagtgccacc tttctcatgc attttttct agtgacaatc acagccaccc    55680
tgtggggcag gagtgtcatc atccccatgt ttcaaatgaa gaattgcagt tcagagaggg   55740
caagtgactg gcccagcctc aacagctagc cagtggaccc caccagggct tctgactcca   55800
gtccgggttc cctttccacc caaatccatg gagggagctg agccgagaac aggtgtcctt   55860
caggaagacg tgaagccaaa gcctccacct ccaaactcag ggggcccaggg agtccaggca  55920 cccatccact cacaaggctg gatatggtgc attccaggag aggggttggg ggcgagtggc   55980
ctctctgtgt acccgtgggg atagatgcgc aagtggcatc gccacatcgt gagtcctggc   56040
ttcatgggtg agctccaggt ccaacgagaa gccaagcagg gggcccttca agctcagctt   56100
tgggcccggt cgggggtaca gggtagagcg ggcctcccca gcccctgcca tgaggccaag   56160
gcagtgcatc gttcgcagcg tacattcaga aaccaaagcc taggagctgg ttatcattcc   56220
ggtttacagc tgatggaaga gcaggtgctt ccgagaaccc acagtgctct ttggccagtg   56280
acccaagggt gcctctgaga ggcctcgcag cacccggagg tgctgctgag caacgccct    56340 gactgtaaga aggaccattc atcccagag agtggccgtg atgctgctgc gacagtccca    56400
ccatccctcc cgactctcac tcccaacaga cttcccactg taaagctgaa ctctccagca   56460
aatcacctct cgccagactc tctcctcact ctctctgggt ccactagagg ttcctcagcc   56520
tctctttgcc ttggttttcc cagctgtaaa atggagcaaa gagggcctat gtacccacaa   56580
aggtgtggtt ggagcgactc ctcctacatt agggcctcga gtggggcttc atgattggtt   56640
ggtggaggtc tccaaaccca cccagtgcca ccgaaggctg agactgcaga tgcaatgcca   56700
caggtgtcct tcctcagcct gggcagctga acatcatgtg taaaacgggg ataataagat   56760
aataacagcc ccttgcacct atgtggctgt gaggattaaa caagataaat gtgtaacagt   56820
gcctggctat agaaatattt actcttgtta ttaagggaag aatatgtgtg gctaaaaagg   56880
gatcgaagat gtaaaagcca atccctcccc ctctagcata tttaagggta atgttgagtt    56940
ggtttgtgga ccatttgctg cctgttagag ctggaaggta gggacccct ctcaacagcg    57000 atgctacaaa ttatacccat tggaggtcaa ccaaaagaca aagcttattg gctggacatg   57060
gtggctcaca cctgtaatcc tagcactttg ggaggccaag gcaggcggat cacttgagat   57120
caggagttcg agaccagcct ggccaacatg gtgaaacccc atccctacta aaaatacaaa   57180
```

```
aattagctgg gcgtggtggt gcacacctgt aatcccagct actcaggagg ctgaggcagg   57240
agaatcacta gaacccagga ggtgaaggtt gcagtgagcc gagatcgcac cactgtactc   57300
aaaccgaggc aacagaggga gacgcaatct caaaaaaaaa gaaaaaaaga caaagcttgt   57360
taataccagc atattgttaa gggaataaag taggctgcag aacaactggt gtaatatggt   57420
gccatgtagg gaaaattaca tgtgtgcata ggagaggggt ctgcaaggtt gtgccctaag   57480
atgttagagt ggttcctttg cttttctctt ttataatttt gtatttgact tttaaataag   57540
gaccataaat cacttttata aaatacattc tctccagccc ctactactcc tttaaagaat   57600
aagagtggtt tgcccaagaa agacagtttt ttttgctctg gttttcttga ttctgacatc   57660
agaggaaact gcttctcatc cacttgggc tctgggttca ggggattcat ttcaggcaga   57720
ttaaagtggt gaccagggc attcgtggac acagggaggg acaggagcac catcagtttg   57780
tctcacacaa ccactgtcat cctcactgaa ggctgttgcc tgatcaaaaa cagtattggg   57840
ccaggcacgg tggctcacac ctgtaatacc accactttgg gaggctgagg tgagtggatc   57900
acttgaggtc aggagttcga gatcaacctg gccaacatgg tgaaaccttg tctctactaa   57960
aagttcaaaa attagccagg cgtggtgggt gcctgtagtc ccagctactt gggaggctga   58020
ggcaggagaa ttgcttgaac ccgagaggta gaggttgcag tgagccgaga tggcaccacc   58080
acactccagc ctgggcgacc gagggggact ctgtcttaaa aaaaaaaaa aaaaatatat   58140
atatatatat atatatatgt caaaaatggg gtagttttta gatctatagt agttctaaaa   58200
acaaaggcca tccaagcatg acagatttac aagcactatt ggctattcca gtagttacaa   58260
tggaggagag aagcttttag ttaaaacaaa caaacaacac aacaaaccca gaaaccttag   58320
gtcaaaacca aaattgtcct ctcagacaca atctgggaat tttctcatga cagtgggcat   58380
tagccaactg acatcagcag caaccatccg tgtgcacaca gtggcaccac ctcctcccaa   58440
aaagcagcct tcatctatgc cctcatacaa tcgttgatta ttctcttttgg attgaggccc   58500
ggaattattt aagtttcttc ttgccagcat gagtcttttcc ttttctgtatg ctccttatct   58560
tctctcttta atttggcagt tctgcttgaa atctgggtct ttcattagta gtagttcaat   58620
ttggttccag aacattctgt ggtgtgatgc aatgtgacca gagctcacac ttcagagctc   58680
ttcaagggcc agtcttactg agcacctccc agtggctgcc tgtgtgctgg gcgccacttg   58740
tggtgggcag gagagaggag gggacacaaa aggagacaca gctccttctt agaagctcaa   58800
agttggggac cagctgccac agaagagtat gtttagcatc tgagacacca agatccagcg   58860
tcacaagggt gtttattaag cctcctcatc tcttctttt tctttttttt tttttttc   58920
ctcaggcagt cttactctgt cacccaggct ggagtgcagt ggcatgatct cggctcactg   58980
catgcaacca ccacctcccg ggtttaagca attctcctgc ctcagcctcc ccagtagctg   59040
ggattacagg tgcccaccac cacacccagc taattttgt gttttagta gagacagggt   59100
ttcaccatgt tggtcaggct ggtctcgaac tcctgacctc agatgattca cccacctcgg   59160
cctcccagtg tgctgggatt acaggtgtga gccaccgcgc ctggccttgc tgttgattca   59220
tctatagtat gtttgacttg atgacctcca gttaccttag acagaggttc tcatctaagc   59280
tccaactttc catttccttt gtcctcgtct ttccccttaa ccctccaca tttctctcaa   59340
aatcacccca cttctaaaaa atactgttta ttttctttt aaatttcaaa ttatctatac   59400
tcattgaaat aaatcaaaat agcatggaat aagcgaaaaa aatggatccc acccttcccc   59460
actcccattc cctagggcta accatagtta accatttaat gactaggttt ttttgttgtt   59520
```

```
gttattttt  atttatttat  tttgagacag  agtcttactc  tgtcacccag  gctggagtgc    59580
agtggtgtga  tctcggctca  ctgcaacctc  tgcctccag   gttcaagcat  tctcctgcct    59640
ctgcctcctg  agtagctggg  attacaggtg  cctgccacca  cacctggcta  attttttgtac   59700 ttttggtaga  gacagggttt  ctcaatgtta  gccaggctgg  tctcgaactc  ctggcctcaa    59760
gtgatctgcc  caccttggcc  ttccaaaata  ctgggattaa  ggtatgagcc  accgcaccca    59820
gccctcctgg  gctcttttcc  tttagttgca  ctcgctcccc  gctcctggag  tagagggatt    59880
tccgagagac  tgtgggctcc  agccttcacc  taggcccagg  actaggatgc  ctgccctaac    59940
atttatcttt  ataccttaaa  gcaaaacagc  tggaccataa  gcattcaaga  acaaactgtg    60000
aataaggaga  aagttctccc  aggaaacaag  agctttagtt  ctgttgggcc  agcccttata    60060
ttccttagct  gttaccagtc  actgcttgat  ttaatctcgg  ctatcacttg  gcctgacagg    60120
tctgctgctg  gtgccaggat  gtctgggttt  tgaagcctgg  ctccattaca  tacttcctgt    60180
gtgaccttgg  gcaacttact  caacctgtct  gttcctcagt  ttccccagct  gtattatgtc    60240
agcataatag  tttgttgtgt  gaattaaatg  aggtaataac  tggaaatgct  tcaaacatgg    60300
ttcctatcat  gagaaatcct  gctttccgcc  taaatgtgct  ggaaaattcc  tggtggtgca    60360
gaacaggaga  ccagagcaaa  ggaaagacag  ggtgcagaag  ccaaaaatta  ccttggagaa    60420
caaagcgcat  gttaaggtta  tttttggatt  ctaggtttat  ctctgcttgg  tcttcagtta    60480
cctgcaagag  atccatttag  gggatttttg  tttgttttta  acgatagctt  tattgagata    60540
taattcatat  gccataaaag  tcactctttt  aaaatgtttc  cggtatattc  acaaggctgt    60600
gcagccttcc  ctgtccttga  ttccagtctg  agttttaac   tgaagggata  aggaggacca    60660
cgctttcccc  agaccagaac  cgcgggccag  ggggcgattc  tgctgagtca  ccgcgggcgc    60720
ctggtgcgcg  gcggcggagc  ccgggacctt  ccttggctgc  ccctagcga   gggccgcagc    60780 gcagcctgag  acacccgccg  gggccgctcc  acggccgtcg  gatttagact  ggaagctcgg    60840
tccaggtccc  cagcttgatg  cgcccgcggt  gtaggagacc  agcccgactc  gggcttcccc    60900
tgagcccctg  gactcttgac  tccagcaggg  cctgggtaat  gaacgtcagc  tccccttttcc   60960 caaaggggtt  gctctgttgg  gaaggcaccc  gtttgataca  gtagcataga  gatgggtttt    61020
agcatcaaaa  tatcagaatt  caagccttgc  tctctgctta  ctagctgtgt  gaccctaaaa    61080
aggtttctga  acgtctctga  gcttcagttt  cctcatcatt  ccttctcacg  gggtggttgt    61140
gagcattaca  gagatcctct  ctgtgaagcc  cctgtgagtg  gctcatcctg  agggctgaaa    61200
taaacatgtt  attaataatc  caaaactggc  aagggatgtt  gactggtccc  cctcccttgc    61260
ccaaggagct  ttctagaacc  tgagttatca  ttaccaaact  gtactgcctt  gagtaagaaa    61320
gttagaagga  atgggaagga  tggtggcagg  tggaggaagg  cggattggtc  atcacctcct    61380
tgcagcaaga  aacagcccca  gatcgtggga  aacctacaga  cctgctagac  agactaggag    61440
caaaagctgg  ggctttaaga  atccccaggg  aggttctcct  gagagagtag  ccagttggat    61500
tttgtaagca  gagatttgtt  tggggaggag  gtgacaacgt  agggagcaga  ggggcaaagc    61560
tgtcgggaat  cctgccttga  gggcagggat  gtgtgttggg  gggagttggg  tcactggggc    61620
tcggtggcct  tgggcaagtt  tctacctctc  aggtccttta  cccacctagg  gtcgccatcc    61680
tgcccacctc  acaggttaca  gtgagcctgg  atgcactgtc  atgggcaggt  gcccaggaaa    61740
atggcagaca  tgttccaaac  agcacgcagc  attcccagt   gatgcccagg  gtcaccttgg    61800
aggtgggcga  gatgcctggg  gtttctcgtc  caccccacaa  cacctcaggg  gacagccaaa    61860 gctgtcccctt  caggtaagct  gcacagaaga  tgtgaactct  gctgcaaaga  ctctattctt    61920
```

```
tgggagcaaa agggacccag ggtctcacct gcacatccct gtccctgagg gcctaggggt    61980
tcttggaggc cccagccttg gcaaaatgag gaagaaggtg aaggttgtct gggccctgc     62040 caggctcctt cctcggccac gcactcccct tcctgcacac acaccttct ccctccaccc     62100 catctccatt gttgtcagaa aagtcacaat aaaaaggtcc atattgtcta gttcccatac    62160
ttttaatttt taaaatttta tttatttatt tatttatgta tttttgaga cagagtctta    62220 acccaggctg gagttcagtg gcatgatcta ggctcactgc aacctctccc tcctgggttc    62280
aagtgattct catgcctcag cctcccgagt agctgagatt acagatatgt gccactatgc    62340
ccagctaatt tttgtatttt tagtagagac ggggtttcac catgttggcc aggctggtct    62400
cgaactcctg gcctcaagtg atctgcctgc ctgagcctcc ggaagtgctg ggatttcagg    62460
tgtgagccac cgcactcggc tccacacttt tcacttatta aaagactgtg gtgtccatca    62520
atggatgaat gaataaacca atgtggacta tccctcccat tacccaagga atgaagcacg    62580
gagccgtgcc aagatctgga ttcacagtga aagaagccag tcaccaaaag ccacgtgctg    62640
tgtgacttcc cttatacgaa atatccagaa gagatacatc catggtgaca gaaagtagat    62700
gagcagctgg ggactggcga aggggagaag ggggagcagc tgtctatgag gtccagcctt    62760
tcttctgggt ttggtgagaa tgttttggaa ctagatagag gtgatagttg tacaacattg    62820
tgaatgtact aaatgccact gaatcattca ttttaaatcg ttctttacgt tgcatgaatt    62880
ttaagtcaat caaaaacagt tgtttgaaaa gagaaaagcc tatgggtagc ggcagcagtg    62940
attggattta tgattcgatt ccatggctca tccctcccct gcctcacccc ctcgccctcc    63000
gacgtcttct tcttttactc tgaactgtta tctttgttct catctctctc tctctctctc    63060
aaccctgcag acacttttcc ctttctttgt ctgcccccac cctccagatt tccgtgtctc    63120
cagtgtctcc ctacgaggca tgaattgaga ctgggagggt gtgattctga agaaggcacc    63180
aacagtgact cagctagccc cttccccac cccgccccc gggcctcaat ttagctaaaa     63240
aaccacaggg acggactcag gaggcaatac cttttccaagg gtccctaaaa aatgtcccat    63300
tttagtgtcc aggtttcact caactttagt gcctccccta aaatgtgttc cttacctccc    63360
accccactgc atctaagtca ctgcctgaga aaacaggatt gaggaaagga gaaggaaga    63420 gagagagaga ggaggagaga gagagagagg gaggaaggct gatggattta gaaaagaaga    63480
aaacaagtgg tctgaggaaa acagccttgg tgtgtttatt ttcctgtctg tgtatcgctt    63540
ctcggccttt tggctaagat caagtgtatt ttcctgtctg tgtgtctcgc ttagattaca    63600
gggatctgtg ggtgatgaca cgtctggtcc aggctgcgta gtcacctcaa gggcatgctt    63660
attgatgtgt ttttcaattc actatctttg catgggagtc ccaggccaag aggcacagct    63720
gcgccatttg tctgttggtt tagatatcct ttatccagtt cttccagaga aatcatcctg    63780
cccttctgga ggaggtgggc agcaggggtc agagatggga gggaaaggaa ggagccaggt    63840
ccttggctag gatgccaggg tcccctgcct ctcacctggc ctgggctgga ggcctcctgc    63900
tgtcctgtca ctgatcacta ccccgcccca gcctcctgag ttagaagaca caggctaaag    63960
tagagtattt cttcattgaa aaacccatac aaaataaagg ttcataaaaa ataaaaattt    64020
agactgggtg ctgtggctca cacctgtgat cccagcactt tgggaggcca aggcaggtgg    64080
atcgcttgag ccctggggtt catgaccagc ctgggcaaca tagtgaaacc ccatctctac    64140
aaaaaataca aaaaattagc caggcatggt ggtgcatacc tgtggtccca gcttctcagc    64200
ctatggaccc acatagaata caatgtcagc ataagaaggg agccctgggg tcaccaaatg    64260
```

```
gtttgggcgg caaagaacct gaaggttgag agaagtggct tggttaccca gctgttggat    64320
gtgagacctg gccactgctt cttccatacc ctagacctgc accctgacat ctcaagtaaa    64380
aagttggggg atgttttatg gtccaggatg aaggaagggc agtgaggggc agcggagcat    64440
cactttgcat ttctgtctgc ctcttactgg ctgtgtgacc tggggcaggt aacttcccag    64500
actcctggga atcataacac ctatgatgat gatgatgatg atgatgatga tgacacctac    64560
ctcaaggatt gccctgaagg gtcacagaga tgcctgcaag gcacctgcat ggagcaagcg    64620 cccttctct ggcaggtgct gggtgagcac tacctgctgc caggccctgg ggctatggca     64680
ctgcgtgacc ctgcaagtcc tacctggcga agctgtcgtt cttgtgctca gtcagtgttg    64740
gttgtaagac tgagaagagt cacttcattt tgctctccag ggacatcttt ctgggtccta    64800
ttttctgcct atgtcaagta gcgcctcaag gatgctcctg aaaatgggct tgtctttctt    64860
aacatggcag gtaggtccca aagcattagc atggggcagc tgacctagcc cagccaatgc    64920
agtgcagtga ctcttgcaac cgagtctaat cagaaggtcc atgaacctac gagcatttcc    64980
tgtcccagga tcagggtgga ggctgagcct ccctgcttag agattcttcc catgcattcc    65040
acttttttcc ccaaaagaaa atattgaccc ttgagaggca cacagtttat ttattttgca    65100
tagtaaatag tagcctgtat tttaaggatg agttgatttc tgcatcagcc cctgtaggtc    65160
atcagccttc tattggtgca tctgactctc tctagccctg cagggatggt ggagggggag    65220
gggaaggagg gatctttatt ggaaaccagg acagtgagac tcattgccct gtcatctgct    65280
ctgtggtgct gaatgaggca gcccaacaga gaaatacact gagcgagcat ccccagcctc    65340
caaaacagtg gcgcattgcc ctgagtcctg ggaatgacct tgattctcc tgctcctgac     65400 ttggaaccca tggaaacctc tagaagcagc tgaggaaaac ccaacatgaa agcagaact     65460 ccacactgag aatataggag gtgatcggaa catacaatga ttcttgctaa gaccgattca    65520 cagttttttct tttttttcga tcgaagaaat actggagaag cctaaagaag gagtctaaaa    65580
actctggcac gtgggccaaa actgtccttg agctaagaat gattttcaca ttttttaagtg   65640 gttgaaaaat gaaataaaat aagatgatgt tttgtgacac atgaaagcta tgggaaattc    65700
aaattctaat atctataaat agtgttttat cagaacacag tcatgctcat ttatttatgc    65760
tcgatggctg cttttcccgct acaattacgt tgagcagtta caacagagac cacgtggccc    65820
acaaagcctt acaatattta ctatctggcc cttttccagaa aaaaatgtgc cgactcttga    65880
ccttaacctc agcaatttgg gaggccgagg caggcggatc gcttgagctc tggagttcat    65940
gaccagcctg gcaacatag taagactcca tctctacaaa aaatacaaaa cattagccag     66000
gcatggtggt gcacacctgt ggtcctagcc actcgggaga ctgaggtggg aggatcgcct    66060
gagcccagga gtcgaggct gcagtgagct gtgatggcac cactgcacct cagcctgggc     66120
gacagagcaa gaccttgtct ccaaataaat aaataatgca aagtaaaata aataaaacca    66180
tataaaaagg aatcaattta aaattataat gaaagctggc cgggcatggt ggctcacgcc    66240
tgtaatccca gcactttggg aggctgaggt gggtggatca cgaggccagg agatcgagac    66300
catcttggct aacacggtga aaccccgtct ctactaaaaa tacaaaaaaa aattagccg     66360 ggcacagtgg cgggcgcctg tagtcccagc tactcgggag gctgaggcag gagaatgtct    66420
tgaacccggg aggtggagct tgcagtgagc cgagatcgtg ccacttgcag tccagcctgg    66480
gcgaaagagc gagactccgt ctcaaaaaca aaacaaaaa caaaaacaaa aaaaattat     66540 aatgaaagcc aaggggcata gtagaacaaa ttttctagag ctcattaagt caaatgagtc    66600
accagttagt aaaacgcagt cacggggaag agagggcagg attctttgaa gcagcggctc    66660
```

```
tcctaaaaac aacccaccct tgtccagctg ccttccctcc tgagggtgtt ccctttgact   66720
gtgtgacccc catccctat ttcccaaccg tccaagccca cctctagcat aatacgagct    66780
tttaatccct ctccctgacc ccaacccgat tttgaagccc agtctagtat tttctcaaat   66840
acacttcttg gctccattcc ttcctttcca tcacctctgc cttttcactg catgcttgga   66900
ccactgcagt cagctccta tgaacagttg ctctctaccc atccaatcgg cccgcctgc     66960 tgctgccaaa ttcaccgagg gcacctctgt ggtgctgcct gtggacaaag tccaagccag   67020
ccacctcacc cacctacagg tgagtgggga gcagccagcg tgtccagtgg tttaccccat   67080
cgccacagac ttggtgatgt gtcgatgtgc agagaagggg tgttggcagc cacaacacaa   67140
gcaaccccgc cccatgtgag atctaagatg ggcgtgctgg gagccacctc tgagaatcca   67200
acagaaggca gagggagaa cggctcacac ggcacaaaca ctccttcctt tttttttttt    67260 cttttcctt tttgaaagga gtctcactct attgcccagg caggagtgca gtggtgcaat    67320
ctcagctcac tgcaacctcc gcctcctagg ttcaagcgat tctccagcct cagcttccca   67380
agtagctggg attacaggta cactccacca tgcccggcta ttttgtgt tttagtaga      67440 gacgggtttt ccctatgttg gccaggctgg tcttgagctc ctgacctcag gtgatctgcc   67500
tgccttggcc tcccaaagtg ctgggattac aggtgtgagc catgggcct agcctccttc    67560 catttaaatg tatgcctaat ttgcccattg agaacggctg agacgcattt taagtggcca   67620
gggtctactt agagttagtg ctcatgacca ggcccaggtc aagcctggct ggccagatgg   67680
tgcctttgac ctgctctgtc tctgtgcaaa ggaatgagct gaaggatggg ggtgcagtgt   67740
gtgggcagtg ggctggggct ggcaggactc agtgactaag ggaagagaac tttcctcact   67800
accagcctgt cttttcaggg caccgcgggg ggctttggga cttggtgatg aacacagcac   67860
agagagctgt ccagcatgcg ggtccctggc ttctcacact tcccaggctc cttcagaggc   67920
tctctccaaa gggagctgct ctctctagaa cccatgaatt tggaatatag gcaaccactg   67980
cattggggac cactgacctc aaacatagag accagagcaa atgggctca tcacgtgaaa    68040 ctcatctgga actctagcag gttcttttat atatatatat atatatatat atatatatat   68100
atatatatat atatatatat tttttattat tatactttaa gttctagggt acatgtgcac   68160
aacatgcagg tttgttacat atgtatacat gtgccatgtt ggtgtgctgc acccattaat   68220
tcatcattta cattaggtat atctcctaat gctatccctc cccactcccc cacccccaca   68280
acaggcccca gtgtgtgatg ttcccccttcc tgtgtccaag tgttctcatt gttcaattcc   68340
cacctacgag tgagaacatg ctgtgtttgg ttttttttgtc cttgcgatag tttgctgaga   68400
atgatggttt ccagcttcat ccatgtccct acaaaggaca tgaactcatc attttttatg   68460
gctgcatagt attccatggt gtatatgtgc cacattttct taatccagtc tatcattgtt   68520
ggacatttgg gttggttcca agtctttgct attgtgaata gtgccgcaat aaacatacgt   68580
gtgcatgtgt cttataaca gcatgattta tattcctttg gttatatacc cagtaatgag    68640
atggctgggt caaatggtat ttctagttct agatccctga ggaatcgcca cactgtcttc   68700
cacaatggtt gaactagttt acagtcctac caacagtgta aaagtgttcc tatttctcca   68760
catcctctcc agcagctgtt gtttcctgac ttttaatga tcgccattct aactggtgtg    68820
agatgttatc tcatggtggt tttgatttgc atttctctga tggccagtga tgatgagcat   68880 ttttcacgt gtctgttggc gaactctagc agcttctttt cacaagttca tggagagagg    68940
tttcccactg agggaatcac atctgtctga tcaaagagg cttgggaaat ggctctcctg    69000
```

```
ttcattccct gaaaacctct gatggaacca ctgccactgt ggcagcccca gcactggcac    69060
cccagccatg attggtgccc cagccacatc tctgctgtga gccccagagc cctggttaat    69120
taatcatcca cgtgttgatg gggagaggcc cattcacaaa agcgacataa agcccaggga    69180
gacgtggccg tggcaagaag ggtgtgggac tacattccgc ccccaactga gagattcaga    69240
aaccagaaaa aaatggaaaa acatactgtg ctcttgggtg ggaaaactaa atatcatgaa    69300
gggagcaatt tttatagttt tggcctataa tacaattcca gccgaaatcc cagtggaact    69360
ttgagaattt gcaggaaaaa aaaaaatgtc taaagtacat ctggaagaca aacttacaag    69420
aaggtcaaat aattttgaaa aagaaaatga tatctaagcc cacctagaga ataagacttg    69480
agatccaaag ctaaatcagg aggctctagc aaaattgaca gataagcagg acagagtgca    69540
tggtgcattc acctgggaa gagggcagat tggtctacaa ataggcctgg gtccactgac     69600
tttagctgtt atatttgggg agaaactttt caacctcact ccatcttaaa cctaaaaata    69660
ttccagatga attaataaat ataaaaaatt agaccactaa aaatgtagaa gaaaatggat    69720
gatctttcta taccatagag caatggaata aatcacaaag gaaaacagat ttgactatat    69780
aaaacttaaa ccctgcccat caaaaaccat cagaaaccaa aataaaaggc aaccaactgg    69840
agaagatagt tgccacaaat atgatcaagg gttaatgtta ttcataaatt aagagcccac    69900
acaagtcatt agaataagca ctgagacctg aacagacaag caaaaagaat gagagtgggt    69960
cggcgcggcg gctcatgcct gtaatcccag cactttggaa ggctgaagca ggcggatcac    70020
ttgatcccag gagttccaac accagcctga gcaacatggt gaaaccctgc ctctacaaaa    70080
gtcataaata ttagccgggt gtgatggcac acgcctgtag tcccagctac tcaggaggct    70140
gaggtgggtg gatcacttga gcccgggagg tagagtctgc agtgagccaa gatcacaccg    70200
ctgcactcca gctggagcaa cagagtgaga ccctgactta aagaaaaaa aaaaaaaag      70260 aggagaaaaa tgctgatctc actagtaatt aaaacatcag gccaggcgca gtggctcaca    70320
cctttaatcc cagcactctg ggaggctgag gcaggcagat cacttgagat caggagttct    70380
agaccagctt ggccaacatg gtgaaatccc gtctctacaa aaaatacaaa aattcgccaa    70440
gcgtggtggc acatgcctgt gatcccagct actcgggagg ctgagacagg agaattgctt    70500
gaacacggga ggcagaggtt gcagtaagct gagatcgtac cattccagtc cagcctgggc    70560
tacagagcga gactctgtcc cagaaaaaat taaaacatca catatttaaa caactctagg    70620
atatcattta aaaaaacatt aatagactgt tttttagagc acttttaggt tcacagtgaa    70680
actgagtgga aggtacagag acttcccgta tgttccctgc cctccacgta cagcctcccc    70740
cactgccaac gtcctgcacc agagtggtac acttgttaca accaatgaat cctcattaac    70800
atatcattat cacccaagtt catagtttac attagtaaaa catcatcttt catctataag    70860
cacaaaaatt ttttggcatt tatttaggtg tatgattaac tcagtgttga caagactcac    70920
acttcatacc cacttgcact gcatctgaga agcaattggt gtctacagcc gctacaccct    70980
caacaagccc gatcttgttt gaaaagcaat tggtgatgct tctcaaaatt ctatggacaa    71040
agtcagccgg gcatggtggc tcatgcctgt aatccctaaa ctttgggagg ccgaggcagg    71100
cagatcacct gaggtctggt gaaaccctgt ctctactaaa aatgcaaaaa ttacccaggc    71160
atggtggctg gggcctgtaa tcccagctac tcggaggct gaggcaggag aatcgcttga     71220
agcaaggagg cggaggtttc agtgagccaa gattgcacca ctgcactcca gcctgggtga    71280
caagagtgaa actccatcta aaaaaaaaa attatgacaa aagttttca aaagatatt        71340 taatgcaact ttatttgtaa tattggaaca tctgaggcca tttcagtgct aactattagg    71400
```

```
ggatggttag gaaaatatgg tacatatgtg gaaaggaaca tttggtagtt agtgccctg    71460 atgtttacaa aggcttttag tgaccaacaa atgctcatgc tataatctta tgtgaaaaaa   71520
gcaagtagca taattgcaac tatattttta atgcatagaa taaaaggcta gaaggaaata   71580
tcacagatcc ttgacataca ttcccaaacc tttgtaaatc cgcggattca tgaaaacaga   71640
cacatttgca caagtgcctg atcttttctg ttatacattc attagaagtc aagccctggt   71700
gccacaaagt atctgccttt tcaaatgtga tcagaatgtt ctcttttgct tcaaggccat   71760
ttttcacgaa gcagtggcat ttttgcctct tcatcagagt caccgtgtgc cctggaggac   71820
tgagaacagc agagccgttt taggatggga cagggcagcc aggaggattg ggctcactcc   71880
ctactgagtg cctcactccc gtacagcccc catagaggaa gaggggttca aatttattcc   71940
tcagccagat ggcatgtgcc gcctgtcctg gaatttcaca tcacttatga tggaccaaaa   72000
ttccaaaagc tgaatccatg attgtcaaag tctggtatgg caggatgtca acagtaatcg   72060
tttctgggca gagggatgat tttctcttcc catcttgctt tgtataaata cattttctat   72120
aataaggttg tattacttt ctcatcaaga aatagcaaag tactgtttta ctcaaaatat   72180
gaatagagcc aggcatggtg gcagcttatg cctgtaatcc caacactttg agaggcggat   72240
atgggaggat cactttagcc caggagtttg agaccagcct gggcaacata gtgagacccc   72300
cgtccccact cccccaaaga aacccacaa agcatttatc ctggattatt cacaggggcc   72360
aaaaaaaaaa aaaaaaattc aggcctccta tagccatgag ctacgaatat gaaaatatgc   72420
aaatgtgtaa gaaaagccag cacatccgat ttttactttt actttcacac ctctgtccac   72480
catgttccaa gagaagaaac ttggtcattg aaaggaatag atcaaatcca agaacaaaa   72540 ccactgtgct cattaaactt cttagtgttc acaaagcttt agctgcaggt tgaatggggc   72600
aacccgaatt ggctggctca cctgggctgc agggagcaga gatcgcgaca ctgcactcca   72660
gcctgggcaa caaagcgaga ctctatctca aaaaaaaaaa agttcataaa ttcaaagtta   72720
tgaattattt ttaaaataat aataatttac aataaagatg aggacaaagt gtgagtaaat   72780
ggtggtttct atccagctct gttgagctga agtggcatct ccctgctggg gcttttgggg   72840
aagaagggtg tgtgttgctc ttcagatccc aagcctcatg cccctactgg gcctgtggg    72900 gtgcttctca gcccaccagg agagccaccg ttgaacaca cacgtggggg acctggtggg    72960
tgccggtgtg gtgaatgggg ccacagcct gactccagga agccagcaaa ctcggagctg    73020
gaggagtcag gacaccccg atgagtcaag agttggtttt gctgccagtt gacatctgat    73080
tgaaccatct cttcacttct ccgtgcctca ctttccttac cagacaggct ctgctgatgc   73140
tgtccctctc ctgttcagtc gtgccctcac cgttaaagag aaagagcaaa ctgctgggca   73200
gcagcattga ttttttttaat gaagtggaaa gagagctggg aataacaagt cgggcccacc   73260
tcacctgcct cacctggtgg gtttatttgt tttgttttt tttttttgtt ttgagacaga    73320
gtttcaccct gtcacccagg ctggagtgca gtggtgtaat ctcagctcac tgcaacctcc   73380
acctgccagg ttcaattgat tctcctgcct cagcctcccc agtagctggg attacaggca   73440
cctgccacat gcctggctaa ttattgtatt tttagtagag atggggtttt accatgttgg   73500
ccaggctggt ctcgatcccc tgacctcagg tgatccaccc acctcggcct cccaaagtgc   73560
tgagatcaca ggcgtgagcc accatgcctg gccgtcacct ggtggtgttg aatatgaact   73620
gctgcggtgt tggtaaatta agcaagcaga tagatgtaaa taacgcttgg gcaggaatat   73680
ggagcacggg atgaggatgg gcggccaact gttagagagg gtagcaggga ggctgagatc   73740
```

```
tgcctgccat gaactgggag gagaggctcc tctctctctt caccccccact ctgcccccca    73800 acactcctca gaacttatcc tctcctcttc tttccccagg tgaactttga accaggatgg    73860
ctgagccccg ccaggagttc gaagtgatgg aagatcacgc tgggacgtac gggttggggg    73920
acaggaaaga tcaggggggc tacaccatgc accaagacca agagggtgac acggacgctg    73980
gcctgaaagg ttagtggaca gccatgcaca gcaggcccag atcactgcaa gccaagggt    74040 ggcgggaaca gtttgcatcc agaattgcaa agaaatttta aatacattat tgtcttagac    74100
tgtcagtaaa gtaaagcctc attaatttga gtgggccaag ataactcaag cagtgagata    74160
atggccagac acggtggctc acgcctgtaa tcccagcact ttggaaggcc caggcaggag    74220
gatcccttga ggccaggaat tgagaccgg cctgggcaac atagcaagac cccgtctcta    74280 aaataaattta aaaattagcc aggtgttgtg gtgcatgtct atagtcctag ctactcagga    74340
tgctgaggca gaaggatcac ttgagcccag gagttcaagg ttgcagtaag ctgtgattat    74400
aaaactgcac tccagcctga gcaacagagc aagaccctgt caaaaaaaaa agaaaagaaa    74460
aaagaaagaa agaaatttac cttgagttac ccacatgagt gaatgtaggg acagagattt    74520
tagggcctta acaatctctc aaatacaggg tacttttga ggcattagcc acacctgtta    74580
gcttataaat cagtggtatt gattagcatg taaaatatgt gactttaaac attgcttttt    74640
atctcttact tagatcaggc ctgagtggcc tctctttagc aagagttggt tagccctggg    74700
attcttactg tagccacatt aataaacaac atcgacttct aaacattcta taataccatc    74760
ttttggccaa attgacttcg cctcttcctc tctctttcca aatgaaatgt gtttcatttc    74820
actgtcagac cacatggttg gggacccac agagcacaca gccctccctc tgccttccca    74880
tgctggccct tcacccactg ctggagtgcc aggttggtcc aagggttgga ccaagttgtc    74940
tgaggttgtc tcaaggttgg tcgaggctgt ctccgcgctg ggttgtgcta caaggagccc    75000 ttcttttccat gggtgtggct ggcagtgagt gctcacagca acagcccaca gtgcagcccg    75060
agggcaggat ggactcagtc cctgcctcca tacccatttc taaggaggca aaatggcaaa    75120
cactctactt ttctcttta atgctaaaaa taagaaaaca ccttgcagcc cagggtatgg    75180
gtagtgcatg gaagccgtgg agttgtgagg tgggaagtga cctctgctgg atatgtctat    75240
tcaggaagat tgctggagtg ggtggggtct ctgggaggtc ccctgagtgt gggaagctgg    75300
gaccaccagc tttctcgcac agggagtggc catcccagct tggagaggtt ccaggactgg    75360
ttgggaggca cgtttcagat ttctatctgt tgaatcagcg aagatattgg attatgagga    75420
atttgggaat taggaaagtg ggtgcaggtg ggttggggggt aggtgaagga agacatgggc    75480
gtattggggg agcagggget gctcagaggt gttccagaag ctctgggtga ggaggtgaga    75540
gggaccgggg aatgcagctc ggcccagcct ccctgcctga ggtcagccat cacgtggtga    75600
tggcaagatg gaaatgtgct ttctgactgc tccagccagt gctgccagat tcagctcccc    75660
agggagggca cctgagaggc tccaagccag gagatctgtt ttctcctttg ttttgttttt    75720
ttttgttttg ttttgtttta ttatactttta agttctaggg tacatgtgca caacgtgcag    75780
gtttgttaca tatgtataca tgtgccatgt tggtgtgctg cacccatcaa cttgtcattt    75840
acattaggta tatctcctaa tgctatccct cccccctccc cccaccccct gttttctcct    75900
ttgaatcctt cttagaggcc gggcgcggtg gctcacgcct gtaatcccag cactttggga    75960
ggctgcggca ggaggattgc ttgagcccag gagttccaga ccagcctggg caacatagtg    76020
agacctcgtc tctacagata ataattttaa aaattatccg gcatagtgg catgcaccta    76080 tagtcccagc tactcaagag gcagaggcag gaggatcact tgagcccagg aggcggaggt    76140
```

```
tgccgtgagc caagatccca ccactgcact ccagcctggg cgacagagac ccccatgtca   76200
aataataata ataataaata aatccttctc agtcccttcc tcactgtgtc ccctccact   76260
gaattttcc acctcctctc ccacttccc cactcccgct ttccctctcc ttctctcccc    76320
actccatctt tttcttctc tgctgtttct cgtccctccc tcctctccat cccacaacac   76380
tgcctaccct gtccctgccc caccctggtg ctcaggatgt gtgaagtgag gggtggtagc   76440
ccccaagacc tcaaccccga aggttagcct gttgaaacca ctttctccca gctgccccc    76500
tggcagttgg tgctgctggg ggaaactggg attgggggcc agattttgcc tcttttcctg   76560
acaaagagag atgaagagtt ctctcaccag gtgcctggga ctgggtgtg ggtgtcccag    76620
cctatcccag cgcatctgtt ctgcatcatg attaatagtg ctgctttcag ccgggcgcgg   76680
tggctcacac ctgtaatccc agcactttgg gaggctaagg tgggcagatc acaaggtcag   76740
gagttcgaga ccagcctggc caacatggtg aaacctcgtc tctactaaaa atacaaaaat   76800
taaccaggtg tggtggtggg tgcctgtagt cccagctact tgggaggctg aggcaggaga   76860
atcacttgaa tctgggaagc agaggttgca gtgagccaag atcgtgccac tgcactccag   76920
cctgggtgac agagtgagac tccgtcctaa aaaaaaagga gttttgctct gtcgcccagg   76980
ctggagtgta gtggcgccat ctcggctcac cgcaacctgc gcctcccggg tgcaagcgat   77040
tctcctgcct cagcctccca gtagctagg attacaggcg cctaccacca cgcctggcca    77100
gttcttgtat ttttagaaga gacggggttt caccctgttg gccaggctcg tctgggactc   77160
ctgacctcag gtaatccgcc cacctcagcc tcccaaagtg ctgggattgc aggcatgagc   77220
caccgtgccc agtcaactcc ttctcaaaaa aaaaaaaata gtgctgcttt ctctttcaag   77280
tgtcctgatt tgggtgatag taaatgccac tctacttata agggatctac ctcagaatgc   77340
taattgggac atttttgtag cactctactg ttggcagcag gtgatgctca caacagcccg   77400
tgagggtgga tgacgtccgc ttcacagatg acaaaggagc ctcatgctca gaccgtgggc   77460
tgccagagca ggtccatggc tgcagcccca catggaccat atttccccct tgtcactctt   77520
tccaccaagc tcccttggaa cttcagttat taagctctct tgggtggaat ccaagttaga   77580
atcacaacat gtgcctcata tggattgtgc cagtgaaaaa tgacattcta tttagaggca   77640
gggcagcctg gcttagagtc agtttaaaat atgtattatg ctgcaacaaa tgtaccatga   77700
tcctgtaaga tgttcacaac aagggaactg gatgtggggt atactgtctg tactaacttc   77760
acaagttttc tgtaaatcta aaactgttcc aaaataacaa gttcgtttaa aattaactcc   77820
aggagaccag gtacggtagc taatgcctat aatcccagca cttcggaagg ctgaggcagg   77880
tggattgctt gagcccagga gtttgagaca agcctgggca acatggtgaa atcctgtctc   77940
taaaaaaat cacaaaaatt agccaggtgt ggtggcgcat tcctgtagtc ccagctactt    78000
gcggggctga ggtgggagaa tcatctgagc ccaggagttt gaggctgcag tgagctgtga   78060
ttgtaccact gcactccaac ctgggcaaca gagcaagacc ctgtctcaaa aaacaaaat    78120
gaaataaagt ccaggaaaga agtaggtttt accactctta ttttctgaag agaaactaa    78180
atttaatgtg taaagtgagg acaagttcac caagttagtg tttgagttgc ctaaaatatg   78240
tttgctaaaa ctattcaaag cttttcacata aacatgatc agaagttcta tgccaaaaca    78300
tatgtgtgtg tatatatata tgcactatat atactgtata taaaaatgca aaatctaaat   78360
tgccaacctt ttgaaaattg ctctgaaagg aaagcatttc aagataattt gcttacccaa   78420
agaatatact ttccaagaaa gcaagtaata cttaaggtgt tcataatcct catcaaatta   78480
```

| | |
|---|---|
| attcttgcta ctgaaagctt acaaggagct gttttgatgt cgggtgtgac aggtttgact | 78540 |
| tggcagaagg tgtcactta ctaacaacat tttaaataag tgacagaaga caagaaacta | 78600 |
| cacgttaaat gccagaacaa agagtgtcta agtggatgct aagagttgaa atatggctgg | 78660 |
| atacctgccc aagagagctg aaaagtagat gaaagttggt tacctataaa ctagtgcacc | 78720 |
| ctaatgaatt aaaaggtgtt gatgagttaa cttgttatgc cttccagata agacatgcaa | 78780 |
| atggggcttc ttcctccttc actacttcca agggatttaa caaggagacc aatgcaaatg | 78840 |
| ataaggactg tagggctcaa gctggggaca gattggggaa aggggaccca tcatgcccat | 78900 |
| atagatgtcc ctgtgccctg gcagtcaagg ctgctgaaaa ataacaaaac ccagaagtct | 78960 |
| gcgtgatgct gcctctccat ttgtccaaag ccttcttgcg gcagtttgca ggcttttgca | 79020 |
| aaagctccag gaccaaggag ctatgttcat gctggaagct tgttcaggat tagctgttct | 79080 |
| ttgtgggatg ggtgcagcca gggccaggtg tccagggaca gtgttttaac aaagggcatg | 79140 |
| aggtgtctga tctcacagtg gaactccact tgccttttt tcatcttctc attctgcttc | 79200 |
| atgcacagaa ccagccccat cctgaaactg actctaaatt actcccgccc caggtggagt | 79260 |
| gcctttctcg gagttcaaca gagccttcct gtcgcccaag ggacaactcc actgaatgcc | 79320 |
| caagccacac ccaaaaccta acaagtaaaa accaaattct gtgctccccc atcctgggcc | 79380 |
| attcctggtt tctctactgc tgttggtgat accaccatca gcttgtccat catgaccctg | 79440 |
| gccagttcct cccacaaccc tccacagcac ccagggacct cacctccatt ccatccgaca | 79500 |
| cagatctcct caccacaaac cttggttttg caacagcagc catgagacct ttacaccctc | 79560 |
| cgcccttcat cctgtccccc actgaggccc cagagccatt ccttaaagca gcgcgccaca | 79620 |
| aactataacc cacaagccaa ttctggtacc cagcctgttt tgcacagcca gtgaactgac | 79680 |
| aatgatcttt tcatacagcc agaaaaacaa aacaaaacaa aaacaacaa aaaaaaccc | 79740 |
| caccattctg agcatgtgac ttccatgttc aagatgtctc atgttcagaa aggcccctgg | 79800 |
| aaaaggagga aggggagctg ggcacaaagg gagaccctct cagctgagct cctcccatcc | 79860 |
| agacattttc ctggacttcc tatccaatga cttcccttag cttcttatca gccaccctg | 79920 |
| tctgcccagg aggctggaag atgtggcctt ttaactgggc acagctctgt cctctatcat | 79980 |
| atcagggctc tgttcccaag gagggtagag agaatggaca ccaggtggac cctcagcagt | 80040 |
| ctgtgccaca gagggagtgt ttgcaatttc cagactaaaa gtccccatgt gcttgacggg | 80100 |
| gtatgtgact acaacgtgat gcttgacttt tcctcatatg accagagcca ctttgtccat | 80160 |
| ctggtacaat gtcagctatc tgctaggggc cctccaggat tcccagtcaa ttccatatct | 80220 |
| gcatcaccac cattggcact aaataaaata aaatactcaa gttcctgctg gtgagcatga | 80280 |
| gcagtgctac actgggccct tcaaccaagg tgacatgata atgactgaaa ataatcactg | 80340 |
| ccacttattg gggacgtctc atctgccagg catggtacaa agtgctttaa ataagcattc | 80400 |
| aacaatttca tgctgacaga agccctgtga gccagtggag ctactactat gcccattata | 80460 |
| caggggagaa aactgaggca gagagaggtt aggtaattcg ctcagcctca cacaaccaat | 80520 |
| aggtggtgga gccaggattt gggccccatc tgcctgactc tctagaggct ctatcttcca | 80580 |
| gtcttccaga gttgagtcta agccatgaat aggacaatta gacagcagag gaaacccatt | 80640 |
| cagccaccat gtgcatgaag agtaaggaat ttctgtcata cagaggggag tgaattcact | 80700 |
| gagctgagag ctgaggaacc attgatctga tggctgagac accactggga agactggaga | 80760 |
| ggcttttctg gcatgcagt gccaggcaca ggaggagctg agggagatg actaagaggt | 80820 |
| actggcaaag aattcagaaa ttctgatgga agctttacat gttaccatca catccatcca | 80880 |

```
tctatccacc catccatcca cccatatctt cctccctcca cccaatcatg catacatcca    80940
gtcatctata caccacccac ccacccatcc atccatccat ccatcccttc atccatccca    81000
tcatccatcc aattatacat acatccaatc atatatctgt acataatcca ttcttccctc    81060
ggttcatcca tccatccatt catccatcca tccacccatc ccttccttca tccttcctat    81120
catccatcca atcatatatc tgtacataat ccattcttcc ctcggttcat ccatccatcc    81180
attcatccat ccatccaccc atcccttcct tcatccttcc tatcatccat ccaatcatac    81240
atatatccaa tcatacatct gcacatcacc agctcatcca tctatccatt tatccatcca    81300
tccttccttc catccatcat tcatccatca tacatacatc taaccataca tctctacatc    81360
attcattctt ccatcgattc atccaattat ccatcattcc ttcctccatc catcccatta    81420
tccatttgat catacatata tcatctatac atcatccatt catccatcca tccatccatc    81480
cacccatatc ttcatccaat caatcataca tacatcgaat catctacaca tcacccatcc    81540
atccatccat ccattcatct atccacccat ccatccatcc atccatccat tcatctatcc    81600
acccatccat ccatccatcc atccatccat ccatgtaacc atccagtcat atatccaatt    81660
acacatccat ccagttatac attcatacat gcatctaatc attcaattat acatacacac    81720
atccatataa ttctacatcc aattatacct ccatccaatt acacattcat acacccacct    81780 aataaaattat taattcatat atccatccat ataattatac atcaattata catccatcta    81840
atcattcagt aattcaccca ccatccagtc atctatccaa taatacattc atccaatcat    81900
ccatccatcc atccacccat tcatccatcc atccgtccgt ccacccatca tggtatgagc    81960
catgatttac cacgatggtc ccctgtggac agcccaggtg gggcagaact gaagggaagc    82020
ccagggctgc ccccataaac atttgcctcc tttacatgga tgagaactag atccacatgt    82080
ataaatcctc atgatttgaa ggtgcttttta ccaacattca ctcatgggat tctcccagga    82140
gctctaggag gaggcaggta gagttgaggt catctcacgc attttacaga tgaggaaacg    82200
gaggccctga gaggcaggtc caaggccacc tgaccagaaa gaagtggaac tgggacttga    82260
acccagccat cttgcccctt ggtcccatgc tctctagcct gtaactcctg cttcctggtg    82320
gggcatctcc aggaggaccc tatcggctgg ccatgggcct gccctggagt cttttgctct    82380
gtgtggccat ccttcctccc tcaggagagt gtgtgctccc agagcacagg ctgtatcttc    82440
tgagcatttt gtcccttccc agtacctagc actcagctct gtatacattg ggctctcaag    82500
aattctcaac cttccagagt gtaaggcctt gacctgctca gccctggata ctgcatgatg    82560
cattgataag cccataaaat aaccagggca gattgactcc cagtggccaa agtgccacag    82620
ggaagggaca attcagccct tctaggagga ggaggaggta gttttctcat ttctattaag    82680
gcaacaaaag ctgccttact aaggacattc ttggtggagg gcgtgactgt caaccactgt    82740
gatcatttgg gcctctcttg cccaggcttc ccattctgaa aggacagttt tattgtaggt    82800
acacatggct gccatttcaa atgtaactca cagcttgtcc atcagtcctt ggaggtcttt    82860
ctatgaaagg agcttggtgg cgtccaaaca ccacccaatg tccacttaga agtaagcacc    82920
gtgtctgccc tgagctgact cctttttccaa ggaaggggtt ggatcgctga gtgttttttcc    82980 aggtgtctac ttgttgttaa ttaatagcaa tgacaaagca gaaggttcat gcgtagctcg    83040
gctttctggt atttgctgcc cgttgaccaa tggaagataa acctttgcct caggtggcac    83100
cactagctgg ttaagaggca cttttgtcctt tcacccagga gcaaacgcac atcacctgtg    83160
tcctcatctg atggccctgg tgtggggcac agtcgtgttg gcaggagggg aggtgggggtt    83220
```

```
ggtcccctttt gtgggtttgt tgcgaggccg tgttccagct gtttccacag ggagcgattt    83280
tcagctccac aggacactgc tccccagttc ctcctgagaa caaaaggggg cgctggggag    83340
aggccaccgt tctgagggct cactgtatgt gttccagaat ctccctgca gacccccact     83400 gaggacggat ctgaggaacc gggctctgaa acctctgatg ctaagagcac tccaacagcg    83460
gaaggtgggc ccccttcag acgccccctc catgcctcca gcctgtgctt agccgtgctt     83520
tgagcctccc tcctggctgc atctgctgct cccctggct gagagatgtg ctcactcctt     83580
cggtgctttg caggacagcg tggtgggagc tgagccttgc gtcgatgcct tgcttgctgg    83640
tgctgagtgt gggcaccttc atcccgtgtg tgctctggag gcagccaccc ttggacagtc    83700
ccgcgcacag ctccacaaag ccccgctcca tacgattgtc ctcccacacc cccttcaaaa    83760 gcccctcct ctctctttct caggggcca gtaggtccca gagcagccat ttggctgagg       83820 gaagggcag gtcagtggac atctgatctt ggtttagtat ccttcatttt gggggctctg     83880
ggtgtggcct gggcctctgg actttggcca cggtgtttgt tccagccctt ctcctaacct    83940
gtcctttcca gacactcggc atctaggtta ttagcacctc gcatactttc tgacatgctc    84000
ctcagtcctg attttgacca tcttctcttg cttcccatct gtgtcagtca agactgcatt    84060
tggctgtaag aaacagaaac cccaactaac tgtggcattt acatgaagag gtttacttttt   84120 ctcacataat cagatgtcta gacttggcca gcacctcaag ggtcattgat gctctcctgt    84180
ctttattttc tgtcatcttt agtggttgga ttgttgcctc atggttacaa agtggctgct   84240
gcacttccag gcatcacatc tgcctttgaa gcaggaacaa gttgcaaagt aaagtggcca    84300
aaagggccct gaaactaaat gtgtccccctt aggaaagcag gagttttctt gcaagtggca   84360
atcttctgct tatgtctcat tggccagagc tgggtcttac ggccacccct tgctgcgagc    84420
aaggctggga cattgagcat tttgccgtcc aacctcttta gcagaataaa ccaaggggga    84480
agaacgttaa tagtggcttt tgagtcacta gttggcagta tctgcccctc tatctttcca    84540
tcctccccat ggagtttcaa ggttcctttc tcagtacttc ttcaggctct gcacgttcat    84600
ttggatcttg tgtcttgggg tgaaaaactg gcccaagtgt ctccccaagc atccacctttt   84660 ggattaattt ggaaaatggc tgtcaagtgc ccgcctcttg cttggtataa tgctacagct    84720
ttagaggacg cagcaggcat gggccttgcc gctgaggttc ttagcctcat gagaatatcc    84780
agatcagatt ctcttggctc cttcttagag ccagtgatgc aagacacttc ctgctcatct    84840
tgtcgggacg gttttacaag ttgcctgcca tcctgagaaa gtctacaaaa cgatgccaga    84900
cctcatgcca gcttcccaag ccttgactct cagtgctccc tcaacaggat tctggaagaa    84960
tctcccaaac aagtcgcaat gccctctgga ccctgtgcag gcatgagact caagagcatt    85020
ggctcccacc cctggtggag ggaacactgc tgggctggg atcttgcctg ttgctccgc      85080 ctgcacccaa gacaaccata attaaaatgt ccttcattga acttggaaag ccttcaaagc    85140
tgacaactcc ttatgtgtac ccggaaaggc ctgggagtgt gccagggcat tgctcggag     85200 ggacgctgat ttggaagcat ttacctgatg agagactgac agcagctcct ggtagccgag    85260
ctttccctcc tgcctctgct gtgaaggtgg accatccaa cagtcaaatg cctgactctg      85320
gacaggagcg gacctattta ttgccatgca agggactctg cacttttgaa ttgtgggtca    85380
tgggcttgga tttagggtt agagctggga gaagtcttgg aagtcaccta gagatgacac      85440
tgccattttg cagatgagga aaccgtccaa tcaaaatgga ccaaggactt gcccaaagcc    85500
tcacagcaaa accataggcc cccgcactaa ccccagagtc cctgtgctgt cttaaggatc    85560
atatagttgt aagcaatcat ctggttttca gtatttcttc ttttaaaatg cctggggcca   85620
```

```
tgcccagcag tctgtttcac tgcagcgttt acacagggct gccgggcttt cctggtggat   85680
gagctgggcg gttcatgagc cagaaccact cagcagcatg tcagtgtgct tcctggggag   85740
ctggtagcag gggctccggg ccctacttca gggctgcttt ctggcatatg gctgatcccc   85800
tcctcactcc tcctccctgc attgctcctg cgcaagaagc aaaggtgagg ggctgggtat   85860
ggctcgtcct ggcccctcta aggtggatct cggtggtttc tagatgtgac agcaccctta   85920
gtggatgagg gagctcccgg caagcaggct gccgcgcagc cccacacgga gatcccagaa   85980
ggaaccacag gtgagggtaa gccccagaga cccccaggca gtcaaggccc tgctgggtgc   86040
cccagctgac ctgtgacaga agtgagggag ctttgcgtgt ttatcctcct gtggggcagg   86100
aacatgggtg gattctggct cctgggaatc ttggttgtg agtagctcga tgccttggtg    86160
ctcagttacc tccctggctg cctgccagcc tctcagagca tttagggcct tctggacttc   86220
tagatgctcc tcatcttgcc tcagtcagcg cgtcagttcc agagacttct ctgcagggtt   86280
ttctggggca ggtggtggca gacccgtgcc ttcttgacac ctgaggtcag tccaccctcc   86340
tgctcagact gcccagcaca gggtcacctc ccaagggtg gaccccaaga tcacctgagc   86400
gcacagaggg tgcagatgac tggaccacac cttttggtga tcttaatgag gtggtcccag   86460
aggagctcag acatgcaatc tagcatccag ttctgggact ctgtctcctt ttcaaacgta   86520
ttcatgtaga acaggcatga cgagaatgcc ttgtcaacat gggtgatggg gaatcaatca   86580
gacagggcgc cgggctcaag gctgcagtca cccaagagtg gctcagccca ccaggcccta   86640
ggaaacgcct gcacagcctg gagctcctgg agtcatttcc ttcatgtctt cttcactgca   86700
cttacgtaaa gatgccagcc attggtttgg tgatttggag ggtgcccagt tgcccaacaa   86760
gaaatgcaga agaggcctag ccaggatttc accagcagtg gagagtagag aagatgtggc   86820
cagaaaagag tttcctttcc ctcctaaaga tggtactccc tgcagctact ggggaagcct   86880
gcagcattct ctagggctct gtgtgttgag agcagcccca ccctggcccc ttctgagtgc   86940
atttctgctt tgtgacttga tccgtgaagt cccctgagat gggcagaggg gatgtcctcg   87000
aagctggggc agagcctcat ccttgaacgt gaaggacgtt tgaagactgt ggcatgatca   87060
caggatgaga tcacagggaa cttgagtttc tctcctcctc tcccttcaca gttatttcac   87120
tgagggaaat ccctcccctg cccagaatga aaactctagc caactcttga cttttccatc   87180
actccaaagt agttgaaagt acattagtct ccacagtggc aaaacagtgt gcaaaagcta   87240
aataattaga acagccagtc ccatgtgaca gtcaaagctt ctaactccat tcaaagttgc   87300
agccattccc ctcgagggct ggcagggagg ggaggggtaa gagaaacagg aaggttctta   87360
ctgagttggt cctggtgtga gctgcgtcac actccctgca gaggtttcaa ggagactctc   87420
tctctctctg tctccatggg gaccttattt gaattcttct actcttaccc cagcctgcca   87480
tctccagcta tcctcccctg aagagccctt ctgctgcgct ggattctggt ggccatgtca   87540
tctcctcggc cccgtgggag tctgaagatc tggctgcagc ctcacctctg aggtcctgct   87600
agttgccacc tcttaaacat gatctgaggc tcccatgcac tctgacctgt gcccacatgg   87660
ggcccacggg aaacacgctg gcaagcaaac tgtgggtgtg cagacggttc tcagggctgc   87720
agcacctgtc ctttgctctg cccccaaagc aaggccagcc catcttccat cctctagtgt   87780
tccttggtgg ggccctgacc acagtccacc aggtccctaa ccagagggga cacacaccag   87840
gtgtcctcaa tgtattgcct tgaaacagtt gtgctgggac tgtgatgggg ggtggccatg   87900
tagccacccc caccaccccc aagccactct ctccaaggaa atcctcctaa agatcccttt   87960
```

| | |
|---|---|
| acatcctcca tgtggtgggg aggttctaga gttgggtgca tgtgtcttca gctactgaca | 88020 |
| atgcagacct tagttggcac ctcgctctgg cctatcctgt ttgctgttct tggcgctcca | 88080 |
| gtgaaactcc ccatgggcca tccagttggg gtgcagtgtg gccacccctt tgcaggttcc | 88140 |
| tgccttgctg gagagcacag ggccctcctg gctcttgtaa aacactcccc atggtacaga | 88200 |
| gaggccagca gtgatgtgag gcccaacctc cctccatggt gttcccaagc agctcccttt | 88260 |
| ctggggtcaa ggggtggcaa agacagtgca gcgtccaatt tctgactcaa gccgggcctg | 88320 |
| gctatcgcag ctctgcactg tgtgtgacag caaggcaact cacccagtgc cgtggcagtg | 88380 |
| accgtgtccg aggaagcctc ctcacaccct ctgtctcaag gactctggca tttagctgga | 88440 |
| cttgctgtag ctctgagcct ttctgccatt gccatcacct tgtcagaaac tcaggccgaa | 88500 |
| tctgcactca gagttgtgcc caggcagttg agccaacact tgctcagcga tattgtcaca | 88560 |
| tgacaaggca ctgtcaccac tgggcatcgt gggtagcgca gtgtcggctg gatggacccg | 88620 |
| gagggtgtct gtgtcatgct agtgctagtg atgggagccc cgtgagccca ttgcccgccc | 88680 |
| tcccatgccc tcagcagctg cctggggaca gccaatggcc tgggtgtttc tgaggctacc | 88740 |
| acatggcttc caggaaactc gagaaccttt ctctcccttg cctacactct tcacacaggc | 88800 |
| ctgtgctggc cagcggtggg gatccggcat tcctatctta ggtgcagaga gtgactgact | 88860 |
| cattgcaggc ctgggagata agactgatgg cccagccagc aagatgtatg gatttctcag | 88920 |
| aggcagtggc ctctgtcatt gtcctcagga aatgctggtg attctggtgg cctgaggtca | 88980 |
| atgcatgtca acgtggccaa cttgccttat aaacttttt tctggacaat gcgtgcact | 89040 |
| gtcctgtaac agtgtcctgt tgtttatgat gcagaaatag gtgtttttaa agcctattga | 89100 |
| ttttggtact attaatgtgg tcaggaactt tctcagtctt tcttgtttgg ggtgagctgt | 89160 |
| ggcttcctaa acaggaaccc aagacacccc caaaagctgc tcaccagcac tgccagcctc | 89220 |
| cctcttacca agtagcaccc gttcaggaca ttctgcgaaa ggcatttgcc cagaagttgg | 89280 |
| gaggaaggaa atgtaacatt ttggggcacc taccatatgc caggcaccag gctaaacgtg | 89340 |
| ttcacacaaa ttctcttact aaccctcacc atccttctac aagacaaact agtatcttca | 89400 |
| tcttggggtt caagatgagg aaatggaggc tcagagaggt tgaatgaatg ccggtgcctg | 89460 |
| gatatgaacc ccatctgcct gactccgcaa cccaggcaaa gtctttcctt gaacttccca | 89520 |
| gcagccactg cttagacaca gcctccacaa ccatggctca gcagcaaatt gcttctctga | 89580 |
| cctcactcag cctgtgtgtc cttgttgagt gaggcattca ggaccctggt cccaaagtgg | 89640 |
| agaaagtctt tcctactagg tcatagctac acctgcatgt gggtgctgtg cctttttgttt | 89700 |
| agtgaacttt tatcaccagc atcctcagca atgacatttg cagagaagcc agagctgagg | 89760 |
| caccttggta ttcttgggat gtgactttcc tgaatgttta agggaaaatg cccgaaggta | 89820 |
| cagagagctt ggtttctagt aaacaataac tgtcttgctt ttacccccct tcatttgctg | 89880 |
| acacatacac cagctgaaga agcaggcatt ggagacaccc ccagcctgga agacgaagct | 89940 |
| gctggtcacg tgacccaagg tcagtgaact ggaattgcct gccatgactt ggggttggg | 90000 |
| gggagggaca tggggtgggc tctgccctga aaagatcatt tggacctgag ctctaattca | 90060 |
| caagtccagg agattttagg gagttggttc ttatcaaagg ttggctactc agatatagaa | 90120 |
| agagccctag tggtttttt ctaataccat ttctgggtaa ttcctaaggc atttagtgtt | 90180 |
| ctgaaagatg ctagccttgt ccagcctggg agttgagaat gaatgtctaa cagaaactct | 90240 |
| aggccgggcc tggtggctca cgcctctaat cccagcacta gggagaccc aggtgggcag | 90300 |
| atcacctgag gtcaggagtt tgagaccagc ctggccaaca tgtgaaatcc tgtctcacta | 90360 |

```
caaataaaaa aattagccgg gtgtggtggt aggtgcctat aatcccagct actcaggagg    90420
ctgaggcagg acaatcgctc gaacccagga ggtggacgtt gcagtgagcc gagatcgcat    90480
cattgcactc cagcctgggc aacaaaagca aaactccgtc tcaaaaaaaa aaaagaaact    90540
caaatatgtg tgacaggcga ttctcactgc aggctgccct gtggctgatc caggagcaag    90600
gccttaacca tgtcatcccc aagcgattgc ttgtaaactt tcttctgtgc agccttcaac    90660
ccttattatg attttcttct caggaaccaa actgctgtat tcaagaaagg cagctttgtg    90720
taatcattta tcataaatat cttaagaaaa atcctagaga ttcctaattt taggaaatgg    90780
gagacctatg gtactgatat aatgtgggct gggcttgttt tctgtcattt gctagataaa    90840
tgaacttgag agcctactgt aaaatgtgga agcttctaga ttgcagaagg gctggaaaga    90900
cactgttctt ttctcccgag tgatgggatc tgtccagtat ttagagctgc ctctgaggcc    90960
atctgattct aggagactct gcctcgttga ggatattttg aggcctaact acacattcct    91020
gcccccagag aggtcacagc ctatagcagg ctgatgtttc tcatgtcaca tggcacagaa    91080
aggcacattt tcgttctcag gctaacaaag agcttcaaaa actattagaa gggacagtgg    91140
ctataagaga agaacctcag tcaatgtgtg aaattaacta ggaacctggc tcctgtttct    91200
tttaggtcat gttttttcagc ttaggtaaaa ctagaggctt tgataaagca tgacctctag    91260
aaatcattgc ttttcataaa tggaagtggg tttgagtttt ttctactgat tgttagtgca    91320
ggtgatgtct acatgccccc agaacatatt ccatgcaaca aaaaagccc aggtcaccgt    91380 ctttgctggg aacttgactt ttgtgctcac tgaattttaa gctttctgac agcagcctgg    91440
aatcatggag ggataaagta cctattagta agatggaaaa aggtgtttca ggttggagct    91500
gcagtctgtt gagagtaagc tatgggaagg cctgtatacg aggggtggac ttttcttctg    91560
taagtgtcca gagaccaggc ctcctgaaga gggcatgggg gcttaactta cctggactac    91620
tgtgtttaca atactcattt atcttgaact cctcctaacc cctgagaatt gctacattta    91680
gtatttgctg agtacttcct agcatcctag ggaatcaata gaacattctc ccaaccaggc    91740
tgggtgcggt ggctcatgtc tgtaatccca gcactttggg aggccaaggt aggcagatcc    91800
cttgaggcca ggagtgcaag actagcctgg ctgacatggt gaaaccccgt ctttactaaa    91860
aatacaaaag ttagccaggc atggtggtac acacctgtaa tcccagctac atgggaggag    91920
taggaggcag gagaattgct tgaacctggg aggtggaggt tgctgtgagc cgagatcatg    91980
ccactgcact ccagcctggg cgacagagtg agtgagactc tgtttaaaaa aaaaaaaaaa    92040
aagaacattc tcctaacctg gcttcttcct ccagggggtgt aattaatcat gtcagtttcc    92100
tcattgatac acacacacac acactacaat cctgtatcca ttacttttca aggtacattt    92160
actatttacg tttggggtcc ttgtctcttt tttaatagtg tttcttaaag tcttgtatta    92220
tatcagagta cagtaacatc ccagtcaaga gcactctagt aagctctagg aggaaagcga    92280
cttccggaag gcagtggaga cctgtcctgt tgggcagca tagggcagc ccctgcctct    92340 ggtcagttct ggcgctcagg ctcagggttg cctctgggct gttcttccca gagactgaca    92400
aagggctccc ataaggcacc tgcagagcct gtgagaagct gaagtcaatg ttttcctgac    92460
accagttgat ctgtgcagga tccattgatt taaccacctg ctgtgtggca tgcactgtgg    92520
tcgatgccag gaacaggaat tggaggggcc catgagcatg ccagtatca caggctggag    92580 gtgctgctgc gctctgaccg ggcctcttgg ggatgagccc atgtcaacca ccttgcctcc    92640
gatggggtcg ggcccacagg ttacctttgt gtgtccatga ccacaccttc ctccccgacc    92700
```

```
tcatccaaat ctctttcttt tccaagcccc tgaatccttc agggctgcag gttttgttta    92760
aagcagagct ggtgagttgc ataggttgtt gcattgggac tagatggggt gttcaaagag    92820
ttgggagtta aaaacataa agggtattta ttaggagaac caaggagtgt aattctcctg     92880
ttcttaatat gcggccaggt taatgaatgt cacgtgaatg aaccagaaaa aaatgaagtg    92940
tgcccttgat cagctgggtt ggtgtgcagc aagctgtgtg accagggggac agcagtggtc   93000 ctgagggccg tcactgtctg ccgtgcagag cccttcctcc cacggggggcc tacctcacct   93060 gtgccaaggg cttgtctgtg gtcagtgacc tggatagatc tgaatggggc ttctttttcg    93120
aggagtctta tggcaggtct ctcagtaaag actccattct tgatgatcac acattttgga    93180
ttttccaaat ctgtcagaga atgggcttga ggcggggttt gtgggcacta gtttcactgg    93240
tttcatttac caaaagggg agcagaagtc aagtatggtg gctcatccct gtaatcccag     93300
aggcaagaga attgcttgag cccaggagtt cgagaccagc ctgagcaaca taaggagacc    93360
ccgtctccac aaaaatgaaa ataacatttt agtcagacg tggtggcatg catctgtggt     93420
cccagctgct tgggagggtg agatggggagg gttgtttgag ccctggagtt aaagttgcaa   93480
tgagctgtga ttgcaccact gcactctagc ctgggtgaca gaacgagacc ctgtctcaaa    93540
aaaaaaaaaa aagaaagaaa gaaaggaaaa aaaaaactca tgcctgtaat cccagcactt    93600
tggggaccgg ggtgggcaga tcacgaggtc aggagatcaa gactatcctg gccaacatgg    93660 tgaaccccg tttctactaa aaatacaaaa attagccagg tgtggtggca cgtgcctgta     93720
atcccagtta ctcggggaggc tgaggcagga gaatcgcttg aaccaggag tcagaggttg    93780 cagtgagctg agatcgtgcc actgtactcc agcctgggcg acagagtgag actctgtctc    93840
aaaccaaaaa aaagggggtgg ggggcggggg caggagaaca gtgagaggta gggagaggaa    93900
aggggattct cgctacaccc aaaccagata ccatctagag gctagaatct ttgggaggct    93960
caaattccct agaaagcagg agaagcttct gtagccctcc cgctttccca gtagattaag    94020
cccagggcgg ctccagatgt gtgacatgct ctgtgcccaa ccagagccca tcataggcag    94080
aggaataaca cccacaccag aagggccctc ggaggtcacc acgtccaaga accctcttta    94140
cagatgagga aactgaggcc cagagagggg agagccacct agcgagctgg tggcggctag    94200
accaggagag ctgtcattcc aagcaagcaa aggcaacgag acgagcccag agctgtgctc    94260
ccatctcttt gttaggggc ctgggatgcc ctctcagtgt cattttgtcc aggatgatgc      94320
tccctctctt aagcgattaa tgcgcccttg ctaaccttt gctatcgctg cctcttcaaa     94380
ccagaggagt tgagagttcc gggccggcag aggaaggcgc ctgaaaggcc cctggccaat    94440
gagattagcg cccacgtcca gcctggaccc tgcggagagg cctctggggt ctctgggccg    94500
tgcctcgggg agaaagagcc agaagctccc gtcccgctga ccgcgagcct tcctcagcac    94560
cgtcccgttt gcccagcgcc tcctccaaca ggaggccctc aggagccctc cctggagtgg    94620
ggacaaaaag gcggggactg ggccgagaag ggtccggcct ttccgaagcc cgccaccact    94680
gcgtatctcc acacagagcc tgaaagtggt aaggtggtcc aggaaggctt cctccgagag    94740
ccaggccccc caggtctgag ccaccagctc atgtccggca tgcctggggc tccctcctg    94800 cctgagggcc ccagagaggc cacacgccaa ccttcgggga caggacctga ggacacagag    94860
ggcggccgcc acgcccctga gctgctcaag caccagcttc taggagacct gcaccaggag    94920
gggccgccgc tgaagggggc agggggcaaa gagaggccgg ggagcaagga ggaggtggat   94980
gaagaccgcg acgtcgatga gtcctccccc caagactccc ctccctccaa ggcctcccca    95040
gcccaagatg ggcggcctcc ccagacagcc gccagagaag ccaccagcat cccaggcttc    95100
```

```
ccagcggagg gtgccatccc cctccctgtg gatttcctct ccaaagtttc cacagagatc   95160
ccagcctcag agcccgacgg gcccagtgta gggcgggcca aagggcagga tgcccccctg   95220
gagttcacgt ttcacgtgga aatcacaccc aacgtgcaga aggagcaggc gcactcggag   95280
gagcatttgg gaagggctgc atttccaggg gcccctggag aggggccaga ggcccggggc   95340
ccctctttgg gagaggacac aaaagaggct gaccttccag agccctctga aaagcagcct   95400
gctgctgctc cgcgggggaa gcccgtcagc cgggtccctc aactcaaagg tctgtgtctt   95460
gagcttcttc gctccttccc tggggacctc ccaggcctcc caggctgcgg gcactgccac   95520
tgagcttcca ggcctcccga ctcctgctgc ttctgacgtt cctaggacgc cactaaatcg   95580
acacctgggt gcagctgctc cactccctcg gcctcctccc gtgctcaggc tgtggccgca   95640
cgcgcccctc acgcttgccc gccactctgc atgtcaccag cacccccgct ccgtgctacc   95700
caccttgttt gactctctgg ccacttgatt tgtccacaac ggcccatcag cccacaggag   95760
gtttggtggg tgccttccac cgacaggatg acgggtgccc tcatggtgtc tagaactctc   95820
caaccctccc atgtaggcat aagcagcccc actttgcaga tgaggaaacg gaggctcaga   95880
gaagtacagt aacttgccga aggccaatga gtagtaagtg acagagccag gtttgggatc   95940
caggtaggtt gtctctgaaa gacacgcctg tcctgcatcc cacaacgcct cccaggaggt   96000
gctggagtgt ggacgcctaa cacagagatg tgcaggcac acacagcagg tgacacacac   96060
agcatccaga ggtggcccag agctcatgct gtgccttttgg cccagtgccc tgcccccacc   96120
cactctgcct tgtggcagga agacaaggag cagacacaag atctccctgg tccacatgcc   96180
accacctccc tctgcagagg acaagggat cctcatgctg gcattggagg gggttgagca   96240
gggcccacct tgagccctca ggagcacgac cacagcagcc ctgcagggag ggattggtgg   96300
gaggagagtc ccaagtatca gggagaggag agttggtgtc ccacaggaga cctcagagcc   96360
acaaggcgag cttgttcata aatttgggac ccttagcatt tcacagttat ttgcagagcc   96420
cagaaatgga tgttactgaa gctcacagtt gcaagcatct gttaaatttt tattagattt   96480
tacttttagg gaaaactttg aaatgctata aagaagcctg tgtttaaaag ttaagacaga   96540 ggctggggc gatggctcac gcctgtaatc tcagcacttt gggaggccaa ggcaggtgga   96600
tcatttgagg ttaggagttc gagaccagcc tggccaacat ggtgagaccc tgtctctact   96660
aaaattacaa aaaattagct gggcgtggtg gcgggcacct gtagtcccag ctactgggga   96720
ggctgaagca ggataagtgc ttgaacccag gaggcagagg ttacagtgag ccaagatcac   96780
accactgtac cctaagcctg ggcgacagag tgagactctg tctcaaaaaa taaaataaaa   96840
taaagttaag agagaaaaaa atatatccta tatcctttgt taaattccaa aacagtaggg   96900
gacaaataac tgacttgaca ggttactaca atatttcctg aaatgatgtt tcttgaata   96960 ctggcctact agaggttcat aggtgtgttt ggattaaaaa agagttccat ggcccagtga   97020 ctggggaaa aaaataaaag actaaagtaa gttaaacagg ctttctgct gcaggacttg   97080 tcagagcctt taatgtacta atggccattg tgaccctctg agaaggtcac agagtgggtt   97140
tcccaaactt acttgattct acctgctaac atttcctgga ggaagtttgg gaaatgccga   97200
tttagcagat tctttgttg tgccgtggat ggtgctggtt gatgtgggca aaacaaagaa   97260
cacgtgagtc agatccgcct ggggctctta ctaaagtgca ggttcccagg tgccacttta   97320
ggcttacaga cccagttgtg gggtaagcct gggagtcttt tagcaggtga ttctgccaca   97380
tagtatagtt ggaaaacctc tgggcatact cattgctggt ccctctagaa atccaggtga   97440
```

```
caatagccaa tgagaagctc caagagaccc agttgtccat ggggtagagg gaatgtgata   97500
ttgaaaccaa agaagaaaat ctatgatcag ttttcagcag tgactgtcaa gagaaggaga   97560
agggtgagtt agcgctgatg ctggctgaca ggtcagcggg ttggtttcac caaggagtgt   97620
gatgaaggct gatgttgtct gtgggaatgt atgatggtaa ctggtttgta gctaatttgg   97680
ggaagcagtg agaattcgtg cccctttgaag accagtaagt ggcaagaaac ccaccaggcc   97740
tggctcaggg ctgggctggg cttggctcgt ctcagagcag ctggggctgg tggccaaagc   97800
caccattagt gagggggcagg ccctgggggt acaaccagca actaggggac aaagacaacc   97860
ctgccagcct ctcctattct ggaggcgtgt gaccagaaat ggagatgggt tggtcagcat   97920
aagatggcca ggaaggtgga aatcaggact gctggcaatc tagccacatg ggcagggggag  97980 ccgggtggtt ccaggcagtt tccaaggcca agagggtgag caggcacctc acagggaatc   98040
agggccaagc ctggctgcag tgtggagaca atgcacccac ccccatcctt ggatcttgca   98100
ggaggctggg tcctcactga gctaccaaca tccatggccc tgaggctttt aaaacaccca   98160
tccatggagt ggggctggtc ccagtggggt gaggctgacc ctggcagaaa cagggcagga   98220
gcctgtgggt tagggagact gcaccttcct tagatagcct ccatgccatc atgtccccgt   98280
gacagtttct gctgcgtccc ctctgcatgg tcccaccctc ggccagcctg ctgccccctc   98340
ttgccaggtt gcgctaatca gtgacccag tgtgctgtgt tgatactaac aatgcgaggc    98400
ctagcagatt caagggaaaa gagaaccaac tgggtttcca ccagacccaa ctaaacaaac   98460
atggacctat cccagagaaa tccagcttca ccacagctgg ctttctgtga acagtgaaaa   98520
tggagtgtga caagcattct tattttatat tttatcagct cgcatggtca gtaaaagcaa   98580
agacgggact ggaagcgatg acaaaaaagc caaggtaagc tgacgatgcc acggagctct   98640
gcagctggtc aagtttacag agaagctgtg ctttatgtct gattcattct catatataat   98700
gtggggagta tttgtcacta aagtacagct gtcatttaaa gtgctttgta ttttggggca   98760
ggcttttaaa aagtccagca tttattagtt ttgatactta ccccagggaa gagcagttgg   98820
caggttcatg aagtcatgct cctaattcca gctttcttag tgtactttca gtgagaccct   98880
gacagtaaat gaaggtgtgt ttgaaaacca aacccaggac agtaaatgaa ggtgtgtttg   98940
aaaaccagcc ctaggacagt aaatgaagcc atcttctcac tgcataaact gcacccagat   99000
cttcgcccat ccttctcagt atttcacttc acccattgtt tactgtctca atgactgggg   99060
aaatgtctgg ggaaatgctc ccgtaattgc acagtggcgt ttttcctgga aaatcccacc   99120
atggctctag ataagaccta ttttttcttaa aggtatctaa aatttccagc ataaattctg   99180
tctgaaacac ctgaattta atcagtactg gagcccggag ggcatctcca gttgccacat   99240
agctctgagc attcagtggt gtgttgaggg ctgctcccgg aagtgcctgc agagtcaggg   99300
ctccccagcc tcatctagtg aggcagtgga agggcctgtg gggatttgga gagctggcct   99360
gggtctctga agtgatagtg acagctgctt gtcaatcacg gtgcacattt agtgctgggg   99420
gcagggggca gggaatacca gcctcatgca tgcatgcatt catttgttcc ttccttcatt   99480
cattcattca gtacacatgg gtacaacatc cctgccctgg agttgcccag agtctaggga   99540
ggggaaagat ctattaccct gggcctcggc cagctgggga gtgctgctgg tggagagggg   99600
ccgtgtgcag cgagggaagg aggagtcgtc aataccccca ccccagctttt gctttcttgt   99660 catcagcccc agggcccag cctgtgtccc tcctctccca ttgctacttc atctcctggg    99720
tcctccttac caagcctgac cacacagagg gccttggccg cttccatggg gaattggaaa   99780
gcaataagat agcatcccct agaagcccag tgaagtctgg gacaggaccc ttctctgagc   99840
```

```
tctgacttgc tcttggaaac acttcgaggc ttagcctccc cactttgttt cccgagagtg   99900
tgacctgttc ccctccaaac accccttct cctccagggc catgcccacc cgtcaaaatc   99960
ccccacgggc aggacgaact gtgggtgtca gtcaccatct atcctgcatc ctggttccag  100020 ggccccccc agccccgcct ccatagggac aggcgtgcag acacccgtcc ctggctgctt  100080
cctcttgtgg aatgggttca aaagtaagca gtgttgttta cactgacaaa ctgaaaaaaa  100140
aagaaaaaga gataacattg gaggcttggc acagtggctc atgcctgtaa tcccagcact  100200 tgggaggct aaggtgggag gatgtcccca gcccaagagt tctagaccag cctgggcaac  100260
atagcaagac cccatctcaa aaaaaaaatt taattggcca ggcagaggtg ggaggatcac  100320
ttgaacccaa agggtggagg ctgcagtgag ccgtgatggc accactgcac tccagccagg  100380
gcaacagagg gagaccctgt ctctaaaaca aacaaacaaa caaacaaaca aaagagttaa  100440
cattggccag attaggattc accagatagt gttaatatta gtttgatttg agactttaat  100500
cagaaagcac atgtgtggtg ggggtgggtg taacctaagt caggtagaat ctttccaact  100560
tggggggggc acactcctga ttgtagccat atgagtctgt cagtgtggtg aagaggcca  100620 tgggttaatg ggcaggtaaa aaagcacctt gcctggaatt gagtagaaag taaggcccctt  100680 cagacccgt gacacacttg gggacatttt cttgagtaac atcctaagat tcatgtacct  100740
tgatgatctc catcaactta ctcatgtgaa gcacctttaa accagtcgtc tccaaattca  100800
ggggcacagt aacatccaac aggctggaga agaacgtac tagaacttcc attccttttt  100860
catgtcctct tctaaaagct ttgtcagggc caggcgcggt ggctcacgcc tgtaatccca  100920
gcactttggg aggccgagac gggtggatca cgaggtcagg agatcgagac catcctggct  100980
aacacagtga aaccccatct ctactaaaaa tacaaaaaaa cgagccgggc gtggtggtgg  101040
gcgcctgtag tcccagctac tcgggaggct gaggcaggag aatggcgtga acccaggagg  101100
cagagcttgc agtgagccga gattgcacca ctgcagtcca gcctgggcga cagagcgaga  101160
ctccgtctca aaaagaaaa agaaaaagaa aagaactgt gattggggag gacggtcact  101220
ttcctgttct tactgatcag aagggatatt aagggtacct gattcaaaca gcctggagat  101280
cactgctttc aaccattacc tgccttattt atttttagtt actgtccttt tttcagtttg  101340
tttccctcct ccatgtgctg acttttattt tgattttatt tatgtttatg tttaagacat  101400
ccacacgttc ctctgctaaa accttgaaaa ataggccttg ccttagcccc aaacacccca  101460
ctcctggtag ctcagaccct ctgatccaac cctccagccc tgctgtgtgc ccagagccac  101520
cttcctctcc taaatacgtc tcttctgtca cttcccgaac tggcagttct ggagcaaagg  101580
agatgaaact caaggtaagg aaaccacctt tgaaagaac caggctgctc tgctgtggtt  101640
tgcaaatgtg gggtttgttt atttgttttt tagcctcaaa gacctttctt caaatgagtt  101700
ctggcataga agcaccgtgt aaaatagtta gaattctggg caagggggaa aagagagctg  101760
ggggccatcc ctctcagcac cccacaggct ctcatagcag cagctcctaa gacacctggt  101820
gggaccttgg tttcgaaatc gctactctaa ggctgggcac ggtggctcac acctgtaatc  101880
ccagctcttt aggaggccga ggagggtgga tcacctgaga tcaggagttc gagaccagcc  101940
tggctaacat ggcaaaaccc tgtctctact aaaaatacaa aaattagccg ggcgtggtgg  102000
tatgcgtggt ggtaatcgca gctactcggg aggctgaggc acaaggattg cttgaacccc  102060
agaggcagag gttgtagtta gctccagctt gggcgacaga gcaagaccct gtcgcaaaaa  102120
ttgtttaaaa aacaaaccca aaattgctac tctcattggg ttcctttgcc cattcctgat  102180
```

```
tttggcaaga gaaatgcttc cagattgccc tgatctgggt aggacagcat cacgccatag   102240
caacactgcc ccgtgagctc actgcccccct caactagctt gtggtccttg gttaatgtca   102300
gtttcttttt tgagtttgtg ttatgtctaa gggtcatctg ctgggtaacg gaacccaggg   102360
actgccctag tccctagact gtgccatgcc cgactctgcc agctttgtca gtgatgctga   102420
tgctcgcctc ctcgggtgct cgcctggtct gagcacaccc aaggagttct tgaggcctta   102480
gggttgtttg cgagagaatg aaagaacacg acctagctct cttagcatc cttggtcagg   102540
ttcaacactg cccccagggg cctctggtgg agccaaccac catcagccaa ataaatccat   102600
aattagagtc agaaaatgga tgtctgcata tgtgtagtgc actaatgtcc tgccgatgat   102660
tgacatggag tggagagtga cctgatcatt gctgtgagct ctgctggcct tggcacaact   102720
catgctgata actaatgcac acagttcctc tgggaggaaa tgtcctcagg gaacttggag   102780
tttgggtggg gatgtgggtt tgtgtgccca gcaagcccct tgtggttgtag cagacactag   102840
tggcatctag gaggcaaagg gtcacccccag tcttagccac gttttgagtc aaggtggcgg   102900
agtgggggctg gtgttgactc ttggtggcag taacttttcc caatggtgaa aaacccctct   102960
atcatgtttc atttacaggg ggctgatggt aaaacgaaga tcgccacacc gcggggagca   103020
gccccctccag gccagaaggg ccaggccaac gccaccagga ttccagcaaa aaccccgccc   103080
gctccaaaga caccaccccag ctctggtaag aagaacgttc tcttgaatct tagaggaagc   103140
tgaagctctc agaggtacag ccttcattt aggaggcctt aggccactga gaatgaataa   103200
cccctggcag ctggtcagca gcttgcagtt tactaagcac tggagtcttc attgccttct   103260
cagtcctttt gatttctgag gcaaatgttg aatccctacc tttttttttt ttttctttt   103320
gagacagagt ttcgcttttg ttatccaggc cggagtgcag tggtgtgatc tcagctcact   103380
gcatcctcca cctcccaggt tcaagcgatt ctcctacctc agcctccta gtagctggga   103440
ttacaggcac ctgccactat gcccggctaa ttttttgtat ttttagtaga cagggtttt   103500
caccatgttg gccaggctgg tctcgaacgc ctgacctcag gtgatccacc tgcctcggcc   103560
tcccaaagtg ctgggattac aggcatgagc caccactccc agcctgaatc ctcactttttt 103620
atcaatgaag aaattgaggc tgattctgca gcatgataaa aaaaaataca gaaaaggaa   103680
aaaaaagaaa gaaatcgagc ctctgagagt ttgcttgact gagtctaacc agctcatttt   103740
aaacccgagg aaaatgcagt cacatgacta ctaagtggca gctctcggag cctctctggc   103800
cccaagtcca gggttccata gaggcagccc cagcatggca tgttttcagt ccccaaatga   103860
gactctggag acaaatgtct ctggagacag agcagcagcc tggataagtc acaatgggtg   103920
acgtcactca gggctcaacc cctgggcagc ttaacttgct agggacgtta ggagtctgct   103980
gcaaaacctg agggtcttag ctgagcagtc acaggctggg cccgttgccc tgggctcctg   104040
tgagtaaaac ccagtcaatt ttgagtaccc agtaaggcat ccattgagtt attttgcagc   104100
caggagtgct attaagaaca gtcgcggctg ggcgtggtgg ctcatgcctg taatcccagc   104160
actttgggag gccaaggtgg gcggatcacc tgaggtcagg agttcgagac cagcttggcc   104220
aacatggcaa aaccccgtct ctaataaaaa tacaaaataa ttagctgggc gtggtggcgg   104280
gcgcctgtaa tccagcttc tcaggagggt gaggaaggaa aatcacttga acccaggagg   104340
cagaggttgc agtgagctga gatcgcacca ttgcactcca gcctggatga caaaagtgag   104400
attccttctc aaaaaaaaaa aaaaaaaaac agtcgtcctc tttggggatt agggacagcc   104460
tgcctgcctg cccgagcact tctctcttcc attgccccag tgaagtattc caggcccctg   104520
ggtttagact ctgcaccatg tagggggtgtc tgacctgcac ttgctccttg gtggcacggg   104580
```

```
cagcctatgg cacttgctgc gggctgtgac caaagcctgg cctggatctt ggatcttggt  104640
gactctgctt ctccctggcc tgagggagct gcccagagcc tgcccaccac ctgctgcgtg  104700
tctttgcggt ggcatttctc gcacacatgc cgtgcagtgg cacccccaag gatggccatt  104760
cactaaggcc cattgttttt gtcttttcgc ttcgtgtttt ctggcctggt gttttctca   104820 tatacatgtg atccagggat aattcccaga attttgacag gattttaagt agcgtttgga  104880
tcctgctgtt ttttttcac ttaacatcgg gccagttgac tcacactctg ttttttgttg   104940 ttgtttttt gagacggagt ctcactgtgt cacccaggct gaagtgcagt ggcacaatct    105000
tggcatactg caacctctgc ttcccaaatt caagcagttt tcctgcctca gcctcctgag  105060
tagctgggac tacaggcaca ggccaccacg ccctgctaat ttttgtattt ttagtaaaga  105120
cagggtttca ccattttggc cagcctagtc tcgaactcct gacctcaagt gatccgccca  105180
cctcggcctc ccaaagtgct gggattacag gggactcaca ctttgtaaca acctgaaaca  105240
acgtgatgca tttcccttttg ggtcttacct gctcttcggt ggctgcctgc aggtggagag  105300
accctccccc ttgggcccct cgaccttgtt tcagaatggg gcccctgctg ggccagctgt   105360
gggtgcctgc cacgtgaagg actcattaag gccctgttta agcctgatga taataaggct  105420
ttcgtggatt tttctcttta agcgactaag caagtccaga gaagaccacc ccctgcaggg  105480
cccagatctg agagaggtac tcgggagcct acttcgctgg gagcagcctc cctttgcgtg  105540
tgtggccatt cactggcttg tgtttctaga gccgggagga ccctttttctg caatgcaggg  105600 ttcacacagg gttcgcagcc tgaagatgga gcagtccgaa ttctcttccc tgtgcagttt   105660
gcgcagctgt gtttgtctga tgggctttct aatcctgtgt gctctccttg acttcaggga  105720
caatggcatt acaggcatga gccaccatgc ctggctgtct ccctatgttt cagatgaaga  105780
cataggctta aggaggtcag gtgacttgcc cacgaccact ctgtaaataa gaggcatgaa  105840
aagtatttgg agccaccacc accaagccca ctggtcaccc tgggtctctg aagtcaggga  105900
ggcaggagga tgggaggtct gaggaggcag agaggctgag cctggaggcc ctggaggccg  105960
aggccccatc tgttgtttcc ttatgtggaa aataagaggc ttcgtttgtc ctattgccac  106020
agagcgtact acttcaggaa catccaagac atggaaatcc gcaggcacg gtggctcacg   106080 tctataatcc cggcactttg ggaggttgag gtgggagaat cgcttgaggc cagaagttca  106140
agaccagcct gagcaacata gtcagacccc gtctctataa aaacattat tttaaaaaa   106200 gacatggaag tcaaattcta aaaactggtg ctggctgggt gcggtggctc atgcctataa  106260
tcccagcact ttgggaggcc gaggcgggtg gatcacctga ggtcaggagt tcaagaccag  106320
cctggccaac atggtaaaac ctctactaaa gaaatctta ctgaaaatac aaaaatccag   106380
tctctactaa aataagtctc tactaaaaat acaaaaatta gccaggcgtg gtgctgcaca  106440
cctgtaatat cagctactcg ggaggctgag gcaggagact cgcttgatcc catgcagcgg  106500
aggttgcagt gagccgagat cacgccattg cactccagcc tgggcatcag aataagactc  106560
cgtctcaaaa aaaaaccac aaaaaaacaa aacaacaaca aaagaaaact agtgcttatt    106620
cgtcactggc caagctgccc attggctaca tgggtgcttc aaagagctgc ccttctccag  106680
gtctggccag caggtatgtg ttacagcaaa tgcctggggc agcggcaggg gcattgctgc  106740
gggaagcttc tggacttgca ggaaagctaa gttctcagac tgcaggggag ctaagcacac  106800
ctcggcacag ggtgaggcct gcggttctca gacttcagtc tttgtggagc ttgagaaaaa  106860
tgaggctttg caggtcccac ccctagagat tctgctctat ccactcttga agggatcga   106920
```

```
gaaatttgca ttttgcaact cccactttcc tccttgaaag ctccggagat tctgacgcag   106980
ggttccgtgg gccacacttt ggaaaataca gacccatgag atagaatacc agactgttga   107040
agtgtaacgg gggcctggga agtgcagtaa cagaagcaag tttgagggta aaggacaccc   107100
agaggaggga gggacagcat ctgcatggag aggagaagag accccccagc agcttccagg   107160
gtgttggaag ggtgcgctag taactgctat gcatggcagg tggggaactg tacgtcaggg   107220
cacagcagca tgaagcggta tggctcgtgt ggacagctag gacaggcag gcgtggagca    107280 ggcatcctgt tctgaaggcc aaatcccaca gaggagccag ggtgctggca ggagccctga   107340
actagccgaa cagctgaaca gctgaacatt caccctgtgg ggaaagggtc agaagcgtcc   107400
aggcttgagg gcacagctgg gtctcgtcac tgcatcaccc ttatttagga taaaggccct   107460
gaagaattgt attagaggtt ggcaaagcat atctaccacc tcctggagcc acgctggccg   107520
cagggattat aattatttcc attttcaaat taaggcctct gagctcagag aggggaagtt   107580
acttgtctga ggccacacag cttgttggag cccatctctt gacccaaaga ctgtggagcc   107640
gagttggcca cctctctggg agcgggtatt ggatggtggt tgatggtttt ccattgcttt   107700
cctgggaaag gggtgtctct gtccctaagc aaaaaggcag ggaggaagag atgcttcccc   107760
agggcagccg tctgctgtag ctgcgcttcc aacctggctt ccacctgcct aacccagtgg   107820
tgagcctggg aatggaccca cgggacaggc agccccagg gccttttctg accccaccca    107880
ctcgagtcct ggcttcactc ccttccttcc ttcccaggtg aacctccaaa atcagggat    107940 cgcagcggct acagcagccc cggctcccca ggcactcccg cagccgctc ccgcaccccg    108000 tcccttccaa ccccacccac ccgggagccc aagaaggtgg cagtggtccg tactccaccc   108060
aagtcgccgt cttccgccaa gagccgcctg cagacagccc ccgtgcccat gccagacctg   108120
aagaatgtca agtccaagat cggctccact gagaacctga agcaccagcc gggaggcggg   108180
aaggtgagag tggctggctg cgcgtggagg tgtggggggc tgcgcctgga ggggtagggc   108240
tgtgcctgga agggtagggc tgcgcctgga ggtgcgcggt tgagcgtgga gtcgtgggac   108300
tgtgcatgga ggtgtggggc tccccgcacc tgagcacccc cgcataacac cccagtcccc   108360
tctggaccct cttcaaggaa gttcagttct ttattgggct ctccactaca ctgtgagtgc   108420
cctcctcagg cgagagaacg ttctggctct tctcttgccc cttcagcccc tgttaatcgg   108480
acagagatgg cagggctgtg tctccacggc cggaggctct catagtcagg gcacccacag   108540
cggttcccca cctgccttct gggcagaata cactgccacc cataggtcag catctccact   108600
cgtgggccat ctgcttaggt tgggttcctc tggattctgg ggagattggg ggttctgttt   108660
tgatcagctg attcttctgg gagcaagtgg gtgctcgcga gctctccagc ttcctaaagg   108720
tggagaagca cagacttcgg gggcctggcc tggatccctt tccccattcc tgtccctgtg   108780
cccctcgtct gggtgcgtta gggctgacat acaaagcacc acagtgaaag aacagcagta   108840
tgcctcctca ctagccaggt gtgggcgggt gggtttcttc caaggcctct ctgtggccgt   108900
gggtagccac ctctgtcctg caccgctgca gtcttccctc tgtgtgtgct cctggtagct   108960
ctgcgcatgc tcatcttctt ataagaacac catggcagct gggcgtagtg gctcacgcct   109020
ataatcccag cactttggga ggctgaggca ggcagatcac gaggtcagga gttcgagacc   109080
aacctgacca acagggtgaa acctcgtctc tactaaaaat acaaaaatac ctgggcgtgg   109140
tggtggtgcg cgcctataat cccagctact caggaggctg aggcaggaga atcgcttgaa   109200
cccaggaggc agaggttgca gtgagccgag atagtgccac tgcactccag tttgagcaac   109260
agagcgagac tctgtctcaa aacaaaataa aacaaaccaa aaaaacccac catggcttag   109320
```

```
ggcccagcct gatgacctca tttttcactt agtcacctct ctaaaggccc tgtctccaaa   109380
tagagtcaca ttctaaggta cggggtgtt ggggagggg gttagggctt caacatgtga   109440
atttgcgggg accacaattc agcccaggac cccgctcccg ccacccagca ctgggagct   109500 ggggaagggt gaagaggagg ctgggggtga aaggaccac agctcactct gaggctgcag   109560
atgtgctggg ccttctgggc actgggcctc ggggagctag ggggctttct ggaaccctgg   109620
gcctgcgtgt cagcttgcct cccccacgca ggcgctctcc acaccattga agttcttatc   109680
acttgggtct gagcctgggg catttggacg gagggtggcc accagtgcac atgggcacct   109740
tgcctcaaac cctgccacct cccccaccc aggatccccc ctgccccga caagcttgt    109800 gagtgcagtg tcacatccca tcgggatgga aatggacggt cgggttaaaa gggacgcatg   109860
tgtagaccct gcctctgtgc atcaggcctc ttttgagagt ccctgcgtgc caggcggtgc   109920
acagaggtgg agaagactcg gctgtgcccc agagcacctc ctctcatcga ggaaaggaca   109980
gacagtggct cccctgtggc tgtgggaca agggcagagc tccctggaac acaggaggga   110040
gggaaggaag agaacatctc agaatctccc tcctgatggc aaacgatccg ggttaaatta   110100
aggtccggcc ttttcctgct caggcatgtg gagcttgtag tggaagaggc tctctggacc   110160
ctcatccacc acagtggcct ggttagagac cttggggaaa taactcacag gtgacccagg   110220
gcctctgtcc tgtaccgcag ctgagggaaa ctgtcctgcg cttccactgg ggacaatgcg   110280
ctccctcgtc tccagacttt ccagtcctca ttcggttctc gaaagtcgcc tccagaagcc   110340
ccatcttggg accaccgtga ctttcattct ccagggtgcc tggccttggt gctgcccaag   110400
accccagagg ggccctcact ggcctttcct gcctttctc ccattgccca cccatgcacc   110460
cccatcctgc tccagcaccc agactgccat ccaggatctc ctcaagtcac ataacaagca   110520
gcacccacaa ggtgctccct tccccctagc ctgaatctgc tgctccccgt ctggggttcc   110580
ccgcccatgc acctctgggg gccctgggt tctgccatac cctgcccgt gtcccatggt   110640 ggggaatgtc cttctctcct tatctcttcc cttcccttaa atccaagttc agttgccatc   110700
tcctccagga agtcttcctg gattcccctc tctcttctta agccctgt aaactctgac    110760 cacactgagc atgtgtctgc tgctccctag tctgggccat gagtgagggt ggaggccaag   110820
tctcatgcat ttttgcagcc cccacaagac tgtgcaggtg gccggccctc attgaatgcg   110880
gggttaattt aactcagcct ctgtgtgagt ggatgattca ggttgccaga gacagaaccc   110940
tcagcttagc atgggaagta gcttccctgt tgaccctgag ttcatctgag gttggcttgg   111000
aaggtgtggg caccatttgg cccagttctt acagctctga agagagcagc aggaatgggg   111060
ctgagcaggg aagacaactt tccattgaag gccctttca gggccagaac tgtccctccc   111120
accctgcagc tgccctgcct ctgcccatga ggggtgagag tcaggcgacc tcatgccaag   111180
tgtagaaagg ggcagatggg agcccaggt tatgacgtca ccatgctggg tggaggcagc   111240
acgtccaaat ctactaaagg gttaaaggag aaagggtgac ttgacttttc ttgagatatt   111300 ttggggacg aagtgtggaa agtggcaga ggacacagtc acagcctccc ttaaatgcca    111360
ggaaagccta gaaaattgt ctgaaactaa acctcagcca taacaaagac caacacatga    111420
atctccagga aaaagaaaa agaaaaatgt catacagggt ccatgcacaa gagcctttaa    111480
aatgacccgc tgaagggtgt caggcctcct cctcctggac tggcctgaag gctccacgag   111540
cttttgctga gaccttttggg tccctgtggc ctcatgtagt acccagtatg cagtaagtgc   111600
tcaataaatg tttggctaca aaagaggcaa agctggcgga gtctgaagaa tccctcaacc   111660
```

```
gtgccggaac agatgctaac accaaaggga aaagagcagg agccaagtca cgtttgggaa   111720
cctgcagagg ctgaaaactg ccgcagattg ctgcaaatca ttgggggaaa aacggaaaac   111780
gtctgttttc ccctttgtgc ttttctctgt tttcttcttt gtgcttttct ctgtttttcag 111840 gatttgctac agtgaacata gattgctttg ggccccaaa tggaattatt ttgaaaggaa   111900
aatgcagata atcaggtggc cgcactggag caccagctgg gtaggggtag agattgcagg   111960
caaggaggag gagctgggtg gggtgccagg caggaagagc ccgtaggccc cgccgatctt   112020
gtgggagtcg tgggtggcag tgttccctcc agactgtaaa agggagcacc tggcgggaag   112080
agggaattct tttaaacatc attccagtgc ccgagcctcc tggacctgtt gtcatcttga   112140
ggtgggcctc ccctgggtga ctctagtgtg cagcctggct gagactcagt ggccctgggt   112200
tcttactgct gacacctacc ctcaacctca accactgcgg cctcctgtgc accctgatcc   112260
agtggctcat tttccacttt cagtcccagc tctatcccta tttgcagttt ccaagtgcct   112320
ggtcctcagt cagctcagac ccagccaggc cagcccctgg ttcccacatc ccctttgcca   112380
agctcatccc cgccctgttt ggcctgcggg agtgggagtg tgtccagaca cagagacaaa   112440
ggaccagctt ttaaaacatt ttgttggggc caggtgtggt ggctcacacc taatcccaac   112500
acctggggag gccaaggcag aaggatcact tgagtccagg agttcaagac cagcctggc   112560 aacataggga gaccctgtct ctacaatttt ttttttaatt agctgggcct gttggcactc   112620
tcctgtagtt ccagctactc tagaggctga ggtgggagga ctgcttgagc ctgggaggtc   112680
agggctgcaa tgagccatgt tcacaccact gaacgccagc ctgggcgaga ccctgtatca   112740
aaaaagtaaa gtaaaatgaa tcctgtacgt tatattaagg tgccccaaat tgtacttaga   112800
aggatttcat agttttaaat acttttgtta tttaaaaaat taaatgactg cagcatataa   112860
attaggttct taatggaggg gaaaagagt acaagaaaag aaataagaat ctagaaacaa   112920
agataagagc agaaataaac cagaaaacac aaccttgcac tcctaactta aaaaaaaaaa   112980
tgaagaaaac acaaccagta aaacaacata taacagcatt aagagctggc tcctggctgg   113040
gcgcggtggc gcatgcctgt aatcccaaca cttgggagg ccgatgctgg aggatcactt   113100
gagaccagga gttcaaggtt gcagtgagct atgatcatac cactcaccc tagcctggc    113160 aacacagtga gactgagact ctattaaaaa aaaaatgctg gttccttcct tatttcattc   113220
ctttattcat tcattcagac aacatttatg gggcacttct gagcaccagg ctctgtgcta   113280
agagcttttg cccccagggt ccaggccagg ggacaggggc aggtgagcag agaaacaggg   113340
ccagtcacag cagcaggagg aatgtaggat ggagagcttg gccaggcaag gacatgcagg   113400
gggagcagcc tgcacaagtc agcaagccag agaagacagg cagaccctg tttgggacct    113460 gttcagtggc ctttgaaagg acagccccca cccggagtgc tgggtgcagg agctgaagga   113520
ggatagtgga acactgcaac gtggagctct tcagagcaaa agcaaaataa acaactggag   113580
gcagctgggg cagcagaggg tgtgtgttca gcactaaggg gtgtgaagct tgagcgctag   113640
gagagttcac actggcagaa gagaggttgg ggcagctgca agcctctgga catcgcccga   113700
caggacagag ggtggtggac ggtggccctg aagagaggct cagttcagct ggcagtggcc   113760
gtgggagtgc tgaagcaggc aggctgtcgg catctgctgg ggacggttaa gcaggggtga   113820
gggcccagcc tcagcagccc ttcttggggg gtcgctggga aacatagagg agaactgaag   113880
aagcagggag tcccagggtc catgcagggc gagagagaag ttgctcatgt ggggcccagg   113940
ctgcaggatc aggagaactg ggacccctgt gactgccagc ggggagaagg gggtgtgcag   114000
gatcatgccc agggaagggc ccaggggccc aagcatgggg gggcctggtt ggctctgaga   114060
```

```
agatggagct aaagtcactt tctcggagga tgtccaggcc aatagttggg atgtgaagac   114120
gtgaagcagc acagagcctg gaagcccagg atggacagaa acctacctga gcagtggggc   114180
tttgaaagcc ttggggcggg gggtgcaata ttcaagatgg ccacaagatg gcaatagaat   114240
gctgtaactt tcttggttct gggccgcagc ctgggtggct gcttccttcc ctgtgtgtat   114300
tgatttgttt ctcttttttg agacagagtc ttgctgggtt gcccaggctg gagtgcagtg   114360
gtgcgatcat agctcactgc agccttgaag tcctgagctc aagagatcct tccacctcag   114420
cctcctgagt agttgggacc acaggcttgc accacagtgc ccaactaatt tcttatattt   114480
tttgtagaga tggggtttca ctgtgtcgcc caggatggtc ttgaactcct gggctcaagt   114540
gatcctcctg cctcagcctc gcaaattgct gggattacag gtgtgagcca ccatgcccga   114600
ccttctcttt taagggcgt gtgtgtgtgt gtgtgtgtgt gggcgcactc tcgtcttcac   114660
cttcccccag ccttgctctg tctctaccca gtcacctctg cccatctctc cgatctgttt   114720
ctctctcctt ttaccoctct ttcctccctc ctcatacacc actgaccatt atagagaact   114780
gagtattcta aaaatacatt ttatttattt attttgagac agagtctcac tctgtcaccc   114840
aggctggagt gcagtggtgc aatctcggct cactgcaacc tccgcctccc aggttgaagc   114900
aactctcctg cctcagcctc cctagtagct gggattacaa gcacacacca ccatgcctag   114960 caaatttta tatttttagt agaggagggg tgtcaccatg tttgccaagc tggtctcaaa   115020
ctcctggcct caggtgatct gcctaccttg gtctcccaaa gtgctgggat tacaggtgtg   115080
agccaccacg cctgccctta aaatacatt atatttaata gcaaagcccc agttgtcact   115140
ttaaaaagca tctatgtaga acatttatgt ggaataaata cagtgaattt gtacgtggaa   115200
tcgtttgcct ctcctcaatc agggccaggg atgcaggtga gcttgggctg agatgtcaga   115260
ccccacagta agtgggggc agagccaggc tgggaccctc ctctaggaca gctctgtaac   115320
tctgagaccc tccaggcatc ttttcctgta cctcagtgct tctgaaaaat ctgtgtgaat   115380
caaatcattt taaaggagct tgggttcatc actgtttaaa ggacagtgta aataattctg   115440
aaggtgactc taccctgtta tttgatctct tctttggcca gctgacttaa caggacatag   115500
acaggttttc ctgtgtcagt tcctaagctg atcaccttgg acttgaagag gaggcttgtg   115560
tgggcatcca gtgcccaccc cgggttaaac tcccagcaga gtattgcact gggcttgctg   115620
agcctggtga ggcaaagcac agcacagcga gcaccaggca gtgctggaga caggccaagt   115680
ctgggccagc ctgggagcca actgtgaggc acggacgggg ctgtggggct gtggggctgc   115740
aggcttgggg ccagggaggg agggctgggc tctttggaac agccttgaga gaactgaacc   115800
caaacaaaac cagatcaagg tctagtgaga gcttagggct gctttgggtg ctccaggaaa   115860
ttgattaaac caagtggaca cacccccca gccccacctc accacagcct ctccttcagg   115920
gtcaaactct gaccacagac atttctcccc tgactaggag ttccctggat caaaattggg   115980
agcttgcaac acatcgttct ctcccttgat ggttttttgtc agtgtctatc cagagctgaa   116040
gtgtaatata tatgttactg tagctgagaa attaaatttc aggattctga tttcataatg   116100
acaaccattc ctcttttctc tcccttctgt aaatctaaga ttctataaac ggtgttgact   116160
taatgtgaca attggcagta gttcaggtct gctttgtaaa tacccttgtg tctattgtaa   116220
aatctcacaa aggcttgttg ccttttttgt ggggttagaa caagaaaaag ccacatggaa   116280
aaaaaatttc ttttttgttt ttttgttttgc ttgttttttt gagacagagt ttcactctgt   116340
cgcccaggct ggagtgcagt ggtgcgatct ccgcccactg caagctccac ctcccgggtt   116400
```

```
catgctattc tcctgtctca gcctcccaag tagctgggac tgcaggtgcc cgccaccaca    116460
cctggctaat ttttttgtat ttttagtaga cacggggttt caccgtgtta gccaggatgg    116520
tctcaatctc ctgacctcgt catctgcctg cctcggcctc ccaaagtgct gagattacag    116580
gcgtgagcca ccgtgcccgg ccagaaaaaa acatttctaa gtatgtggca gatactgaat    116640
tattgcttaa tgtcctttga ttcatttgtt taatttcttt aatggattag tacagaaaac    116700
aaagttctct tccttgaaaa actggtaagt tttctttgtc agataaggag agttaaataa    116760
cccatgacat ttccctttt gcctcggctt ccaggaagct caaagttaaa tgtaatgatc    116820
actcttgtaa ttatcagtgt tgatgccctt cccttcttct aatgttactc tttacatttt    116880
cctgctttat tattgtgtgt gttttctaat tctaagctgt tcccactcct ttctgaaagc    116940
aggcaaatct tctaagcctt atccactgaa aagttatgaa taaaaatga tcgtcaagcc    117000 tacaggtgct gaggctactc cagaggctga ggccagagga ccacttgagc ccaggaattt    117060
gagacctggg ctgggcagca tagcaagact ctatctccat taaaactatt ttttttatt    117120 taaaaaataa tccgcaaaga aggagtttat gtgggattcc ttaaaatcgg agggtggcat    117180
gaattgattc aaagacttgt gcagagggcg acagtgactc cttgagaagc agtgtgagaa    117240
agcctgtccc acctccttcc gcagctccag cctgggctga ggcactgtca cagtgtctcc    117300
ttgctggcag gagagaattt caacattcac caaaaagtag tattgttttt attaggttta    117360
tgaggctgta gccttgagga cagcccagga caactttgtt gtcacataga tagcctgtgg    117420
ctacaaactc tgagatctag attcttctgt ggctgcttct gacctgagaa agttgcggaa    117480
cctcagcgag cctcacatgg cctccttgtc cttaacgtgg ggacggtggg caagaaaggt    117540
gatgtggcac tagagattta tccatctcta aaggaggagt ggattgtaca ttgaaacacc    117600
agagaaggaa ttacaaagga agaatttgag tatctaaaaa tgtaggtcag gcgctcctgt    117660
gttgattgca gggctattca caatagccaa gatttggaag caacccaagt gtccatcaac    117720
agacaaatgg ataagaaaa tgtggtgcat atacacaatg gaatactatt cagccatgaa    117780
aaagaatgag aatctgtcat ttgaaacaac atggatggaa ctggaggaca ttatgttaag    117840
tgaaataagc cagacagaag gacagacttc acatgttctc acacatttgt gggagctaaa    117900
aattaaactc atggagatag agagtagaag gatggttacc agaggctgag gagggtggag    117960
gggagcaggg agaaagtagg gatggttaat gggtacaaaa acgtagttag catgcataga    118020
tctagtattg gatagcacag cagggtgacg acagccaaca gtaatttata gtacatttaa    118080
aaacaactaa aagagtgtaa ttggactggc taacatggtg aaaccccgtc tctactaaaa    118140
atacaaaaat tagctgggca tggtggctca cgcctgtaat cccagcactt tgggaggccg    118200
aggcgggccg atcacgaggt caggagatcg agaccatcct agctaacatg gtgaaacccc    118260
gtctctacta caaatacaaa aaaagaaaa aattagccgg gcatggtggt gggcgcctgt    118320
agtcccagct actcgggagg ctgaggcagg agaatggcgt gaacccggga ggcggagctt    118380
gcagtgagcc gagatcgcgc cactgcactc cagcctgggc gacaaggcaa gattctatct    118440 caaaaaata aaaataaaat aaaataaaat aataaaataa aataaaataa aataaaataa    118500
ataaaataaa ataaaatgta taattggaat gtttataaca caagaaatga taaatgcttg    118560
aggtgataga taccccattc accgtgatgt gattattgca caatgtatgt ctgtatctaa    118620
atatctcatg taccccacaa gtatatacac ctactatgta cccatataaa tttaaaatta    118680
aaaaattata aaacaaaaat aaataagtaa attaaaatgt aggctggaca ccgtggttca    118740
cgcctgtaat cccagtgctt tgtgaggctg aggtgagaga atcacttgag cccaggagtt    118800
```

```
tgagaccggc ctgggtgaca tagcgagacc ccatcatcac aaagaatttt taaaaattag 118860
ctgggcgtgg tagcacatac cggtagttcc agctacttgg gagaccgagg caggaggatt 118920
gcttgagccc aggagtttaa ggctgcagtg agctacgatg gcgccactgc attccagcct 118980
gggtgacaga gtgagagctt gtctctattt taaaaataat aaaagaata aataaaaata 119040 aattaaaatg taaatatgtg catgttagaa aaaatacacc catcagcaaa aaggggtaa 119100 aggagcgatt tcagtcataa ttggagagat gcagaataag ccagcaatgc agtttctttt 119160
attttggtca aaaaaaataa gcaaaacaat gttgtaaaca cccagtgctg cagcaatgt 119220 ggtgaggctg gctctctcac cagggctcac agggaaaact catgcaaccc ttttagaaag 119280
ccatgtggag agttgtaccg agaggtttta gaatatttat aactttgacc cagaaattct 119340
attctaggac tctgtgttat gaaataacc catcatatgg aaaagctcc tttcagaaag 119400 aggttcatgg gaggctgttt gtattttttt tttctttgca tcaaatccag ctcctgcagg 119460
actgtttgta ttattgaagt acaaagtgga atcaatacaa atgttggata gcaggggaac 119520
aatattcaca aaatggaatg ggacatagta ttaaacatag tgcttctgat gaccgtagac 119580
catagacaat gcttaggata tgatatcact tcttttgttg tttttttgtat tttgagacga 119640 agtctcattc tgtcacccag gctggagttc agtggcgcca tctcagctca ctgcaaccct 119700
catctcccgg gttcaagcta ttctccttcc tcaacctccc gagtagctgg gttgcgcacc 119760
accatgcctg gctaacttt gtattttag tacagacggg gtttcaccac gttggccagg 119820
ctgctcttga actcctgacg tcaggtgatc caccagcctt gacctcccaa agtgctagga 119880
ttacaggagc cactgtaccc agcctaggat atgatatcac ttcttagagc aagatacaaa 119940
attgcatgtg cacaataatt ctaccaagta taggtataca ggggtagtta tatataaatg 120000
agacttcaag gaaatacaac aaaatgcaat cgtgattgtg ttagggtggt aagaaaacgg 120060 ttttttgcttt gatgagctct gtttttttaaa atcgttatat tttctaataa aaatacatag 120120
tcttttgaag gaacataaaa gattatgaag aaatgagtta gatattgatt cctattgaag 120180
attcagacaa gtaaaattaa ggggaaaaaa aacgggatga accagaagtc aggctggagt 120240
tccaacccca gatccgacag cccaggctga tggggcctcc agggcagtgg tttccaccca 120300
gcattctcaa aagagccact gaggtctcag tgccattttc aagatttcgg aagcggcctg 120360
ggcacggctg gtccttcact gggatcacca cttggcaatt atttacacct gagacgaata 120420
aaaaccagag tgctgagatt acaggcatgg tggcttacgc ttgtaatcgg ctttgggaag 120480
ccgaggtggg ctgattgctt gagcccagga gtttcaaact atcctggaca acatagcatg 120540
acctcgtctc tacaaaaaat acaaaaaatt tgccaggtgt ggtggcatgt gcctgtggtc 120600
ccagctactt gggaggctga gtaggagaa tcccctgagc cctgggaagt cgaggctgca 120660
ctgagccgtg atggtgtcac tgcactccag cctgggtgac aaagtgagac cctatctcac 120720
aaagaaaaaa aacaaaacaa aaacccaaa gcacactgtt tccactgttt ccagagttcc 120780
tgagaggaaa ggtcaccggg tgaggaagac gttctcactg atctggcaga gaaaatgtcc 120840 agttttttcca actccctaaa ccatggtttt ctatttcata gttcttaggc aaattggtaa 120900
aaatcatttc tcatcaaaac gctgatattt tcacacctcc ctggtgtctg cagaaagaac 120960
cttccagaaa tgcagtcgtg ggagacccat ccaggccacc cctgcttatg aagagctga 121020 gaaaaagccc cacgggagca tttgctcagc ttccgttacg cacctagtgg cattgtgggt 121080
gggagagggc tggtgggtgg atggaaggag aaggcacagc ccccccttgc agggacagag 121140
```

-continued

```
ccctcgtaca gaagggacac cccacatttg tcttccccac aaagcggcct gtgtcctgcc 121200
tacggggtca gggcttctca aacctggctg tgtgtcagaa tcaccagggg aacttttcaa 121260
aactagagag actgaagcca gactcctaga ttctaattct aggtcagggc tagggctga  121320
gattgtaaaa atccacaggt gattctgatg cccggcaggc ttgagaacag ccgcagggag 121380
ttctctggga atgtgccggt gggtctagcc aggtgtgagt ggagatgccg ggaacttcc  121440
tattactcac tcgtcagtgt ggccgaacac attttcact tgacctcagg ctggtgaacg   121500
ctcccctctg gggttcaggc ctcacgatgc catccttttg tgaagtgagg acctgcaatc 121560
ccagcttcgt aaagcccgct ggaaatcact cacacttctg ggatgccttc agagcagccc 121620
tctatccctt cagctcccct gggatgtgac tcaacctccc gtcactcccc agactgcctc 121680
tgccaagtcc gaaagtggag gcatccttgc gagcaagtag gcgggtccag ggtggcgcat 121740
gtcactcatc gaaagtggag gcgtccttgc gagcaagcag gcgggtccag ggtggcgtgt 121800
cactcatcct tttttctggc taccaaaggt gcagataatt aataagaagc tggatcttag 121860
caacgtccag tccaagtgtg gctcaaagga taatatcaaa cacgtcccgg gaggcggcag 121920
tgtgagtacc ttcacacgtc ccatgcgccg tgctgtggct tgaattatta ggaagtggtg 121980
tgagtgcgta cacttgcgag acactgcata gaataaatcc ttcttgggct ctcaggatct 122040
ggctgcgacc tctgggtgaa tgtagcccgg ctccccacat tccccacac  ggtccactgt 122100
tcccagaagc cccttcctca tattctagga ggggtgtcc  cagcatttct gggtccccca  122160
gcctgcgcag gctgtgtgga cagaataggg cagatgacgg accctctctc cggaccctgc 122220
ctgggaagct gagaataccc atcaaagtct ccttccactc atgcccagcc ctgtcccag  122280
gagccccata gccattgga  agttgggctg aaggtggtgg cacctgagac tgggctgccg 122340
cctcctcccc cgacacctgg gcaggttgac gttgagtggc tccactgtgg acaggtgacc 122400
cgtttgttct gatgagcgga caccaaggtc ttactgtcct gctcagctgc tgctcctaca 122460
cgttcaaggc aggagccgat tcctaagcct ccagcttatg cttagcctgc gccaccctct 122520
ggcagagact ccagatgcaa agagccaaac caaagtgcga caggtccctc tgcccagcgt 122580
tgaggtgtgg cagagaaatg ctgcttttgg ccctttttaga tttggctgcc tcttgccagg 122640
agtggtggct cgtgcctgta attccagcac tttgggagac taaggcggga ggttcgcttg 122700
agcccaggag ttcaagacca gcctgggcaa caatgagacc cctgtgtcta caaaagaat  122760
taaaattagc caggtgtggt ggcacgcacc tgtagtccca gctacttggg aggctgaggt 122820
gggaggattg cctgagtccg ggaggcggaa gttgcaagga gccatgatcg cgccactgca 122880
cttcaaccta ggcaacagag tgagactttg tctcaaaaaa caatcatata ataattttaa 122940
aataaataga tttggcttcc tctaaatgtc cccggggact ccgtgcatct tctgtggagt 123000
gtctccgtga gattcgggac tcagatcctc aagtgcaact gacccacccg ataagctgag 123060
gcttcatcat cccctggccg gtctatgtcg actgggcacc cgaggctcct ctcccaccag 123120
ctctcttggt cagctgaaag caaactgtta cacccctggg gagctggacg tatgagaccc 123180
ttggggtggg aggcgttgat ttttgagagc aatcacctgg ccctggctgg cagtaccggg 123240
acactgctgt ggctccgggg tgggctgtct ccagaaaatg cctggcctga ggcagccacc 123300
cgcatccagc ccagagggtt tattcttgca atgtgctgct gcttcctgcc ctgagcacct 123360
ggatcccggc ttctgccctg aggcccttg  agtccacag  gtagcaagcg cttgccctgc 123420
ggctgctgca tggggctaac taacgcttcc tcaccagtgt ctgctaagtg tctcctctgt 123480
ctcccacgcc ctgctctcct gtcccccag  tttgtctgct gtgaggggac agaagaggtg 123540
```

```
tgtgccgccc ccacccctgc ccgggcccett gttcctggga ttgctgtttt cagctgtttg   123600
agctttgatc ctggttctct ggcttcctca aagtgagctc ggccagagga ggaaggccat   123660
gtgctttctg gttgaagtca agtctggtgc cctggtggag ctgtgctgc tgaggcggag    123720 ctggggagag agtgcacacg ggctgcgtgg ccaacccctc tgggtagctg atgcccaaag   123780
acgctgcagt gcccaggaca tctgggacct ccctggggcc cgcccgtgtg tcccgcgctg   123840
tgttcatctg cgggctagcc tgtgacccgc gctgtgctcg tctgcgggct agcctgtgtc   123900
ccgcgctctg cttgtctgcg gtctagcctg tgacctggca gagagccacc agatgtcccg   123960
ggctgagcac tgccctctga gcaccttcac aggaagccct tctcctggtg agaagagatg   124020
ccagcccctg gcatctgggg gcactggatc cctggcctga gccctagcct ctccccagcc   124080
tgggggcccc ttcccagcag gctggccctg ctccttctct acctgggacc cttctgcctc   124140
ctggctggac cctggaagct ctgcagggcc tgctgtcccc ctccctgccc tccaggtatc   124200
ctgaccaccg gccctggctc ccactgccat ccactcctct cctttctggc cgttccctgg   124260
tccctgtccc agccccctc ccctctcac gagttacctc acccaggcca gagggaagag    124320
ggaaggaggc cctggtcata ccagcacgtc ctcccacctc cctcggccct ggtccacccc   124380
ctcagtgctg gcctcagagc acagctctct ccaagccagg ccgcgcgcca tccatcctcc   124440
ctgtccccca acgtccttgc cacagatcat gtccgccctg acacacatgg gtctcagcca   124500
tctctgcccc agttaactcc ccatccataa agagcacatg ccagctgaca ccaaaataat   124560
tcgggatggt tccagtttag acctaagtgg aaggagaaac caccacctgc cctgcacctt   124620 gtttttttggt gaccttgata aaccatcttc agccatgaag ccagctgtct cccaggaagc   124680
tccagggcgg tgcttcctcg ggagctgact gataggtggg aggtggctgc ccccttgcac   124740
cctcaggtga ccccacacaa ggccactgct ggaggccctg gggactccag gaatgtcaat   124800
cagtgacctg ccccccaggc cccacacagc catggctgca tagaggcctg cctccaaggg   124860
acctgtctgt ctgccactgt ggagtcccta cagcgtgccc cccacagggg agctggttct   124920
ttgactgaga tcagctggca gctcagggtc atcattccca gagggagcgg tgccctggag   124980
gccacaggcc tcctcatgtg tgtctgcgtc cgctcgagct tactgagaca ctaaatctgt   125040
tggtttctgc tgtgccacct acccacccctg ttggtgttgc tttgttccta ttgctaaaga   125100
caggaatgtc caggacactg agtgtgcagg tgcctgctgg ttctcacgtc cgagctgctg   125160
aactccgctg ggtcctgctt actgatggtc tttgctctag tgctttccag ggtccgtgga   125220 agctttttcct ggaataaagc ccacgcatcg accctcacag cgcctcccct ctttgaggcc   125280
cagcagatac cccactcctg cctttccagc aagattttc agatgctgtg catactcatc    125340
atattgatca cttttttctt catgcctgat tgtgatctgt caatttcatg tcaggaaagg   125400
gagtgacatt tttacactta agcgtttgct gagcaaatgt ctgggtcttg cacaatgaca   125460
atgggtccct gttttcccca gaggctcttt tgttctgcag ggattgaaga cactccagtc   125520
ccacagtccc cagctcccct ggggcagggt tggcagaatt tcgacaacac attttttccac  125580 cctgactagg atgtgctcct catggcagct gggaaccact gtccaataag gcctgggct    125640 tacacagctg cttctcattg agttacaccc ttaataaaat aatcccattt tatccttttt   125700
gtctctctgt cttcctctct ctctgccttt cctcttctct ctcctcctct ctcatctcca   125760
ggtgcaaata gtctacaaac cagttgacct gagcaaggtg acctccaagt gtggctcatt   125820
aggcaacatc catcataaac caggtagccc tgtggaaggt gagggttggg acgggagggt   125880
```

-continued

```
gcagggggtg gaggagtcct ggtgaggctg gaactgctcc agacttcaga aggggctgga    125940
aaggatattt taggtagacc tacatcaagg aaagtgttga gtgtgaaact tgcgggagcc    126000
caggaggcgt ggtggctcca gctcgctcct gcccaggcca tgctgcccaa gacaaggtga    126060
ggcgggagtg aagtgaaata aggcaggcac agaaagaaag cacatattct cggccgggcg    126120
ctgtggctca cgcctgtaat tccagcactt tgggaggcca aggtgggtgg atcatgaggt    126180
caggagattg agaccatcct ggctaacaca gtgaaacccc gtctctacta aaaatacaaa    126240
aaattagccg ggcgtggtgg tgggcgcctg tagtcccagc tactccggag gctgaggcag    126300
gaaaatggcg tgaacccgga aggcggagct tgcagtgagc ggagtgagca gagatcgcgc    126360
cactgcactc cagcctgggc gacagagcga gactccgtct caaaaaaaaa aagcacatgt    126420
tctcgcttct ttgtgggatc caggagatag agaatagaag gatggttacc agaggctggg    126480
aagggtagtg aggggatggt gggggatgg tcaatgggta caaaaaaaat agaataagac    126540
ctagtatttg atagtgcaac agggtgacta tagtcaataa taatttaatt gtacatttaa    126600
aaataactaa aagatagccg ggtgcagtgg cttacgtctg taatcccagt actttgggag    126660
gctgaggtgg gcgtttgaga ccagcctggc caacatggtg aaaccccatc tctactaaaa    126720
atacaaaaat tagccaggca tggtggcggg cgcctgtaat cccagctact cgggaggctg    126780
aggcaggaga atcacttgaa cctgggaggc agaggttgca gtgagccgag atcttgccac    126840
tgcactccag cctgggtgac agtgaaactc cgtctcaaaa ataaaaataa aatacagct    126900 gggcacggtg gctcacgcct gtaatcccag ctactttggga ggccgaggcg agcggatcac    126960
aaggtcagga gatatagacc atcctggcta acacggtgaa accggtctc tactaaaaat    127020 acaaaaaatt agccaggcgt ggtggcaggt gcctatagtc ccagctactc acaaggctga    127080
ggcaggagaa tggcatgaac ctgggaggcg gagcttgcag tgagccgaga ttgtgccact    127140
gcactccagc ctgggcgaga gagtgagact ccgtctcaaa acaaaaacaa aaacaaaaac    127200
aaaaacaaac acacaacaaa aacctaaaag aatataaatg gattgtttgt aacacaaagg    127260
acaaatgttt gaggggatgg ataccccatt ttccatgatg tgattattat acattgtgtg    127320
tctgtatcaa aacatctcat gagccccata aatatataca cctaactatg tacccacaaa    127380
aattaaaaaa atatatttttt taaggtgaag agggaggcga gatgctggcc ttaaccccta    127440
acccgttgtt ctccctgcaa gctgtccaca gggcctctca gactcgaggt tcagctatat    127500
ggatgcatga gcttggtccc cagccaacat gggagacact tcaccatcgg cagcagctac    127560
agcacaggaa ccctgggtca ctgccatgtc ccctctgtga cttttgttta acagaaatg    127620 atgctctggg ccggctgtgg tggcccacac ctataatccc agcaccttgg gaggcggggg    127680
tgggcagatt gcctgaggtc aggagttgga gatcagcctg gccgacatgg cgaaacccca    127740
tgtctactaa aaatacaaaa actagccagg catggtggca catgcctgta atcccagcta    127800
cttgggaggc tgaagcagga gaatcacttg aacccaggag gcagaggctg agtgagccaa    127860
gatcgtgcca atgcactcca gcttgggtga gggagtgaga ctccgtctca aaaaaaaaaa    127920
aaaagaaaga aaagaaaag aaagtgatcc tactggaacc atgcttactc ccctccccac    127980
ctcacactgt gtagaaatta gtgctgtcgg ccaggcgcgg tggctcatgc ctgtaatcgc    128040
agcactttgg gaggccaagg caggcggatc acgaggtcag gagatcaaga ccatcctggc    128100
taacacagtg aaaccctgtc tctactaaaa atacaaaaaa ttagccgggc atggtggcag    128160
gcacctgtag tcccaactac ttgggaggct gaggcaggaa aatggcatga acctgggagg    128220
cggagcttgc agtgagccaa gatcgcgcca ctgcatacca gcctaggtga cagagtgaga    128280
```

```
ctcagcaaaa aaagaaagaa agaaagaaag aaatcagtgc tgtctatact tctttctgca  128340
gtgatggaaa tattctgtat ctgtgctgtc cagtatagta gccactagct acatgtggca  128400
cttgaaacat ggctggtaca gttgaggaag agtggctgcc atatcggacg acacagctat  128460
agattctgtc accccacccc gagagtccag agcggggact tctgccttag ccctattca   128520
gggctgattt ttacttgaac ccttactgtg ggaagagaag gccatgagaa gttcagtcta  128580
gaatgtgact ccttattttc tggctccctt ggacactttg tgggatttag tctccctgtg  128640
gaaagtattc cacaagtggt gccaccaccc cagctgtgag agcagctggg agctgctttt  128700
gtcatctttc cctggaaagt cctgtgggct gtctcttcct catgccttgt cccatgcttg  128760
ggcatggtgt caagcgtcag gagggagaaa gggtccttat ttatttattt agagagggac  128820
ccttcttctg ttcccaggct ggagtgcagt ggtgcgatct cggctcactg caacctccgc  128880
ctcctgggtt caagtgattc tcctgcctca gcctcctgag tagctgagat tacaggcaca  128940
tgccaacatg cctggctaat ttttttttt tttttttttt ttttttttg agatggagtt    129000
gtactctcat tgcccaggct ggaatgtaat ggcacaatct cggctcactg caacctccac  129060
ctcctggatt caagcaattc tcctgtctca gcttcccaag tagctgggat tacaggtgcc  129120
cgccaccatg ctcaactaat ttttgtattt tttttttagt agagacgagg tttcaccatg  129180
ttggtcagac tggtctcaaa ctcctgacct caggtgatcc acctgcctcg gcctcccaaa  129240
gtgctaggat tacaggcatg agccaccacg cccggcctga aagggttctt atttagtgtg  129300
catttttgaca ttcaatttaa ttccaaggtc ttgtggggtc atggtttaca ggatgttgat  129360
atagaaaga cttcacttaa tgggccgggc gcagtggctc atgcctgtaa tcccagcact  129420
ttgggaggcc gaggcaggca gatcaggagg tcaggagatt gagaccatcc tggctaacac  129480
agtgaaaccc catctctact gaaaatacaa aaaattagct gggcgtggtg gcaggcacct  129540
gtagtcccag ccactcggtt ggctgaggca ggagaatggc atgaacccgg gaggcggagc  129600
ttgcagtgag cagagaccat gccactgcac tccagcctgg gcgacagagc aagactctgt  129660
ctcaagaaaa aaaaaaaaaa aacagacttt acttactgga agccaaccaa tgtatattta  129720
gagtaatttt tcctgggctg agctgtcatt tacttttgca gtatctcaag aagaagagtt  129780
tacagtgtaa atatttgatg cacactttga ttatatagat gaagcaaact attttcaaga  129840
gctttgcaag gacttacttg tatccaaaca ccattctaaa ggagtcttac ctacttctaa  129900
aggctggtct ctacttggaa ccacttgctt ggccctggtt caagtcctgc tgcaaacctg  129960
gaagtcctgt cattgtcttc ttccctccag agcagtggca cccaatctaa ttttttgctgt  130020
gccccagcag cccctggcac tttgccctgt agactgcaga cctcatgtaa tgtatgttaa  130080
gtccacagaa ccacagaaga tgatggcaag atgctcttgt gtgtgttgtg ttctaggagg  130140
tggccaggtg gaagtaaaat ctgagaagct tgacttcaag gacagagtcc agtcgaagat  130200
tgggtccctg gacaatatca cccacgtccc tggcggagga aataaaaagg taagggggt   130260
agggtgggtt ggatgctgcc cttgggtata tgggcattaa tcaagttgag tggacaaagg  130320
ctggtccagt tcccagagga ggaaaacaga ggcttctgtg ttgactggct ggatgtgggc  130380
cctcagcagc atccagtggg tctccactgc ctgtctcaat cacctggagc tttagcacgt  130440
ttcacacctg ggccccaacc tggagaggct gaccaatggg tctcaggggc agctcggttg  130500
ctggagtttt tgtttttatt tattttttatg tatttaaggc agggtctctg tattagtcca  130560
ttctcacact gctaataaag acatacccaa gactgggtaa tttataaagg aaagaggttt  130620
```

```
aatggactca cagttccaca tggctgggga ggcctcaaaa tcatggcgga aggcaaagga    130680
gaagcaaagg catttcttac atggcgacag gcaagagagc gtgtgcaggg gaactcccat    130740
ttataaaacc atcagacctc atgagattta ttcactatca tgagaacagc atgggaaaga    130800
cccgccccca tgattcagtt acctcccact gggtccctcc catgacacat ggaattatgg    130860
gagctacaat tcaagatgag atttgggtgg ggacacagcc aaaccatatc agtctccctc    130920
tgtcatccag gctggagtgc actggcatga tctcggctca ctgcagcctc tacctccctg    130980
ggtcaggtga tcttcccacc tcagcctccc aggtagctgg aactacaggt acctgccact    131040
atgcctggct aaatattttg tatttcctgt ggagacgagg ttttgccacg ttgcccaggc    131100
tggtcttgaa ctcctgaggt caagcaatat gcccacctcg gcctcccaag gtgctgggat    131160
tacaggtgtg agccacagtg ctcggcctaa gtcactgcag tttttaaagc tcccaggtga    131220
ttcttcagtg cagtcaaaag tgagaactgg ctgggtgcgg tggctcatgc ctgtaatccc    131280
agcaccttgg gaggcgaagg tgggcagatg gcttgaggtc aggagttcaa gaccagcctg    131340
gccaacatgg taaaacccca tctctactaa aaatacaaaa gttagctggg tgtggtggtg    131400
cgtgcctgta atcccagcta cttgggaggc tgaggcatga gaattgcttg aacccagggg    131460
acagaggttg tagtgagccg agatcgtgcc actgcactcc agcctgggca acagagtgag    131520
attccatctc acaaaaaaaa aaaaaaagc gagaaccact gtcctaggcc ctgatgtttg    131580
caggcaacta aaaaggaag tggacatccc cagtcagctg tggcgcacca agaacaagtc    131640
atgggaacat aacctaattt tctaaatggg ttactaggca cttagagcaa acaatgatg    131700 ccgaaatcct gatttcagca aagcctctgc ctgcctgtct tggaagtatc cacatggagc    131760
tgctggggcc ttggtgtccc cagcagtttc tagtctctag gtcttgctgt gggtgtctgt    131820
gcagtgaggg tgtgtgtggc gctgggtgag ctctgtctag gcctggcaca ggatgcggtc    131880
tggtagctgc tgcttctctt ctgcagaagc gcagccaagc accctctggg gtttcaggcc    131940
cacacccagc ctgaagttct gggagtggct cactttccaa ccttcagggt ctcccagcag    132000
ctgactgggg agtggtggag ggaaaaggga ttgtattagt ccgttttcac gccgctgatg    132060
aagacatacc cgatactggg cagtctaaaa gatagaggtc tgatggactc acagttccac    132120
gtgactgggg aggcctgaca atcatggtgg aaggtgaaag gcttgtctca cacggtggca    132180
gacaagagaa aagagcttgt gcaggggaac tcccctttat aaaaccatca gatctcggga    132240
gacttattca ctatcatgag aacagcacgg gaaagaccct cctctatgat tcaattacct    132300
cccaccaggt ccctcccaca acatgtagga attgtgggaa ctacaattca agatgacatt    132360
tgggtgggga cacagccaaa ccatatcagg gcgtcccaga aagggtatag ggtctgagac    132420
ccaagtcagc atgagaaagt atgcttctca tggtggccca gttgggtgga agtggcagcc    132480
gggccgtctt tccaccaggc cactcaagta gcagctgaga gaccctgcc ctggccagtc    132540 cccgccctcc cctcttgcca ctgcctctgg ttctgaacag atgggcaccc tcatcttgta    132600
tttgtgatta atgtctaaca atgtagtttt gtgagaaggg tttgctgata cagccttgct    132660
gcagatgctg cgaactgtgg cctggggcag accttacctc cagacacgcc ctgaggcagg    132720
ggagggcact ggcccgtagc tggccgagag ctctcgggtt gcgcgacagg gatactttc    132780 agcggctggg tcgctatcca aagtgagaaa acgaggaggg accaggaggc tgtccgcctc    132840
aagagatgtg ggggccaggt ccagttatct ggggaagcag taagcttctc tgctgtttct    132900
aaccccaggc ctcccctggt ctaaggcagg gcctcccagc ctcggggcac tttaaagata    132960
tctgggcctg gccccatccc cacagtctga ctgagtgggt ctggataggg cctgagcatt    133020
```

```
ggtgatttcc tgggtgaaag gaggcccctc acagtctctg gaagcttctc tgtgttagga   133080
aaagctctgg gcttgactct gctttgaaag tcaagatccg caaatcctct cagcctcagt   133140
ttctccttca gcaagatgaa atggaaatgc tgtacctacg tcccggggtg gttgtgagac   133200
ccaaaaaaga caatgttctg gaaggttcct ggtgcgttgc agtcctctaa gaacctgagt   133260
tagagccacg ctgagtctca gcttcttggc tccttctgtt tcaaactcgt ccatgtgata   133320
gctcaggaag ggtaggcagg gccctgcccc tactcagaa acaccatcc tggtcctggg    133380 gatccccgca gcattagtcc cctgttttcc cagtgtattg agaaaaattg ctaacaagca   133440
gtggggcaca ccaccagcct cctgggttcc tttcagtttg gggattttg gacattccca    133500 ggaatgtctt aaaaaacact tcaaaaaaca ttaacataaa tatttttatc aaagcctgta   133560
ttaaatggtc tttcaagaaa atacagtaac aggtcaggca tggtggctca tgcctgtaac   133620
cccagcactt tgggaggcca aggcaggcag atcacctgaa atcaggagtt caagaccaac   133680
ctggccaaca cagccaaatc ccatctctac aaaaaataca aaaattagct gggtgtggtg   133740
gcacacacct gtagtcccag ctacttggga ggccgaggca ggagaattgc ttgatcccgg   133800
aggcggaggt tgcagtgagc tgagatcgtg ccactgcact ccagcgtggg tgacaaggtg   133860
aatctttgtc tcaaaaaaa aaaaaaaaa aagataaaat acagtataca gtaatagaga    133920
acaatccttt tttcaaagta gtgaccccaa atgaacaaaa tatgcatcta gcttaaatgc   133980
gaacctggtt ttctctacgc ccattcaagc ccctgcaata ggggcccttc accccgcatc   134040
catggactcc taaaattata tggaaaatgg ctgtgtgtga gtgtggatgg acatgtgcac   134100
acatattttt ggctttacca gatgctcaaa gagcctagga cccaaaaagg gctgagaatg   134160
accgtgtcgg ccacttcagg gtcatcagga attgctgtgc actgctcact tctccagtga   134220
acactttctg cttctgtgtt tcctggtatc ctttgggact cctggctagg tcatgtgttt   134280
ctctactttc aaaagggctt cagccaggca cgatggcatg agcctgtagt cccagttgct   134340
ctggaggtta aggtgggaag attgcttgag cccaggaatt tgaggccagc ctgggcaagt   134400
agataggtag atgattgata gatagataga tagataaata gatggataga taagtcgcta   134460
gacagtcatc catccaccca tccacacata aaaaggcctt tgtcatgtca tgttttgtgg   134520
cccacctgcc agtgttgccc acagttgctg cccctccaaa ctcatcagtc actggcaaac   134580
aggaggaatg tgtggctcat gtctgggcat cagtggctgt gggagacatc cttgatcttc   134640
tccagcttct ccttccacat tttcctttgc aatctggcaa tatctattaa aataaaatgt   134700
gcatgccttt tgacctaaga gcttcacttc taggacccac ttacacgtgt gtgacatgat   134760
gttcatacgg gtttatttat ctgaggttgt tcatacacac cattgcctgt aatcactaaa   134820
ggcgggagca gcctacacat ccatccacag aggagtagat gccttttggt acatccgtgg   134880
cgacggaata ctaagcagcc tgtgtatcta tacactcaca cgtgtttgtt tatgtgtgga   134940
atatctctgg agggtacaca agaaacttaa aatgatcact gtctctgggg agggtacctg   135000
ggtgcctggg aggcaggtca gggaaggagt gggcacaggt attaccaatt ggaagacaat   135060
aaaaacaaca gctcctggcc aggcgcagtg gctcacgcct gtaatggcag cactctgaga   135120
ggctgaggcg ggcagattgc ttgcgtccag gagttcaaga ccagcctggg caacatagca   135180 aaacccgtt tctattaaaa atacaaaaaa ttagccaggt gtggtggcat gcacctgtaa   135240
tcccagctac tcgggaggct gaggtgggag aatcacctga gctgggagg tcaaggctgc    135300 agtgaggtga gattgtgcca ccgcactcta gcctgggcga tagagcaaga ccctgtctca   135360
```

```
aaaacaaaca aaaaacagtc cctggcactc tgggccaggc ctggcagggc agttggcagg    135420
gctggtctttt ctctggcact tcatctcacc ctccctccct tcctcttctt gcagattgaa    135480
acccacaagc tgaccttccg cgagaacgcc aaagccaaga cagaccacgg ggcggagatc    135540
gtgtacaagt cgccagtggt gtctggggac acgtctccac ggcatctcag caatgtctcc    135600
tccaccggca gcatcgacat ggtagactcg ccccagctcg ccacgctagc tgacgaggtg    135660
tctgcctccc tggccaagca gggtttgtga tcaggcccct ggggcggtca ataattgtgg    135720
agaggagaga atgagagagt gtggaaaaaa aaagaataat gacccggccc ccgccctctg    135780
cccccagctg ctcctcgcag ttcggttaat tggttaatca cttaacctgc ttttgtcact    135840
cggctttggc tcgggacttc aaaatcagtg atgggagtaa gagcaaattt catctttcca    135900
aattgatggg tgggctagta ataaaatatt taaaaaaaaa cattcaaaaa catgccaca    135960
tccaacattt cctcaggcaa ttccttttga ttcttttttc ttccccctcc atgtagaaga    136020
gggagaagga gaggctctga aagctgcttc tggggatttt caaggactg ggggtgccaa    136080
ccacctctgg ccctgttgtg ggggtgtcac agaggcagtg gcagcaacaa aggatttgaa    136140
acttggtgtg ttcgtggagc cacaggcaga cgatgtcaac cttgtgtgag tgtgacgggg    136200
gttgggtgg ggcgggaggc cacggggggag gccgaggcag gggctgggca gaggggagag    136260
gaagcacaag aagtgggagt gggagaggaa gccacgtgct ggagagtaga catcccctc    136320
cttgccgctg ggagagccaa ggcctatgcc acctgcagcg tctgagcggc cgcctgtcct    136380
tggtggccgg gggtgggggc ctgctgtggg tcagtgtgcc accctctgca gggcagcctg    136440
tgggagaagg gacagcgggt aaaaagagaa ggcaagctgg caggagggtg gcacttcgtg    136500
gatgacctcc ttagaaaaga ctgaccttga tgtcttgaga gcgctggcct cttcctccct    136560
ccctgcaggg tagggggcct gagttgaggg gcttccctct gctccacaga aaccctgttt    136620
tattgagttc tgaaggttgg aactgctgcc atgattttgg ccactttgca gacctgggac    136680
tttaggctga accagttctc tttgtaagga cttgtgcctc ttgggagacg tccaccgtt    136740
tccaagcctg ggccactggc atctctggag tgtgtggggg tctgggaggc aggtcccgag    136800
cccctgtcc ttcccacggc cactgcagtc acccgctg cgccgctgtg ctgttgtctg    136860
ccgtgagagc ccaatcactg cctatacccc tcatcacacg tcacaatgtc ccgaattccc    136920
agcctcacca cccttctca gtaatgaccc tggttggttg caggagtac ctactccata    136980
ctgagggtga aattaaggga aggcaaagtc caggcacaag agtgggaccc cagcctctca    137040
ctctcagtc cactcatcca actgggaccc tcaccacgaa tctcatgatc tgattcggtt    137100
ccctgtctcc tcctcccgtc acagatgtga gccagggcac tgctcagctg tgaccctagg    137160
tgttctgcc ttgttgacat ggagagagcc ctttcccctg agaaggcctg gcccttcct    137220
gtgctgagcc cacagcagca ggctgggtgt cttggttgtc agtggtggca ccaggatgga    137280
agggcaaggc acccagggca ggcccacagt cccgctgtcc cccacttgca ccctagcttg    137340
tagctgccaa cctcccagac agcccagccc gctgctcagc tccacatgca agtatcagc    137400
cctccacacc cgacaaaggg gaacacaccc ccttggaaat ggttctttc cccagtccc    137460
agctggaagc catgctgtct gttctgctgg agcagctgaa catatacata gatgttgccc    137520
tgccctcccc atctgcaccc tgttgagttg tagttggatt tgtctgttta tgcttggatt    137580
caccagagtg actatgatag tgaaaagaaa aaaaaaaaaa aaaaaggacg catgtatctt    137640
gaaatgcttg taaagaggtt tctaacccac cctcacgagg tgtctctcac ccccacactg    137700
ggactcgtgt ggcctgtgtg gtgccaccct gctgggggcct cccaagtttt gaaaggcttt    137760
```

```
cctcagcacc tgggacccaa cagagaccag cttctagcag ctaaggaggc cgttcagctg   137820
tgacgaaggc ctgaagcaca ggattaggac tgaagcgatg atgtcccctt ccctacttcc   137880
ccttggggct ccctgtgtca gggcacagac taggtcttgt ggctggtctg gcttgcggcg   137940
cgaggatggt tctctctggt catagcccga agtctcatgg cagtcccaaa ggaggcttac   138000
aactcctgca tcacaagaaa aaggaagcca ctgccagctg gggggatctg cagctcccag   138060
aagctccgtg agcctcagcc acccctcaga ctgggttcct ctccaagctc gccctctgga   138120
ggggcagcgc agcctcccac caagggccct gcgaccacag cagggattgg gatgaattgc   138180
ctgtcctgga tctgctctag aggcccaagc tgcctgcctg aggaaggatg acttgacaag   138240
tcaggagaca ctgttcccaa agccttgacc agagcacctc agcccgctga ccttgcacaa   138300
actccatctg ctgccatgag aaagggaag ccgcctttgc aaaacattgc tgcctaaaga   138360
aactcagcag cctcaggccc aattctgcca cttctggttt gggtacagtt aaaggcaacc   138420
ctgagggact tggcagtaga aatccagggc ctccccctgg gctggcagct tcgtgtgcag   138480
ctagagcttt acctgaaagg aagtctctgg gcccagaact ctccaccaag agcctccctg   138540
ccgttcgctg agtcccagca attctcctaa gttgaaggga tctgagaagg agaaggaaat   138600
gtggggtaga tttggtggtg gttagagata tgcccccctc attactgcca acagtttcgg   138660
ctgcatttct tcacgcacct cggttcctct tcctgaagtt cttgtgccct gctcttcagc   138720
accatgggcc ttcttatacg gaaggctctg ggatctcccc cttgtggggc aggctcttgg   138780
ggccagccta agatcatggt ttagggtgat cagtgctggc agataaattg aaaaggcacg   138840
ctggcttgtg atcttaaatg aggacaatcc ccccagggct gggcactcct cccctcccct   138900
cacttctccc acctgcagag ccagtgtcct tgggtgggct agataggata tactgtatgc   138960
cggctccttc aagctgctga ctcactttat caatagttcc atttaaattg acttcagtgg   139020
tgagactgta tcctgtttgc tattgcttgt tgtgctatgg ggggaggggg gaggaatgtg   139080
taagatagtt aacatgggca aagggagatc ttggggtgca gcacttaaac tgcctcgtaa   139140
ccctttcat gatttcaacc acatttgcta gagggaggga gcagccacgg agttagaggc   139200
ccttggggtt tctcttttcc actgacaggc tttcccaggc agctggctag ttcattccct   139260
ccccagccag gtgcaggcgt aggaatatgg acatctggtt gctttggcct gctgccctct   139320
ttcagggtc ctaagcccac aatcatgcct ccctaagacc ttggcatcct tccctctaag   139380
ccgttggcac ctctgtgcca cctctcacac tggctccaga cacacagcct gtgcttttgg   139440
agctgagatc actcgcttca ccctcctcat ctttgttctc caagtaaagc cacgaggtcg   139500
gggcgagggc agaggtgatc acctgcgtgt cccatctaca gacctgcagc ttcataaaac   139560
ttctgatttc tcttcagctt tgaaaagggt taccctgggc actggcctag agcctcacct   139620
cctaatagac ttagccccat gagtttgcca tgttgagcag gactatttct ggcacttgca   139680
agtcccatga tttcttcggt aattctgagg gtggggggag ggacatgaaa tcatcttagc   139740
ttagctttct gtctgtgaat gtctatatag tgtattgtgt gttttaacaa atgatttaca   139800
ctgactgttg ctgtaaaagt gaatttggaa ataaagttat tactctgatt aaataaggtc   139860
tccattcatg gattccaagg acaagaaagt catatagaat gtctattttt taagttcttt   139920
cccacgcacc cttagataat ttagctcaga acaggaaatg atagtattaa taaaagctgg   139980
acatcaggat taacagctct ctctggggcc ctgaaggtga gagttctcag acttgctcat   140040
ttgcagttgc ttctttgtga tgctggcaaa ccatcctagt cccattcaaa gggcaataca   140100
```

```
aagccttgtg gctgacctca cgatgcagca ctcagtttgc aagaccggca ccagtgtatg   140160
caaacctgag aaggttgggg atgaggatat gggatctttc atccctggaa atttagtcca   140220
gaggcctggg gctggagcag aacaccaagc caatcagctt aatgaatggc ttagattcct   140280
gctaggtttg cagagctgcc ttctttcctt tggtaccttc ttatagattg aggagtattt   140340
ctgctaaacc aagatagggc taaccagata gcatcttcat agcaatgcca caaggaaaa    140400 caaaaacaaa acagtaatcc atcatattat tccttagtaa ctatgccaag gtcatgatac   140460
tgaatcctta gattgtttca aaatactact tttctttgct cttcctgatg tgtttgccac   140520
cgcaggcaga tgtttaagta aaacagattt taactgcagc tacaaaagca gcaacaggcc   140580
agcaaaagag aagtgctatc tcagagagca tggctttcag agccacaaga gacagcctca   140640
ctggctgttt cagcttgact gccatgcaaa gaagagagca gagggagaac cagccccacc   140700
cacttattca tcttgtacaa aaaaaaagca cctaccagcc taggctacat agtgagacac   140760
tatctccaca aaaaacccac gaaaactagc tgggtatggt ggcacatgcc tacagtccca   140820
gctactggta aggctgtggt gggaggatct cttgaggcca ggaaggagat ccaggctgca   140880
gtgagccaag attgcaccac tgcactccag tctggacaat cgagcaagat cccatctcaa   140940
acaataaaaa aaaaagcgt gtaacctcct cagaagaaag atgttataat ctcaggcagc   141000
a                                                                  141001

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
cactgagaac ctgaagcacc                                                       20

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
ggactggacg ttgctaagat c                                                     21

<210> SEQ ID NO 4
<211> LENGTH: 26
<212> TYPE: DNA
<213> ORGANISM: Artificial sequence
<220> FEATURE:
<223> OTHER INFORMATION: Probe

<400> SEQUENCE: 4
ttaattatct gcaccttccc gcctcc                                                26

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
ggataatatc aaacacgtcc cg                                                    22
```

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tgcctaatga gccacacttg                                                    20

<210> SEQ ID NO 7
<211> LENGTH: 24
<212> TYPE: DNA
<213> ORGANISM: Artificial sequence
<220> FEATURE:
<223> OTHER INFORMATION: Probe

<400> SEQUENCE: 7
gtctacaaac cagttgacct gagc                                               24

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
cccgcctact tgctcgca                                                      18

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 9
tggacccgcc tacttgct                                                      18

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
accctggacc cgcctact                                                      18

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
catgcgccac cctggacc                                                      18

<210> SEQ ID NO 12
<211> LENGTH: 18
<212> TYPE: DNA
<213> ORGANISM: Artificial sequence
<220> FEATURE:

```
<223> OTHER INFORMATION: Synthetic oligonucleotide

<400> SEQUENCE: 12
gtgacatgcg ccaccctg                                                 18

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 13
atgagtgaca tgcgccac                                                 18

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 14
ttcgatgagt gacatgcg                                                 18

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
cactttcgat gagtgaca                                                 18

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
cctccacttt cgatgagt                                                 18

<210> SEQ ID NO 17
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 17
gacgcctcca ctttcgat                                                 18

<210> SEQ ID NO 18
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 18
caaggacgcc tccacttt                                                 18
```

```
<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
ctcgcaagga cgcctcca                                              18

<210> SEQ ID NO 20
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 20
cttgctcgca aggacgcc                                              18

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
cctgcttgct cgcaagga                                              18

<210> SEQ ID NO 22
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 22
cccgcctgct tgctcgca                                              18

<210> SEQ ID NO 23
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 23
tggacccgcc tgcttgct                                              18

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
accctggacc cgcctgct                                              18

<210> SEQ ID NO 25
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 25
cgccaccctg gacccgcc                                                18

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26
gacacgccac cctggacc                                                18

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
gagtgacacg ccaccctg                                                18

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 28
ggatgagtga cacgccac                                                18

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 29
aaaaggatga gtgacacg                                                18

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
agaaaaaagg atgagtga                                                18

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 31
agccagaaaa aaggatga                                                18

<210> SEQ ID NO 32
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 32
tggtagccag aaaaaagg                                                   18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
ttatcctttg agccacac                                                   18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
gatattatcc tttgagcc                                                   18

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
gtttgatatt atcctttg                                                   18

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 36
acgtgtttga tattatcc                                                   18

<210> SEQ ID NO 37
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 37
cgggacgtgt ttgatatt                                                   18

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38
```
ctcccgggac gtgtttga                                                    18

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
ccgcctcccg ggacgtgt                                                    18

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 40
actgccgcct cccgggac                                                    18

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 41
tcacactgcc gcctcccg                                                    18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
gtactcacac tgccgcct                                                    18

<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
gaaggtactc acactgcc                                                    18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 44
gtgtgaaggt actcacac                                                    18

<210> SEQ ID NO 45
<211> LENGTH: 18
<212> TYPE: DNA
<213> ORGANISM: Artificial sequence -continued

```
<220> FEATURE:
<223> OTHER INFORMATION: Synthetic oligonucleotide

<400> SEQUENCE: 45
ggacgtgtga aggtactc                                                18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 46
catgggacgt gtgaaggt                                                18

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
ggcgcatggg acgtgtga                                                18

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
gcacggcgca tgggacgt                                                18

<210> SEQ ID NO 49
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 49
cacagcacgg cgcatggg                                                18

<210> SEQ ID NO 50
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 50
aagccacagc acggcgca                                                18

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 51
attcaagcca cagcacgg                                                18
```

```
<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 52
aataattcaa gccacagc                                                 18

<210> SEQ ID NO 53
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 53
tcctaataat tcaagcca                                                 18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
cacttcctaa taattcaa                                                 18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55
acaccacttc ctaataat                                                 18

<210> SEQ ID NO 56
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 56
actcacacca cttcctaa                                                 18

<210> SEQ ID NO 57
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 57
gtgtacgcac tcacacca                                                 18

<210> SEQ ID NO 58
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 58
gcaagtgtac gcactcac                                                18

<210> SEQ ID NO 59
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 59
tctcgcaagt gtacgcac                                                18

<210> SEQ ID NO 60
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 60
agtgtctcgc aagtgtac                                                18

<210> SEQ ID NO 61
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 61
atgcagtgtc tcgcaagt                                                18

<210> SEQ ID NO 62
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 62
ttctatgcag tgtctcgc                                                18

<210> SEQ ID NO 63
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 63
tttattctat gcagtgtc                                                18

<210> SEQ ID NO 64
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 64
aggatttatt ctatgcag                                                18

<210> SEQ ID NO 65
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 65
aagaaggatt tattctat                                                 18

<210> SEQ ID NO 66
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 66
gcccaagaag gatttatt                                                 18

<210> SEQ ID NO 67
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 67
gagagcccaa gaaggatt                                                 18

<210> SEQ ID NO 68
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 68
tcctgagagc ccaagaag                                                 18

<210> SEQ ID NO 69
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 69
cagatcctga gagcccaa                                                 18

<210> SEQ ID NO 70
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 70
cctttggtag ccagaaaa                                                 18

<210> SEQ ID NO 71
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 71
```
tgcacctttg gtagccag                                                 18

<210> SEQ ID NO 72
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 72
taattatctg cacctttg                                                 18

<210> SEQ ID NO 73
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 73
ttcttaatta tctgcacc                                                 18

<210> SEQ ID NO 74
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 74
cttcttctta attatctg                                                 18

<210> SEQ ID NO 75
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 75
ccagcttctt cttaatta                                                 18

<210> SEQ ID NO 76
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 76
agatccagct tcttctta                                                 18

<210> SEQ ID NO 77
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 77
gctaagatcc agcttctt                                                 18

<210> SEQ ID NO 78
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 78
cgttgctaag atccagct                                                   18

<210> SEQ ID NO 79
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 79
tggacgttgc taagatcc                                                   18

<210> SEQ ID NO 80
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 80
ggactggacg ttgctaag                                                   18

<210> SEQ ID NO 81
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 81
acttggactg gacgttgc                                                   18

<210> SEQ ID NO 82
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 82
ccacacttgg actggacg                                                   18

<210> SEQ ID NO 83
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 83
tgagccacac ttggactg                                                   18

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 84
aaaaaggatg agtgacac                                                   18
```

<210> SEQ ID NO 85
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 85
aaaaaaggat gagtgaca                                                18

<210> SEQ ID NO 86
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 86 gaaaaagga tgagtgac                                                 18

<210> SEQ ID NO 87
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 87 cagaaaaag gatgagtg                                                 18

<210> SEQ ID NO 88
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 88
ccagaaaaaa ggatgagt                                                18

<210> SEQ ID NO 89
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 89
gccagaaaaa aggatgag                                                18

<210> SEQ ID NO 90
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 90
tagccagaaa aaaggatg                                                18

<210> SEQ ID NO 91
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 91
gtagccagaa aaaggat                                                    18

<210> SEQ ID NO 92
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 92
ggtagccaga aaaagga                                                    18

<210> SEQ ID NO 93
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 93
ttggtagcca gaaaaaag                                                   18

<210> SEQ ID NO 94
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 94
tttggtagcc agaaaaaa                                                   18

<210> SEQ ID NO 95
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 95
ctttggtagc cagaaaaa                                                   18

<210> SEQ ID NO 96
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 96
acctttggta gccagaaa                                                   18

<210> SEQ ID NO 97
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 97
cacctttggt agccagaa                                                   18

```
<210> SEQ ID NO 98
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 98
gcacctttgg tagccaga                                                 18

<210> SEQ ID NO 99
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 99
ctgcaccttt ggtagcca                                                 18

<210> SEQ ID NO 100
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 100 tctgcaccttt tggtagcc                                                18

<210> SEQ ID NO 101
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 101
atctgcacct ttggtagc                                                 18

<210> SEQ ID NO 102
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 102
tatctgcacc tttggtag                                                 18

<210> SEQ ID NO 103
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 103
ttatctgcac ctttggta                                                 18

<210> SEQ ID NO 104
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 104
attatctgca cctttggt                                                   18

<210> SEQ ID NO 105
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 105
aattatctgc acctttgg                                                   18

<210> SEQ ID NO 106
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 106
ttaattatct gcaccttt                                                   18

<210> SEQ ID NO 107
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 107
attaattatc tgcacctt                                                   18

<210> SEQ ID NO 108
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 108
tattaattat ctgcacct                                                   18

<210> SEQ ID NO 109
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 109
ttattaatta tctgcacc                                                   18

<210> SEQ ID NO 110
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 110
cttattaatt atctgcac                                                   18

<210> SEQ ID NO 111
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 111
tcttattaat tatctgca                                                 18

<210> SEQ ID NO 112
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 112
ttcttattaa ttatctgc                                                 18

<210> SEQ ID NO 113
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 113
cttcttatta attatctg                                                 18

<210> SEQ ID NO 114
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 114
gcttcttatt aattatct                                                 18

<210> SEQ ID NO 115
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 115
agcttcttat taattatc                                                 18

<210> SEQ ID NO 116
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 116
cagcttctta ttaattat                                                 18

<210> SEQ ID NO 117
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 117
```
ccagcttctt attaatta                                              18

<210> SEQ ID NO 118
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 118
tccagcttct tattaatt                                              18

<210> SEQ ID NO 119
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 119
atccagcttc ttattaat                                              18

<210> SEQ ID NO 120
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 120
gatccagctt cttattaa                                              18

<210> SEQ ID NO 121
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 121
agatccagct tcttatta                                              18

<210> SEQ ID NO 122
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 122
aagatccagc ttcttatt                                              18

<210> SEQ ID NO 123
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 123
taagatccag cttcttat                                              18

<210> SEQ ID NO 124
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 124
ctaagatcca gcttctta                                                   18

<210> SEQ ID NO 125
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 125
tgctaagatc cagcttct                                                   18

<210> SEQ ID NO 126
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 126
ttgctaagat ccagcttc                                                   18

<210> SEQ ID NO 127
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 127
gttgctaaga tccagctt                                                   18

<210> SEQ ID NO 128
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 128
acgttgctaa gatccagc                                                   18

<210> SEQ ID NO 129
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 129
gacgttgcta agatccag                                                   18

<210> SEQ ID NO 130
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 130
ggacgttgct aagatcca                                                   18
```

<210> SEQ ID NO 131
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 131
ctggacgttg ctaagatc                                                   18

<210> SEQ ID NO 132
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 132
actggacgtt gctaagat                                                   18

<210> SEQ ID NO 133
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 133
gactggacgt tgctaaga                                                   18

<210> SEQ ID NO 134
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 134
tggactggac gttgctaa                                                   18

<210> SEQ ID NO 135
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 135
ttggactgga cgttgcta                                                   18

<210> SEQ ID NO 136
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 136
cttggactgg acgttgct                                                   18

<210> SEQ ID NO 137
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 137
cacttggact ggacgttg                                              18

<210> SEQ ID NO 138
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 138
acacttggac tggacgtt                                              18

<210> SEQ ID NO 139
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 139
cacacttgga ctggacgt                                              18

<210> SEQ ID NO 140
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 140
gccacacttg gactggac                                              18

<210> SEQ ID NO 141
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 141
agccacactt ggactgga                                              18

<210> SEQ ID NO 142
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 142
gagccacact tggactgg                                              18

<210> SEQ ID NO 143
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 143
ttgagccaca cttggact                                              18

<210> SEQ ID NO 144
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 144
tttgagccac acttggac                                                 18

<210> SEQ ID NO 145
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 145
ctttgagcca cacttgga                                                 18

<210> SEQ ID NO 146
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 146
cctttgagcc acacttgg                                                 18

<210> SEQ ID NO 147
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 147
tcctttgagc cacacttg                                                 18

<210> SEQ ID NO 148
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 148
atcctttgag ccacactt                                                 18

<210> SEQ ID NO 149
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 149
tatcctttga gccacact                                                 18

<210> SEQ ID NO 150
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 150
```
attatccttt gagccaca                                          18

<210> SEQ ID NO 151
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 151
tattatcctt tgagccac                                          18

<210> SEQ ID NO 152
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 152
atattatcct ttgagcca                                          18

<210> SEQ ID NO 153
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 153
tgatattatc ctttgagc                                          18

<210> SEQ ID NO 154
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 154
ttgatattat cctttgag                                          18

<210> SEQ ID NO 155
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 155
tttgatatta tcctttga                                          18

<210> SEQ ID NO 156
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 156
tgtttgatat tatccttt                                          18

<210> SEQ ID NO 157
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 157
gtgtttgata ttatcctt                                                 18

<210> SEQ ID NO 158
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 158
cgtgtttgat attatcct                                                 18

<210> SEQ ID NO 159
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 159
gacgtgtttg atattatc                                                 18

<210> SEQ ID NO 160
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 160
ggacgtgttt gatattat                                                 18

<210> SEQ ID NO 161
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 161
gggacgtgtt tgatatta                                                 18

<210> SEQ ID NO 162
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 162
ccgggacgtg tttgatat                                                 18

<210> SEQ ID NO 163
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 163
cccgggacgt gtttgata                                                 18
```

```
<210> SEQ ID NO 164
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 164
tcccgggacg tgtttgat                                                 18

<210> SEQ ID NO 165
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 165
cactgccgcc tcccggga                                                 18

<210> SEQ ID NO 166
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 166
acactgccgc ctcccggg                                                 18

<210> SEQ ID NO 167
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 167
cacactgccg cctcccgg                                                 18

<210> SEQ ID NO 168
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 168
ctcacactgc cgcctccc                                                 18

<210> SEQ ID NO 169
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 169
actcacactg ccgcctcc                                                 18

<210> SEQ ID NO 170
<211> LENGTH: 18
<212> TYPE: DNA
<213> ORGANISM: Artificial sequence
<220> FEATURE:
```

<223> OTHER INFORMATION: Synthetic oligonucleotide

<400> SEQUENCE: 170
tactcacact gccgcctc                                                      18

<210> SEQ ID NO 171
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 171
ggtactcaca ctgccgcc                                                      18

<210> SEQ ID NO 172
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 172
aggtactcac actgccgc                                                      18

<210> SEQ ID NO 173
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 173
aaggtactca cactgccg                                                      18

<210> SEQ ID NO 174
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 174
tgaaggtact cacactgc                                                      18

<210> SEQ ID NO 175
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 175
gtgaaggtac tcacactg                                                      18

<210> SEQ ID NO 176
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 176
tgtgaaggta ctcacact                                                      18

<210> SEQ ID NO 177
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 177
cgtgtgaagg tactcaca                                                 18

<210> SEQ ID NO 178
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 178
acgtgtgaag gtactcac                                                 18

<210> SEQ ID NO 179
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 179
gacgtgtgaa ggtactca                                                 18

<210> SEQ ID NO 180
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 180
gggacgtgtg aaggtact                                                 18

<210> SEQ ID NO 181
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 181
tgggacgtgt gaaggtac                                                 18

<210> SEQ ID NO 182
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 182
atgggacgtg tgaaggta                                                 18

<210> SEQ ID NO 183
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 183
gcatgggacg tgtgaagg                                               18

<210> SEQ ID NO 184
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 184
cgcatgggac gtgtgaag                                               18

<210> SEQ ID NO 185
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 185
gcgcatggga cgtgtgaa                                               18

<210> SEQ ID NO 186
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 186
cggcgcatgg gacgtgtg                                               18

<210> SEQ ID NO 187
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 187
acggcgcatg ggacgtgt                                               18

<210> SEQ ID NO 188
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 188
cacggcgcat gggacgtg                                               18

<210> SEQ ID NO 189
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 189
agcacggcgc atgggacg                                               18

<210> SEQ ID NO 190
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 190
cagcacggcg catgggac                                                     18

<210> SEQ ID NO 191
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 191
acagcacggc gcatggga                                                     18

<210> SEQ ID NO 192
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 192
atcctgagag cccaagaa                                                     18

<210> SEQ ID NO 193
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 193
gatcctgaga gcccaaga                                                     18

<210> SEQ ID NO 194
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 194
agatcctgag agcccaag                                                     18

<210> SEQ ID NO 195
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 195
ccagatcctg agagccca                                                     18

<210> SEQ ID NO 196
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 196
```
gccagatcct gagagccc                                                    18

<210> SEQ ID NO 197
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 197
agccagatcc tgagagcc                                                    18

<210> SEQ ID NO 198
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 198
ugaagguacu cacacugccg c                                                21

<210> SEQ ID NO 199
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 199
uaucugcacc uuugguag                                                    18

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
tcttattaat tatctgcacc                                                  20

<210> SEQ ID NO 201
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 201
acgcactcac accacttc                                                    18

<210> SEQ ID NO 202
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 202
cgcctacttg ctcgcaag                                                    18

<210> SEQ ID NO 203
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 203
gacccgccta cttgctcg                                                  18

<210> SEQ ID NO 204
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 204
gacccgcctg cttgctcg                                                  18

<210> SEQ ID NO 205
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 205
cctggacccg cctgcttg                                                  18

<210> SEQ ID NO 206
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 206
cgccuacuug cucgcaag                                                  18

<210> SEQ ID NO 207
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (17)..(17)
<223> OTHER INFORMATION: bases at these positions are DNA

<400> SEQUENCE: 207
ccuggacccg ccugcutg                                                  18

<210> SEQ ID NO 208
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are DNA

<400> SEQUENCE: 208
tgauauuauc cuuugagc                                                  18

<210> SEQ ID NO 209
<211> LENGTH: 18
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are DNA

<400> SEQUENCE: 209
ttgauauuau ccuuugag                                              18

<210> SEQ ID NO 210
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are DNA

<400> SEQUENCE: 210
ttugauauua uccuuuga                                              18

<210> SEQ ID NO 211
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 211
cacuuccuaa uaauucaa                                              18

<210> SEQ ID NO 212
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (18)..(18)
<223> OTHER INFORMATION: bases at these positions are DNA

<400> SEQUENCE: 212
acaccacuuc cuaauaat                                              18

<210> SEQ ID NO 213
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 213
acucacacca cuuccuaa                                              18

<210> SEQ ID NO 214
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 214
cccgccuacu ugcucgca                                              18
```

```
<210> SEQ ID NO 215
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 215
gacccgccua cuugcucg                                                    18

<210> SEQ ID NO 216
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 216
gacccgccug cuugcucg                                                    18

<210> SEQ ID NO 217
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are DNA
<220> FEATURE:
<221> NAME/KEY: misc_feature
<222> LOCATION: (18)..(18)
<223> OTHER INFORMATION: bases at these positions are DNA

<400> SEQUENCE: 217
tggacccgcc ugcuugct                                                    18

<210> SEQ ID NO 218
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 218
ucuuauuaau uaucugcacc                                                  20

<210> SEQ ID NO 219
<211> LENGTH: 20
<212> TYPE: DNA
<213> ORGANISM: Artificial sequence
<220> FEATURE:
<223> OTHER INFORMATION: Primer

<400> SEQUENCE: 219
cactgagaac ctgaagcacc                                                  20

<210> SEQ ID NO 220
<211> LENGTH: 21
<212> TYPE: DNA
<213> ORGANISM: Artificial sequence
<220> FEATURE:
<223> OTHER INFORMATION: Primer

<400> SEQUENCE: 220
```
gttgctaaga tccagcttct t                                             21

<210> SEQ ID NO 221
<211> LENGTH: 26
<212> TYPE: DNA
<213> ORGANISM: Artificial sequence
<220> FEATURE:
<223> OTHER INFORMATION: Probe

<400> SEQUENCE: 221
ttaattatct gcaccttccc gcctcc                                        26

<210> SEQ ID NO 222
<211> LENGTH: 22
<212> TYPE: DNA
<213> ORGANISM: Artificial sequence
<220> FEATURE:
<223> OTHER INFORMATION: Primer

<400> SEQUENCE: 222
aatatcaaac acgtcccggg ag                                            22

<210> SEQ ID NO 223
<211> LENGTH: 20
<212> TYPE: DNA
<213> ORGANISM: Artificial sequence
<220> FEATURE:
<223> OTHER INFORMATION: Primer

<400> SEQUENCE: 223
tgcctaatga gccacacttg                                               20

<210> SEQ ID NO 224
<211> LENGTH: 24
<212> TYPE: DNA
<213> ORGANISM: Artificial sequence
<220> FEATURE:
<223> OTHER INFORMATION: Probe

<400> SEQUENCE: 224
gtctacaaac cagttgacct gagc                                          24

<210> SEQ ID NO 225
<211> LENGTH: 21
<212> TYPE: DNA
<213> ORGANISM: Artificial sequence
<220> FEATURE:
<223> OTHER INFORMATION: Primer

<400> SEQUENCE: 225
aagattgggt ccctggacaa t                                             21

<210> SEQ ID NO 226
<211> LENGTH: 26
<212> TYPE: DNA
<213> ORGANISM: Artificial sequence
<220> FEATURE:
<223> OTHER INFORMATION: Primer

<400> SEQUENCE: 226
agcttgtggg tttcaatctt tttatt                                        26

<210> SEQ ID NO 227
<211> LENGTH: 19
<212> TYPE: DNA
<213> ORGANISM: Artificial sequence

```
<220> FEATURE:
<223> OTHER INFORMATION: Probe

<400> SEQUENCE: 227
cacccacgtc cctggcgga                                                  19

<210> SEQ ID NO 228
<211> LENGTH: 20
<212> TYPE: DNA
<213> ORGANISM: Artificial sequence
<220> FEATURE:
<223> OTHER INFORMATION: Primer

<400> SEQUENCE: 228
ggcaaattca acggcacagt                                                 20

<210> SEQ ID NO 229
<211> LENGTH: 20
<212> TYPE: DNA
<213> ORGANISM: Artificial sequence
<220> FEATURE:
<223> OTHER INFORMATION: Primer

<400> SEQUENCE: 229
gggtctcgct cctggaagat                                                 20

<210> SEQ ID NO 230
<211> LENGTH: 27
<212> TYPE: DNA
<213> ORGANISM: Artificial sequence
<220> FEATURE:
<223> OTHER INFORMATION: Probe

<400> SEQUENCE: 230
aaggccgaga atgggaagct tgtcatc                                         27

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
ccagcttctt attaattatc                                                 20

<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
taagatccag cttcttatta                                                 20
```